US010329563B2

(12) United States Patent
Chen et al.

(10) Patent No.: US 10,329,563 B2
(45) Date of Patent: Jun. 25, 2019

(54) ORGANIC COMPOSITIONS TO TREAT HSF1-RELATED DISEASES

(71) Applicant: Arrowhead Pharmaceuticals, Inc., Pasadena, CA (US)

(72) Inventors: Jinyun Chen, Chestnut Hill, MA (US); Kalyani Gampa, Natick, MA (US); Dieter Huesken, Freiburg (DE); Frank Stegmeier, Acton, MA (US); Mark Stump, Lexington, MA (US); Chandra Vargeese, Schwenksville, PA (US); Jan Weiler, Lorrach-Haagen (DE); Wenlai Zhou, Newton, MA (US)

(73) Assignee: Arrowhead Pharmaceuticals, Inc., Pasadena, CA (US)

( * ) Notice: Subject to any disclaimer, the term of this patent is extended or adjusted under 35 U.S.C. 154(b) by 0 days.

(21) Appl. No.: 15/587,538

(22) Filed: May 5, 2017

(65) Prior Publication Data

US 2017/0298354 A1 Oct. 19, 2017

Related U.S. Application Data

(62) Division of application No. 14/342,193, filed as application No. PCT/IB2012/054455 on Aug. 30, 2012, now abandoned.

(60) Provisional application No. 61/598,453, filed on Feb. 14, 2012, provisional application No. 61/530,532, filed on Sep. 2, 2011.

(51) Int. Cl.
*C07H 21/04* (2006.01)
*C12N 15/113* (2010.01)
*A61K 31/5377* (2006.01)
*A61K 31/713* (2006.01)
*A61K 45/06* (2006.01)

(52) U.S. Cl.
CPC ........ *C12N 15/113* (2013.01); *A61K 31/5377* (2013.01); *A61K 31/713* (2013.01); *A61K 45/06* (2013.01); *C12N 2310/14* (2013.01); *C12N 2310/321* (2013.01); *C12N 2310/322* (2013.01); *C12N 2310/333* (2013.01); *C12N 2310/334* (2013.01); *C12N 2310/335* (2013.01); *C12N 2310/336* (2013.01); *C12N 2310/351* (2013.01); *C12N 2320/31* (2013.01)

(58) Field of Classification Search
None
See application file for complete search history.

(56) References Cited

U.S. PATENT DOCUMENTS

| 6,506,559 | B1 | 1/2003 | Fire et al. |
| 6,573,099 | B2 | 6/2003 | Graham et al. |
| 7,053,052 | B2 | 5/2006 | Voellmy et al. |
| 7,250,496 | B2 | 7/2007 | Bentwich |
| 7,691,997 | B2 | 4/2010 | Khvorova et al. |
| 7,858,592 | B2 | 12/2010 | Shames et al. |
| 8,090,542 | B2 | 1/2012 | Khvorova et al. |
| 8,168,606 | B2 | 5/2012 | Van Heeke et al. |
| 2004/0029275 | A1* | 2/2004 | Brown ............... C12N 15/111 435/375 |
| 2005/0255487 | A1* | 11/2005 | Khvorova ............ A61K 31/713 435/6.11 |
| 2007/0135372 | A1* | 6/2007 | MacLachlan ........ C12N 15/113 514/44 A |
| 2007/0238682 | A1 | 10/2007 | Nudler et al. |
| 2009/0092600 | A1 | 4/2009 | Kufe |

FOREIGN PATENT DOCUMENTS

| WO | 2003/000861 A2 | 1/2003 |
| WO | 2006/110688 A2 | 10/2006 |
| WO | 2007/002528 A1 | 1/2007 |
| WO | 2007/041294 A2 | 4/2007 |
| WO | 2008/022035 A2 | 2/2008 |
| WO | 2008/141074 A1 | 11/2008 |
| WO | 2009/103067 A2 | 8/2009 |
| WO | 2010135669 A1 | 11/2010 |
| WO | 2011073326 A2 | 6/2011 |

OTHER PUBLICATIONS

Abravaya et al.; "The human heat shock protein hsp70 interacts with HSF, the transcription factor that regulates heat shock gene expression"; Genes Dev.; 6:1153-1164 (1992).
Cen et al.; "Induction of HSF1 expression is associated with sporadic colorectal cancer"; World J Gastroenterol; 10(21):3122-3126 (2004).
Cervantes-Gomez et al.; "Transcription Inhibition of Heat Shock Proteins: A Strategy for Combination of 17-Allylamino-17-Demethoxygeldanamycin and Actinomycin D"; Cancer Res—Research Article; 69(9):3947-3954 (2009).
Chu et al.; "Sequential Phosphorylation by Mitogen-activated Protein Kinase and Glycogen Synthase Kinase 3 Represses Transcriptional Activation by Heat Shock Factor-1"; The Journal of Biological Chemistry; 271(48):30847-30857 (1996).
Ciocca et al.; "Heat shock proteins in cancer: diagnostic, prognostic, predictive, and treatment implications"; Cell Stress & Chaperones; 10(2):86-103 (2005).
Dai et al.; "Heat Shock Factor 1 Is a Powerful Multifaceted Modifier of Carcinogenesis"; Cell; 130:1005--1018 (2007).
Dokladny et al.; "Cellular and Molecular Mechanisms of Heat Stress-Induced Up-Regulation of Occludin Protein Expression: Regulatory Role of Heat Shock Factor-1"; The American Journal of Pathology—Epithelial and Mesenchymal Cell Biology; 172(3):659-670 (2008).
Elbashir et al., "Fuctional Anatomy of siRNAs for Mediating Efficient RNAi in *Drosophila melanogaster* embryo lysate" EMBO J., 20 (23): 6877-6888 (2001).

(Continued)

*Primary Examiner* — Kimberly Chong
(74) *Attorney, Agent, or Firm* — Robert M. Teigen; Paul VanderVelde

(57) ABSTRACT

The present disclosure relates to methods of treating heat stock factor 1 (HSF1)-related diseases such as cancer, autoimmune and viral diseases, using a therapeutically effective amount of a RNAi agent to HSF.

13 Claims, 5 Drawing Sheets

Specification includes a Sequence Listing.

(56) References Cited

OTHER PUBLICATIONS

Elbashir et al., "Duplexes of 21-nucleotide RNAs mediate RNA interference in cultured mammalian cells" Nature, 411: 494-498 (2001).
Ferrarini et al.; "Unusual Expression and Localization of Heat-Shock Proteins in Human Tumor Cells"; Int. J. Cancer; 51:613-619 (1992).
Fuller et al.; "Cancer and the Heat Shock Response"; European Journal of Cancer—Feature Articles; 30A (12):1884-1891 (1994).
Green et al.; "A Heat Shock-Responsive Domain of Human HSF1 That Regulates Transcription Activation Domain Function"; Molecular and Cellular Biology; 15(6):3354-3362 (1995).
He et al.; "Elevated Expression of Heat Shock Factor (HSF) 2A Stimulates HSF1-induced Transcription during Stress"; The Journal of Biological Chemistry; 278(37):35465-35475 (2003).
Helmbrecht et al.; "Chaperones in cell cycle regulation and mitogenic signal transduction: a review"; Cell Prolif.—Review Article; 33:341-365 (2000).
Hoang et al.; "A Novel Association between the Human Heat Shock Transcription Factor 1 (HSF1) and Prostate Adenocarcinoma"; American Journal of Pathology; 156(3):857-864 (2000).
Homma et al.; "Demyelination, Astrogliosis, and Accumulation of Ubiquitinated Proteins, Hallmarks of CNS Disease in hsf1-Deficient Mice"; The Journal of Neuroscience; 27(30):7974-7986 (2007).
Hu et al.; "HSF-1 Interacts with Ral-binding Protein 1 in a Stress-responsive, Multiprotein Complex with HSP90 in Vivo"; The Journal of Biological Chemistry; 278(19):17299-17306 (2003).
Huang et al.; "Heat Shock Transcription Factor 1 Binds Selectively in Vitro to Ku Protein and the Catalytic Subunit of the DNA-dependent Protein Kinase"; The Journal of Biological Chemistry; 272(41):26009-26016 (1997).
Jacobs et al.; "Heat Shock Factor 1 Attenuates 4-Hydroxynonenal-mediated Apoptosis: Critical Role for Heat Shock Protein 70 Induction and Stabilization of Bcl-XL"; The Journal of Biological Chemistry; 282(46):33412-33420 (2007).
Jaattela; "Escaping Cell Death: Survival Proteins in Cancer"; Experimental Cell Research—Minireview; 248:30-43 (1999).
Jolly et al.; "Role of the Heat Shock Response and Molecular Chaperones in Oncogenesis and Cell Death"; Journal of the National Cancer Institute—Review; 92(19):1564-1572 (2000).
Kim et al.; "Update on Hsp90 Inhibitors in Clinical Trial"; Current Topics in Medicinal Chemistry; 9:1479-1492 (2009).
Kline et al.; "Repression of the Heat Shock Factor 1 Transcriptional Activation Domain Is Modulated by Constitutive Phosphorylation"; Molecular and Cellular Biology; 17(4):2107-2115 (1997).
Kraynack et al., "Small interfering RNAs containing full 2'-0-methylribonucleotide-modified sense strands display Argonaute2/eIF2C2-dependent activity" RNA: vol. 12, pp. 163-176; (2006).
Macario et al.; "Mechanisms of Disease: Sick Chaperones, Cellular Stress, and Disease"; The New England Journal of Medicine—Review Article; 353(14):1489-1501 (2005).
Min et al.; "Selective suppression of lymphomas by functional loss of Hsf1 in a p53-deficient mouse model for spontaneous tumors"; Oncogene; 26:5086-5097 (2007).
Mosser et al.; "Molecular chaperones and the stress of oncogenesis"; Oncogene; 23:2907-2918 (2004).
Nair et al.; "A pathway of multi-chaperone interactions common to diverse regulatory proteins: estrogen receptor, Fes tyrosine kinase, heat shock transcription factor Hsf1, and the aryl hydrocarbon receptor"; Cell Stress & Chaperones; 1(4):237-250 (1996).
Newton et al.; "The Regulatory Domain of Human Heat Shock Factor 1 Is Sufficient to Sense Heat Stress"; Molecular and Cellular Biology; 16(3):839-846 (1996).
Nunes et al.; "Heat Shock Factor-1 and the Heat Shock Cognate 70 Protein Associate in High Molecular Weight complexes in the Cytoplasm of NIH-3T3 Cells"; Biochemical and Biophysical Research Communications; 213(1):1-6 (1995).
Page et al.; "Genome-wide analysis of human HSF1 signaling reveals a transcriptional program linked to cellular adaptation and survival"; Mal. BioSyst.; 2:627-639 (2006).
Page et al.; "Genome-wide analysis of human HSF1 signaling reveals a transcriptional program linked to cellular adaptation and survival"; Mal. BioSyst.; 2:627-639 (2006). [Supplemental Material—Table 1].
Parrish et al., "Fuctional Anatomy of a dsRNA Trigger: Differential Requirement for the Two Trigger Strands in RNA Interference" Molecular Cell, vol. 6, pp. 1077-1087, (2000).
Powers et al.; "Inhibitors of the heat shock response: Biology and pharmacology"; FEBS Letters-. Minireview; 581 :3758-3769 (2007).
Powers et al.; "Dual Targeting of HSC70 and HSP72 Inhibits HSP90 Function and Induces Tumor-Specific Apoptosis"; Cancer Cell; 14:250-262 (2008).
Rabindran et al.; "Molecular cloning and expression of a human heat shock factor, HSF1"; Proc. Nat Acad. Sci. USA; 88:6906-6910 (1991).
Rossi et al.; "Targeting the Heat Shock Factor 1 by RNA Interference: A Potent Tool to Enhance Hyperthermochemotherapy Efficacy in Cervical Cancer"; Cancer Res; 66:7678-7685 (2006).
Satyal et al.; "Negative regulation of the heat shock transcriptional response by?HSBP1"; Genes Dev.; 12:1962-1974 (1998).
Saetrom, "Predicting the efficacy of short oligonucleotides in antisense and RNAi experiments with boosted genetic programming" Bioinformatics, vol. 20, No. 17, pp. 3055-3063, (2004).
Schett et al.; "Enhanced Expression of Heat Shock Protein 70 (hsp70) and Heat Shock Factor 1 (HSF1) Activation in Rheumatoid Arthritis Synovial Tissue—Differential Regulation of hsp70 Expression and HSF1 Activation in Synovial Fibroblasts by Proinflammatory Cy1okines, Shear Stress, and Antiinflammatory Drugs"; J. Clin. Invest.; 102(2):302-311 (1998).
Shamovsky et al.; "New insights into the mechanism of heat shock response activation"; Cell. Mal. Life Sci.—Visions & Reflections (Minireview); 65:855-861 (2008).
Shi et al.; "The Carboxyl-Terminal Transactivation Domain of Heat Shock Factor 1 Is Negatively Regulated and Stress Responsive"; Molecular and Cellular Biology; 15(8):4309-4318 (1995).
Shi et al.; "Molecular chaperones as HSF1-specific transcriptional repressors"; Genes & Development; 12:654-666 (1998).
Sioud; "Induction of Inflammatory Cy1okines and Interferon Responses by Double-stranded and Single-stranded siRNAs is Sequence-dependent and Requires Endosomal Localization"; J. Mol. Biol.; 348:1079-1090 (2005).
Tang et al.; "Expression of heat shock proteins and heat shock protein messenger ribonucleic acid in human prostate carcinoma in vitro and in tumors in vivo"; Cell Stress & Chaperones; 10(1 ):46-58 (2005).
Wang et al.; "Expression of a Dominant Negative Heat Shock Factor-1 Construct Inhibits Aneuploidy in Prostate Carcinoma Cells"; The Journal of Biological Chemistry; 279(31 ):32651-32659 (2004).
Wei et al.; "Both Strands of siRNA Have Potential to Guide Posttranscriptional Gene Silencing in Mammalian Cells"; PLoS One; 4(4):e5382[1-10] (2009).
Whitesell et al.; "Inhibiting the transcription factor HSF1 as an anticancer strategy"; Expert Opin. Ther. Targets—Review; 13(4 ):469-478 (2009).
Xie et al.; "Heat Shock Factor 1 Represses Transcription of the IL-1beta Gene through Physical Interaction with the Nuclear Factor of Interleukin 6"; The Journal of Biological Chemistry; 277(14):11802-11810 (2002).
Xing et al.; "HSF1 Modulation of Hsp70 mRNA Polyadenylation via Interaction with Symplekin"; The Journal of Biological Chemistry; 279(11):10551-10555 (2004).
Office Action for corresponding Eurasian Application No. 201490553, dated Mar. 29, 2016.
Patent Examination Report No. 3 for corresponding Australian Application No. 2012303650 dated Mar. 30, 2016.
Office Action dated Jul. 7, 2016 (dated Jul. 12, 2016) for corresponding Japanese Patent Application No. 2014-527791.
Third Office Action for corresponding Chinese Application No. 201280053243.0 dated Jun. 7, 2016.

(56) References Cited

OTHER PUBLICATIONS

Patent Examination Report No. 1 for corresponding Australian Patent Application No. 2016202437 dated Oct. 24, 2016.
European Search Report for corresponding European Application No. EP 16179166 dated Oct. 17, 2016.
Yin, C. et al.; "Silencing heat shock factor 1 by small interfering RNA abrogates heat shock-induced cardioprotection against ischemia-reperfusion injury in mince"; Journal of Molecular and Cellular Cardiology vol. 39; Issue 4; pp. 681-689; (2005).
Du, Z-X. et al.; "Proteasome Inhibitor MG 132 Induces BAG3 Expression Through Activation of Heat Shock Factor 1"; Journal of Cellular Physiology; vol. 218; Issue 3; pp. 631-637; (2009).

* cited by examiner

ORGANIC COMPOSITIONS TO TREAT HSF1-RELATED DISEASES

PRIORITY

This application is a divisional of U.S. patent application Ser. No. 14/342,193, filed Aug. 20, 2015, which is a § 371 U.S. National Application of PCT/IB2012/054455, filed Aug. 30, 2012, which claims priority to U.S. Provisional Patent Application No. 61/598,453, filed Feb. 14, 2012, and U.S. Provisional Patent Application No. 61/530,532, filed Sep. 2, 2011, the entire contents of each of which are incorporated herein by reference.

SEQUENCE LISTING

This application contains a Sequence Listing which has been submitted electronically in ASCII format. The ASCII copy, created on May 4, 2017, is named "Sequence_54711_US2.txt" and is 92 kb in size.

BACKGROUND OF THE INVENTION

HSF1 is the master regulator of the heat shock response, in which multiple genes are induced in response to temperature increase and other stresses. At non-shock temperatures in humans and other vertebrates, HSF1 is produced constitutively, but is inactive and bound by protein HSP90. At an elevated temperature, HSF1 is released by HSP90, moves from the cytoplasm to the nucleus, and trimerizes. This active HSF1 binds to sequences called heat shock elements (HSE) in DNA and activates transcription of heat shock genes by RNA polymerase II. The HSE has a consensus sequence of three repeats of NGAAN and is present in the promoter regions of the HSP90, HSP70 and HSP27 genes. During cessation of the heat shock response, HSF1 is phosphorylated by mitogen-activated protein kinases (MAPKs) and glycogen synthase kinase 3 (GSK3) and returns to an inactive state. The biochemistry of HSF1 is described, inter alia, in Chu et al. 1996 J. Biol. Chem. 271:30847-30857; Huang et al. 1997 J. Biol. Chem. 272: 26009-26016; and Morimoto et al. 1998 Nat. Biotech. 16: 833-838.

HSF1 interacts with additional factors. HSF1 binds to DNA-dependent protein kinase (DNA-PK), which is involved in DNA repair. HSF1 is a target of mitogen-activated protein kinases, and its activity is down-regulated when the RAS signaling cascade is active.

Additional heat shock factor proteins in humans include HSF2, HSF3, and HSF4. HSF1, HSF2, and HSF3 are positive regulators of heat shock gene expression, while HSF4 is a negative regulator. HSF1, HSF2 and HSF4 play a role in transcriptional control of other heat shock proteins. The various HSF proteins share about 40% sequence identity.

HSF1 has been implicated in several diseases, including cancer, and autoimmune, and viral diseases. HSF1 and other heat shock proteins (whose expression is increased by HSF1) are over-expressed in, or have otherwise been implicated in, breast, endometrial, fibrosarcoma, gastric, kidney, liver, lung, lymphoma, neuroectodermal, neuroblastoma, Ewing's sarcoma, prostate, skin, squamous cell, and testicular cancers, leukemia (e.g., promyelocytic leukemia), and Hodgkin's disease.

Without wishing to be bound by any particular theory, the present disclosure contemplates that heat shock proteins (HSP) may block the pathways of apoptosis and permit malignant cells to arise despite the triggering of apoptotic signals during transformation. HSP expression may also afford protection to cancer cells from treatments such as chemotherapy and hyperthermia by thwarting the pro-apoptotic influence of these modalities.

Because HSF1 positively regulates HSPs, a need exists for therapeutics that modulate HSF1.

BRIEF SUMMARY OF THE INVENTION

The present disclosure provides RNAi (RNA interference) agents, for inhibition of HSF1. HSF1 is the master regulator of the heat shock response, in which multiple genes are induced in response to temperature increase and other stresses.

HSF1 has been implicated in several HSF1-related diseases, including cancer, and autoimmune, and viral diseases. HSF1 and other heat shock proteins (whose expression is increased by HSF1) are over-expressed in, or have otherwise been implicated in, breast, endometrial, fibrosarcoma, gastric, kidney, liver, lung, lymphoma, neuroectodermal, neuroblastoma, Ewing's sarcoma, prostate, skin, squamous cell, and testicular cancers, leukemia (e.g., promyelocytic leukemia), and Hodgkin's disease. RNAi agents to HSF1 are useful in treating these diseases.

Because HSF1 positively regulates HSPs, a need exists for therapeutics that modulate HSF1. The RNAi agents of the present disclosure are specific to HSF1 and can reduce expression of HSF1. These RNAi agents are therefore useful in treating cancer, and autoimmune, and viral diseases.

The present disclosure provides specific RNAi agents and methods that are useful in reducing HSF1 levels in a subject, e.g., a mammal, such as a human. The present disclosure specifically provides double-stranded RNAi agents for RNA interference-mediated inhibition of the HSF1 gene, comprising at least 15 or more contiguous nucleotides of HSF1. In particular, the present disclosure provides agents comprising sequences of 15 or more contiguous nucleotides differing by 0, 1, 2 or 3 from those of the RNAi agents provided, e.g., in Tables A1, 1, 2, 3, 4, 5, 6, or 7 (or, if DNA sequences are provided, the RNA equivalent of or RNA corresponding to these sequences, e.g., with RNA nucleotides rather than DNA, and U instead of T). The RNAi agents particularly can in one embodiment comprise less than 30 nucleotides per strand, e.g., such as 18-23 nucleotides, and/or 19-21 nucleotides, and/or such as those provided, e.g., in Tables A1, 1, 2, 3, 4, 5, 6, or 7 (or, if DNA sequences are provided, the RNA equivalent of or RNA corresponding to these sequences, e.g., with RNA nucleotides rather than DNA, and U instead of T).

The double-stranded RNAi agents can have one or two blunt end(s) and/or overhang(s) of 1, 2, 3 or 4 nucleotides (i.e., 1-4 nt [nucleotides]) from one or both 3' and/or 5' ends. The double-stranded RNAi agents can also optionally comprise one or two 3' caps and/or one or more modified nucleotides. Modified variants of sequences as provided herein include those that are otherwise identical but contain substitutions of a naturally occurring nucleotide for a corresponding modified nucleotide. Seven modifications of each of several duplex nucleotide sequences are provided. Any RNAi agent sequence(s) provided herein can be used in combination with any modification(s) or set of modification(s), 5' and/or 3' end caps, blunt end(s), and/or additional overhang(s) on one or both 5' and/or 3' end(s), ligand(s), pharmaceutical carrier(s) or additional treatment(s), provided that such combinations are not mutually exclusive (e.g., a RNAi agent comprising two strands cannot by definition simultaneously have two blunt ends and two overhangs).

The RNAi agent can either contain only naturally-occurring ribonucleotide subunits, or one or more modifications to the sugar, phosphate or base of one or more of the replacement nucleotide subunits, whether they comprise ribonucleotide subunits or deoxyribonucleotide subunits. In one embodiment, modified variants of the disclosed RNAi agents include RNAi agents with the same sequence (e.g., the same sequence of bases), but with one or more modifications to one or more of the sugar or phosphate of one or more of the nucleotide subunits. In one embodiment, the modifications improve efficacy, stability and/or reduce immunogenicity of the RNAi agent. One aspect of the present disclosure relates to a double-stranded oligonucleotide comprising at least one non-natural nucleobase. In certain embodiments, the non-natural nucleobase is difluorotolyl, nitroindolyl, nitropyrrolyl, or nitroimidazolyl. In a particular embodiment, the non-natural nucleobase is difluorotolyl. In certain embodiments, only one of the two oligonucleotide strands contains a non-natural nucleobase. In certain embodiments, both of the oligonucleotide strands contain a non-natural nucleobase.

The RNAi agent(s) can optionally be attached to a ligand selected to improve one or more characteristic, such as, e.g., stability, distribution and/or cellular uptake of the agent, e.g., cholesterol or a derivative thereof. The RNAi agent(s) can be isolated or be part of a pharmaceutical composition used for the methods described herein. Particularly, the pharmaceutical composition can be formulated for delivery to the lungs or nasal passage or formulated for parental administration. The pharmaceutical compositions can optionally comprise two or more RNAi agents, each one directed to the same, overlapping or a different segment of the HSF1 mRNA. If the composition comprises two or more RNAi agents targeting the same sequence, the two or more RNAi agents can, for example, differ in modifications. Optionally, the pharmaceutical compositions can further comprise or be used in conjunction with any known treatment for any HSF1-related disease.

The present disclosure further provides methods for reducing the level of HSF1 mRNA in a cell, particularly in the case of a disease characterized by over-expression or hyper-activity of HSF1. The present disclosure also encompasses a method of treating a human subject having a pathological state mediated at least in part by HSF1 expression, over-expression or hyper-activity (e.g., increased or excessive activity), the method comprising the step of administering to the subject a therapeutically effective amount of a RNAi agent HSF1. Such methods comprise the step of administering one of the RNAi agents of the present disclosure to a subject, as further described below. The present methods utilize the cellular mechanisms involved in RNA interference to selectively degrade the target RNA in a cell and are comprised of the step of contacting a cell with one of the RNAi agents of the present disclosure. Such methods can be performed directly on a cell or can be performed on a mammalian subject by administering to a subject one of the RNAi agents/pharmaceutical compositions of the present disclosure. Reduction of target HSF1 mRNA in a cell results in a reduction in the amount of encoded HSF1 protein produced.

The methods and compositions of the present disclosure, e.g., the methods and HSF1 RNAi agent compositions, can be used with any dosage and/or formulation described herein, as well as with any route of administration described herein.

The details of one or more embodiments of the present disclosure are set forth in the accompanying drawings and the description below. Elements of the various embodiments (e.g., modifications, end caps, ligands, sequences, combinations of RNAi agents, etc.) which are not mutually exclusive can be combined with each other. Thus, the disclosure complements any composition comprising one or more HSF1 RNAi agent comprising a first strand and a second strand, wherein (1) (a) the sequence of the first strand comprises 15 contiguous nt differing by 0, 1, 2, or 3 nt from the sequence of the first strand of any RNAi agent disclosed herein; or (b) the sequence of the first strand comprises 15 contiguous nt of the sequence of the first strand of any RNAi agent disclosed herein; or (c) the sequence of the first strand comprises the sequence of the first strand of any RNAi agent disclosed herein; or (d) the sequence of the first strand is the sequence of the first strand of any RNAi agent disclosed herein; wherein (2) the RNAi agent can have any modification(s), blunt end(s), overhang(s), 5' end cap(s), 3' end cap(s), ligand(s) or any other variation or modification disclosed herein, or any combinations thereof, provided that such combinations are not mutually exclusive (e.g., a RNAi comprising two strands cannot by definition comprise both two overhangs and two blunt ends). Other features, objects, and advantages of the present disclosure will be apparent from this description, the drawings, Tables, sequences, Examples, abstract, and claims. For example, any RNAi agent sequence disclosed herein can be combined with any set of modifications or endcaps disclosed herein. Any combination of modifications, 5' end caps, and/or 3' end caps can be used with any RNAi agent sequence disclosed herein. Any RNAi agent disclosed herein (with any combination of modifications or endcaps or without either modifications or endcaps) can be combined with any other RNAi agent or other treatment composition or method disclosed herein.

DETAILED DESCRIPTION OF THE INVENTION

Figure 1:
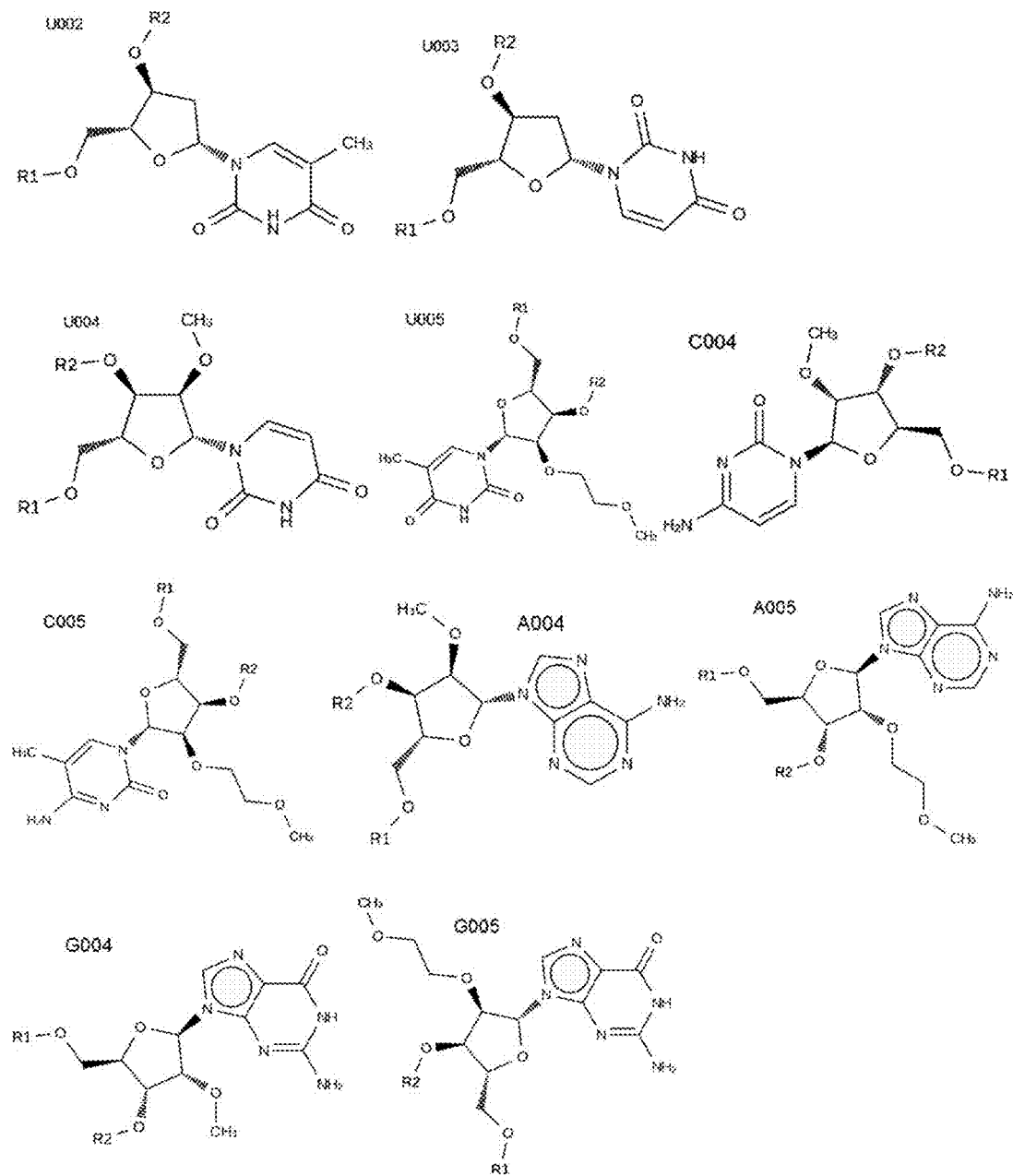
FIG. 1 illustrates various modified nucleotides: U002, U003, U004, U005, C004, C005, A004, A005, G005, and G004, which can be used in the RNAi agents disclosed herein.

The present disclosure encompasses RNAi agents to HSF1, which are useful in treatment of HSF1-related diseases (e.g., diseases associated with mutations in and/or altered expression, level and/or activity of HSF1, and/or diseases treatable by modulating the expression, level and/or activity of HSF1), such as cancer, and autoimmune, and viral diseases. The present disclosure also provides methods of treating a human subject having a pathological state mediated at least in part by HSF1 expression, the method comprising the step of administering to the subject a therapeutically effective amount of a RNAi agent HSF1.

Various Embodiments of the Disclosure Include the Following

In one embodiment, the present disclosure relates to a composition comprising an RNAi agent for RNA interference-mediated inhibition of the HSF1 gene, comprising an antisense strand, wherein the antisense strand comprises at least 15 contiguous nucleotides differing by 0, 1, 2, or 3 nucleotides from the antisense strand of an RNAi agent to HSF1 selected of any sequence provided herein (e.g., in Tables A1, 1, 2, 3, 4, 5, 6, or 7 [or, if DNA sequences are provided, the RNA equivalent of or RNA corresponding to these sequences, e.g., with RNA nucleotides rather than DNA, and U instead of]). In another embodiment, the present disclosure relates to a composition comprising an RNAi agent comprising a sense strand and an antisense strand, wherein the antisense strand comprises at least 15 contiguous nucleotides differing by 0, 1, 2, or 3 nucleotides from the antisense strand of an RNAi agent to HSF1 of any sequence provided herein (or, if DNA sequences are provided, the RNA equivalent of or RNA corresponding to these sequences, e.g., with RNA nucleotides rather than DNA, and U instead of T). In another embodiment, the present disclosure relates to a composition comprising an RNAi agent comprising a sense strand and an antisense strand, wherein the sense strand comprises at least 15 contiguous nucleotides differing by 0, 1, 2, or 3 nucleotides from the sense strand and the antisense strand comprises at least 15 contiguous nucleotides differing by 0, 1, 2, or 3 nucleotides from the antisense strand of an RNAi agent to HSF1 of any sequence provided herein (or, if DNA sequences are provided, the RNA equivalent of or RNA corresponding to these sequences, e.g., with RNA nucleotides rather than DNA, and U instead of T). In another embodiment, the present disclosure relates to a composition comprising an RNAi agent comprising a first strand and a second strand, wherein the sequence of the first strand comprises the sequence of the first strand of an RNAi agent to HSF1 of any sequence provided herein (or, if DNA sequences are provided, the RNA equivalent of or RNA corresponding to these sequences, e.g., with RNA nucleotides rather than DNA, and U instead of T). In another embodiment, the present disclosure relates to a composition comprising an RNAi agent comprising a first strand and a second strand, wherein the sequence of the first strand is the sequence of the first strand of an RNAi agent to HSF1 of any sequence provided herein (or, if DNA sequences are provided, the RNA equivalent of or RNA corresponding to these sequences, e.g., with RNA nucleotides rather than DNA, and U instead of T).

HSF1 RNAi agents are presented in the following Tables:
Table A1. SEQ ID NOs and positions of various HSF1 RNAi agents.
Table 1. HSF1 RNAi agent target sequences.
Table 2. Unmodified HSF1 RNAi agent sequences.
Table 3. Example modified HSF1 RNAi agent sequences.
Table 4. Sets of HSF1 RNAi agents comprising overlapping sequences.
Table 5. Activity of HSF1 RNAi agents in vitro on GTL-16 cells.
Table 6. Activity of HSF1 RNAi agents in vitro on SK-BR-3 cells.
Table 7. Activity of HSF1 RNAi agents in vitro on GTL-16 and SK-BR-3 cells.

Various Embodiments of the Present Disclosure

In one embodiment, the present disclosure relates to particular compositions comprising an RNAi agent comprising an antisense strand, wherein the antisense strand comprises at least 15 contiguous nucleotides differing by 0, 1, 2, or 3 nucleotides from the antisense strand of an RNAi agent to HSF1 selected from any one or more of the sequences in Tables A1, 1, 2, 3, 4, 5, 6, or 7 (or, if DNA sequences are provided, the RNA equivalent of or RNA corresponding to these sequences, e.g., with RNA nucleotides rather than DNA, and U instead of T). In another embodiment, the present disclosure relates to a composition comprising an RNAi agent comprising a sense strand and an antisense strand, wherein the antisense strand comprises at least 15 contiguous nucleotides differing by 0, 1, 2, or 3 nucleotides from the antisense strand of an RNAi agent to HSF1 listed in any one or more of Tables A1, 1, 2, 3, 4, 5, 6, or 7 (or, if DNA sequences are provided, the RNA equivalent of or RNA corresponding to these sequences, e.g., with RNA nucleotides rather than DNA, and U instead of T). In another embodiment, the present disclosure relates to a composition comprising an RNAi agent comprising a sense strand and an antisense strand, wherein the sense strand comprises at least 15 contiguous nucleotides differing by 0, 1, 2, or 3 nucleotides from the sense strand and the antisense strand comprises at least 15 contiguous nucleotides differing by 0, 1, 2, or 3 nucleotides from the antisense strand of an RNAi agent to HSF1 listed in any one or more of Tables A1, 1, 2, 3, 4, 5, 6, or 7 (or, if DNA sequences are provided, the RNA equivalent of or RNA corresponding to these sequences, e.g., with RNA nucleotides rather than DNA, and U instead of T). Particular duplexes include those specific duplexes provided above and as listed in any one or more of Tables A1, 1, 2, 3, 4, 5, 6, or 7 (or, if DNA sequences are provided, the RNA equivalent of or RNA corresponding to these sequences, e.g., with RNA nucleotides rather than DNA, and U instead of T). Additional modified variants (e.g., variants comprising one or more modified base) of each of the compositions above are also contemplated as part of the disclosure. RNAi agents comprising a first strand and a second strand, wherein the first strand and/or the second strand comprises the sequence of the first and/or second strand of any RNAi agent to HSF1 listed herein are also contemplated. In various embodiments, the RNAi agent is for inhibition of the HSF1 gene.

Table A1, below, provides the SEQ ID NOs for the target and unmodified and example modified variants of the sense and an anti-sense strands of various RNAi agents to HSF1. The positions for each RNAi agent within the HSF1 gene are also provided in Table A1; the position within the HSF1 gene corresponds to the prefix of the nickname of the HSF1 RNAi agent.

The target sequence for various RNAi agents is provided in Table 1; the unmodified variant for the various RNAi agents is provided in Table 2; example modified variants for each specific RNAi agent are provided in Table 3; and overlapping portions of these RNAi agents are provided in Table 4. Activity levels for various RNAi agents are provided in Tables 5 to 7.

Note that the RNAi agents listed in the Tables herein comprise sets of duplexes, wherein each duplex within the set has a particular set of modifications. For example, all RNAi agents with the prefix hs_HSF1_175 have the same sequence (e.g., nucleotide sequence or sequence of bases), though hs_HSF1_175_A22_S26, hs_HSF1_175_A25_S27, hs_HSF1_175_A81_S26, hs_HSF1_175_A48_S26, hs_HSF1_175_A82_S36, hs_HSF1_175_A83_S36, and hs_HSF1_175_A84_S36 may have different sets of modifications.

Similarly:

All the RNAi agents with the prefix hs_HSF1_517 have the same nucleotide sequence, though they may have different modifications.

All the RNAi agents with the prefix hs_HSF1_562 have the same nucleotide sequence, though they may have different modifications.

All the RNAi agents with the prefix hs_HSF1_751 have the same nucleotide sequence, though they may have different modifications.

All the RNAi agents with the prefix hs_HSF1_755 have the same nucleotide sequence, though they may have different modifications.

All the RNAi agents with the prefix hs_HSF1_846 have the same nucleotide sequence, though they may have different modifications.

All the RNAi agents with the prefix hs_HSF1_1360 have the same nucleotide sequence, though they may have different modifications.

All the RNAi agents with the prefix hs_HSF1_2030 have the same nucleotide sequence, though they may have different modifications.

All the RNAi agents with the prefix hs_HSF1_2034 have the same nucleotide sequence, though they may have different modifications.

All the RNAi agents with the prefix hs_HSF1_2138 have the same nucleotide sequence, though they may have different modifications.

All the RNAi agents with the prefix hs_HSF1_2153 have the same nucleotide sequence, though they may have different modifications.

All the RNAi agents with the prefix hs_HSF1_2154 have the same nucleotide sequence, though they may have different modifications.

Particular duplexes include the following, wherein each duplex targets a sequence comprising a set of SEQ ID NOs, wherein the first SEQ ID NO corresponds to the first strand of the target (e.g., an antisense) and the second SEQ ID NO corresponds to the second strand of the target (e.g., a sense strand): hs_HSF1_175_A22_S26 (SEQ ID NOs. 12 and 96); hs_HSF1_175_A25_S27 (SEQ ID NOs. 24 and 108); hs_HSF1_175_A81_S26 (SEQ ID NOs. 36 and 120); hs_HSF1_175_A48_S26 (SEQ ID NOs. 48 and 132); hs_HSF1_175_A82_S36 (SEQ ID NOs. 60 and 144); hs_HSF1_175_A83_S36 (SEQ ID NOs. 72 and 156); hs_HSF1_175_A84_S36 (SEQ ID NOs. 84 and 168); hs_HSF1_517_A22_S26 (SEQ ID NOs. 4 and 88); hs_HSF1_517_A25_S27 (SEQ ID NOs. 16 and 100); hs_HSF1_517_A81_S26 (SEQ ID NOs. 28 and 112); hs_HSF1_517_A48_S26 (SEQ ID NOs. 40 and 124); hs_HSF1_517_A82_S36 (SEQ ID NOs. 52 and 136); hs_HSF1_517_A83_S36 (SEQ ID NOs. 64 and 148); hs_HSF1_517_A84_S36 (SEQ ID NOs. 76 and 160); hs_HSF1_562_A22_S26 (SEQ ID NOs. 1 and 85); hs_HSF1_562_A25_S27 (SEQ ID NOs. 13 and 97); hs_HSF1_562_A81_S26 (SEQ ID NOs. 25 and 109); hs_HSF1_562_A48_S26 (SEQ ID NOs. 37 and 121); hs_HSF1_562_A82_S36 (SEQ ID NOs. 49 and 133); hs_HSF1_562_A83_S36 (SEQ ID NOs. 61 and 145); hs_HSF1_562_A84_S36 (SEQ ID NOs. 73 and 157); hs_HSF1_751_A22_S26 (SEQ ID NOs. 2 and 86); hs_HSF1_751_A25_S27 (SEQ ID NOs. 14 and 98); hs_HSF1_751_A81_S26 (SEQ ID NOs. 26 and 110); hs_HSF1_751_A48_S26 (SEQ ID NOs. 38 and 122); hs_HSF1_751_A82_S36 (SEQ ID NOs. 50 and 134); hs_HSF1_751_A83_S36 (SEQ ID NOs. 62 and 146); hs_HSF1_751_A84_S36 (SEQ ID NOs. 74 and 158); hs_HSF1_755_A22_S26 (SEQ ID NOs. 3 and 87); hs_HSF1_755_A25_S27 (SEQ ID NOs. 15 and 99); hs_HSF1_755_A81_S26 (SEQ ID NOs. 27 and 111); hs_HSF1_755_A48_S26 (SEQ ID NOs. 39 and 123); hs_HSF1_755_A82_S36 (SEQ ID NOs. 51 and 135); hs_HSF1_755_A83_S36 (SEQ ID NOs. 63 and 147); hs_HSF1_755_A84_S36 (SEQ ID NOs. 75 and 159); hs_HSF1_846_A22_S26 (SEQ ID NOs. 5 and 89); hs_HSF1_846_A25_S27 (SEQ ID NOs. 17 and 101); hs_HSF1_846_A81_S26 (SEQ ID NOs. 29 and 113); hs_HSF1_846_A48_S26 (SEQ ID NOs. 41 and 125); hs_HSF1_846_A82_S36 (SEQ ID NOs. 53 and 137); hs_HSF1_846_A83_S36 (SEQ ID NOs. 65 and 149); hs_HSF1_846_A84_S36 (SEQ ID NOs. 77 and 161); hs_HSF1_1360_A22_S26 (SEQ ID NOs. 6 and 90); hs_HSF1_1360_A25_S27 (SEQ ID NOs. 18 and 102); hs_HSF1_1360_A81_S26 (SEQ ID NOs. 30 and 114); hs_HSF1_1360_A48_S26 (SEQ ID NOs. 42 and 126); hs_HSF1_1360_A82_S36 (SEQ ID NOs. 54 and 138); hs_HSF1_1360_A83_S36 (SEQ ID NOs. 66 and 150); hs_HSF1_1360_A84_S36 (SEQ ID NOs. 78 and 162); hs_HSF1_2030_A22_S26 (SEQ ID NOs. 7 and 91); hs_HSF1_2030_A25_S27 (SEQ ID NOs. 19 and 103); hs_HSF1_2030_A81_S26 (SEQ ID NOs. 31 and 115); hs_HSF1_2030_A48_S26 (SEQ ID NOs. 43 and 127); hs_HSF1_2030_A82_S36 (SEQ ID NOs. 55 and 139); hs_HSF1_2030_A83_S36 (SEQ ID NOs. 67 and 151); hs_HSF1_2030_A84_S36 (SEQ ID NOs. 79 and 163); hs_HSF1_2034_A22_S26 (SEQ ID NOs. 8 and 92); hs_HSF1_2034_A25_S27 (SEQ ID NOs. 20 and 104); hs_HSF1_2034_A81_S26 (SEQ ID NOs. 32 and 116); hs_HSF1_2034_A48_S26 (SEQ ID NOs. 44 and 128); hs_HSF1_2034_A82_S36 (SEQ ID NOs. 56 and 140); hs_HSF1_2034_A83_S36 (SEQ ID NOs. 68 and 152); hs_HSF1_2034_A84_S36 (SEQ ID NOs. 80 and 164); hs_HSF1_2138_A22_S26 (SEQ ID NOs. 9 and 93); hs_HSF1_2138_A25_S27 (SEQ ID NOs. 21 and 105); hs_HSF1_2138_A81_S26 (SEQ ID NOs. 33 and 117); hs_HSF1_2138_A48_S26 (SEQ ID NOs. 45 and 129); hs_HSF1_2138_A82_S36 (SEQ ID NOs. 57 and 141); hs_HSF1_2138_A83_S36 (SEQ ID NOs. 69 and 153); hs_HSF1_2138_A84_S36 (SEQ ID NOs. 81 and 165); hs_HSF1_2153_A22_S26 (SEQ ID NOs. 10 and 94); hs_HSF1_2153_A25_S27 (SEQ ID NOs. 22 and 106); hs_HSF1_2153_A81_S26 (SEQ ID NOs. 34 and 118); hs_HSF1_2153_A48_S26 (SEQ ID NOs. 46 and 130); hs_HSF1_2153_A82_S36 (SEQ ID NOs. 58 and 142); hs_HSF1_2153_A83_S36 (SEQ ID NOs. 70 and 154); hs_HSF1_2153_A84_S36 (SEQ ID NOs. 82 and 166); hs_HSF1_2154_A22_S26 (SEQ ID NOs. 11 and 95); hs_HSF1_2154_A25_S27 (SEQ ID NOs. 23 and 107); hs_HSF1_2154_A81_S26 (SEQ ID NOs. 35 and 119); hs_HSF1_2154_A48_S26 (SEQ ID NOs. 47 and 131); hs_HSF1_2154_A82_S36 (SEQ ID NOs. 59 and 143); hs_HSF1_2154_A83_S36 (SEQ ID NOs. 71 and 155); hs_HSF1_2154_A84_S36 (SEQ ID NOs. 83 and 167).

Particular duplexes include the following wherein each duplex (e.g., RNAi agent) comprises a set of SEQ ID NOs, wherein the first SEQ ID NO corresponds to a first strand and the second SEQ ID NO corresponds to a second strand, wherein the sequences are not necessarily modified: hs_HSF1_175_A22_S26 (SEQ ID NOs. 180 and 264); hs_HSF1_175_A25_S27 (SEQ ID NOs. 192 and 276); hs_HSF1_175_A81_S26 (SEQ ID NOs. 204 and 288); hs_HSF1_175_A48_S26 (SEQ ID NOs. 216 and 300); hs_HSF1_175_A82_S36 (SEQ ID NOs. 228 and 312); hs_HSF1_175_A83_S36 (SEQ ID NOs. 240 and 324); hs_HSF1_175_A84_S36 (SEQ ID NOs. 252 and 336); hs_HSF1_517_A22_S26 (SEQ ID NOs. 172 and 256); hs_HSF1_517_A25_S27 (SEQ ID NOs. 184 and 268); hs_HSF1_517_A81_S26 (SEQ ID NOs. 196 and 280);

hs_HSF1_517_A48_S26 (SEQ ID NOs. 208 and 292);
hs_HSF1_517_A82_S36 (SEQ ID NOs. 220 and 304);
hs_HSF1_517_A83_S36 (SEQ ID NOs. 232 and 316);
hs_HSF1_517_A84_S36 (SEQ ID NOs. 244 and 328);
hs_HSF1_562_A22_S26 (SEQ ID NOs. 169 and 253);
hs_HSF1_562_A25_S27 (SEQ ID NOs. 181 and 265);
hs_HSF1_562_A81_S26 (SEQ ID NOs. 193 and 277);
hs_HSF1_562_A48_S26 (SEQ ID NOs. 205 and 289);
hs_HSF1_562_A82_S36 (SEQ ID NOs. 217 and 301);
hs_HSF1_562_A83_S36 (SEQ ID NOs. 229 and 313);
hs_HSF1_562_A84_S36 (SEQ ID NOs. 241 and 325);
hs_HSF1_751_A22_S26 (SEQ ID NOs. 170 and 254);
hs_HSF1_751_A25_S27 (SEQ ID NOs. 182 and 266);
hs_HSF1_751_A81_S26 (SEQ ID NOs. 194 and 278);
hs_HSF1_751_A48_S26 (SEQ ID NOs. 206 and 290);
hs_HSF1_751_A82_S36 (SEQ ID NOs. 218 and 302);
hs_HSF1_751_A83_S36 (SEQ ID NOs. 230 and 314);
hs_HSF1_751_A84_S36 (SEQ ID NOs. 242 and 326);
hs_HSF1_755_A22_S26 (SEQ ID NOs. 171 and 255);
hs_HSF1_755_A25_S27 (SEQ ID NOs. 183 and 267);
hs_HSF1_755_A81_S26 (SEQ ID NOs. 195 and 279);
hs_HSF1_755_A48_S26 (SEQ ID NOs. 207 and 291);
hs_HSF1_755_A82_S36 (SEQ ID NOs. 219 and 303);
hs_HSF1_755_A83_S36 (SEQ ID NOs. 231 and 315);
hs_HSF1_755_A84_S36 (SEQ ID NOs. 243 and 327);
hs_HSF1_846_A22_S26 (SEQ ID NOs. 173 and 257);
hs_HSF1_846_A25_S27 (SEQ ID NOs. 185 and 269);
hs_HSF1_846_A81_S26 (SEQ ID NOs. 197 and 281);
hs_HSF1_846_A48_S26 (SEQ ID NOs. 209 and 293);
hs_HSF1_846_A82_S36 (SEQ ID NOs. 221 and 305);
hs_HSF1_846_A83_S36 (SEQ ID NOs. 233 and 317);
hs_HSF1_846_A84_S36 (SEQ ID NOs. 245 and 329);
hs_HSF1_1360_A22_S26 (SEQ ID NOs. 174 and 258);
hs_HSF1_1360_A25_S27 (SEQ ID NOs. 186 and 270);
hs_HSF1_1360_A81_S26 (SEQ ID NOs. 198 and 282);
hs_HSF1_1360_A48_S26 (SEQ ID NOs. 210 and 294);
hs_HSF1_1360_A82_S36 (SEQ ID NOs. 222 and 306);
hs_HSF1_1360_A83_S36 (SEQ ID NOs. 234 and 318);
hs_HSF1_1360_A84_S36 (SEQ ID NOs. 246 and 330);
hs_HSF1_2030_A22_S26 (SEQ ID NOs. 175 and 259);
hs_HSF1_2030_A25_S27 (SEQ ID NOs. 187 and 271);
hs_HSF1_2030_A81_S26 (SEQ ID NOs. 199 and 283);
hs_HSF1_2030_A48_S26 (SEQ ID NOs. 211 and 295);
hs_HSF1_2030_A82_S36 (SEQ ID NOs. 223 and 307);
hs_HSF1_2030_A83_S36 (SEQ ID NOs. 235 and 319);
hs_HSF1_2030_A84_S36 (SEQ ID NOs. 247 and 331);
hs_HSF1_2034_A22_S26 (SEQ ID NOs. 176 and 260);
hs_HSF1_2034_A25_S27 (SEQ ID NOs. 188 and 272);
hs_HSF1_2034_A81_S26 (SEQ ID NOs. 200 and 284);
hs_HSF1_2034_A48_S26 (SEQ ID NOs. 212 and 296);
hs_HSF1_2034_A82_S36 (SEQ ID NOs. 224 and 308);
hs_HSF1_2034_A83_S36 (SEQ ID NOs. 236 and 320);
hs_HSF1_2034_A84_S36 (SEQ ID NOs. 248 and 332);
hs_HSF1_2138_A22_S26 (SEQ ID NOs. 177 and 261);
hs_HSF1_2138_A25_S27 (SEQ ID NOs. 189 and 273);
hs_HSF1_2138_A81_S26 (SEQ ID NOs. 201 and 285);
hs_HSF1_2138_A48_S26 (SEQ ID NOs. 213 and 297);
hs_HSF1_2138_A82_S36 (SEQ ID NOs. 225 and 309);
hs_HSF1_2138_A83_S36 (SEQ ID NOs. 237 and 321);
hs_HSF1_2138_A84_S36 (SEQ ID NOs. 249 and 333);
hs_HSF1_2153_A22_S26 (SEQ ID NOs. 178 and 262);
hs_HSF1_2153_A25_S27 (SEQ ID NOs. 190 and 274);
hs_HSF1_2153_A81_S26 (SEQ ID NOs. 202 and 286);
hs_HSF1_2153_A48_S26 (SEQ ID NOs. 214 and 298);
hs_HSF1_2153_A82_S36 (SEQ ID NOs. 226 and 310);
hs_HSF1_2153_A83_S36 (SEQ ID NOs. 238 and 322);
hs_HSF1_2153_A84_S36 (SEQ ID NOs. 250 and 334);
hs_HSF1_2154_A22_S26 (SEQ ID NOs. 179 and 263);
hs_HSF1_2154_A25_S27 (SEQ ID NOs. 191 and 275);
hs_HSF1_2154_A81_S26 (SEQ ID NOs. 203 and 287);
hs_HSF1_2154_A48_S26 (SEQ ID NOs. 215 and 299);
hs_HSF1_2154_A82_S36 (SEQ ID NOs. 227 and 311);
hs_HSF1_2154_A83_S36 (SEQ ID NOs. 239 and 323); and
hs_HSF1_2154_A84_S36 (SEQ ID NOs. 251 and 335). In these various embodiments, the first strand and the second strand are the antisense and sense strand, respectively, or the second and the first strand are the antisense and sense strand, respectively. The disclosure also encompasses modified variants of these duplexes (e.g., duplexes with one or more modifications).

Particular duplexes include the following wherein each duplex (e.g., RNAi agent) comprises a set of SEQ ID NOs, wherein the first SEQ ID NO corresponds to a first strand and the second SEQ ID NO corresponds to a second strand, wherein the sequences ARE modified:
hs_HSF1_175_A22_S26 (SEQ ID NOs. 348 and 432);
hs_HSF1_175_A25_S27 (SEQ ID NOs. 360 and 444);
hs_HSF1_175_A81_S26 (SEQ ID NOs. 372 and 456);
hs_HSF1_175_A48_S26 (SEQ ID NOs. 384 and 468);
hs_HSF1_175_A82_S36 (SEQ ID NOs. 396 and 480);
hs_HSF1_175_A83_S36 (SEQ ID NOs. 408 and 492);
hs_HSF1_175_A84_S36 (SEQ ID NOs. 420 and 504);
hs_HSF1_517_A22_S26 (SEQ ID NOs. 340 and 424);
hs_HSF1_517_A25_S27 (SEQ ID NOs. 352 and 436);
hs_HSF1_517_A81_S26 (SEQ ID NOs. 364 and 448);
hs_HSF1_517_A48_S26 (SEQ ID NOs. 376 and 460);
hs_HSF1_517_A82_S36 (SEQ ID NOs. 388 and 472);
hs_HSF1_517_A83_S36 (SEQ ID NOs. 400 and 484);
hs_HSF1_517_A84_S36 (SEQ ID NOs. 412 and 496);
hs_HSF1_562_A22_S26 (SEQ ID NOs. 337 and 421);
hs_HSF1_562_A25_S27 (SEQ ID NOs. 349 and 433);
hs_HSF1_562_A81_S26 (SEQ ID NOs. 361 and 445);
hs_HSF1_562_A48_S26 (SEQ ID NOs. 373 and 457);
hs_HSF1_562_A82_S36 (SEQ ID NOs. 385 and 469);
hs_HSF1_562_A83_S36 (SEQ ID NOs. 397 and 481);
hs_HSF1_562_A84_S36 (SEQ ID NOs. 409 and 493);
hs_HSF1_751_A22_S26 (SEQ ID NOs. 338 and 422);
hs_HSF1_751_A25_S27 (SEQ ID NOs. 350 and 434);
hs_HSF1_751_A81_S26 (SEQ ID NOs. 362 and 446);
hs_HSF1_751_A48_S26 (SEQ ID NOs. 374 and 458);
hs_HSF1_751_A82_S36 (SEQ ID NOs. 386 and 470);
hs_HSF1_751_A83_S36 (SEQ ID NOs. 398 and 482);
hs_HSF1_751_A84_S36 (SEQ ID NOs. 410 and 494);
hs_HSF1_755_A22_S26 (SEQ ID NOs. 339 and 423);
hs_HSF1_755_A25_S27 (SEQ ID NOs. 351 and 435);
hs_HSF1_755_A81_S26 (SEQ ID NOs. 363 and 447);
hs_HSF1_755_A48_S26 (SEQ ID NOs. 375 and 459);
hs_HSF1_755_A82_S36 (SEQ ID NOs. 387 and 471);
hs_HSF1_755_A83_S36 (SEQ ID NOs. 399 and 483);
hs_HSF1_755_A84_S36 (SEQ ID NOs. 411 and 495);
hs_HSF1_846_A22_S26 (SEQ ID NOs. 341 and 425);
hs_HSF1_846_A25_S27 (SEQ ID NOs. 353 and 437);
hs_HSF1_846_A81_S26 (SEQ ID NOs. 365 and 449);
hs_HSF1_846_A48_S26 (SEQ ID NOs. 377 and 461);
hs_HSF1_846_A82_S36 (SEQ ID NOs. 389 and 473);
hs_HSF1_846_A83_S36 (SEQ ID NOs. 401 and 485);
hs_HSF1_846_A84_S36 (SEQ ID NOs. 413 and 497);
hs_HSF1_1360_A22_S26 (SEQ ID NOs. 342 and 426);
hs_HSF1_1360_A25_S27 (SEQ ID NOs. 354 and 438);
hs_HSF1_1360_A81_S26 (SEQ ID NOs. 366 and 450);
hs_HSF1_1360_A48_S26 (SEQ ID NOs. 378 and 462);
hs_HSF1_1360_A82_S36 (SEQ ID NOs. 390 and 474);
hs_HSF1_1360_A83_S36 (SEQ ID NOs. 402 and 486);
hs_HSF1_1360_A84_S36 (SEQ ID NOs. 414 and 498);

hs_HSF1_2030_A22_S26 (SEQ ID NOs. 343 and 427);
hs_HSF1_2030_A25_S27 (SEQ ID NOs. 355 and 439);
hs_HSF1_2030_A81_S26 (SEQ ID NOs. 367 and 451);
hs_HSF1_2030_A48_S26 (SEQ ID NOs. 379 and 463);
hs_HSF1_2030_A82_S36 (SEQ ID NOs. 391 and 475);
hs_HSF1_2030_A83_S36 (SEQ ID NOs. 403 and 487);
hs_HSF1_2030_A84_S36 (SEQ ID NOs. 415 and 499);
hs_HSF1_2034_A22_S26 (SEQ ID NOs. 344 and 428);
hs_HSF1_2034_A25_S27 (SEQ ID NOs. 356 and 440);
hs_HSF1_2034_A81_S26 (SEQ ID NOs. 368 and 452);
hs_HSF1_2034_A48_S26 (SEQ ID NOs. 380 and 464);
hs_HSF1_2034_A82_S36 (SEQ ID NOs. 392 and 476);
hs_HSF1_2034_A83_S36 (SEQ ID NOs. 404 and 488);
hs_HSF1_2034_A84_S36 (SEQ ID NOs. 416 and 500);
hs_HSF1_2138_A22_S26 (SEQ ID NOs. 345 and 429);
hs_HSF1_2138_A25_S27 (SEQ ID NOs. 357 and 441);
hs_HSF1_2138_A81_S26 (SEQ ID NOs. 369 and 453);
hs_HSF1_2138_A48_S26 (SEQ ID NOs. 381 and 465);
hs_HSF1_2138_A82_S36 (SEQ ID NOs. 393 and 477);
hs_HSF1_2138_A83_S36 (SEQ ID NOs. 405 and 489);
hs_HSF1_2138_A84_S36 (SEQ ID NOs. 417 and 501);
hs_HSF1_2153_A22_S26 (SEQ ID NOs. 346 and 430);
hs_HSF1_2153_A25_S27 (SEQ ID NOs. 358 and 442);
hs_HSF1_2153_A81_S26 (SEQ ID NOs. 370 and 454);
hs_HSF1_2153_A48_S26 (SEQ ID NOs. 382 and 466);
hs_HSF1_2153_A82_S36 (SEQ ID NOs. 394 and 478);
hs_HSF1_2153_A83_S36 (SEQ ID NOs. 406 and 490);
hs_HSF1_2153_A84_S36 (SEQ ID NOs. 418 and 502);
hs_HSF1_2154_A22_S26 (SEQ ID NOs. 347 and 431);
hs_HSF1_2154_A25_S27 (SEQ ID NOs. 359 and 443);
hs_HSF1_2154_A81_S26 (SEQ ID NOs. 371 and 455);
hs_HSF1_2154_A48_S26 (SEQ ID NOs. 383 and 467);
hs_HSF1_2154_A82_S36 (SEQ ID NOs. 395 and 479);
hs_HSF1_2154_A83_S36 (SEQ ID NOs. 407 and 491); and
hs_HSF1_2154_A84_S36 (SEQ ID NOs. 419 and 503). In these various embodiments, the first strand and the second strand are the antisense and sense strand, respectively, or the second and the first strand are the antisense and sense strand, respectively. The disclosure also encompasses different modifications of these duplexes (e.g., duplexes with the same nucleotide sequence, but with different modifications).

In addition to the described example modifications, other modified variants can be made using the nucleotide sequences provided.

TABLE A1

SEQ ID NOs. for RNAi Agents to HSF1.

| Nickname | TARGET | | RNAI AGENT (NOT MODIFIED) | | RNAI AGENT (MODIFIED) | | Position |
|---|---|---|---|---|---|---|---|
| | AS SEQ ID NO: | SENSE SEQ ID NO: | AS SEQ ID NO: | SENSE SEQ ID NO: | AS SEQ ID NO: | SENSE SEQ ID NO: | |
| 175_A22_S26 | 12 | 96 | 180 | 264 | 348 | 432 | 175 |
| 175_A25_S27 | 24 | 108 | 192 | 276 | 360 | 444 | 175 |
| 175_A81_S26 | 36 | 120 | 204 | 288 | 372 | 456 | 175 |
| 175_A48_S26 | 48 | 132 | 216 | 300 | 384 | 468 | 175 |
| 175_A82_S36 | 60 | 144 | 228 | 312 | 396 | 480 | 175 |
| 175_A83_S36 | 72 | 156 | 240 | 324 | 408 | 492 | 175 |
| 175_A84_S36 | 84 | 168 | 252 | 336 | 420 | 504 | 175 |
| 517_A22_S26 | 4 | 88 | 172 | 256 | 340 | 424 | 517 |
| 517_A25_S27 | 16 | 100 | 184 | 268 | 352 | 436 | 517 |
| 517_A81_S26 | 28 | 112 | 196 | 280 | 364 | 448 | 517 |
| 517_A48_S26 | 40 | 124 | 208 | 292 | 376 | 460 | 517 |
| 517_A82_S36 | 52 | 136 | 220 | 304 | 388 | 472 | 517 |
| 517_A83_S36 | 64 | 148 | 232 | 316 | 400 | 484 | 517 |
| 517_A84_S36 | 76 | 160 | 244 | 328 | 412 | 496 | 517 |
| 562_A22_S26 | 1 | 85 | 169 | 253 | 337 | 421 | 562 |
| 562_A25_S27 | 13 | 97 | 181 | 265 | 349 | 433 | 562 |
| 562_A81_S26 | 25 | 109 | 193 | 277 | 361 | 445 | 562 |
| 562_A48_S26 | 37 | 121 | 205 | 289 | 373 | 457 | 562 |
| 562_A82_S36 | 49 | 133 | 217 | 301 | 385 | 469 | 562 |
| 562_A83_S36 | 61 | 145 | 229 | 313 | 397 | 481 | 562 |
| 562_A84_S36 | 73 | 157 | 241 | 325 | 409 | 493 | 562 |
| 751_A22_S26 | 2 | 86 | 170 | 254 | 338 | 422 | 751 |
| 751_A25_S27 | 14 | 98 | 182 | 266 | 350 | 434 | 751 |
| 751_A81_S26 | 26 | 110 | 194 | 278 | 362 | 446 | 751 |
| 751_A48_S26 | 38 | 122 | 206 | 290 | 374 | 458 | 751 |
| 751_A82_S36 | 50 | 134 | 218 | 302 | 386 | 470 | 751 |
| 751_A83_S36 | 62 | 146 | 230 | 314 | 398 | 482 | 751 |
| 751_A84_S36 | 74 | 158 | 242 | 326 | 410 | 494 | 751 |
| 755_A22_S26 | 3 | 87 | 171 | 255 | 339 | 423 | 755 |
| 755_A25_S27 | 15 | 99 | 183 | 267 | 351 | 435 | 755 |
| 755_A81_S26 | 27 | 111 | 195 | 279 | 363 | 447 | 755 |
| 755_A48_S26 | 39 | 123 | 207 | 291 | 375 | 459 | 755 |
| 755_A82_S36 | 51 | 135 | 219 | 303 | 387 | 471 | 755 |
| 755_A83_S36 | 63 | 147 | 231 | 315 | 399 | 483 | 755 |
| 755_A84_S36 | 75 | 159 | 243 | 327 | 411 | 495 | 755 |
| 846_A22_S26 | 5 | 89 | 173 | 257 | 341 | 425 | 846 |
| 846_A25_S27 | 17 | 101 | 185 | 269 | 353 | 437 | 846 |
| 846_A81_S26 | 29 | 113 | 197 | 281 | 365 | 449 | 846 |
| 846_A48_S26 | 41 | 125 | 209 | 293 | 377 | 461 | 846 |
| 846_A82_S36 | 53 | 137 | 221 | 305 | 389 | 473 | 846 |
| 846_A83_S36 | 65 | 149 | 233 | 317 | 401 | 485 | 846 |

TABLE A1-continued

SEQ ID NOs. for RNAi Agents to HSF1.

| Nickname | TARGET | | RNAI AGENT (NOT MODIFIED) | | RNAI AGENT (MODIFIED) | | Position |
|---|---|---|---|---|---|---|---|
| | AS SEQ ID NO: | SENSE SEQ ID NO: | AS SEQ ID NO: | SENSE SEQ ID NO: | AS SEQ ID NO: | SENSE SEQ ID NO: | |
| 846__A84__S36 | 77 | 161 | 245 | 329 | 413 | 497 | 846 |
| 1360__A22__S26 | 6 | 90 | 174 | 258 | 342 | 426 | 1360 |
| 1360__A25__S27 | 18 | 102 | 186 | 270 | 354 | 438 | 1360 |
| 1360__A81__S26 | 30 | 114 | 198 | 282 | 366 | 450 | 1360 |
| 1360__A48__S26 | 42 | 126 | 210 | 294 | 378 | 462 | 1360 |
| 1360__A82__S36 | 54 | 138 | 222 | 306 | 390 | 474 | 1360 |
| 1360__A83__S36 | 66 | 150 | 234 | 318 | 402 | 486 | 1360 |
| 1360__A84__S36 | 78 | 162 | 246 | 330 | 414 | 498 | 1360 |
| 2030__A22__S26 | 7 | 91 | 175 | 259 | 343 | 427 | 2030 |
| 2030__A25__S27 | 19 | 103 | 187 | 271 | 355 | 439 | 2030 |
| 2030__A81__S26 | 31 | 115 | 199 | 283 | 367 | 451 | 2030 |
| 2030__A48__S26 | 43 | 127 | 211 | 295 | 379 | 463 | 2030 |
| 2030__A82__S36 | 55 | 139 | 223 | 307 | 391 | 475 | 2030 |
| 2030__A83__S36 | 67 | 151 | 235 | 319 | 403 | 487 | 2030 |
| 2030__A84__S36 | 79 | 163 | 247 | 331 | 415 | 499 | 2030 |
| 2034__A22__S26 | 8 | 92 | 176 | 260 | 344 | 428 | 2034 |
| 2034__A25__S27 | 20 | 104 | 188 | 272 | 356 | 440 | 2034 |
| 2034__A81__S26 | 32 | 116 | 200 | 284 | 368 | 452 | 2034 |
| 2034__A48__S26 | 44 | 128 | 212 | 296 | 380 | 464 | 2034 |
| 2034__A82__S36 | 56 | 140 | 224 | 308 | 392 | 476 | 2034 |
| 2034__A83__S36 | 68 | 152 | 236 | 320 | 404 | 488 | 2034 |
| 2034__A84__S36 | 80 | 164 | 248 | 332 | 416 | 500 | 2034 |
| 2138__A22__S26 | 9 | 93 | 177 | 261 | 345 | 429 | 2138 |
| 2138__A25__S27 | 21 | 105 | 189 | 273 | 357 | 441 | 2138 |
| 2138__A81__S26 | 33 | 117 | 201 | 285 | 369 | 453 | 2138 |
| 2138__A48__S26 | 45 | 129 | 213 | 297 | 381 | 465 | 2138 |
| 2138__A82__S36 | 57 | 141 | 225 | 309 | 393 | 477 | 2138 |
| 2138__A83__S36 | 69 | 153 | 237 | 321 | 405 | 489 | 2138 |
| 2138__A84__S36 | 81 | 165 | 249 | 333 | 417 | 501 | 2138 |
| 2153__A22__S26 | 10 | 94 | 178 | 262 | 346 | 430 | 2153 |
| 2153__A25__S27 | 22 | 106 | 190 | 274 | 358 | 442 | 2153 |
| 2153__A81__S26 | 34 | 118 | 202 | 286 | 370 | 454 | 2153 |
| 2153__A48__S26 | 46 | 130 | 214 | 298 | 382 | 466 | 2153 |
| 2153__A82__S36 | 58 | 142 | 226 | 310 | 394 | 478 | 2153 |
| 2153__A83__S36 | 70 | 154 | 238 | 322 | 406 | 490 | 2153 |
| 2153__A84__S36 | 82 | 166 | 250 | 334 | 418 | 502 | 2153 |
| 2154__A22__S26 | 11 | 95 | 179 | 263 | 347 | 431 | 2154 |
| 2154__A25__S27 | 23 | 107 | 191 | 275 | 359 | 443 | 2154 |
| 2154__A81__S26 | 35 | 119 | 203 | 287 | 371 | 455 | 2154 |
| 2154__A48__S26 | 47 | 131 | 215 | 299 | 383 | 467 | 2154 |
| 2154__A82__S36 | 59 | 143 | 227 | 311 | 395 | 479 | 2154 |
| 2154__A83__S36 | 71 | 155 | 239 | 323 | 407 | 491 | 2154 |
| 2154__A84__S36 | 83 | 167 | 251 | 335 | 419 | 503 | 2154 |

Provided in Table A1 are: Nickname for the sequence (wherein each sequence nickname begins with hs__HSF1__*, where * is the nickname provided in each row; e.g., "175__A22__S26" is the same as "hs__HSF1__175__A22__S26", etc.); target sequence (AS, antisense; and Sense strand); RNAi agent sequence provided as a sequence which is not modified (antisense and sense); RNAi agent sequence provided as an example modified variant (antisense and sense); and Position within the HSF1 gene. Note that at time duplexes are referred to by their position; e.g., "hs_HSF1__175" is sometimes referred to as simply HSF1-175; "hs_HSF1__517" is sometimes referred to as simply "HSF1-517," etc.

Note that in some texts the nickname may contain an underscore after "hs". This underscore is insignificant; e.g., "hs_HSF1_562_A22_S26" is identical to "hsHSF1_562_A22_S26". Sequence nicknames may also appear with internal spaces ( ) after the underscores (_); these too are not significant. In addition, some RNAi agents to HSF1 have multiple designations. hs_HSF1_2138 is also known as HSF1_2138, HSF1_2138_NBC, and HSF1_2120_ALNY. Similarly, other RNAi agents may have the "hs_" portion of the prefix deleted or an additional suffix "NBC" appended. RNAi agent hs_HSF1_562 is also known as HSF-544 or HSF-544-1. hs_HSF1_562_ is also known as AD-20487-b1 and AD-30071; hs_HSF1_751_ is also known as AD-20560-b1 and AD-37739; hs_HSF1_755_ is also known as AD-20564 and AD-36971; and hs_HSF1_517_ is also known as AD-20397-b1. The suffix "b" followed by a number indicates batch number; thus, "b1" indicates batch 1. However, note that the batch number does not affect the nucleotide sequence; e.g., AD-20397-b1 has the same nucleotide sequence as AD-20397.

An RNAi Agent Comprising an Antisense Strand of an RNAi Agent Described Herein.

In one particular specific embodiment, the present disclosure relates to a composition comprising an RNAi agent comprising an antisense strand, wherein the antisense strand comprises at least 15 contiguous nucleotides differing by 0, 1, 2, or 3 nucleotides from the antisense strand of an RNAi agent to HSF1 selected from those antisense strands in the specific duplexes provided above and as listed in Tables A1, 1, 2, 3, 4, 5, 6, or 7.

Various particular specific embodiments of this embodiment are described below.

In one embodiment, the composition further comprises a second RNAi agent to HSF1. In various embodiments, the second RNAi agent is physically separate from the first, or the two are physically connected (e.g., covalently linked or otherwise conjugated). In various embodiments, the first and second RNAi agents are co-administered, or administered simultaneously or sequentially.

In one embodiment, the antisense strand is about 30 or fewer nucleotides in length.

In one embodiment, the antisense strand forms a duplex region with a sense strand, wherein the duplex region is about 15 to 30 nucleotide pairs in length.

In one embodiment, the antisense strand is about 15 to about 30 nucleotides in length, including about 19 to about 49, about 19 to about 30, about 19 to about 23 nucleotides in length. In one embodiment, the antisense strand has at least the length selected from about 15 nucleotides, about 16 nucleotides, about 17 nucleotides, about 18 nucleotides, about 19 nucleotides, about 20 nucleotides, about 21 nucleotides, about 22 nucleotides, about 23 nucleotides, about 24 nucleotides, about 25 nucleotides, about 26 nucleotides, about 27 nucleotides, about 28 nucleotides, about 29 nucleotides and 30 nucleotides.

In one embodiment, the RNAi agent comprises a modification that causes the RNAi agent to have increased stability in a biological sample or environment, e.g., blood serum or intestinal lavage fluid.

In one embodiment, the RNAi agent comprises at least one sugar backbone modification (e.g., phosphorothioate linkage) or at least one 2'-modified nucleotide. In various embodiments, one, more than one, or all the pyrimidines are 2' O-methyl-modified nucleotides.

In one embodiment, the RNAi agent comprises: at least one 5'-uridine-adenine-3' (5'-ua-3') dinucleotide, wherein the uridine is a 2'-modified nucleotide; at least one 5'-uridine-guanine-3' (5'-ug-3') dinucleotide, wherein the 5'-uridine is a 2'-modified nucleotide; at least one 5'-cytidine-adenine-3' (5'-ca-3') dinucleotide, wherein the 5'-cytidine is a 2'-modified nucleotide; or at least one 5'-uridine-uridine-3' (5'-uu-3') dinucleotide, wherein the 5'-uridine is a 2'-modified nucleotide. These dinucleotide motifs are particularly prone to scrum nuclease degradation (e.g. RNase A). Chemical modification at the 2'-position of the first pyrimidine nucleotide in the motif prevents or slows down such cleavage. This modification recipe is also known under the term 'endo light'.

In one embodiment, the RNAi agent comprises a 2'-modification selected from the group consisting of: 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA). In one embodiment, all pyrimidines (uridine and cytidine) are 2' O-methyl-modified nucleosides.

In one embodiment, the RNAi agent comprises at least one blunt end.

In one embodiment, the RNAi agent comprises an overhang having 1 nt to 4 nt unpaired.

In one embodiment, the RNAi agent comprises an overhang at the 3'-end of the antisense strand of the RNAi agent.

In one embodiment, the RNAi agent is ligated to one or more diagnostic compound, reporter group, cross-linking agent, nuclease-resistance conferring moiety, natural or unusual nucleobase, lipophilic molecule, cholesterol, lipid, lectin, steroid, uvaol, hecigenin, diosgenin, terpene, triterpene, sarsasapogenin, Friedelin, epifriedelanol-derivatized lithocholic acid, vitamin, carbohydrate, dextran, pullulan, chitin, chitosan, synthetic carbohydrate, oligo lactate 15-mer, natural polymer, low- or medium-molecular weight polymer, inulin, cyclodextrin, hyaluronic acid, protein, protein-binding agent, integrin-targeting molecule, polycationic, peptide, polyamine, peptide mimic, and/or transferrin.

In one embodiment, the RNAi agent is capable of inhibiting expression of HSF1 by at least about 60% in HeLa, GTL-16, or SK-BR-3 cells in vitro, or Hep3B tumor cells in vitro.

In one embodiment, the RNAi agent is capable of inhibiting expression of HSF1 by at least about 70% in HeLa, GTL-16, or SK-BR-3 cells in vitro, or Hep3B tumor cells in vitro.

In one embodiment, the RNAi agent is capable of inhibiting expression of HSF1 by at least about 75% in HeLa, GTL-16, or SK-BR-3 cells in vitro, or Hep3B tumor cells in vitro.

In one embodiment, the RNAi agent is capable of inhibiting expression of HSF1 by at least about 80% in HeLa, GTL-16, or SK-BR-3 cells in vitro, or Hep3B tumor cells in vitro.

In one embodiment, the RNAi agent is capable of inhibiting expression of HSF1 by at least about 90% in HeLa, GTL-16, or SK-BR-3 cells in vitro, or Hep3B tumor cells in vitro.

In one embodiment, the RNAi agent is capable of inhibiting expression of HSF1 by at least about 95% in HeLa, GTL-16, or SK-BR-3 cells in vitro, or Hep3B tumor cells in vitro.

In one embodiment, the RNAi agent is capable of inhibiting expression of HSF1 by at least about 99% in HeLa, GTL-16, or SK-BR-3 cells in vitro, or Hep3B tumor cells in vitro.

In one embodiment, the RNAi has an EC50 of no more than about 0.1 nM. EC50 is effective concentration to reduce gene expression by 50%.

In one embodiment, the RNAi has an EC50 of no more than about 0.01 nM.

In one embodiment, the RNAi has an EC50 of no more than about 0.001 nM.

An RNAi Agent Comprising a First and Second Strand of an RNAi Described Herein.

In one particular specific embodiment, the present disclosure relates to a composition comprising an RNAi agent comprising a first strand and an second strand, wherein the first strand and second strand comprise at least 15 contiguous nucleotides differing by 0, 1, 2, or 3 nucleotides from the first and second strand, respectively, of an RNAi agent to HSF1 selected from the specific duplexes provided above and as listed in Tables A1, 1, 2, 3, 4, 5, 6, or 7. In one particular specific embodiment, the present disclosure relates to a composition comprising an RNAi agent comprising a first strand and an second strand, wherein the first strand and second strand comprise at least 15 contiguous nucleotides from the first and second strand, respectively, of an RNAi agent to HSF1 selected from the specific duplexes provided above and as listed in Tables A1, 1, 2, 3, 4, 5, 6, or 7. In one particular specific embodiment, the present disclosure relates to a composition comprising an RNAi agent comprising a first strand and an second strand, wherein the sequence of the first strand comprises the sequence of the first strand of an RNAi agent to HSF1 selected from the specific duplexes provided above and as listed in Tables A1, 1, 2, 3, 4, 5, 6, or 7. In one particular specific embodiment, the present disclosure relates to a composition comprising an RNAi agent comprising a first strand and an second strand, wherein the sequence of the first strand is the sequence of the first strand of an RNAi agent to HSF1 selected from the specific duplexes provided above and as listed in Tables A1, 1, 2, 3, 4, 5, 6, or 7. In one particular specific embodiment, the present disclosure relates to a composition comprising an RNAi agent comprising a first strand and an second strand, wherein the sequence of the first and/or second strand comprises the sequence of the first and/or second strand of an RNAi agent to HSF1 selected from the specific duplexes provided above and as listed in Tables A1, 1, 2, 3, 4, 5, 6, or 7. In one particular specific embodiment, the present disclosure relates to a composition comprising an RNAi agent comprising a first strand and an second strand, wherein the sequence of the first and/or second strand is the sequence of the first and/or second strand of an RNAi agent to HSF1 selected from the specific duplexes provided above and as listed in Tables A1, 1, 2, 3, 4, 5, 6, or 7. In one particular specific embodiment, the present disclosure relates to a composition comprising an RNAi agent comprising a first strand and an second strand, wherein the sequence of the first and/or second strand is the sequence of the first and/or second strand of an RNAi agent to HSF1 selected from the specific duplexes provided above and as listed in Tables A1, 1, 2, 3, 4, 5, 6, or 7, wherein the sequence of the first and/or second strand further comprises 1 to 20 nt.

Various particular specific embodiments of these embodiments are described below.

In one embodiment, the composition comprises a second RNAi agent to HSF1. In various embodiments, the second RNAi agent is physically separate from the first, or the two are physically connected (e.g., chemically linked or otherwise conjugated). In various embodiments, the first and second RNAi agents are co-administered, or administered simultaneously or sequentially.

In one embodiment, the second strand is about 30 or fewer nucleotides in length.

In one embodiment, the first strand and the second strand form a duplex region about 15 to about 30 nucleotide pairs in length.

In one embodiment, the antisense strand is about 15 to about 30 nucleotides in length, including about 19 to about 49, about 19 to about 30, about 19 to about 23 nucleotides in length. In one embodiment, the antisense strand has at least the length selected from about 15 nucleotides, about 16 nucleotides, about 17 nucleotides, about 18 nucleotides, about 19 nucleotides, about 20 nucleotides, about 21 nucleotides, about 22 nucleotides, about 23 nucleotides, about 24 nucleotides, about 25 nucleotides, about 26 nucleotides, about 27 nucleotides, about 28 nucleotides, about 29 nucleotides and 30 nucleotides.

In one embodiment, the RNAi agent comprises a modification that causes the RNAi agent to have increased stability in a biological sample or environment, e.g., blood serum or intestinal lavage fluid.

In one embodiment, the RNAi agent comprises at least one sugar backbone modification (e.g., phosphorothioate linkage) or at least one 2'-modified nucleotide. In various embodiments, one, more than one, or all the pyrimidines are 2' O-methyl-modified nucleosides.

In one embodiment, the RNAi agent comprises: at least one 5'-uridine-adenine-3' (5'-ua-3') dinucleotide, wherein the uridine is a 2'-modified nucleotide; at least one 5'-uridine-guanine-3' (5'-ug-3') dinucleotide, wherein the 5'-uridine is a 2'-modified nucleotide; at least one 5'-cytidine-adenine-3' (5'-ca-3') dinucleotide, wherein the 5'-cytidine is a 2'-modified nucleotide; or at least one 5'-uridine-uridine-3' (5'-uu-3') dinucleotide, wherein the 5'-uridine is a 2'-modified nucleotide.

In one embodiment, the RNAi agent comprises a 2'-modification selected from the group consisting of: 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA). In one embodiment, all pyrimidines (uridine and cytidine) are 2' O-methyl-modified nucleosides.

In one embodiment, the RNAi agent comprises at least one blunt end.

In one embodiment, the RNAi agent comprises an overhang having 1 to 4 nt unpaired.

In one embodiment, the RNAi agent comprises an overhang at the 3'-end of the second strand of the RNAi agent.

In one embodiment, the RNAi agent is ligated to one or more diagnostic compound, reporter group, cross-linking agent, nuclease-resistance conferring moiety, natural or unusual nucleobase, lipophilic molecule, cholesterol, lipid, lectin, steroid, uvaol, hecigenin, diosgenin, terpene, triterpene, sarsasapogenin, Friedelin, epifriedelanol-derivatized lithocholic acid, vitamin, carbohydrate, dextran, pullulan, chitin, chitosan, synthetic carbohydrate, oligo lactate 15-mer, natural polymer, low- or medium-molecular weight polymer, inulin, cyclodextrin, hyaluronic acid, protein, protein-binding agent, integrin-targeting molecule, polycationic, peptide, polyamine, peptide mimic, and/or transferrin.

In one embodiment, the RNAi agent is capable of inhibiting expression of HSF1 by at least about 60% in HeLa, GTL-16, or SK-BR-3 cells in vitro, or Hep3B tumor cells in vitro.

In one embodiment, the RNAi agent is capable of inhibiting expression of HSF1 by at least about 70% in HeLa, GTL-16, or SK-BR-3 cells in vitro, or Hep3B tumor cells in vitro.

In one embodiment, the RNAi agent is capable of inhibiting expression of HSF1 by at least about 80% in HeLa, GTL-16, or SK-BR-3 cells in vitro, or Hep3B tumor cells in vitro.

In one embodiment, the RNAi agent is capable of inhibiting expression of HSF1 by at least about 90% in HeLa, GTL-16, or SK-BR-3 cells in vitro, or Hep3B tumor cells in vitro.

In one embodiment, the RNAi agent is capable of inhibiting expression of HSF1 by at least about 95% in HeLa, GTL-16, or SK-BR-3 cells in vitro, or Hep3B tumor cells in vitro.

In one embodiment, the RNAi agent is capable of inhibiting expression of HSF1 by at least about 99% in HeLa, GTL-16, or SK-BR-3 cells in vitro, or Hep3B tumor cells in vitro.

In one embodiment, the RNAi has an EC50 of no more than about 0.1 nM.

In one embodiment, the RNAi has an EC50 of no more than about 0.01 nM.

In one embodiment, the RNAi has an EC50 of no more than about 0.001 nM.

Treatment Using an RNAi Agent Comprising a RNAi Agent Described Herein.

In one particular specific embodiment, the present disclosure relates to a method of treating a HSF1-related disease in an individual, comprising the step of administering to the individual a therapeutically effective amount of a composition comprising an RNAi agent comprising an antisense strand, wherein the antisense strand comprises at least 15 contiguous nucleotides differing by 0, 1, 2, or 3 nucleotides from the antisense strand of an RNAi agent to HSF1 selected from those specific duplexes provided herein and as listed in Tables A1, 1, 2, 3, 4, 5, 6, or 7. In one embodiment of this method, the RNAi agent to HSF1 comprises an antisense strand duplexed with a sense strand, wherein the sense and antisense strands are selected from one or more of the sequences provided in Tables A1, 1, 2, 3, 4, 5, 6, or 7. In one particular specific embodiment of this method, the present disclosure relates to a composition comprising an RNAi agent comprising a first strand and an second strand, wherein the first strand and second strand comprise at least 15 contiguous nucleotides differing by 0, 1, 2, or 3 nucleotides from the first and second strand, respectively, of an RNAi agent to HSF1 selected from the specific duplexes provided above and as listed in Tables A1, 1, 2, 3, 4, 5, 6, or 7. In one particular specific embodiment of this method, the present disclosure relates to a composition comprising an RNAi agent comprising a first strand and an second strand, wherein the first strand and second strand comprise at least 15 contiguous nucleotides from the first and second strand, respectively, of an RNAi agent to HSF1 selected from the specific duplexes provided above and as listed in Tables A1, 1, 2, 3, 4, 5, 6, or 7. In one particular specific embodiment of this method, the present disclosure relates to a composition comprising an RNAi agent comprising a first strand and an second strand, wherein the sequence of the first strand comprises the sequence of the first strand of an RNAi agent to HSF1 selected from the specific duplexes provided above and as listed in Tables A1, 1, 2, 3, 4, 5, 6, or 7. In one particular specific embodiment of this method, the present disclosure relates to a composition comprising an RNAi agent comprising a first strand and an second strand, wherein the sequence of the first strand is the sequence of the first strand of an RNAi agent to HSF1 selected from the specific duplexes provided above and as listed in Tables A1, 1, 2, 3, 4, 5, 6, or 7. In one particular specific embodiment of this method, the present disclosure relates to a composition comprising an RNAi agent comprising a first strand and an second strand, wherein the sequence of the first and/or second strand comprises the sequence of the first and/or second strand of an RNAi agent to HSF1 selected from the specific duplexes provided above and as listed in Tables A1, 1, 2, 3, 4, 5, 6, or 7. In one particular specific embodiment of this method, the present disclosure relates to a composition comprising an RNAi agent comprising a first strand and an second strand, wherein the sequence of the first and/or second strand is the sequence of the first and/or second strand of an RNAi agent to HSF1 selected from the specific duplexes provided above and as listed in Tables A1, 1, 2, 3, 4, 5, 6, or 7. In one particular specific embodiment of this method, the present disclosure relates to a composition comprising an RNAi agent comprising a first strand and an second strand, wherein the sequence of the first and/or second strand is the sequence of the first and/or second strand of an RNAi agent to HSF1 selected from the specific duplexes provided above and as listed in Tables A1, 1, 2, 3, 4, 5, 6, or 7, wherein the sequence of the first and/or second strand further comprises 1 to 20 nt.

Various particular specific embodiments of these embodiments are described below.

In one embodiment, the HSF1-related disease is proliferative disease such as, e.g., a cancer, or is an autoimmune disease, or is a viral disease.

In one embodiment, the HSF1-related disease is cancer selected from the list of bladder, bone, breast, cervical, colon, colorectal, endometrial, fibrosarcoma, gastric, haematopoietic, intestine, kidney, liver, lung, lymphoma, neuroectodermal, neuroblastoma, Ewing's sarcoma, osteosarcoma, ovary, pancreas, pleura, prostate, skin, squamous cell, stomach, and testicular cancers, leukemia, promyelocytic leukemia, and Hodgkin's disease.

In one embodiment, the method further comprises the step of administering an additional cancer treatment.

In one embodiment, the method further comprises the step of administering an additional cancer treatment selected from the list of actinomycin D, an inhibitor of HSP90 (heat shock protein 90), AUY922 (NVP-AUY922) (a HSP90 inhibitor), 17-AAG (tanespimycin), 17-DMAG (alvespimycin), IPI-504 (retaspimycin), IPI-493, SNX-5422 mesylate, AUY922, BIB021 CNF-2024, BIIB028, STA-9090, KW-2478, ATI3387, XL888, HSP990, MPC-3100, ABI-010 (as reviewed in Kim et al. 2009 Curr. Topics in Med. Chem. 9: 1479-1492), or 2-chlorodeoxyadenosine, 5-azacitidine, 5-fluoro-29-deoxyuridine, 5-fluorouracil, 6-mercaptopurine, 6-thioguanine, 7-hydroxystaurosporine, 13-cis-retinoic acid, a goserlin implant, alemtuzumab, alitretinoin, all-trans retinoic acid, alpha interferon, altretamine, amifostine, aminoglutethimide, anagrelide, anastrozole, arabinosylcytosine, arsenic trioxide, asparaginase, bacillus calmette-guerin, bendamustine, bevacizumab, bexarotene, bicalutamide, bleomycin, bortezomib, busulfan, camptothecin, capecitabine, carboplatin, carmustine, cetuximab, chlorambucil, cisplatin, cladribine, colcemid, Cycloheximide, cyclophosphamide, cytarabine, cytosine arabinoside (Ara-C), dacarbazine, dactinomycin, dasatinib, daunorubicin liposomal, daunorubicin, decitabine, denileukin diftitox, dexamethazone, docetaxel, doxorubicin, edelfosine, ehlorambucil, epipodophyllotoxin, epirubicin, erlotinib, estramustine, etoposide, everolimus, exemestane, fenretinide, finasteride, flavopiridol, floxuridine, fludarabine, fluorouracil, fluoxymesterone, flutamide, fulvestrant, gefitinib, gemcitabine, gemtuzumab ozogamicin, goserelin, hexamethylmelamine, hydrocortisone, hydroxyurea, ibritumomab tiuxetan, ibtritumomab, idarubicin, ifosfamide, imatinib, imidazole carboxamide, interleukin-11, interleukin-2, irinotecan, ixabepilone, lapatinib, L-asparaginase, lenalidomide, letrozole, leukovorin, leuprolide, mechlorethamine, megestrol, melphalan, mercaptopurine, methotrexate, methylprednisolone, mitixantrone, mitomycin, mitoxantrone, nelarabine, nitrogen mustard, octreotide, oxaliplatin, paclitaxel, paclitaxel-albumin formulations, paclitaxel-protein formulations, pamidronate, panitumumab, pemetrexed, pentostatin, phenylalanine mustard, pirubicin, prednisolone, prednisone, procarbazine, Puromycin, raloxifene, rituxan, rubidomycin, sargramostim, sorafenib, staurosporine, steroids, streptozocin, sunitinib, tamoxifen, Taxol, tegafur, temozolomide, temsirolimus, teniposide, thalidomide, thiophosphoamide, thiotepa, topotecan, toremifene, tositumomab, trastuzumab, tretinoin, UFT, vinblastine, vincristine, vinorelbine, vorinostat, and/or zoledronic acid. A RNAi agent to HSF1 can be used in conjunction with any additional treatment disclosed herein, as appropriate for the disease, optionally, in further conjunction with one or more additional RNAi agents to HSF1.

In one embodiment, the HSF1-related disease is a viral disease.

In one embodiment, the HSF1-related disease is a viral disease selected from the list of viral diseases mediated in whole or in part by adenovirus, herpes simplex virus, human cytomegalovirus, HTLV-1, SV40, polyoma virus, HIV, and/or Epstein-Barr virus.

In one embodiment, the method further comprises the step of administering an additional viral disease treatment.

In one embodiment, the method further comprises the step of administering an additional viral disease treatment selected from the list of Abacavir, Aciclovir, acyclovir (acycloguanosine), Adefovir, Amantadine, Ampligen, Amprenavir, Arbidol, Atazanavir, Atripla, bevirimat, Boceprevir, broad spectrum inhibitor, Cidofovir, Combivir, Darunavir, Delavirdine, Didanosine, Docosanol, Edoxudine, Efavirenz, Emtricitabine, Enfuvirtide, Entecavir, Entry inhibitors, Entry or fusion inhibitor, Famciclovir, Fomivirsen, Fosamprenavir, Foscarnet, Fosfonet, Fusion inhibitor, Ganciclovir, Ibacitabine, Idoxuridine, Imiquimod, Imunovir, Indinavir, Inosine, Integrase inhibitor, Integrase inhibitor, Interferon, Interferon type I, Interferon type II, Interferon type III, Lamivudine, Lopinavir, Loviride, Maraviroc, Maturation inhibitor, Moroxydine, Nelfinavir, Nevirapine, Nexavir, Non-nucleoside reverse transcriptase inhibitor, NOV-205, Nucleoside analogues, Nucleotide analog reverse transcriptase inhibitor, Oseltamivir (Tamiflu), Pcginterferon alfa-2a, Penciclovir, Peramivir, Pleconaril, Podophyllotoxin, Protease inhibitor, Protease inhibitor, Raltegravir, Raltegravir, Reverse transcriptase inhibitor, Reverse transcriptase inhibitor, Ribavirin, Rimantadine, Ritonavir, Saquinavir, Saquinavir, Stavudine, Synergistic enhancer (antiretroviral), Tenofovir, Tenofovir disoproxil, Tipranavir, Trifluridine, Trizivir, Tromantadine, Truvada, Valaciclovir (Valtrex), Valganciclovir, Vicriviroc, Vidarabine, Viramidine, Zalcitabine, Zanamivir (Relenza), and Zidovudine. It will be understood that references to any additional treatment (e.g., viral disease treatment or cancer treatment or autoimmune disease treatment, etc.) are meant to also include the pharmaceutically acceptable salts of any of the active substances. If active substances comprised by components (a) and/or (b) have, for example, at least one basic center, they can form acid addition salts. Corresponding acid addition salts can also be formed having, if desired, an additionally present basic center. Active substances having an acid group, e.g., COOH, can form salts with bases. The active substances comprised in components (a) and/or (b) or a pharmaceutically acceptable salts thereof may also be used in form of a hydrate or include other solvents used for crystallization.

In one embodiment, the HSF1-related disease is an autoimmune disease.

In one embodiment, the HSF1-related disease is lupus or rheumatoid arthritis.

In one embodiment, the composition comprises a second RNAi agent to HSF1. In various embodiments, the second RNAi agent is physically distinct from the first, or the two are physically connected (e.g., linked or conjugated).

Inhibiting HSF1 Expression Using an RNAi Comprising an RNAi Agent.

In one particular specific embodiment, the present disclosure relates to a method of inhibiting the expression of HSF1 in an individual, comprising the step of administering to the individual a therapeutically effective amount of a composition comprising an RNAi agent of the disclosure. In one embodiment of this method, the RNAi comprises a sense strand and an antisense strand, wherein the antisense strand comprises at least 15 contiguous nucleotides differing by 0, 1, 2, or 3 nucleotides from the antisense strand of an RNAi agent to HSF1 selected from those specific duplexes provided above and as listed in Tables A1, 1, 2, 3, 4, 5, 6, or 7. In one particular specific embodiment of this method, the present disclosure relates to a composition comprising an RNAi agent comprising a first strand and an second strand, wherein the first strand and second strand comprise at least 15 contiguous nucleotides differing by 0, 1, 2, or 3 nucleotides from the first and second strand, respectively, of an RNAi agent to HSF1 selected from the specific duplexes provided above and as listed in Tables A1, 1, 2, 3, 4, 5, 6, or 7. In one particular specific embodiment of this method, the present disclosure relates to a composition comprising an RNAi agent comprising a first strand and an second strand, wherein the first strand and second strand comprise at least 15 contiguous nucleotides from the first and second strand, respectively, of an RNAi agent to HSF1 selected from the specific duplexes provided above and as listed in Tables A1, 1, 2, 3, 4, 5, 6, or 7. In one particular specific embodiment of this method, the present disclosure relates to a composition comprising an RNAi agent comprising a first strand and an second strand, wherein the sequence of the first strand comprises the sequence of the first strand of an RNAi agent to HSF1 selected from the specific duplexes provided above and as listed in Tables A1, 1, 2, 3, 4, 5, 6, or 7. In one particular specific embodiment of this method, the present disclosure relates to a composition comprising an RNAi agent comprising a first strand and an second strand, wherein the sequence of the first strand is the sequence of the first strand of an RNAi agent to HSF1 selected from the specific duplexes provided above and as listed in Tables A1, 1, 2, 3, 4, 5, 6, or 7. In one particular specific embodiment of this method, the present disclosure relates to a composition comprising an RNAi agent comprising a first strand and an second strand, wherein the sequence of the first and/or second strand comprises the sequence of the first and/or second strand of an RNAi agent to HSF1 selected from the specific duplexes provided above and as listed in Tables A1, 1, 2, 3, 4, 5, 6, or 7. In one particular specific embodiment of this method, the present disclosure relates to a composition comprising an RNAi agent comprising a first strand and an second strand, wherein the sequence of the first and/or second strand is the sequence of the first and/or second strand of an RNAi agent to HSF1 selected from the specific duplexes provided above and as listed in Tables A1, 1, 2, 3, 4, 5, 6, or 7. In one particular specific embodiment of this method, the present disclosure relates to a composition comprising an RNAi agent comprising a first strand and an second strand, wherein the sequence of the first and/or second strand is the sequence of the first and/or second strand of an RNAi agent to HSF1 selected from the specific duplexes provided above and as listed in Tables A1, 1, 2, 3, 4, 5, 6, or 7, wherein the sequence of the first and/or second strand further comprises 1 to 20 nt.

Various particular specific embodiments of these embodiments are described below.

In one embodiment, the individual is afflicted with or susceptible to an HSF1-related disease.

In one embodiment, the HSF1-related disease is proliferative disease, such as, e.g., a cancer.

In one embodiment, the HSF1-related disease is cancer selected from the list of bladder, bone, breast, cervical, colon, colorectal, endometrial, fibrosarcoma, gastric, haematopoietic, intestine, kidney, liver, lung, lymphoma, neuroectodermal, neuroblastoma, Ewing's sarcoma, osteosarcoma, ovary, pancreas, pleura, prostate, skin, squamous cell, stomach, and testicular cancers, leukemia, promyelocytic leukemia, and Hodgkin's disease.

In one embodiment, the method further comprises the step of administering an additional cancer treatment.

In one embodiment, the method further comprises the step of administering an additional cancer treatment selected from the list of any cancer treatment listed herein, or known in the art.

In one embodiment, the HSF1-related disease is a viral disease.

In one embodiment, the HSF1-related disease is a viral disease selected from the list of viral diseases mediated in whole or in part by adenovirus, herpes simplex virus, human cytomegalovirus, HTLV-1, SV40, polyoma virus, HIV, and/or Epstein-Barr virus.

In one embodiment, the method further comprises the step of administering an additional viral disease treatment.

In one embodiment, the method further comprises the step of administering an additional viral disease treatment selected from the list of any viral disease treatment listed herein.

In one embodiment, the HSF1-related disease is an autoimmune disease.

In one embodiment, the HSF1-related disease is lupus or rheumatoid arthritis.

In one embodiment, the composition further comprises a second RNAi agent to HSF1. In various embodiments, the second RNAi agent is physically distinct from the first, or the two are physically connected (e.g., linked or conjugated).

Pharmaceutical Formulations of a RNAi Agent to HSF1.

In one particular specific embodiment, the present disclosure relates to a composition comprising a RNAi agent of the present disclosure. In one embodiment, the RNAi agent comprises at least an anti-sense strand, and/or comprises a sense and an anti-sense strand, wherein the anti-sense strand comprises at least 15 contiguous nucleotides differing by 0, 1, 2, or 3 nucleotides from the anti-sense strand of a RNAi agent to HSF1 selected from those specific duplex provided herein and as listed, e.g., in a Table herein, wherein the composition is in a pharmaceutically effective formulation. In one particular specific embodiment, the present disclosure relates to a composition comprising an RNAi agent comprising a first strand and an second strand, wherein the first strand and second strand comprise at least 15 contiguous nucleotides differing by 0, 1, 2, or 3 nucleotides from the first and second strand, respectively, of an RNAi agent to HSF1 selected from the specific duplexes provided above and as listed in Tables A1, 1, 2, 3, 4, 5, 6, or 7. In one particular specific embodiment, the present disclosure relates to a composition comprising an RNAi agent comprising a first strand and an second strand, wherein the first strand and second strand comprise at least 15 contiguous nucleotides from the first and second strand, respectively, of an RNAi agent to HSF1 selected from the specific duplexes provided above and as listed in Tables A1, 1, 2, 3, 4, 5, 6, or 7. In one particular specific embodiment, the present disclosure relates to a composition comprising an RNAi agent comprising a first strand and an second strand, wherein the sequence of the first strand comprises the sequence of the first strand of an RNAi agent to HSF1 selected from the specific duplexes provided above and as listed in Tables A1, 1, 2, 3, 4, 5, 6, or 7. In one particular specific embodiment, the present disclosure relates to a composition comprising an RNAi agent comprising a first strand and an second strand, wherein the sequence of the first strand is the sequence of the first strand of an RNAi agent to HSF1 selected from the specific duplexes provided above and as listed in Tables A1, 1, 2, 3, 4, 5, 6, or 7. In one particular specific embodiment, the present disclosure relates to a composition comprising an RNAi agent comprising a first strand and an second strand, wherein the sequence of the first and/or second strand comprises the sequence of the first and/or second strand of an RNAi agent to HSF1 selected from the specific duplexes provided above and as listed in Tables A1, 1, 2, 3, 4, 5, 6, or 7. In one particular specific embodiment, the present disclosure relates to a composition comprising an RNAi agent comprising a first strand and an second strand, wherein the sequence of the first and/or second strand is the sequence of the first and/or second strand of an RNAi agent to HSF1 selected from the specific duplexes provided above and as listed in Tables A1, 1, 2, 3, 4, 5, 6, or 7. In one particular specific embodiment, the present disclosure relates to a composition comprising an RNAi agent comprising a first strand and an second strand, wherein the sequence of the first and/or second strand is the sequence of the first and/or second strand of an RNAi agent to HSF1 selected from the specific duplexes provided above and as listed in Tables A1, 1, 2, 3, 4, 5, 6, or 7, wherein the sequence of the first and/or second strand further comprises 1 to 20 nt.

In one embodiment, the present disclosure pertains to the use of a RNAi agent in the manufacture of a medicament for treatment of a HSF1-related disease, wherein the RNAi agent comprises a sense strand and an antisense strand, wherein the antisense strand comprises at least 15 contiguous nucleotides differing by 0, 1, 2, or 3 nucleotides from the antisense strand of a RNAi agent to HSF1 selected from those specific duplex provided herein and as listed, e.g., in a Table herein. In one particular specific embodiment, the present disclosure relates to a composition comprising an RNAi agent comprising a first strand and an second strand, wherein the first strand and second strand comprise at least 15 contiguous nucleotides differing by 0, 1, 2, or 3 nucleotides from the first and second strand, respectively, of an RNAi agent to HSF1 selected from the specific duplexes provided above and as listed in Tables A1, 1, 2, 3, 4, 5, 6, or 7. In one particular specific embodiment, the present disclosure relates to a composition comprising an RNAi agent comprising a first strand and an second strand, wherein the first strand and second strand comprise at least 15 contiguous nucleotides from the first and second strand, respectively, of an RNAi agent to HSF1 selected from the specific duplexes provided above and as listed in Tables A1, 1, 2, 3, 4, 5, 6, or 7. In one particular specific embodiment, the present disclosure relates to a composition comprising an RNAi agent comprising a first strand and an second strand, wherein the sequence of the first strand comprises the sequence of the first strand of an RNAi agent to HSF1 selected from the specific duplexes provided above and as listed in Tables A1, 1, 2, 3, 4, 5, 6, or 7. In one particular specific embodiment, the present disclosure relates to a composition comprising an RNAi agent comprising a first strand and an second strand, wherein the sequence of the first strand is the sequence of the first strand of an RNAi agent to HSF1 selected from the specific duplexes provided above and as listed in Tables A1, 1, 2, 3, 4, 5, 6, or 7. In one particular specific embodiment, the present disclosure relates to a composition comprising an RNAi agent comprising a first strand and an second strand, wherein the sequence of the first and/or second strand comprises the sequence of the first and/or second strand of an RNAi agent to HSF1 selected from the specific duplexes provided above and as listed in Tables A1, 1, 2, 3, 4, 5, 6, or 7. In one particular specific embodiment, the present disclosure relates to a composition comprising an RNAi agent comprising a first strand and an second strand, wherein the sequence of the first and/or second strand is the sequence of the first and/or second strand of an RNAi agent to HSF1 selected from the specific duplexes provided above and as listed in Tables A1, 1, 2, 3, 4, 5, 6, or 7. In one particular specific embodiment, the present disclosure relates to a composition comprising an RNAi agent comprising a first strand and an second strand, wherein the sequence of the first and/or second strand is the sequence of the first and/or second strand of an RNAi agent to HSF1 selected from the specific duplexes provided above and as listed in Tables A1, 1, 2, 3, 4, 5, 6, or 7, wherein the sequence of the first and/or second strand further comprises 1 to 20 nt.

Other Embodiments

Various particular specific embodiments of this disclosure are described below.

In one embodiment, the disclosure pertains to a composition according to any of the above embodiments, for use in a method of treating a HSF1-related disease in an individual, the method comprising the step of administering to the individual a therapeutically effective amount of a composition according to any of the claims.

Various particular specific embodiments of this embodiment are described below.

In one embodiment, the disclosure pertains to the composition according to any of the above embodiments, for use in a method of inhibiting the expression of HSF1 in an individual, the method comprising the step of administering to the individual a therapeutically effective amount of a composition according to any of the above embodiments.

One embodiment of the disclosure is the use of a composition according to any of the above embodiments, in the manufacture of a medicament for treatment of an HSF1-related disease.

In one embodiment, the HSF1-related disease is selected from cancer, viral disease or autoimmune disease.

In one embodiment, the disclosure pertains to the composition of any of the above embodiments, for use in the treatment of an HSF1-related disease.

In one embodiment, the HSF1-related disease is selected from cancer, viral disease or autoimmune disease.

In one embodiment, the disclosure relates to a method of inhibiting the expression of HSF1 in an cell, comprising the step of introducing into the cell a composition comprising an RNAi agent comprising an antisense strand, wherein the antisense strand comprises at least 15 contiguous nucleotides differing by 0, 1, 2, or 3 nucleotides from the antisense strand of an RNAi agent to HSF1 selected from the HSF1 siRNAs disclosed herein.

In one embodiment, the disclosure relates to a method of inhibiting the expression of HSF1 in an cell, comprising the step of introducing into the cell a composition comprising an RNAi agent comprising a sense strand and an antisense strand, wherein the antisense strand comprises at least 15 contiguous nucleotides differing by 0, 1, 2, or 3 nucleotides from the antisense strand, and the sense strand comprises at least 15 contiguous nucleotides differing by 0, 1, 2, or 3 nucleotides from the sense strand of an RNAi agent to HSF1 selected from the HSF1 siRNAs disclosed herein.

Definitions

Heat Shock Factor 1 (HSF1).

By "HSF1" is meant the gene or mRNA or protein (or any nucleic acid encoding the protein) heat shock factor 1, or heat shock transcription factor 1 (HSTF1). HSF1 is the master regulator of the heat shock response, in which multiple genes are induced in response to temperature increase and other stresses. HSF1 has been designated HGNC ID HGNC:5224, on Chromosome 8q24.3. It (including homologues) is also identified as: GeneID: 3297; RefSeq IDs NM_005526; AccNo. M64673; Mouse Genome Database ID MGI:96238; Rat Genome Database ID RGD: 620913; Entrez Gene ID 3297; CCDS IDs CCDS6419.1; Pubmed IDs 1871105; Ensembl ID ENSG00000185122; OMIM ID (NCBI) 140580; UCSC ID (UCSC) uc003zbt.2; and/or UniProt ID (mapped data supplied by UniProt) Q00613.

The amino acid sequence of human HSF1 is provided as SEQ ID NO: 505:

(SEQ ID NO: 505)
MDLPVGPGAAGPSNVPAFLTKLWTLVSDPDTDALICWSPSGNSFHVFDQ

GQFAKEVLPKYFKHNNMASFVRQLNMYGFRKVVHIEQGGLVKPERDDTE

FQHPCFLRGQEQLLENIKRKVTSVSTLKSEDIKIRQDSVTKLLTDVQLM

KGKQECMDSKLLAMKHENEALWREVASLRQKHAQQQKVVNKLIQFLISL

VQSNRILGVKRKIPLMLNDSGSAHSMPKYSRQFSLEHVHGSGPYSAPSP

AYSSSSLYAPDAVASSGPIISDITELAPASPMASPGGSIDERPLSSSPL

VRVKEEPPSPPQSPRVEEASPGRPSSVDTLLSPTALIDSILRESEPAPA

SVTALTDARGHTDTEGRPPSPPPTSTPEKCLSVACLDKNELSDHLDAMD

SNLDNLQTMLSSHGFSVDTSALLDLFSPSVTVPDMSLPDLDSSLASIQE

LLSPQEPPRPPEAENSSPDSGKQLVHYTAQPLFLLDPGSVDTGSNDLPV

LFELGEGSYFSEGDGFAEDPTISLLTGSEPPKAKDPTVS

The functional domains of HSF1 have been delineated by mutagenesis. A sequence near the N terminus forms the DNA binding domain (numbered approximately aa 13-121). Adjacent to this is a hydrophobic region comprising three "leucine zippers" that mediate monomerization and trimerization (numbered approximately aa 126-217). A fourth hydrophobic patch or leucine zipper lies at approximately aa 378-407; this region is involved in negative regulation under non-stress conditions. The central part of the molecule contains a region that regulates the activity of transcriptional activation domains in response to stress. Sequences within the regulatory domain undergo specific phosphorylation and dephosphorylation in response to stress. This regulatory domain, which is rich in serines and prolines, lies at approximately aa 221-310. The C-terminal portion of HSF1 contains the main transcriptional activation regions; this comprises the 100 most C-terminal amino acids, or aa 395-503, particularly aa 401-420. These domains are described in, inter alia, Green et al. 1995 Mol. Cell. Biol. 15: 3354-3362; and Shi et al. 1995 Mol. Cell. Biol. 15: 4309-4318, which references provide slightly different boundaries for the different regions. The HSF1 RNAi agent of the present disclosure can interact with a specific functional domain or domains of HSF1.

In various embodiments, the RNAi agents of the present disclosure specifically bind to HSF1 mRNA, in a sequence corresponding to a functional domain, e.g., in a sequence near the N terminus that forms the DNA binding domain; in the 4/3 hydrophobic repeat or "leucine zipper" that mediates trimerization; in the first, second, third or fourth leucine zipper; in the central part of the molecule that contains several elements that maintain HSF1 in its latent form, or that regulate the activity of transcriptional activation domains in response to stress; in sequences within the regulatory domain that undergo specific phosphorylation and dephosphorylation in response to stress; in the C-terminal portion of HSF1 that contains the main transcriptional activation regions; in the arrays of amphipathic alpha-helical residues in the amino-terminal domain of HSF family proteins that interact to form coiled coils; and/or in the fourth region of amphipathic alpha-helix in the carboxyl-terminal domain. In other embodiments, the RNAi agents of the present disclosure bind to the 5' or 3' UTR [untranslated region(s)].

In various embodiments, the RNAi agents of the present disclosure bind to HSF1 mRNA, but not in a sequence corresponding to a functional domain, e.g., not in a sequence near the N terminus that forms the DNA binding domain; not in the 4/3 hydrophobic repeat or "leucine zipper" that mediates trimerization; not in the first, second, third or fourth leucine zipper; not in the central part of the molecule that contains several elements that maintain HSF1 in its latent form, or that regulate the activity of transcriptional activation domains in response to stress; not in sequences within the regulatory domain that undergo specific phosphorylation and dephosphorylation in response to stress; not in the C-terminal portion of HSF1 that contains the main transcriptional activation regions; not in the arrays of amphipathic alpha-helical residues in the amino-terminal domain of HSF family proteins that interact to form coiled coils; not in the fourth region of amphipathic alpha-helix in the carboxyl-terminal domain; or not in the 5' or 3' UTRs. In another embodiment, the RNAi agents of the present disclosure bind to the HSF1 mRNA, but neither strand of the RNAi agent comprises the entirety of the sequence spanning nt 322 to 340 downstream of the gene transcription start site as described by Rossi et al. 2006 Cancer Res. 66:7678-7685.

HSF1-Related Diseases.

As used herein, the phrase a "HSF1-related disease" means one or more of the following: a proliferative disease, including, e.g., a cancer, wherein the cancer is selected from one or more of cancers of bladder, bone, breast, cervical, colon, colorectal, endometrial, fibrosarcoma, gastric, haematopoietic, intestine, kidney, liver, lung, lymphoma, neuroectodermal, neuroblastoma, Ewing's sarcoma, osteosarcoma, ovary, pancreas, pleura, prostate, skin, squamous cell, stomach, and testicular cancers, leukemia, promyelocytic leukemia, and Hodgkin's disease; a viral disease, wherein the viral disease is selected from one or more of viral diseases mediated in whole or in part by adenovirus, herpes simplex virus, human cytomegalovirus, HTLV-1, SV40, polyoma virus, HIV, and/or Epstein-Barr virus; and an autoimmune disease, wherein the autoimmune disease is selected from one or more of lupus and a rheumatoid arthritis.

HSF1 has been implicated in several diseases, including cancer and viral diseases. HSF1 and other heat shock proteins (whose expression is increased by HSF1) are over-expressed in, or have otherwise been implicated in, bladder, bone, breast, cervical, colon, colorectal, endometrial, fibrosarcoma, gastric, haematopoietic, intestine, kidney, liver, lung, lymphoma, neuroectodermal, neuroblastoma, Ewing's sarcoma, osteosarcoma, ovary, pancreas, pleura, prostate, skin, squamous cell, stomach, and testicular cancers, leukemia (e.g., promyelocytic leukemia), and Hodgkin's disease. HSF1 is over-expressed in metastatic prostate carcinoma cell line PC-3M (as compared to the non-metastatic PC-3 line), and other prostate cancer cells.

The over-expression of HSF1 is correlated with an up-relation of heat shock protein HSP27. Hoang et al. 2000 Am. J. Pathol. 156: 857-864. HSP27 up-regulation is also associated with increased tumorigenicity and invasiveness of some cancers, including colon, breast, promyelocytic leukemia, testicular and prostate. HSF1 also plays a functional role in cancer cells under non-stress conditions; a dominant-negative HSF1 alters DNA content in PC-3 cell populations and inhibits ancuploidy. Wang et al. 2004 J. Biol. Chem. 279: 32651-32659. Many tumor types contain high concentrations of heat shock protein of the HSP27, HSP70, and HSP90 families, which are up-regulated by HSF1. Without wishing to be bound by any particular theory, applicants note that it has been suggested that heat shock proteins (HSP) may block the pathways of apoptosis and permit malignant cells to arise despite the triggering of apoptotic signals during transformation. HSP expression may also afford protection of cancer cells from treatments such as chemotherapy and hyperthermia by thwarting the pro-apoptotic influence of these modalities. Tang et al. 2005 Cell Stress Chaperones 10: 46-58 and references therein. Rossi et al. also showed that decreasing HSF1 levels increased the sensitivity of uterine cervix carcinoma cells to cisplatin associated with hyperthermia. Over-expression of heat shock proteins is also associated with protection of cancer cells against doxorubicin and hyperthermia and other anti-cancer treatments. Helmbrecht et al. 2000 Cell Prolif. 33: 341-365.

Over-expression of heat shock proteins is also associated with viral infections, including those mediated by adenovirus, herpes simplex virus, human cytomegalovirus, HTLV-1, SV40, polyoma virus, HIV, Epstein-Barr virus. High heat shock protein levels are also associated with autoimmune diseases, including lupus and rheumatoid arthritis. Inhibition of HSF1, e.g., via use of an anti-HSF1 RNAi agent, can thus be an effective treatment against cancer, and viral and other diseases. Few HSP inhibitors are known, but they include quercetin, a flavonoid that inhibits the HSF1. Zanini et al. 2007 J. Neurochem. 103:1344-354 and references therein. Quercetin can thus be used as a positive control for RNAi agents that inhibit HSF1 in treating a viral disease or cancer.

HSF1 Gene Sequences in Various Species.

The human HSF1 gene has been cloned. Rabindran et al. 1991 Proc. Natl. Acad. Sci USA 88: 6906-6910. Various sequences are available for human HSF1, including Genbank identifier NM_005526.2. The mouse (*Mus musculus*) HSF1 gene is, for example, Genbank id NM_008296.2. Another mouse HSF1 sequence is available as Acc. Number XM_128055 (as used in Yin et al. 2005 J. Mol. Cell. Card. 39: 681-689).

The Cynomolgus monkey ("Cyno", or *Macaca fascicularis*) HSF1 sequence (SEQ ID NO: 506), compared to the human sequence (SEQ ID NO: 513), is presented below:

```
human  GCGGCGGGAGCGCGCCCGTTGCAAGATGGCGGCGGCCATGCTGGGCCCCGGGGCTGTGTG
cyno   ----------CGCGCCCGTTGCAAGATGGCGGCGGCAAAGCTGGGCCTTGGGGCTGGGGG
                 ************************ * ****** ***** * * human  TGCGCAGCGGGCGGCGGCGCGGCCCGGAAGGCTGGCGCGGCGACGGCGTTAGCCCGGCCC
cyno   GGCGCAGGGGGAGGCGGNNNNNNNNNNNNNNNNNNNNNNNNNNNNNNNNNNNNNNNNNNN
        ****** *** *****
```

```
                                                          Start->
human TCGGCCCCTCTTTGCGGCCGCTCCCTCCGCCTATTCCCTCCTTGCTCGAGATGGATCTGC
cyno  NNNNNNNNNNNNNNNNNNNNNNNNNNNNNNNNNNNNNNNNNNNNNNNNNNNNCGAGATGGATCTGC
                                                          ************** human CCGTGGGCCCCGGCGCGGCGGGGCCCAGCAAC-GTCCCGGCCTTCCTGACCAAGCTGTGG
cyno  CCGTGGGCCCCGGTGCGGCGGGGCCCAGCAANCGTCCCGGCCTTCCTGACCAAGCTGTGG
      ***********  ************  ************************* human ACCCTCGTGAGCGACCCGGACACCGACGCGCTCATCTGCTGGAGCCCGAGCGGGAACAGC
cyno  ACCCTCGTGAGCGACCCGGACACCGACGCGCTCATCTGCTGGAGCCCGAGTGGGAACAGC
      ************************************************ ****** human TTCCACGTGTTCGACCAGGGCCAGTTTGCCAAGGAGGTGCTGCCCAAGTACTTCAAGCAC
cyno  TTCCATGTGTTCGACCAGGGCCAGTTTGCCAAGGAGGTGCTGCCCAAGTATTTCAAGCAC
      *** **************************************** ******* human AACAACATGGCCAGCTTCGTGCGGCAGCTCAACATGTATGGCTTCCGGAAAGTGGTCCAC
cyno  AACAACATGGCCAGCTTCGTGCGGCAGCTCAACATGTATGGTTTCCGGAAAGTGGTCCAC
      *************************************** **************** human ATCGAGCAGGGCGGCCTGGTCAAGCCAGAGAGAGACGACACGGAGTTCCAGCACCCATGC
cyno  ATCGAGCAGGGTGGCCTGGTCAAGCCAGAGAGAGACGACACGGAGTTCCAGCACCCGTGC
      ********* *************************************** * human TTCCTGCGTGGCCAGGAGCAGCTCCTTGAGAACATCAA-GAGGAAAGTGACCAGTGTGTC
cyno  TTCCTGCGCGGCCAGGAGCAGCTCCTTGAGAACATCANAGAGGAAAGTGACCAGTGTGTC
      ****** ************************ ******************** human CACCCTGAAGAGTGAAGACATAAAGATCCGCCAGGACAGCGTCACCAAGCTGCTGACGGA
cyno  CACCCTGAAGAGTGAAGACATAAAGATCCGTCAGGACAGTGTCACCAAGCTGCTGACGGA
      **************************** **** ****************** human CGTGCAGCTGATGAAGGGGAAGCAGGAGTGCATGGACTCCAAGCTCCTGGCCATGAAGCA
cyno  CGTGCAGCTGATGAAGGGGAAGCAGGAGTGCATGGACTCCAAGCTCCTGGCCATGAAGCA
      ************************************************************ human TGAGAATGAGGCTCTGTGGCGGGAGGTGGCCAGCCTTCGGCAGAAGCATGCCCAGCAACA
cyno  TGAGAATGAGGCTCTGTGGCGGGAGGTGGCCAGCCTTCGGCAGAAGCATGCCCAGCAACA
      ************************************************************ human GAAAGTCGTCAACAAGCTCATTCAGTTCCTGATCTCACTGGTGCAGTCAAACCGGATCCT
cyno  GAAAGTCGTCAACAAGCTCATTCAGTTCCTGATCTCACTGGTGCAGTCAAACCGGATCCT
      ************************************************************ human GGGGGTGAAGAGAAAGATCCCCCTGATGCTGAACGACAGTGGCTCAGCACATTCCATGCC
cyno  GGGGGTGAAGAGAAAGATCCCCCTGATGCTGAACGACAGTGGCTCAGCACATTCCATGCC
      ************************************************************ human CAAGTATAGCCGGCAGTTCTCCCTGGAGCACGTCCACGGCTCGGGCCCCTACTCGGCCCC
cyno  CAAGTATGGCCGGCAGTTCTCCCTGGAGCACGTCCACGGCTCGGGCCCCTACTCGGCCCC
      ***** ************************************************** human CTCCCCAGCCTACAGCAGCTCCAGCCTCTACGCCCCTGATGCTGTGGCCAGCTCTGGACC
cyno  CTCCCCAGCCTACAGTAGCTCCAGCCTCTACGCCCCCGATTCTGTGGCCAACTCCGGACC
      ************* ****************  * ******* * ***** human CATCATCTCCGACATCACCGAGCTGGCTCCTGCCAGCCCCATGGCCTCCCCCGGCGGGAG
cyno  CATCATCTCCGACATCACCGAGCTGGCTCCTGCCAGCCCCGTGGCCTCCCCTGGCGGGAG
      ************************************** ****** ****** human CATAGACGAGAGGCCCCTATCCAGCAGCCCCCTGGTGCGTGTCAAGGAGGAGCCCCCCAG
cyno  CATAGACGAGAGGCCCCTGTCTAGCAGCCCCCTGGTGCGTGTCAAAGAGGAGCCCCCCAG
      ****************   ******************** ************ human CCCGCCTCAGAGCCCCCGGGTAGAGGAGGCGAGTCCCGGGCGCCCATCTTCCGTGGACAC
cyno  CCCGCCTCAGAGCCCCCGGGTAGAGGAGGCGAGTCCCGGGCGCCCATCTTCCGTGGACAC
      ************************************************************ human CCTCTTGTCCCCGACCGCCCTCATTGACTCCATCCTGCGGGAGAGTGAACCTGCCCCCGC
cyno  CCTCTTGTCCCCGACCGCCCTCATTGACTCCATCCTGCGGGAGAGTGAACCTACCCCCGC
      ************************************************** ***** human CTCCGTCACAGCCCTCACGGACGCCAGGGGCCACACGGACACCGAGGGCCGGCCTCCCTC
cyno  CTCCGCCACAGCCCTCACCGATGCCAGGGGCCACACGGACACCGAGGGCCGGCCTCCCTC
      *** ********  ************************************** human CCCCCCGCCCACCTCCACCCCTGAAAAGTGCCTCAGCGTAGCCTGCCTGGACAAGAATGA
cyno  ACCCCCGCCCACCTCCACCCCTGAAAAGTGCCTCAGCGTAGCCTGCCTGGACAAGAATGA
       ***********************************************************
```

```
                              -continued
human  GCTCAGTGACCACTTGGATGCTATGGACTCCAACCTGGATAACCTGCAGACCATGCTGAG
cyno   GCTCAGTGATCACTTGGATGCTATGGACTCCAACCTGGACAACCTGCAGACCATGCTGAG
       ******* *************************** **************** human  CAGCCACGGCTTCAGCGTGGACACCAGTGCCCTGCTGGACCTGTTCAGCCCCTCGGTGAC
cyno   CAGCCACGGCTTCAGCGTGGACACCAGCGCCCTGCTGGACCTGTTCAGCCCCTCGGTGAC
       ************************* ****************************** human  CGTGCCCGACATGAGCCTGCCTGACCTTGACAGCAGCCTGGCCAGTATCCAAGAGCTCCT
cyno   CGTGCCCGACATGAGCCTGCCTGACCTTGACAGCAGCCTGGCTAGTATCCAAGAGCTCCT
       **************************************** *************** human  GTCTCCCCAGGAGCCCCCCAGGCCTCCCGAGGCAGAGAACAGCAGCCCGGATTCAGGGAA
cyno   GTCTCCCCAGGAGCCCTCCAGGCCTCCCGAGGCAGAGAACAGCAGCCCGGATTCAGGGAA
       ************** ***************************************** human  GCAGCTGGTGCACTACACAGCGCAGCCGCTGTTCCTGCTGGACCCCGGCTCCGTGGACAC
cyno   GCAGCTGGTGCACTACACAGCACAGCCACTGTTCCTGCTCGACCCCGGCTCCGTGGGCAC
       ******************* * ******* ************ * human  CGGGAGCAACGACCTGCCGGTGCTGTTTGAGCTGGGAGAGGGCTCCTACTTCTCCGAAGG
cyno   CGGGAGCAGCGACTTGCCGGTGCTGTTTGAGCTGGGGGAGGGCTCCTACTTCTCCGAAGG
       ******  ****************** ********************* human  GGACGGCTTCGCCGAGGACCCCACCATCTCCCTGCTGACAGGCTCGGAGCCTCCCAAAGC
cyno   GGACGGCTTCGCAGAGGACCCCACCATCTCCCTGCTGACAGGCTCAGAGCCTCCCAAAGC
       ************ ******************************** **************
                                STOP
human  CAAGGACCCCACTGTCTCCTAGAGGCCCCGGAGGAGCTGGGCCAGCCGCCCACCCCCACC
cyno   CAAGGACCCCACTGTCTCCTAGGCGCCCGGGAGGAGCTGGGCCAGCCGCCCACCCCCACC
       *******************  ******************************* human  CCCAGTGCAGGGCTGGTCTTGGGGAGGCAG-GGCAGCCTCGCGGTCTTGGGCACTGGTGG
cyno   CCCAGTGCAGGGCTGGCCTTGGGGAGGAAGAGGCAGCCTCGAGGTCCTGGGCACTGGTGG
       ************** ******  ********  *********** human  GTCGGCCGCCATAGCCCCAGTAGGACAAAC--GGGCTCGGGTCTGGGCAGCACCTCTGGT
cyno   GTTGGCCACCACAGCCCCAGTAGGACAAACAGGGGCTCAGGTCTGGGCAGCACCTCTGGT
         * **************** ** ******************** human  CAGGAGGGTCACCCTGGCCTGCCAGTCTGCCTTCCCCCAACCCCGTGTCCTGTGGTTTGG
cyno   CAGGAGGGTCACCCCGGCCTCCCAGTCTGCCTTCCCCCAACCCCGTGTCCTGTGGTTTGG
       ************ * ************************************* human  TTGGGGCTTCACAGCCACACCTGGACTGACCCTGCAGGTTGTTCATAGTCAGAATTGTAT
cyno   TTGGGGCTTCGTAGCCACACCTGGACTGACCCTGCAGGTTGTTCATAATCAGAATTGTAT
       ******** ******************************** ********** human  TTTGGATTTTTACACAACTGTCCCGTTCCCCGCTCCACAGAGATACACAGATATATACAC
cyno   TTTGGATTTTTACACAACTGTCCCATTCCCTGTTCCATAGAGATATACAGATATATACAC
       ********************** *** * ** *** ************ human  ACAG-TGGATGGACGGACAAGACAGGCAGAGATCTATAAACAGACAGGCTCTATGCTAAA
cyno   ACAGGTGGATGGACGGACAAGACAGGCAGAGATCTATAAACAGACAG-------------
       ** **************************************** human  AAAAAAAAAAAA (SEQ ID NO: 513)
cyno   ------------ (SEQ ID NO: 506)
The start (ATG) and stop (TAG) of the human HSF1 sequence and putative
start and stop of the cyno HSF1 sequence are indicated in bold underlined.
N indicates that the nucleotide was not determined at that position in the
sequencing experiment.
Nucleotides matching between the human and cyno sequences are marked with
an asterick (*).
```

In one embodiment, the HSF1 RNAi agent of the present disclosure comprises a sequence which is identical in the human, rat, mouse and cyno HSF1 gene. This sequence identity facilitates animal testing prior to human testing. In one embodiment, the HSF1 RNAi agent of the present disclosure comprises a sequence which is identical in the human, mouse and cyno HSF1 gene. In one embodiment, the HSF1 RNAi agent of the present disclosure comprises a sequence which is identical in the human and cyno HSF1 gene. In one embodiment, the HSF1 RNAi agent of the present disclosure comprises a sequence which is identical in the human and rat HSF1 gene. In one embodiment, the HSF1 RNAi agent of the present disclosure comprises a sequence which is identical in the human and mouse HSF1 gene.

Additional Embodiments of a RNAi Agent to HSF1

In one embodiment, the HSF1 RNAi agent comprises a sequence which does not match that of any other gene. In one embodiment, the HSF1 RNAi agent comprises a sequence which differs from all other known non-HSF1 genes by at least 0, 1, 2 or 3 nucleotides.

In one embodiment, the HSF1 RNAi agent comprises a sequence which is identical to that in HSF2, HSF3 or HSF4.

In one embodiment, the HSF1 RNAi agent comprises a sequence which is not identical to any in HSF2, HSF3 or HSF4.

HSF1 RNAi Agent for Use in Treating Various HSF1-Related Diseases

In one embodiment, the HSF1 RNAi agent of the present disclosure comprises a sequence disclosed herein and is administered to a patient in need thereof (e.g., a patient suffering from cancer and/or a viral disease and/or autoimmune disease and/or HSF1-related disease). In one embodiment, the HSF1 RNAi agent of the present disclosure is administered to a patient in need thereof, along with one or more additional pharmaceutical agent appropriate for that disease. For example, a patient suffering from cancer can be administered a pharmacologically effective amount of one or more HSF1 RNAi agent along with a pharmacologically effective amount of one or more of any cancer treatment listed herein, and/or any other cancer treatment known in the art.

A patient suffering from a viral disease can be administered one or more RNAi agent to HSF1 and one or more additional viral disease treatment. This additional treatment can be selected from the list of any viral disease treatment listed herein, and/or any anti-viral known in the art.

The patient can also be administered more than one RNAi agent to HSF1.

In the case of cancer, and autoimmune and viral diseases, the RNAi agent(s) and additional disease treatment(s) can be administered in any order, simultaneously or sequentially, or in multiple doses over time. Administration of the RNAi agent and the additional treatment can be, for example, simultaneous, concurrent, separate or sequential.

In at least some cases, knockdown of HSF1 by itself may not have anti-tumor effects. However, knockdown of HSF1 may be able to sensitize cancer cells (e.g., liver cancer cells or melanoma cells) to HSP90 inhibitors. In other words, a HSF1 RNAi agent may not inhibit cell proliferation, but may synergize cancer cells to apoptosis with one or more HSP90 inhibitors. These HSP90 inhibitors include, as non-limiting examples, actinomycin D and AUY922 (also known as NVP-AUY922). See, for example, Jensen et al. 2008 Breast Cancer Res. 10(2): R33; Gaspar et al. 2010 Mol. Cancer Ther. 9: 1219-1233; Okui et al. 2011 Anticancer Res. 31: 1194-204; and Eccles et al. Cancer Res. 68: 2850-2860. In some embodiments, the disease treatment regimen includes both at least one RNAi agent to HSF1 and AUY922, wherein the administration of these agents in simultaneous, sequential, or separate.

Simultaneous administration may, e.g., take place in the form of one fixed combination with two or more active ingredients, or by simultaneously administering two or more active ingredients that are formulated independently. Sequential use (administration) preferably means administration of one (or more) components of a combination at one time point, other components at a different time point, that is, in a chronically staggered manner, preferably such that the combination shows more efficiency than the single compounds administered independently (especially showing synergism). Separate use (administration) preferably means administration of the components of the combination independently of each other at different time points, preferably meaning that the components (a) and (b) are administered such that no overlap of significant measurable blood levels of both compounds are present in an overlapping manner (at the same time).

Also combinations of two or more of sequential, separate and simultaneous administration are possible, preferably such that the combination component-drugs show a joint therapeutic effect that exceeds the effect found when the combination component-drugs are used independently at time intervals so large that no mutual effect on their therapeutic efficiency can be found, a synergistic effect being especially preferred.

The term "delay of progression" as used herein means administration of the combination to patients being in a pre-stage or in an early phase, of the first manifestation or a relapse of the disease to be treated, in which patients, e.g., a pre-form of the corresponding disease is diagnosed or which patients are in a condition, e.g., during a medical treatment or a condition resulting from an accident, under which it is likely that a corresponding disease will develop.

"Jointly therapeutically active" or "joint therapeutic effect" means that the compounds may be given separately (in a chronically staggered manner, especially a sequence-specific manner) in such time intervals that they preferably, in the warm-blooded animal, especially human, to be treated, still show a (preferably synergistic) interaction (joint therapeutic effect). Whether this is the case, can inter alia be determined by following the blood levels, showing that both compounds are present in the blood of the human to be treated at least during certain time intervals.

Additional Definitions

For convenience, the meaning of certain terms and phrases used in the specification, examples, and appended claims, are provided below. If there is an apparent discrepancy between the usage of a term in other parts of this specification and its definition provided in this document, the definition in this document shall prevail.

As used throughout this disclosure, articles such as "a" and "an" refer to one or more than one (at least one) of the grammatical object of the article.

RNAi Agent

In one embodiment, the present disclosure pertains to a HSF1 RNAi agent or other composition comprising at least one nucleic acid sequence complementary to a HSF1 nucleic acid (or portion thereof), or pertains to a recombinant expression vector encoding at least one strand of the siRNA (RNAi agent) or a composition comprising the antisense nucleic acid that can function as an RNAi agent as defined below. As used herein, an "antisense" nucleic acid comprises a nucleotide sequence complementary to a "sense" nucleic acid encoding the HSF1 protein (e.g., complementary to the coding strand of a double-stranded DNA, complementary to an mRNA or complementary to the coding strand of a HSF1 gene or nucleic acid).

As used herein, the term "RNAi agent," "RNAi agent to HSF1", "RNAi agent specific to HSF1", "iRNA agent to HSF1", "siRNA to HSF1", "HSF1 siRNA" and the like refer to an siRNA (short inhibitory RNA), shRNA (short or small hairpin RNA), iRNA (interference RNA) agent, RNAi (RNA interference) agent, dsRNA (double-stranded RNA), microRNA, and the like, and/or refer to a composition which specifically targets, is specific to, and/or specifically binds to the HSF1 mRNA or a portion thereof. As used herein, the term "antisense nucleic acid" or "composition comprising an anti-sense nucleic acid" and the like is broadly meant to encompass any composition comprising at least one nucleic acid strand which is anti-sense to its target; this includes, but is not limited to, any siRNA, shRNA, iRNA, dsRNA, microRNA, antisense oligonucleotide, and any other composition comprising an anti-sense nucleic acid. As used herein, the terms "iRNA" and "RNAi" refers to an agent that contains RNA (or a derivative thereof), and which mediates the targeted cleavage of another RNA transcript via an RNA-induced silencing complex (RISC) pathway. In one embodiment, the RNAi agent is an oligonucleotide composition that activates the RISC complex/pathway. In another embodiment, the RNAi agent comprises an antisense strand sequence (antisense oligonucleotide). In one embodiment, the RNAi comprises a single strand. This single-stranded RNAi agent oligonucleotide or polynucleotide can comprise the sense or antisense strand, as described by Sioud 2005 J. Mol. Biol. 348:1079-1090, and references therein. Thus the disclosure encompasses RNAi agents with a single strand comprising either the sense or antisense strand of an RNAi agent described herein. It should also be clear that a single or double-stranded RNA molecule or strand (e.g., a siRNA, shRNA, dsRNA, microRNA, etc., or either or both strand thereof) can comprise one or more nucleotides which are not RNA. For example, a siRNA, shRNA, dsRNA, microRNA, etc., or either or both strand thereof, or the like, can comprise one or two or more terminal or internal nucleotides which are DNA. For example, a siRNA can comprise a terminal dinucleotide TT which is DNA. In no case does the present disclosure contemplate a molecule in which both strands are fully DNA (e.g., a double-stranded DNA molecule). In another non-limiting example, a siRNA can comprise one or two or a few other nucleotides which are DNA instead of RNA. In addition, the present disclosure contemplates a functional equivalent of a siRNA which is a molecule comprising any sequence disclosed herein, but wherein the components are not RNA and/or DNA nucleotides but rather PNA, LNA, TNA, GNA, FANA, or other nucleic acid substitutes.

RNA interference (RNAi) is a post-transcriptional, targeted gene-silencing technique that uses double-stranded RNA (dsRNA) to degrade messenger RNA (mRNA) containing the same sequence as the dsRNA. The process of RNAi occurs when ribonuclease III (Dicer) cleaves the longer dsRNA into shorter fragments called siRNAs. siRNAs (small interfering RNAs) are typically produced by Dicer to be about 21 to 23 nucleotides long and comprise about 19 base pair duplexes (though artificial RNAi agents can be shorter and/or blunt-ended). The smaller RNA segments then mediate the degradation of the target mRNA. Dicer has also been implicated in the excision of 21- and 22-nucleotide small temporal RNAs (stRNAs) from precursor RNA of conserved structure that are implicated in translational control. Hutvagner et al. 2001, Science, 293, 834. The RNAi response also features an endonuclease complex, commonly referred to as an RNA-induced silencing complex (RISC), which mediates cleavage of single-stranded mRNA complementary to the antisense strand of the siRNA. Cleavage of the target RNA takes place in the middle of the region complementary to the antisense strand of the siRNA duplex.

Kits for RNAi synthesis are commercially available, e.g., from New England Biolabs and Ambion.

The RNAi agent(s) of the present disclosure target (e.g., bind to, anneal to, etc.) the HSF1 mRNA. The use of the RNAi agent to HSF1 results in a decrease of HSF1 activity, level and/or expression, e.g., a "knock-down" or "knock-out" of the target gene or target sequence. Particularly, in one embodiment, in the case of a disease state characterized by over-expression or hyper-activity of HSF1, administration of a RNAi agent to HSF1 knocks down the HSF1 target enough to restore a normal level of HSF1 activity.

A suitable RNAi agent can be selected by any process known in the art or conceivable by one of ordinary skill in the art. For example, the selection criteria can include one or more of the following steps: initial analysis of the HSF1 gene sequence and design of RNAi agents; this design can take into consideration sequence similarity across species (human, cynomolgus, mouse, etc.) and dissimilarity to other (non-HSF1) genes; screening of RNAi agents in vitro (e.g., at 10 nM in WI-38 cells); determination of EC50 in HeLa cells; determination of viability of WI-38, HeLa and GTL16 cells treated with RNAi agents, wherein it is desired that the RNAi agent to HSF1 not inhibit the viability of these cells; testing with human PBMC (peripheral blood mononuclear cells), e.g., to test levels of TNF-alpha to estimate immunogenicity, wherein immunostimulatory sequences are less desired; testing in human whole blood assay, wherein fresh human blood is treated with an RNAi agent and cytokine/chemokine levels are determined [e.g., TNF-alpha (tumor necrosis factor-alpha) and/or MCP1 (monocyte chemotactic protein 1)], wherein Immunostimulatory sequences are less desired; determination of gene knockdown in vivo using Hep3B subcutaneous tumors in test animals; HSF1 target gene modulation analysis, e.g., using a pharmacodynamic (PD) marker, for example, HSP70 or HSP27, wherein HSF1 knockdown leads to a dose-dependent reduction of HSP70 and HSP27 expression in A375 cells; and optimization of specific modifications of the RNAi agents.

Targets and Sequences.

As used herein, "target sequence" or "target gene" refer to a contiguous portion of the nucleotide sequence of an mRNA molecule formed during the transcription of a gene, e.g., a HSF1 gene, including mRNA that is a product of RNA processing of a primary transcription product. The target portion of the sequence will be at least long enough to serve as a substrate for iRNA-directed cleavage at or near that portion. For example, the target sequence will generally be from about 9-36 nucleotides ("nt") in length, e.g., about 15-30 nucleotides in length, including all sub-ranges therebetween. As non-limiting examples, the target sequence can be from about 15-30 nt, about 15-26 nt, about 15-23 nt, about 15-22 nt, about 15-21 nt, about 15-20 nt, about 15-19 nt, about 15-18 nt, about 15-17 nt, about 18-30 nt, about 18-26 nt, about 18-23 nt, about 18-22 nt, about 18-21 nt, about 18-20 nt, about 19-30 nt, about 19-26 nt, about 19-23 nt, about 19-22 nt, about 19-21 nt, about 19-20 nt, about 20-30 nt, about 20-26 nt, about 20-25 nt, about 20-24 nt, about 20-23 nt, about 20-22 nt, about 20-21 nt, about 21-30 nt, about 21-26 nt, about 21-25 nt, about 21-24 nt, about 21-23 nt, or about 21-22 nt.

As used herein, the term "strand comprising a sequence" refers to an oligonucleotide comprising a chain of nucleotides that is described by the sequence referred to using the standard nucleotide nomenclature.

As used herein, and unless otherwise indicated, the term "complementary" refers to the ability of an oligonucleotide or polynucleotide comprising a first nucleotide sequence to hybridize and form a duplex structure under certain conditions with an oligonucleotide or polynucleotide comprising a second nucleotide sequence. Such conditions can, for example, be stringent, e.g., 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides. The present disclosure contemplates any RNAi agent comprising a first and a second strand wherein the first and/or second strand are complementary to any sequence disclosed herein (e.g., the first and/or second strand are anti-parallel to and have or comprise a sequence of bases which hydrogen bind to the sequence of bases of any sequence disclosed herein). It is also noted that RNA sequences are complementary to any DNA sequence disclosed herein.

Complementary sequences within an iRNA, e.g., within a dsRNA as described herein, include base-pairing of the oligonucleotide or polynucleotide comprising a first nucleotide sequence to an oligonucleotide or polynucleotide comprising a second nucleotide sequence over the entire length of one or both sequences. Such sequences can be referred to as "fully complementary" with respect to each other herein. However, where a first sequence is referred to herein as "substantially complementary" with respect to a second sequence, the two sequences can be fully complementary, or they may form one or more, but generally not more than 5, 4, 2 or 2 mismatched base pairs upon hybridization for a duplex up to 30 base pairs, while retaining the ability to hybridize under the conditions most relevant to their ultimate application, e.g., inhibition of gene expression via a RISC pathway. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nt in length and another oligonucleotide 23 nt in length, wherein the longer oligonucleotide comprises a sequence of 21 nt that is fully complementary to the shorter oligonucleotide, may yet be referred to as "fully complementary" for the purposes herein.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled. Such non-Watson-Crick base pairs includes, but are not limited to, G:U Wobble or Hoogstein base pairing.

The terms "complementary," "fully complementary" and "substantially complementary" herein may be used with respect to the base matching between the sense strand and the antisense strand of a dsRNA, or between the antisense strand of an RNAi agent and a target sequence, as will be understood from the context of their use.

As used herein, a polynucleotide that is "substantially complementary to at least part of" a messenger RNA (mRNA) refers to a polynucleotide that is substantially complementary to a contiguous portion of the mRNA of interest (e.g., an mRNA encoding HSF1). For example, a polynucleotide is complementary to at least a part of a HSF1 mRNA if the sequence is substantially complementary to a non-interrupted portion of an mRNA encoding HSF1.

In various embodiments, one or both strands are nicked.

In one embodiment, the RNAi agent comprises a single strand (such as an shRNA, as described herein). In one embodiment, the RNAi agent comprises a single strand, the sequence of which comprises the sequences of both the sense and antisense strand (or first and second strand) of any RNAi agent disclosed herein.

In one embodiment, a single-stranded RNAi agent oligonucleotide or polynucleotide can comprise the sense and/or antisense strand. See, e.g., Sioud 2005 J. Mol. Biol. 348: 1079-1090, and references cited therein. Thus the present disclosure encompasses RNAi agents with a single strand comprising either the sense or antisense strand of a RNAi agent described herein.

siRNAs that are particularly useful for this disclosure include those which can bind specifically to a region of the HSF1 mRNA, and have one or more of the following qualities: binding in the coding segment of HSF1; binding at or near the junction of the 5' untranslated region and the start of the coding segment; binding at or near the translational start site of the mRNA; binding at, across or near junctions of exons and introns; little or no binding to the mRNAs or transcripts of other genes (little or no "off-target effects"); binding to the HSF1 mRNA in or near a region or regions that is not double-stranded or a stem region, e.g., in a loop or single-stranded portion; eliciting little or no immunogenicity; binding in a segment of the HSF1 mRNA sequence which is conserved among various animal species (including human, mouse, rat, cyno, etc.), as the presence of a conserved sequence facilitates testing using various laboratory animals; binding to double-stranded region(s) of the mRNA; binding to an AT-rich region (e.g., at least about 50, 51, 52, 53, 54, 55, 56, 57, 58, 59, or 60% AT-rich); and/or lacking particular sequences known or suspected to decrease siRNA activity, e.g., the presence of a GG sequence at the 5' end, which may decrease separation of the double-stranded portion of the siRNA. In one embodiment, the RNAi agent specific to HSF1 can be a double-stranded RNA having any one or more of these qualities.

Double-Stranded RNA.

The term "double-stranded RNA" or "dsRNA," as used herein, refers to an RNAi agent comprising a first and a second strand; e.g., a composition that includes an RNA molecule or complex of molecules having a hybridized duplex region that comprises two anti-parallel and substantially complementary nucleic acid strands, which will be referred to as having "sense" and "antisense" orientations with respect to a target RNA. The antisense strand, with respect to the mRNA target, is also called the "guide" strand, and the sense strand is also called the "passenger" strand. The passenger strand can include at least one or more of the following: one or more extra nucleotides (e.g., a bulge or 1 nt loop) compared to the other strand, a nick, a gap, etc., compared to the other strand. In various embodiments, the first strand is the sense strand and the second strand is the anti-sense strand. In other embodiments, the first strand is the anti-sense strand, and the second strand is the sense strand.

The duplex region can be of any length that permits specific degradation of a desired target RNA through a RISC pathway, but will typically range from 9 to 36 base pairs ("bp") in length, e.g., 15-30 base pairs in length. Considering a duplex between 9 and 36 base pairs, the duplex can be any length in this range, for example, 9, 10, 11, 12, 13, 14, 15, 16, 17, 18, 19, 20, 21, 22, 23, 24, 25, 26, 27, 28, 29, 30, 31, 32, 33, 34, 35, or 36 bp and any sub-range therebetween, including, but not limited to 15-30 base pairs, 15-26 bp, 15-23 bp, 15-22 bp, 15-21 bp, 15-20 bp, 15-19 bp, 15-18 bp, 15-17 bp, 18-30 bp, 18-26 bp, 18-23 bp, 18-22 bp, 18-21 bp, 18-20 bp, 19-30 bp, 19-26 bp, 19-23 bp, 19-22 bp, 19-21 bp, 19-20 bp, 19 bp, 20-30 bp, 20-26 bp, 20-25 bp, 20-24 bp, 20-23 bp, 20-22 bp, 20-21 bp, 20 bp, 21-30 bp, 21-26 bp, 21-25 bp, 21-24 bp, 21-23 bp, 21-22 bp, 21 bp, 22 bp, or 23 bp. The dsRNAs generated in the cell by processing with Dicer and similar enzymes are generally in the range of about 19 to about 22 base pairs in length (although artificial RNAi agents can be shorter or longer and/or blunt-ended or have modification(s), 5' and/or 3' endcap(s), and/or other variations). One strand of the duplex region of a dsRNA comprises a sequence that is substantially complementary to a region of a target RNA. The two strands forming the duplex structure can be from a single RNA molecule having at least one self-complementary duplex region, or can be formed from two or more separate RNA molecules that hybridize to form the duplex. Where the duplex region is formed from two self-complementary regions of a single molecule, the molecule can have a duplex region separated by a single stranded chain of nucleotides (herein referred to as a "hairpin loop", e.g., such as found in an shRNA construct) between the 3'-end of one strand and the 5'-end of the respective other strand forming the duplex structure. The hairpin loop can comprise at least one unpaired nucleotide; in some embodiments the hairpin loop can comprise at least 3, at least 4, at least 5, at least 6, at least 7, at least 8, at least 9, at least 10, at least 20, at least 23 or more unpaired nucleotides. Where the two substantially complementary strands of a dsRNA are comprised by separate RNA molecules, those molecules need not, but can be covalently connected. Where the two strands are connected covalently by a hairpin loop, the construct is generally referred to herein and in the art as a "shRNA". Where the two strands are connected covalently by means other than a hairpin loop, the connecting structure is referred to as a "linker." The term "siRNA" is also used herein to refer to a dsRNA as described above.

In one aspect, an RNA interference agent includes a single stranded RNA that interacts with a target RNA sequence to direct the cleavage of the target RNA. Without wishing to be bound by theory, the present disclosure contemplates that long double stranded RNA introduced into plants and invertebrate cells is broken down into siRNA by a Type III endonuclease known as Dicer (Sharp et al., Genes Dev. 2001, 15:485). Dicer, a ribonuclease-III-like enzyme, processes the dsRNA into 19-23 base pair short interfering RNAs with characteristic two base 3' overhangs (Bernstein, et al., (2001) Nature 409:363). The siRNAs are then incorporated into an RNA-induced silencing complex (RISC) where one or more helicases unwind the siRNA duplex, enabling the complementary antisense strand to guide target recognition (Nykanen, et al., (2001) Cell 107:309). Upon binding to the appropriate target mRNA, one or more endonucleases within the RISC cleaves the target to induce silencing (Elbashir, et al., (2001) Genes Dev. 15:188). Thus, in one aspect the disclosure relates to a single stranded RNA that promotes the formation of a RISC complex to effect silencing of the target gene.

Down-Regulation of HSF1.

As used herein, "down-regulates" refers to any statistically significant decrease in a biological activity and/or expression of HSF1, including full blocking of the activity (i.e., complete inhibition) and/or expression. For example, "down-regulation" can refer to a decrease of at least about 10, 20, 30, 40, 50, 60, 70, 80, 90 or 100% in HSF1 activity and/or expression.

As used herein, the term "inhibit" or "inhibiting" HSF1 refers to any statistically significant decrease in biological activity and/or expression of HSF1, including full blocking of the activity and/or expression. For example, "inhibition" can refer to a decrease of at least about 10, 20, 30, 40, 50, 60, 70, 80, 90 or 100% in HSF1 activity and/or expression. As used herein, the term "inhibit" similarly refers to a significant decrease in activity and/or expression, while referring to any other biological agent or composition.

By "level", it is meant that the HSF1 RNAi agent can interfere with the detectable level of HSF1, e.g., the level of HSF1 mRNA or the level of HSF1 protein.

By "activity," it is meant that the HSF1 RNAi agent can alter any known activity of HSF1, as described herein or as known in the literature.

By "heat shock" (HS) and "heat shock response" (HSR) is meant the biochemical response to environmental stress, such as elevated temperature. In the laboratory, experimental animals and cells can be maintained at a "non-shock" temperature (37° C. or lower) and heat shock can be induced at an elevated temperature (e.g., 40, 41, 42, 43, 44, or 45 degrees C. or higher). Experimentally, heat shock is typically induced at 42, 43 or 44 degrees C.

Heat shock is characterized by misfolding, denaturation and aggregation of various proteins; the induced heat shock proteins (HSP or HSPs) include chaperone proteins (chaperonins) and others which repair and/or remove these proteins. Genes induced during the heat shock response include, inter alia, HSP90, HSP70 and HSP27. The heat shock response can also be induced (or mimicked) by additional environmental conditions, such as oxidative stress, chemical stress, free radicals, ATP depletion, acidosis, heavy metals, alcohols, presence of antibiotics, inhibitors of energy metabolism, pathological conditions such as ischemia and reperfusion, inflammation, tissue damage, infection and mutant proteins associated with genetic diseases. Jolly et al. 2000 J. Natl. Cancer Inst. 92: 1564-1572; Dai et al. 2007 Cell 130: 1005-1018. The RNAi agents of the present disclosure thus down-regulate heat shock or the heat shock response.

The RNAi Agent to HSF1.

In one embodiment, the disclosure pertains to a HSF1 RNAi agent or other antisense nucleic acid complementary to a HSF1 gene (or portion thereof), or a recombinant expression vector encoding the antisense nucleic acid. As used herein, an "antisense" nucleic acid comprises a nucleotide sequence complementary to a "sense" nucleic acid encoding the HSF1 protein (e.g., complementary to the coding strand of a double-stranded DNA, complementary to an mRNA or complementary to the coding strand of a HSF1 gene).

The use of antisense nucleic acids to down-modulate the expression of a particular protein in a cell is well known in the art. An antisense nucleic acid comprises a sequence complementary to, and is capable of hydrogen binding to, the coding strand of another nucleic acid (e.g., an mRNA). Antisense sequences complementary to an mRNA can be complementary to the coding region, the 5' or 3' untranslated region of the mRNA, and/or a region bridging the coding and untranslated regions, and/or portions thereof. Furthermore, an antisense nucleic acid can be complementary to a regulatory region of the gene encoding the mRNA, for instance a transcription or translation initiation sequence or regulatory element. Preferably, an antisense nucleic acid can be complementary to a region preceding or spanning the initiation codon on the coding strand or in the 3' untranslated region of an mRNA.

Antisense nucleic acids can be designed according to the rules of Watson and Crick base pairing. The antisense nucleic acid molecule can be complementary to the entire coding region of HSF1 mRNA, but in at least one embodiment is an oligonucleotide which is antisense to only a portion of the coding or non-coding region of HSF1 mRNA. For example, the antisense oligonucleotide can be complementary to the region surrounding the translation start site of HSF1 mRNA. An antisense oligonucleotide can be, for example, about 5, about 10, about 15, about 16, about 17, about 18, about 19, about 20, about 21, about 22, about 23, about 24, about 25, about 30, about 35, about 40, about 45 or about 50 nt in length, or 5, 10, 15, 16, 17, 18, 19, 20, 21, 22, 23, 24, 25, 30, 35, 40, 45 or 50 nt in length.

siRNA may have modifications internally, or at one or both ends. Example modifications at the 5' end are illustrated in FIG. 1. These include: C6-alkyl (5'-hexylphosphate), 5'-Methyoxy; 5'-inverted dT (idT), and 5'-beta-L-uridine. The modifications at the ends can help stabilize the siRNA, protecting it from degradation by nucleases in the blood. The siRNAs may optionally be directed to regions of the HSF1 mRNA known or predicted to be near or at splice sites of the gene; e.g., exon-intron junctions. The siRNAs can also optionally be designed to anneal to known or predicted exposed and/or single-stranded regions of the mRNA (e.g., loops).

An antisense nucleic acid can be constructed using chemical synthesis and enzymatic ligation reactions using procedures known in the art. For example, an antisense nucleic acid (e.g., an antisense oligonucleotide) can be chemically synthesized using naturally-occurring nucleotides or variously modified nucleotides designed to decrease off-target effects, and/or increase the biological stability of the molecules or to increase the physical stability of the duplex formed between the antisense and sense nucleic acids. In at least one embodiment a modified sugar backbone, including a phosphorothioate linkage or its derivatives, and acridine substituted nucleotides can be used.

Each of "G," "C," "A," "T" and "U" generally stand for a nucleotide that contains guanine, cytosine, adenine, thymidine and uracil as a base, respectively. However, the term "ribonucleotide" or "nucleotide" can also refer to a modified nucleotide or a surrogate replacement moiety. The skilled person is well aware that guanine, cytosine, adenine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine may be replaced in the nucleotide sequences of dsRNA featured in the disclosure by a nucleotide containing, for example, inosine. In another example, adenine and cytosine anywhere in the oligonucleotide can be replaced with guanine and uracil, respectively to form G-U Wobble base pairing with the target mRNA. Sequences containing such replacement moieties are suitable for the compositions and methods featured in the disclosure.

Modifications.

The skilled artisan will recognize that the term "RNA molecule" or "ribonucleic acid molecule" encompasses not only RNA molecules as expressed or found in nature, but also analogs and derivatives of RNA comprising one or more ribonucleotide/ribonucleoside analogs or derivatives as described herein or as known in the art. Strictly speaking, a "ribonucleoside" includes a nucleoside base and a ribose sugar, and a "ribonucleotide" is a ribonucleoside with one, two or three phosphate moieties. However, the terms "ribonucleoside" and "ribonucleotide" can be considered to be equivalent as used herein. The RNA can be modified in the nucleobase structure or in the ribose-phosphate backbone structure, e.g., as described herein below. However, the molecules comprising ribonucleoside analogs or derivatives must retain the ability to form a duplex. As non-limiting examples, an RNA molecule can also include at least one modified ribonucleoside, including but not limited to a 2'-O-methyl modified nucleotide, a nucleoside comprising a 5' phosphorothioate linkage group, a terminal nucleoside linked to a cholesteryl derivative or dodecanoic acid bisdecylamide group, a locked nucleoside, an abasic nucleoside, a 2'-deoxy-2'-fluoro modified nucleoside, a 2'-aminomodified nucleoside, 2'-alkyl-modified nucleoside, morpholino nucleoside, an unlocked ribonucleotide (e.g., an acyclic nucleotide monomer, as described in WO 2008/147824), a phosphoramidate or a non-natural base comprising nucleoside, or any combination thereof. Alternatively, an RNA molecule can comprise at least two modified ribonucleosides, at least 3, at least 4, at least 5, at least 6, at least 7, at least 8, at least 9, at least 10, at least 15, at least 20 or more, up to the entire length of the dsRNA molecule. The modifications need not be the same for each of such a plurality of modified ribonucleosides in an RNA molecule. In one embodiment, modified RNAs contemplated for use in methods and compositions described herein are peptide nucleic acids (PNAs) that have the ability to form the required duplex structure and that permit or mediate the specific degradation of a target RNA via a RISC pathway.

Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

In one aspect, a modified ribonucleoside includes a deoxyribonucleoside. In such an instance, an RNAi agent can comprise one or more deoxynucleosides, including, for example, a deoxynucleoside overhang(s), or one or more deoxynucleosides within the double stranded portion of a dsRNA. A portion of the RNAi agent can be double-stranded DNA, while another portion is double-stranded RNA, forming a DNA-RNA chimera (See, for example, Yamato et al. 2011. Cancer Gene Ther. 18: 587-597). However, it is self-evident that under no circumstances is a double stranded DNA molecule encompassed by the term "iRNA."

Other modifications and/or other changes can be made to the RNAi agent. The antisense nucleic acid molecule can also comprise a 2'-o-methylribonucleotide (Inoue et al. 1987 Nucleic Acids Res. 15: 6131-6148) or a chimeric RNA-DNA analogue (Inoue et al. 1987 FEBS Lett. 215: 327-330).

In another embodiment, the RNAi agent has a single-stranded nick (e.g., a break or missing bond in the backbone). In various embodiments, a single-stranded nick can be in either the sense or anti-sense strand, or both.

This nick can be, for example, in the sense strand, producing a small internally segmented interfering RNA, or sisiRNA, which may have less off-target effects than the corresponding RNAi agent without a nick. See, for example, WO 2007/107162 to Wengels and Kjems.

The antisense nucleic acid or RNAi agent can also have an alternative backbone such as locked nucleic acids (LNA), Morpholinos, peptidic nucleic acids (PNA), threose nucleic acid (TNA), or glycol nucleic acid (GNA), or FANA and/or it can be labeled (e.g., radiolabeled or otherwise tagged). FANA are described in Dowler et al. 2006 Nucl. Acids Res. 34: 1669-1675.

One or both strands can comprise an alternative backbone.

Mismatches between the guide and passenger stand can also be introduced, though some positions may be better suited than others (See, for example, U.S. Patent App. No. 2009/0209626 to Khvorova). The passenger strand can also be shortened, to as short as 15 or 16 nt, while the guide strand remains 19 nt or longer (See, for example, Sun et al. 2008 Nature Biotech. 26: 1379-1382; and Chu and Rana 2008 RNA 14: 1714-1719). This can increase incorporation of the guide strand into the RNA-induced Silence Complex (RISC), and decrease incorporation of the passenger strand, than reducing off-target effects. In some cases, the passenger strand may be more amenable to modification (e.g., single-stranded nicking, nucleotide modifications, and shortening) than the guide strand. These and many other modifications can be made once a functional guide strand is identified.

Modified siRNAs or iRNA agents can be produced using any sequence provided herein with any one or more of these modifications (2' modifications, mismatches, nicks, RNA-DNA hybrid, LNA, PNA, GNA, TNA, or FANA, etc.), provided that the modifications are not mutually exclusive and produce a functional iRNA agent (e.g., an agent which mediates RNA interference activity against the target HSF1).

Replacing the 3'-terminal nucleotide overhanging segments of a 21-mer siRNA duplex having two-nucleotide 3'-overhangs with deoxyribonucleotides does not have an adverse effect on RNAi activity. Replacing up to four nucleotides on each end of the siRNA with deoxyribonucleotides has been well tolerated, whereas complete substitution with deoxyribonucleotides results in no RNAi activity. International PCT Publication No. WO 00/44914, and Beach et al. International PCT Publication No. WO 01/68836 preliminarily suggest that siRNA may include modifications to either the phosphate-sugar backbone or the nucleoside to include at least one of a nitrogen or sulfur heteroatom. Kreutzer et al. Canadian Patent Application No. 2,359,180, also describe certain chemical modifications for use in dsRNA constructs in order to counteract activation of double-stranded RNA-dependent protein kinase PKR, specifically 2'-amino or 2'-O-methyl nucleotides, and nucleotides containing a 2'-0 or 4'-C methylene bridge. Additional 3'-terminal nucleotide overhangs include dT (deoxythimidine), 2'-0,4'-C-ethylene thymidine (eT), and 2-hydroxyethyl phosphate (hp).

Parrish et al. (2000 Molecular Cell 6: 1077-1087) tested certain chemical modifications targeting the unc-22 gene in *C. elegans* using long (>25 nt) siRNA transcripts. The authors describe the introduction of thiophosphate residues into these siRNA transcripts by incorporating thiophosphate nucleotide analogs with T7 and T3 RNA polymerase and observed that RNAs with two phosphorothioate modified bases also had substantial decreases in effectiveness as RNAi. Further, Parrish et al. reported that phosphorothioate modification of more than two residues greatly destabilized the RNAs in vitro such that interference activities could not be assayed. Id. at 1081. The authors also tested certain modifications at the 2'-position of the nucleotide sugar in the long siRNA transcripts and found that substituting deoxynucleotides for ribonucleotides produced a substantial decrease in interference activity, especially in the case of Uridine to Thymidine and/or Cytidine to deoxy-Cytidine substitutions. Id. In addition, the authors tested certain base modifications, including substituting, in sense and antisense strands of the siRNA, 4-thiouracil, 5-bromouracil, 5-iodouracil, and 3-(aminoallyl)uracil for uracil, and inosine for guanosine. Whereas 4-thiouracil and 5-bromouracil substitution appeared to be tolerated, Parrish reported that inosine produced a substantial decrease in interference activity when incorporated in either strand. Parrish also reported that incorporation of 5-iodouracil and 3-(aminoallyl)uracil in the antisense strand resulted in a substantial decrease in RNAi activity as well.

Those skilled in the art will appreciate that it is possible to synthesize and modify the siRNA as desired, using any conventional method known in the art (see Henschel et al. 2004 DEQOR: a web-based tool for the design and quality control of siRNAs. Nucleic Acids Research 32 (Web Server Issue): W113-W120). Further, it will be apparent to those skilled in the art that there are a variety of regulatory sequences (for example, constitutive or inducible promoters, tissue-specific promoters or functional fragments thereof, etc.) which are useful for the antisense oligonucleotide, siRNA, or shRNA expression construct/vector.

There are several examples in the art describing sugar, base, phosphate and backbone modifications that can be introduced into nucleic acid molecules with significant enhancement in their nuclease stability and efficacy. For example, oligonucleotides are modified to enhance stability and/or enhance biological activity by modification with nuclease resistant groups, for example, 2'-amino, 2'-C-allyl, 2'-flouro, 2'-O-methyl, 2'-O-allyl, 2'-H, nucleotide base modifications (for a review see Usman and Cedergren 1992 TIBS. 17: 34; Usman et al. 1994 Nucleic Acids Symp. Ser. 31: 163; Burgin et al. 1996 Biochemistry 35: 14090). Sugar modifications of nucleic acids have been extensively described in the art.

Additional modifications and conjugations of RNAi agents have been described. Soutschek et al. 2004 Nature 432: 173-178 presented conjugation of cholesterol to the 3'-end of the sense strand of a siRNA molecule by means of a pyrrolidine linker, thereby generating a covalent and irreversible conjugate. Chemical modifications (including conjugation with other molecules) of siRNA may also be made to improve the in vivo pharmacokinetic retention time and efficiency.

In various embodiments, the RNAi agent to HSF1 comprises at least one 5'-uridine-adenine-3' (5'-ua-3') dinucleotide, wherein the uridine is a 2'-modified nucleotide; at least one 5'-uridine-guanine-3' (5'-ug-3') dinucleotide, wherein the 5'-uridine is a 2'-modified nucleotide; at least one 5'-cytidine-adenine-3' (5'-ca-3') dinucleotide, wherein the 5'-cytidine is a 2'-modified nucleotide; or at least one 5'-uridine-uridine-3' (5'-uu-3') dinucleotide, wherein the 5'-uridine is a 2'-modified nucleotide.

In various embodiments, the RNAi agent comprises a 2'-modification selected from the group consisting of: 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA).

In another embodiment, the RNAi comprises a gap or missing base. For example, the phosphate-sugar backbone may be present, but the base missing.

In another embodiment, the RNAi agent has a single-stranded nick (e.g., a break or missing bond in the backbone). This nick can be, for example, in the sense strand, producing a small internally segmented interfering RNA, or sisiRNA, which may have less off-target effects than the corresponding RNAi agent without a nick.

The antisense nucleic acid or RNAi agent can also have an alternative backbone (or comprise mostly RNA with a small number of individual nucleotide substitutions) such as: locked nucleic acids (LNA), Morpholinos, peptidic nucleic acids (PNA), threose nucleic acid (TNA), boranophosphate-RNA, 2'-deoxy-2'-fluoro-β-D-arabinonucleic acid (FANA), and/or glycol nucleic acid (GNA), and/or it can be labeled (e.g., radiolabeled or otherwise tagged). One or both strands can comprise an alternative backbone or have a small number (e.g., 1 to 10) of substitutions which are LNA, PNA, TNA, boranophosphate RNA, FANA, and/or GNA, etc.

In yet another embodiment, the antisense nucleic acid molecule employed by the methods of the present disclosure can include an α-anomeric nucleic acid molecule. An α-anomeric nucleic acid molecule forms specific double-stranded hybrids with complementary RNA in which, contrary to the usual β-units, the strands run parallel to each other. Gaultier et al. 1987 Nucleic Acids. Res. 15: 6625-6641. The antisense nucleic acid molecule can also comprise a 2'-o-methylribonucleotide (Inoue et al. 1987 Nucleic Acids Res. 15: 6131-6148) or a chimeric RNA-DNA analogue (Inoue et al. 1987 FEBS Lett. 215: 327-330).

Alternatively, gene expression can be inhibited by targeting nucleotide sequences complementary to the regulatory region of HSF1 (e.g., the promoter and/or enhancers) to form triple helical structures that prevent transcription of the HSF1 gene. See generally, Helene 1991 Anticancer Drug Des. 6(6): 569-84; Helene et al. 1992 Ann. N.Y. Acad. Sci. 660: 27-36; and Maher 1992, Bioassays 14(12): 807-15.

Alternatively, the antisense nucleic acid can be produced biologically using an expression vector into which a nucleic acid has been subcloned in an antisense orientation (i.e., RNA transcribed from the inserted nucleic acid will be in an antisense orientation to a target nucleic acid of interest).

The antisense nucleic acid molecules of the present disclosure are typically administered to a subject or generated in situ such that they hybridize with cellular mRNA and/or genomic DNA encoding HSF1, and inhibit expression by inhibiting transcription and/or translation. An example of a route of administration of antisense nucleic acid molecules includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using vectors well known in the art and described in, for example, US20070111230, the entire contents of which are incorporated herein. To achieve sufficient intracellular concentrations of the antisense molecules, vector constructs in which the antisense nucleic acid molecule is placed under the control of a strong pol II or pol III promoter can be used.

RNA Interference.

RNA interference (RNAi) is a post-transcriptional, targeted gene-silencing technique that uses double-stranded RNA (dsRNA) to degrade messenger RNA (mRNA) containing the same sequence as the dsRNA. The process of RNAi occurs when ribonuclease III (Dicer) cleaves the longer dsRNA into shorter fragments called siRNAs. siRNAs (small interfering RNAs) produced in this way are typically about 21 to 23 nucleotides long and comprise about 19 base pair duplexes (although effective artificial siRNAs can be significantly longer or shorter). The smaller RNA segments then mediate the degradation of the target mRNA. Dicer has also been implicated in the excision of 21- and 22-nucleotide small temporal RNAs (stRNAs) from precursor RNA of conserved structure that are implicated in translational control. Hutvagner et al. 2001, Science, 293, 834. The RNAi response also features an endonuclease complex, commonly referred to as an RNA-induced silencing complex (RISC), which mediates cleavage of single-stranded mRNA complementary to the antisense strand of the siRNA. Cleavage of the target RNA takes place in the middle of the region complementary to the antisense strand of the siRNA duplex.

In one aspect, an RNA interference agent includes a single-stranded RNA that interacts with a target RNA sequence to direct the cleavage of the target RNA. Without wishing to be bound by theory, the present disclosure contemplates that long double-stranded RNA introduced into plants and invertebrate cells is broken down into siRNA by a Type III endonuclease known as Dicer (Sharp et al., Genes Dev. 2001, 15: 485). Dicer, a ribonuclease-III-like enzyme, processes the dsRNA into 19-23 base pair short interfering RNAs with characteristic two base 3' overhangs (Bernstein, et al., (2001) Nature 409:363) (although artificial RNAi agents can be shorter and/or blunt-ended). The siRNAs are then incorporated into an RNA-induced silencing complex (RISC) where one or more helicases unwind the siRNA duplex, enabling one of the now unpaired siRNA strands to act as a "guide" strand to guide target recognition (Nykanen, et al., (2001) Cell 107:309). Upon binding of the antisense guide strand to the appropriate target mRNA, one or more endonucleases within the RISC cleaves the target to induce silencing (Elbashir, et al., (2001) Genes Dev. 15:188). Thus, in one aspect the present disclosure relates to a single-stranded RNA that promotes the formation of a RISC complex to effect silencing of the target gene.

RNA interference has also been studied in a variety of systems. Work in *Drosophila* embryonic lysates (Elbashir et al. 2001 EMBO J. 20: 6877 and Tuschl et al. International PCT Publication No. WO 01/75164) has revealed certain requirements for siRNA length, structure, chemical composition, and sequence that are essential to mediate efficient RNAi activity in a variety of systems, including especially mammals. These studies have shown that 21-nucleotide siRNA duplexes are particularly active when containing 3'-terminal dinucleotide overhangs, though other studies have shown that blunt-ended siRNAs can also be effective.

The dsRNA molecules (RNAi agents) described herein are thus useful in RNA interference of HSF1.

The present disclosure also encompasses RNAi agents comprising any sequence disclosed herein, e.g., as part of a longer sequence. For example, the disclosure encompasses longer RNAi agents comprising two strands, wherein the sequence of either or both of the strands comprises the sequence of a strand provided herein. Several studies have shown that longer strands can be effective in RNA interference, even though they are half a dozen nt or bp longer than a 19 nt RNAi agent, or even up to about 49, about 200, about 500, or even about 700 bp long or longer. See Elbashir et al. 2001 EMBO J. 23: 6877-6888; WO 00/44914; WO 01/36646; and WO 00/63364. Most importantly for therapeutic use, however, siRNA duplexes shorter than 50 bp or so are less likely to activate the interferon response in mammalian cells. See, e.g., Tuschl et al., WO 01/752164.

RNAi Agents to HSF1.

RNAi agents that are particularly useful for this disclosure include those which can bind specifically to a region of the HSF1 mRNA, and have one or more of the following qualities: binding in the coding segment of HSF1; binding at or near the junction of the 5' untranslated region and the start of the coding segment; binding at or near the translational start site of the snRNA; binding at or near junctions of exons and introns; little or no binding to the mRNAs of other genes (little or no "off-target effects"); binding to the HSF1 mRNA in or near a region or regions that is not double-stranded or a stem region, e.g., in a loop or single-stranded portion; eliciting little or no immunogenicity; binding in a segment of the HSF1 mRNA sequence which is conserved among various animal species (including human, mouse, rat, cynomolgus monkey, etc.), as the presence of a conserved sequence facilitates testing using various laboratory animals; binding to double-stranded region(s) of the mRNA; binding to an AT-rich region (e.g., at least about 50, 51, 52, 53, 54, 55, 56, 57, 58, 59, or 60% AT-rich); and lacking particular sequences known or suspected to decrease siRNA activity, e.g., the presence of a GG sequence at the 5' end, which may decrease separation of the double-stranded portion of the siRNA.

RNAi agents can be designed as HSF1 RNAi agents which bind to and assist in degradation of HSF1 mRNA. The anti-HSF1 RNAi agents can be designed to bind to the coding segment or non-coding segment (e.g., the 5' or 3' untranslated regions, or UTRs). Preferably, the RNAi agent binds to the coding segment of the mRNA. The RNAi agents can have double-stranded regions of, for example, about 17, 18, 19, 20, 21, 22, 23, or 24 bp. Preferably, the RNAi agent comprises about 19, 20 or 21 bp. The RNAi agents can be longer (e.g., up to 49 bp), as incorporated into a construct suitable for shortening by the Dicer complex. The RNAi can also be incorporated into a longer construct for expression prior to further shortening and processing.

RNAi Agents Lowering HSF1 Level, Expression and/or Activity.

RNAi agents for targeting HSF1 include those which bind to a HSF1 sequence provided herein and which work to reduce HSF1 through a RNAi mechanism. Example siRNAs to HSF1 are provided, e.g., in Tables A1, 1, 2, 3, 4, 5, 6, or 7.

The RNAi agents of the present disclosure silence, inhibit the expression of, down-regulate the expression of, and/or suppress the expression of the HSF1 gene, such that an approximately normal level of HSF1 activity, expression and/or level is achieved.

In addition, in various embodiments, depending on the disease condition and biological context, it is acceptable to use the RNAi agents of the present disclosure to establish a level of HSF1 expression, activity and/or level which is below the normal level, or above the normal level.

Features of a RNAi Agent: Sense Strand and Antisense Strand.

In various embodiments, the RNAi agents comprise a first strand and a second strand, e.g., a sense strand and an antisense strand and, optionally, one or both ends of the duplex containing unpaired nucleotides referred to herein as overhangs, and, optionally, 3' and/or 5' end caps.

The term "antisense strand" refers to the strand of a RNAi agent which includes a region that is substantially complementary to a target sequence. As used herein, the term "region of complementarity" refers to the region on the antisense strand that is substantially complementary to a sequence, for example a target sequence, as defined herein. Where the region of complementarity is not fully complementary to the target sequence, the mismatches may be in the internal or terminal regions of the molecule. Generally, the most tolerated mismatches are in the terminal regions, e.g., within 5, 4, 3, or 2 nucleotides of the 5' and/or 3' terminus.

The term "sense strand," as used herein, refers to the strand of a RNAi agent that includes a region that is substantially complementary to a region of the antisense strand as that term is defined herein.

The sequence of a gene may vary from individual to individual, especially at wobble positions within the coding segment, or in the untranslated region; individuals may also differ from each other in coding sequence, resulting in additional differences in mRNA. The sequence of the sense and antisense strands of the RNAi agent can thus be designed to correspond to that of an individual patient, if and where needed. RNAi agents can also be modified in sequence to reduce immunogenicity, binding to undesired mRNAs (e.g., "off-target effects") or to increase stability in the blood. These sequence variants are independent of chemical modification of the bases or 5' or 3' or other end-caps of the RNAi agents.

Overhangs, Blunt Ends and Caps.

The RNAi agents can also have 0, 1, or 2 overhangs; in the case of 0 overhangs, they are blunt-ended. A RNAi agent can have 0, 1 or 2 blunt ends. In a "blunt-ended RNAi agent" both strands terminate in a base-pair; thus a blunt-ended molecule lacks either 3' or 5' single-stranded nucleotide overhangs.

The terms "blunt" or "blunt-ended" as used herein in reference to a dsRNA mean that there are no unpaired nucleotides or nucleotide analogs at a given terminal end of a dsRNA, i.e., no nucleotide overhang. One or both ends of a dsRNA can be blunt. Where both ends of a dsRNA are blunt, the dsRNA is said to be blunt ended. To be clear, a "blunt ended" dsRNA is a dsRNA that is blunt at both ends, i.e., no nucleotide overhang at either end of the molecule. Most often such a molecule will be double-stranded over its entire length.

As used herein, the term "overhang" or "nucleotide overhang" refer to at least one unpaired nucleotide that protrudes from the end of at least one of the two strands of the duplex structure of a RNAi agent. For example, when a 3'-end of one strand of a dsRNA extends beyond the 5'-end of the other strand, or vice versa, the unpaired nucleotide(s) form the overhang. A dsRNA can comprise an overhang of at least one nucleotide; alternatively the overhang can comprise at least two nucleotides, at least three nucleotides, at least four nucleotides, at least five nucleotides or more. An overhang can comprise or consist of a nucleotide/nucleoside analog, including a deoxynucleotide/nucleoside. The overhang(s) may be on the sense strand, the antisense strand or any combination thereof. Furthermore, the nucleotide(s) of an overhang can be present on the 5' end, 3' end or both ends of either an antisense or sense strand of a dsRNA.

An example overhang is 3'-terminal dinucleotide such as dithymidine (TT), dTdT, sdTsdT, UU, etc. The 3'-terminal dinucleotide overhangs can be effective for increasing nuclease resistance, though they may not contribute to target recognition (Elbashir et al. 2001 Nature 411: 494-498). This is consistent with reports that the overhangs can be deleted in many cases, and can be replaced with a 3' endcap that increases nuclease resistance, WO 2005/021749 and WO 2007/128477. A suitable 3' endcap ideally performs at least two functions: (1) increasing stability, e.g., against nucleases, e.g., in blood serum or intestinal fluid; and (2) allowing RNA interference activity. Substitution of the 3'-terminal siRNA overhang nucleotides with 2'-deoxy nucleotides (2'-H) was also tolerated. In addition, a 5'-phosphate on the target-complementary strand of a siRNA duplex is usually required for siRNA activity.

The RNAi agent can thus optionally comprise a cap. The term "cap" and the like include a chemical moiety attached to the end of a double-stranded nucleotide duplex, but is used herein to exclude a chemical moiety that is a nucleotide or nucleoside. A "3' Cap" is attached at the 3' end of a nucleotide or oligonucleotide. A "5' Cap" is attached at the 5' end of a nucleotide or oligonucleotide. In one embodiment, 3' end caps are as disclosed in, for example, WO 2005/021749 and WO 2007/128477. A 3' and/or 5' end cap can be used in addition to an overhang or as a replacement to the overhang (e.g., on a blunt-end of a RNAi agent). In one embodiment, a blunt end of an RNAi duplex is chemically modified by the addition of a 3' cap, e.g., those described in WO 2005/021749 and WO 2007/128477. In such embodiments, the 3' caps are non-nucleotidic, and thus do not constitute an overhang.

The present disclosure thus contemplates a RNAi agent specific to HSF1 comprising an antisense strand (which may be contiguous or connected via a linker or loop) in a RNAi agent. In a more specific embodiment, an RNAi agent comprises an antisense strand and a sense strand which together comprise a double-stranded or complementary region. In one embodiment, it can also optionally comprise one or two overhangs and/or one or two caps.

Target and Complementary Sequences.

The RNAi agents of the present disclosure target (e.g., specifically bind to, anneal to, etc.) the mRNA encoding the gene HSF1. The use of the RNAi agent specific to HSF1 results in a decrease of HSF1 activity, level and/or expression, e.g., a "knock-down" or "knock-out" of the target gene or target sequence. Particularly in one embodiment, in the case of a disease state characterized by over-expression or hyper-activity of HSF1, administration of a RNAi agent to HSF1 knocks down the HSF1 gene enough to restore a normal level of HSF1 activity and/or a normal level of Na$^+$ reabsorption.

As used herein, "target sequence" or "target gene" refer to a contiguous portion of the nucleotide sequence of an mRNA molecule formed during the transcription of a gene, e.g., a HSF1 gene, including mRNA that is a product of RNA processing of a primary transcription product. The target portion of the sequence will be at least long enough to serve as a substrate for iRNA-directed cleavage at or near that portion. For example, the target sequence will generally be from 9-36 nucleotides ("nt") in length, e.g., 15-30 nt in length, including all sub-ranges therebetween. As non-limiting examples, the target sequence can be from 15-30 nt, 15-26 nt, 15-23 nt, 15-22 nt, 15-21 nt, 15-20 nt, 15-19 nt, 15-18 nt, 15-17 nt, 18-30 nt, 18-26 nt, 18-23 nt, 18-22 nt, 18-21 nt, 18-20 nt, 19-30 nt, 19-26 nt, 19-23 nt, 19-22 nt, 19-21 nt, 19-20 nt, 19 nt, 20-30 nt, 20-26 nt, 20-25 nt, 20-24 nt, 20-23 nt, 20-22 nt, 20-21 nt, 20 nt, 21-30 nt, 21-26 nt, 21-25 nt, 21-24 nt, 21-23 nt, or 21-22 nt, 21 nt, 22 nt, or 23 nt. The sense and antisense strands of the RNAi comprise a sequence complementary to that of the target nucleic acid, HSF1. In considering the "sequence" of a target, a strand or an RNAi agent, neither the end-caps nor modifications of the RNAi agent, as described herein, are considered a part of the sequence.

As used herein, and unless otherwise indicated, the term "complementary" refers to the ability of an oligonucleotide or polynucleotide comprising a first nucleotide sequence to hybridize and form a duplex structure under certain conditions with an oligonucleotide or polynucleotide comprising a second nucleotide sequence. Such conditions can, for example, be stringent, e.g., 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled. Such non-Watson-Crick base pairs includes, but are not limited to, G:U Wobble or Hoogstein base pairing.

The terms "complementary," "fully complementary" and "substantially complementary" herein may furthermore be used with respect to the base matching between the sense strand and the antisense strand of a dsRNA, or between the antisense strand of a RNAi agent and a target sequence, as will be understood from the context of their use.

As used herein, a polynucleotide that is "substantially complementary to at least part of" a messenger RNA (mRNA) refers to a polynucleotide that is substantially complementary to a contiguous portion of the mRNA of interest (e.g., an mRNA encoding HSF1). For example, a polynucleotide is complementary to at least a part of a HSF1 mRNA if the sequence is substantially complementary to a non-interrupted portion of an mRNA encoding HSF1.

Complementary sequences within a RNAi agent, e.g., within a dsRNA as described herein, include base-paired oligonucleotides or polynucleotides comprising a first nucleotide sequence to an oligonucleotide or polynucleotide comprising a second nucleotide sequence over the entire length of one or both nucleotide sequences. Such sequences can be referred to as "fully complementary" with respect to each other herein. However, where a first sequence is referred to as "substantially complementary" with respect to a second sequence herein, the two sequences can be fully complementary, or they may form one or more, but generally not more than 5, 4, 3 or 2 mismatched base pairs upon hybridization for a duplex up to 30 base pairs, while retaining the ability to hybridize under the conditions most relevant to their ultimate application, e.g., inhibition of gene expression via a RISC pathway. However, where two oligonucleotides are designed to form, upon hybridization, one or more single-stranded overhangs, such overhangs shall not be regarded as mismatches with regard to the determination of complementarity.

For example, a duplex comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes described herein. The term overhang describes an unpaired nucleotide at the 3' or 5' end of a double-stranded nucleotide duplex, as described above. In one embodiment, the overhang is 0 to 4 nt long and is on the 3' end.

Thus, the RNAi agent of the present disclosure is complimentary or substantially complimentary to a target sequence in the target HSF1 and is double-stranded, comprising a sense and an antisense strand (which can be contiguous, linked via a loop, or otherwise joined), where the double-stranded region an be 9 to 36 bp long (particularly for example, 19-22 bp or 19-23 bp long), and can furthermore optionally comprise a 3' or 5' overhang, and the RNAi agent can furthermore comprise a 3' cap. The RNAi agent mediates RNA interference, down-regulating or inhibiting the level, expression and/or activity of HSF1, and/or establishing or re-establishing an approximately normal level of HSF1 and/or HSF1 activity, or other biological function related to HSF1.

Types of RNAi Agents and Modification Thereof.

The use of RNAi agents or compositions comprising an antisense nucleic acid to down-modulate the expression of a particular protein in a cell is well known in the art. A RNAi agent comprises a sequence complementary to, and is capable of hydrogen binding to, the coding strand of another nucleic acid (e.g., an mRNA). Thus, in various embodiments, the RNAi agents of the present disclosure encompass any RNAi agents which target (e.g., are complementary, capable of hydrogen binding to, etc.) any sequence presented, e.g., in Tables A1, 1, 2, 3, 4, 5, 6, or 7.

Antisense sequences complementary to an mRNA can be complementary to the coding region, the 5' or 3' untranslated region of the mRNA, and/or a region bridging the coding and untranslated regions, and/or portions thereof. Furthermore, a RNAi agent or a portion thereof can be complementary to a regulatory region of the gene encoding the mRNA, for instance a transcription or translation initiation sequence or regulatory element. Particularly, a RNAi agent or a portion thereof can be complementary to a region preceding or spanning the initiation codon on the coding strand or in the 3' untranslated region of an mRNA.

RNAi agent molecules can be designed according to the rules of Watson and Crick base pairing. The RNAi agent can be complementary to the entire coding region of HSF1 mRNA, but more particularly is an oligonucleotide which is antisense to only a portion of the coding or non-coding region of HSF1 mRNA. For example, the antisense oligonucleotide can be complementary to the region surrounding the translation start site of HSF1 mRNA. An antisense oligonucleotide can be, for example, about 5, 10, 15, 19, 20, 21, 22, 23, 24, 25, 30, 35, 40, 45 or 50 nucleotides in length.

The RNAi agent may have modifications internally, or at one or both ends. The modifications at the ends can help stabilize the RNAi agent, protecting it from degradation by nucleases in the blood. The RNAi agents may optionally be directed to regions of the HSF1 mRNA known or predicted to be near or at splice sites of the gene; e.g., exon-intron junctions (as described in, for example, Saxena et al. 1998).

The RNAi agents can also optionally be designed to anneal to known or predicted exposed and/or single-stranded regions of the mRNA (e.g., loops).

A RNAi agent can be constructed using chemical synthesis and enzymatic ligation reactions using procedures known in the art. For example, RNAi agent can be chemically synthesized using naturally-occurring nucleotides or variously modified nucleotides designed to decrease off-target effects, and/or increase the biological stability of the molecules or to increase the physical stability of the duplex formed between the antisense and sense nucleic acids, e.g., phosphorothioate derivatives and acridine substituted nucleotides can be used.

"G," "C," "A," "T" and "U" each generally stand for a nucleotide that contains guanine, cytosine, adenine, thymidine and uracil as a base, respectively. However, the term "ribonucleotide" or "nucleotide" can also refer to a modified nucleotide or a surrogate replacement moiety. The skilled person is well aware that guanine, cytosine, adenine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine may be replaced in the nucleotide sequences of dsRNA featured in the present disclosure by a nucleotide containing, for example, inosine. In another example, adenine and cytosine anywhere in the oligonucleotide can be replaced with guanine and uracil, respectively to form G-U Wobble base pairing with the target mRNA. Sequences containing such replacement moieties are suitable for the compositions and methods featured in the present disclosure.

The skilled artisan will recognize that the term "RNA molecule" or "ribonucleic acid molecule" encompasses not only RNA molecules as expressed or found in nature (i.e., are naturally occurring), but also non-naturally occurring analogs and derivatives of RNA comprising one or more ribonucleotide/ribonucleoside analogs or derivatives as described herein or as known in the art. Strictly speaking, a "ribonucleoside" includes a nucleoside base and a ribose sugar, and a "ribonucleotide" is a ribonucleoside with one, two or three phosphate moieties. However, the terms "ribonucleoside" and "ribonucleotide" can be considered to be equivalent as used herein. The RNA can be modified in the nucleobase structure or in the ribose-phosphate backbone structure, e.g., as described herein below. However, the molecules comprising ribonucleoside analogs or derivatives must retain the ability to form a duplex. As non-limiting examples, an RNA molecule can also include at least one modified ribonucleoside, including but not limited to a 2'-O-methyl modified nucleotide, a nucleoside comprising a 5' phosphorothioate group, a terminal nucleoside linked to a cholesteryl derivative or dodecanoic acid bisdecylamide group, a locked nucleoside, an abasic nucleoside, a 2'-deoxy-2'-fluoro modified nucleoside, a 2'-amino-modified nucleoside, 2'-alkyl-modified nucleoside, morpholino nucleoside, an unlocked ribonucleotide (e.g., an acyclic nucleotide monomer, as described in WO 2008/147824), a phosphoramidate or a non-natural base comprising nucleoside, or any combination thereof. Alternatively, an RNA molecule can comprise at least two modified ribonucleosides, at least 3, at least 4, at least 5, at least 6, at least 7, at least 8, at least 9, at least 10, at least 15, at least 20 or more, up to the entire length of the dsRNA molecule. The modifications need not be the same for each of such a plurality of modified ribonucleosides in an RNA molecule. In one embodiment, modified RNAs contemplated for use in methods and compositions described herein are peptide nucleic acids (PNAs) that have the ability to form the required duplex structure and that permit or mediate the specific degradation of a target RNA via a RISC pathway.

Examples of modified nucleotides which can be used to generate the RNAi agent include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

In one embodiment, the present disclosure encompasses modified any modified variant of any RNAi agent disclosed herein. The modified variant contains the same sequence, but can be modified to contain modifications in the phosphate, sugar, base, nucleotide, etc. For example, the modified variant can contain one or more of the modified nucleotides listed herein, for example a C replaced by a 2'-modified C.

In one aspect, a modified ribonucleoside includes a deoxyribonucleoside. In such an instance, a RNAi agent can comprise one or more deoxynucleosides, including, for example, a deoxynucleoside overhang(s), or one or more deoxynucleosides within the double-stranded portion of a dsRNA. However, it is self-evident that under no circumstances is a double-stranded DNA molecule encompassed by the term "RNAi agent."

Replacing the 3'-terminal nucleotide overhanging segments of a 21-mer siRNA duplex having two-nucleotide 3'-overhangs with deoxyribonucleotides does not have an adverse effect on RNAi activity. Replacing up to four nucleotides on each end of the siRNA with deoxyribonucleotides has been well tolerated, whereas complete substitution with deoxyribonucleotides results in no RNAi activity. International PCT Publication No. WO 00/44914, and Beach et al. International PCT Publication No. WO 01/68836 preliminarily suggest that siRNA may include modifications to either the phosphate-sugar backbone or the nucleoside to include at least one of a nitrogen or sulfur heteroatom. Kreutzer et al. Canadian Patent Application No. 2,359,180, also describe certain chemical modifications for use in dsRNA constructs in order to counteract activation of double-stranded RNA-dependent protein kinase PKR, specifically 2'-amino or 2'-O-methyl nucleotides, and nucleotides containing a 2'-0 or 4'-C methylene bridge. Additional 3'-terminal nucleotide overhangs include dT (deoxythimidine), 2'-0,4'-C-ethylene thymidine (eT), and 2-hydroxyethyl phosphate (hp).

Parrish et al. 2000 Molecular Cell 6: 1077-1087 tested certain chemical modifications targeting the unc-22 gene in C. elegans using long (>25 nt) siRNA transcripts. The authors describe the introduction of thiophosphate residues into these siRNA transcripts by incorporating thiophosphate nucleotide analogs with T7 and T3 RNA polymerase and observed that RNAs with two phosphorothioate modified bases also had substantial decreases in effectiveness as RNAi. Further, Parrish et al. reported that phosphorothioate modification of more than two residues greatly destabilized the RNAs in vitro such that interference activities could not be assayed. Id. at 1081. The authors also tested certain modifications at the 2'-position of the nucleotide sugar in the long siRNA transcripts and found that substituting deoxynucleotides for ribonucleotides produced a substantial decrease in interference activity, especially in the case of Uridine to Thymidine and/or Cytidine to deoxy-Cytidine substitutions. Id. In addition, the authors tested certain base modifications, including substituting, in sense and antisense strands of the siRNA, 4-thiouracil, 5-bromouracil, 5-iodouracil, and 3-(aminoallyl) uracil for uracil, and inosine for guanosine. Whereas 4-thiouracil and 5-bromouracil substitution appeared to be tolerated, Parrish reported that inosine produced a substantial decrease in interference activity when incorporated in either strand. Parrish also reported that incorporation of 5-iodouracil and 3-(aminoallyl)uracil in the antisense strand resulted in a substantial decrease in RNAi activity as well.

Those skilled in the art will appreciate that it is possible to synthesize and modify the siRNA as desired, using any conventional method known in the art (see Henschel et al. 2004 DEQOR: a web-based tool for the design and quality control of siRNAs. Nucleic Acids Research 32 (Web Server Issue): W113-W120). Further, it will be apparent to those skilled in the art that there are a variety of regulatory sequences (for example, constitutive or inducible promoters, tissue-specific promoters or functional fragments thereof, etc.) which are useful for the antisense oligonucleotide, siRNA, or shRNA expression construct/vector.

There are several examples in the art describing sugar, base, phosphate and backbone modifications that can be introduced into nucleic acid molecules with significant enhancement in their nuclease stability and efficacy. For example, oligonucleotides are modified to enhance stability and/or enhance biological activity by modification with nuclease resistant groups, for example, 2'-amino, 2'-C-allyl, 2'-flouro, 2'-O-methyl, 2'-O-allyl, 2'-H, nucleotide base modifications (for a review see Usman and Cedergren 1992 TIBS. 17: 34; Usman et al. 1994 Nucleic Acids Symp. Ser. 31: 163; Burgin et al. 1996 Biochemistry 35: 14090). Sugar modification of nucleic acid molecules are extensively described in the art.

Additional modifications and conjugations of RNAi agents have been described. Soutschek et al. 2004 Nature 432: 173-178 presented conjugation of cholesterol to the 3'-end of the sense strand of a siRNA molecule by means of a pyrrolidine linker, thereby generating a covalent and irreversible conjugate. Chemical modifications (including conjugation with other molecules) of RNAi agents may also be made to improve the in vivo pharmacokinetic retention time and efficiency.

In various embodiments, the RNAi agent to HSF1 is ligated to one or more diagnostic compound, reporter group, cross-linking agent, nuclease-resistance conferring moiety, natural or unusual nucleobase, lipophilic molecule, cholesterol, lipid, lectin, steroid, uvaol, hecigenin, diosgenin, terpene, triterpene, sarsasapogenin, Friedelin, epifriedelanol-derivatized lithocholic acid, vitamin, carbohydrate, dextran, pullulan, chitin, chitosan, synthetic carbohydrate, oligo lactate 15-mer, natural polymer, low- or medium-molecular weight polymer, inulin, cyclodextrin, hyaluronic acid, protein, protein-binding agent, integrin-targeting molecule, polycationic, peptide, polyamine, peptide mimic, and/or transferrin.

Various modifications of the RNAi agent can be produced. In various embodiments, the RNAi agent to HSF1 comprises at least one 5'-uridine-adenine-3' (5'-ua-3') dinucleotide, wherein the uridine is a 2'-modified nucleotide; at least one 5'-uridine-guanine-3' (5'-ug-3') dinucleotide, wherein the 5'-uridine is a 2'-modified nucleotide; at least one 5'-cytidine-adenine-3' (5'-ca-3') dinucleotide, wherein the 5'-cytidine is a 2'-modified nucleotide; and/or at least one 5'-uridine-uridine-3' (5'-uu-3') dinucleotide, wherein the 5'-uridine is a 2'-modified nucleotide.

In various embodiments, the RNAi agent comprises a 2'-modification selected from the group consisting of: 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA).

In another embodiment, the RNAi comprises a gap or missing base. For example, the phosphate-sugar backbone may be present, but the base missing.

In another embodiment, the RNAi agent has a single-stranded nick (e.g., a break or missing bond in the backbone). In various embodiments, a single-stranded nick can be in either the sense or anti-sense strand, or both.

This nick can be, for example, in the sense strand, producing a small internally segmented interfering RNA, or sisiRNA, which may have less off-target effects than the corresponding RNAi agent without a nick.

The antisense nucleic acid or RNAi agent can also have an alternative backbone (or comprise mostly RNA with a small number of individual nucleotide substitutions) such as: locked nucleic acids (LNA), Morpholinos, peptidic nucleic acids (PNA), threose nucleic acid (TNA), boranophosphate-RNA, 2'-deoxy-2'-fluoro-β-D-arabinonucleic acid (FANA), and/or glycol nucleic acid (GNA), and/or it can be labeled (e.g., radiolabeled or otherwise tagged).

One or both strands can comprise an alternative backbone.

In yet another embodiment, the RNAi agent employed by the methods of the present disclosure can include an α-anomeric nucleic acid molecule. An α-anomeric nucleic acid molecule forms specific double-stranded hybrids with complementary RNA in which, contrary to the usual β-units, the strands run parallel to each other. Gaultier et al. 1987 Nucleic Acids. Res. 15: 6625-6641.

The antisense nucleic acid molecule can also comprise a 2'-o-methylribonucleotide (Inoue et al. 1987 Nucleic Acids Res. 15: 6131-6148) or a chimeric RNA-DNA analogue (Inoue et al. 1987 FEBS Lett. 215: 327-330).

Alternatively, gene expression can be inhibited by targeting nucleotide sequences complementary to the regulatory region of HSF1 (e.g., the promoter and/or enhancers) to form triple helical structures that prevent transcription of the HSF1 gene.

Production of RNAi Agents.

The RNAi agent can be produced biologically using an expression vector into which a nucleic acid has been subcloned in an antisense orientation (i.e., RNA transcribed from the inserted nucleic acid will be in an antisense orientation to a target nucleic acid of interest). The RNAi agent can also be produced biologically using an expression vector into which a nucleic acid has been subcloned as an shRNA construct (i.e., RNA transcribed from the inserted nucleic acid will have a first region in an antisense orientation to a target nucleic acid of interest, a second region that comprises a loop or hinge, and a third region in a sense orientation to the target nucleic acid of interest, wherein the first and third regions of the transcript preferably hybridizes with itself, thereby forming a stem-and-loop structure).

Methods of producing RNAi agents are well-known in the art and available to persons of ordinary skill in the art.

Kits for synthesis of RNAi are commercially available from, e.g., New England Biolabs and Ambion.

Delivery Vehicles for RNAi Agents.

RNAi agents of the present disclosure can be delivered or introduced (e.g., to a cell in vitro, to a test animal, or to a human) by any means known in the art.

The RNAi agents of the present disclosure are typically administered to a subject or generated in situ such that they can hybridize with cellular mRNA and/or genomic DNA encoding HSF1, and inhibit expression by inhibiting transcription and/or translation. An example of a route of administration of the RNAi agent includes direct injection at a tissue site. Alternatively, RNAi agents can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using vectors well known in the art and described in, for example, US20070111230, the entire contents of which are incorporated herein. To achieve sufficient intracellular concentrations of the antisense molecules, vector constructs in which the antisense nucleic acid molecule is placed under the control of a strong pol II or pol III promoter are preferred.

"Introducing into a cell," when referring to a RNAi agent, means facilitating or effecting uptake or absorption into the cell, as is understood by those skilled in the art. Absorption or uptake of a RNAi agent can occur through unaided diffusive or active cellular processes, or by auxiliary agents or devices. The meaning of this term is not limited to cells in vitro; a RNAi agent may also be "introduced into a cell," wherein the cell is part of a living organism. In such an instance, introduction into the cell will include the delivery to the organism. For example, for in vivo delivery, a RNAi agent can be injected into a tissue site or administered systemically. In vivo delivery can also be by a beta-glucan delivery system, such as those described in U.S. Pat. Nos. 5,032,401 and 5,607,677, and U.S. Publication No. 2005/0281781. In vitro introduction into a cell includes methods known in the art such as electroporation and lipofection. Further approaches are described herein or known in the art.

Delivery of RNAi agent to tissue is a problem both because the material must reach the target organ and must also enter the cytoplasm of target cells. RNA cannot penetrate cellular membranes, so systemic delivery of naked RNAi agent is unlikely to be successful. RNA is degraded by RNAse activity in serum (although the use of particular 3' end caps on siRNAs may reduce or limit this degradation; see, for example, WO 2005/021749 and WO 2007/128477). For these reasons, other mechanisms to deliver RNAi agent to target cells has been devised. Methods known in the art include but are not limited to: viral delivery (retrovirus, adenovirus, lentivirus, baculovirus, AAV); liposomes (Lipofectamine, cationic DOTAP, neutral DOPC) or nanoparticles (cationic polymer, PEI), bacterial delivery (tkRNAi), and also chemical modification (LNA) of siRNA to improve stability. Xia et al. 2002 Nat. Biotechnol. 20 and Devroe et al. 2002. BMC Biotechnol. 2 1: 15, disclose incorporation of siRNA into a viral vector. Porphysomes can also be used to deliver RNAi agents. Lovell et al. 2001 Nature Mater. 10: 324-32; and WO 2011/044671. Other systems for delivery of RNAi agents are contemplated and the RNAi agents of the present disclosure can be delivered by various methods yet to be found and/or approved by the FDA or other regulatory authorities.

RNAi agents of the present disclosure can delivered in a suitable pharmaceutical composition. Several of these are described in greater detail, below.

Pharmaceutical Compositions of RNAi Agents.

As used here, a "pharmaceutical composition" comprises a pharmaceutically effective amount of one or more HSF1 RNAi agent, a pharmaceutically acceptable carrier, and, optionally, an additional disease treatment which works synergistically with the RNAi agent. As used herein, "pharmacologically effective amount," "therapeutically effective amount" or simply "effective amount" refers to that amount of a RNAi agent effective to produce the intended pharmacological, therapeutic or preventive result. For example, if a given clinical treatment is considered effective where there is at least a 10% reduction in a measurable parameter associated with a disease or disorder, a therapeutically effective amount of a drug for the treatment of that disease or disorder is the amount necessary to effect at least a 10% reduction in that parameter. In this embodiment, a therapeutically effective amount of a RNAi agent targeting HSF1 can reduce HSF1 protein levels by at least 10%. In additional embodiments, a given clinical treatment is considered effective where there is at least a 15, 20, 25, 30, 35, 40, 45, 50, 55, 60, 65, 70, 75, 80, 85, 90 or 95% reduction in a measurable parameter associated with a disease or disorder, and the therapeutically effective amount of a drug for the treatment of that disease or disorder is the amount necessary to effect at least a 15, 20, 25, 30, 35, 40, 45, 50, 55, 60, 65, 70, 75, 80, 85, 90 or 95% reduction, respectively, in that parameter.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract. Agents included in drug formulations are described further herein.

The pharmaceutical compositions comprising a HSF1 RNAi agent can be in solid form, for example, powders, granules, tablets, pills, gelcaps, gelatin capsules, liposomes, suppositories, chewable forms, or patches. The pharmaceutical compositions comprising a HSF1 RNAi agent can also be presented in liquid form, for example, solutions, emulsions, suspensions, elixirs, or syrups. Appropriate liquid supports can be, for example, water, organic solvents such as polyol, such as glycerol or glycols, including propylene glycol and polyethylene glycol, or ethanol, Cremophor EL, or mixtures thereof, in varying proportions, in water. The compositions can comprise nano-sized amorphous or crystalline granules coated with albumin or a surfactant.

Appropriate supports can include, for example, antibacterial and antifungal agents, buffering agents, calcium phosphate, cellulose, methyl cellulose, chlorobutanol, cocoa butter, colorings, dextrin, emulsifiers, enteric coatings, flavorings, gelatin, isotonic agents, lecithin, magnesium stearate, perfuming agents, polyalcohols such as mannitol, injectable organic esters such as ethyl oleate, paraben, phenol sorbic acid, polyethylene glycol, polyvinylpyrrolidine, phosphate buffered saline (PBS), preserving agents, propylene glycol, sodium carboxymethylcellulose, sodium chloride, sorbitol, various sugars (including, but not limited to, sucrose, fructose, galactose, lactose and trehalose), starch, suppository wax, talc, vegetable oils, such as olive oil and corn oil, vitamins, wax, and/or wetting agents. For HSF1 RNAi agents, a preferred support comprises dextran and water, e.g. 5% dextrose in water (D5W).

The biologically inert portion of the pharmaceutical composition can optionally be erodible, allowing timed release of the RNAi agent.

The pharmaceutical composition can comprise additional components which aid in delivery, stability, efficacy, or reduction of immunogenicity.

Additional Components of a Pharmaceutical Composition Comprising a RNAi Agent to HSF1.

Additional components of a pharmaceutical composition comprising a RNAi Agent to HSF1 can be added to aid in delivery, stability, efficacy, or reduction of immunogenicity.

Liposomes have been used previously for drug delivery (e.g., delivery of a chemotherapeutic). Liposomes (e.g., cationic liposomes) are described in PCT publications WO02/100435A1, WO03/015757A1, and WO04029213A2; U.S. Pat. Nos. 5,962,016; 5,030,453; and 6,680,068; and U.S. Patent Application 2004/0208921. A process of making liposomes is also described in WO04/002453A1. Furthermore, neutral lipids have been incorporated into cationic liposomes (e.g., Farhood et al. 1995).

Cationic liposomes have been used to deliver RNAi agent to various cell types (Sioud and Sorensen 2003; U.S. Patent Application 2004/0204377; Duxbury et al., 2004; Donze and Picard, 2002).

Use of neutral liposomes disclosed in Miller et al. 1998, and U.S. Patent Application 2003/0012812.

As used herein, the term "SNALP" refers to a stable nucleic acid-lipid particle. A SNALP represents a vesicle of lipids coating a reduced aqueous interior comprising a nucleic acid such as an iRNA or a plasmid from which an iRNA is transcribed. SNALPs are described, e.g., in U.S. Patent Application Publication Nos. 20060240093, 20070135372, and in International Application No. WO 2009082817.

Chemical transfection using lipid-based, amine-based and polymer-based techniques, is disclosed in products from Ambion Inc., Austin, Tex.; and Novagen, EMD Biosciences, Inc, an Affiliate of Merck KGaA, Darmstadt, Germany); Ovcharenko D (2003) "Efficient delivery of siRNAs to human primary cells." Ambion TechNotes 10 (5): 15-16). Additionally, Song et al. (Nat Med. published online (Fete 10, 2003) doi: 10.1038/nm828) and others [Caplen et al. 2001 Proc. Natl. Acad. Sci. (USA), 98: 9742-9747; and McCaffrey et al. Nature 414: 34-39] disclose that liver cells can be efficiently transfected by injection of the siRNA into a mammal's circulatory system.

A variety of molecules have been used for cell-specific RNAi agent delivery. For example, the nucleic acid-condensing property of protamine has been combined with specific antibodies to deliver siRNAs. Song et al. 2005 Nat Biotech. 23: 709-717. The self-assembly PEGylated polycation polyethylenimine (PEI) has also been used to condense and protect siRNAs. Schiffelers et al. 2004 Nucl. Acids Res. 32: e149, 141-110.

The siRNA-containing nanoparticles were then successfully delivered to integrin-overexpressing tumor neovasculature. Hu-Lieskovan et al. 2005 Cancer Res. 65: 8984-8992.

The RNAi agents of the present disclosure can be delivered via, for example, Lipid nanoparticles (LNP); neutral liposomes (NL); polymer nanoparticles; double-stranded RNA binding motifs (dsRBMs); or via modification of the RNAi agent (e.g., covalent attachment to the dsRNA).

Lipid nanoparticles (LNP) are self-assembling cationic lipid based systems. These can comprise, for example, a neutral lipid (the liposome base); a cationic lipid (for siRNA loading); cholesterol (for stabilizing the liposomes); and PEG-lipid (for stabilizing the formulation, charge shielding and extended circulation in the bloodstream).

The cationic lipid can comprise, for example, a headgroup, a linker, a tail and a cholesterol tail. The LNP can have, for example, good tumor delivery, extended circulation in the blood, small particles (e.g., less than 100 nm), and stability in the tumor microenvironment (which has low pH and is hypoxic).

Neutral Liposomes (NL) are Non-Cationic Lipid Based Particles.

Polymer nanoparticles are self-assembling polymer-based particles.

Double-stranded RNA binding motifs (dsRBMs) are self-assembling RNA binding proteins, which will need modifications.

The RNAi agents of the present disclosure can be prepared in a pharmaceutical composition comprising various components appropriate for the particular method of administration of the RNAi agent.

Any of the pharmaceutically acceptable carriers or pharmaceutical compositions described herein can be used with an iRNA agent of any sequence described herein. These carriers and compositions can also be used with an iRNA agent having any modification, 3' end cap, 5' end cap, or other alteration described herein. For example, any liposome described herein can be used in combination with an iRNA agent of any sequence described herein.

Administration of a RNAi Agent.

The pharmaceutical composition comprising a HSF1 can be administered by buccal, inhalation (including insufflation and deep inhalation), nasal, oral, parenteral, implant, injection or infusion via epidural, intra-arterial, intra-articular, intra-capsular, intra-cardiac, intra-cerebroventricular, intracranial, intradermal, intramuscular, intra-orbital, ocular, intra-peritoneal, intra-spinal, intrasternal, intrathecal, intravenous, subarachnoid, sub-capsular, subcutaneous, sub-cuticular, transendothelial, transtracheal, transvascular, rectal, sublingual, topical, and/or vaginal routes. This may be by injection, infusion, dermal patch, or any other method known in the art. The formulation can be powdered, nebulized, aerosolized, granulized or otherwise appropriately prepared for delivery. The administration, if liquid, may be slow or via bolus, though, under some circumstances known in the art, bolus injections may lead to loss of material through the kidneys.

The pharmaceutical compositions comprising a HSF1 RNAi agent can be administered with medical devices known in the art. For example, in a particular embodiment, a RNAi agent can be administered with a needle-less hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the present disclosure include: U.S. Pat. No. 4,487,603, which discloses an implantable micro-infusion pump for dispensing medication at a controlled rate; U.S. Pat. No. 4,486,194, which discloses a therapeutic device for administering medications through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

In certain embodiments, the pharmaceutical compositions comprising a RNAi agent can be formulated to ensure proper distribution in vivo. Administration of a RNAi agent to HSF1 can be systemic (whole-body) or, particularly, targeted to tissues or organs that express (or over-express or demonstrate a hyper-activity of) HSF1. Methods for targeting these particular tissues or organs are described herein, and/or are known in the art. For example, they can be formulated in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) J. Clin. Pharmacol. 29: 685).

Example targeting moieties include folate or biotin (see, e.g., U.S. Pat. No. 5,416,016 to Low et al.); mannosides (Umezawa et al., (1988) Biochem. Biophys. Res. Commun. 153: 1038); antibodies (P. G. Bloeman et al. (1995) FEBS Lett. 357: 140; M. Owais et al. (1995) Antimicrob. Agents Chemother. 39: 180); surfactant protein A receptor (Briscoe et al. (1995) Am. J. Physiol. 1233: 134), different species of which may comprise the formulations of the present disclosures, as well as components of the invented molecules; p120 (Schreier et al. (1994) J. Biol. Chem. 269: 9090); see also K. Keinanen; M. L. Laukkanen (1994) FEBS Lett. 346: 123; J. J. Killion; I. J. Fidler (1994) Immunomethods 4: 273.

The present disclosure thus encompasses pharmaceutical compositions comprising one or more RNAi agents to HSF1, which can optionally comprise various modifications and/or additional components, for use in treatment of HSF1-related diseases.

Measuring the Effect of an RNAi Agent on HSF1 Activity, Level and/or Expression

Any method known in the art can be use to measure changes in HSF1 activity, level and/or expression induced by a HSF1siRNA. Measurements can be performed at multiple timepoints, prior to, during and after administration of the siRNA, to determine the effect of the siRNA.

The terms "silence," "inhibit the expression of," "down-regulate the expression of," "suppress the expression of," and the like, in so far as they refer to a HSF1 gene, herein refer to the at least partial suppression of the expression of a HSF1 gene, as manifested by a reduction of the amount of HSF1 mRNA which may be isolated from or detected in a first cell or group of cells in which a HSF1 gene is transcribed and which has or have been treated such that the expression of a HSF1 gene is inhibited, as compared to a second cell or group of cells substantially identical to the first cell or group of cells but which has or have not been so treated (control cells). The degree of inhibition is usually expressed in terms of $$\frac{(mRNA \text{ in control cells}) - (mRNA \text{ in treated cells})}{(mRNA \text{ in control cells})} \cdot 100\% \quad \text{Equation 1}$$

Alternatively, the degree of inhibition may be given in terms of a reduction of a parameter that is functionally linked to HSF1 gene expression, e.g., the amount of protein encoded by a HSF1 gene, etc. In principle, HSF1 gene silencing may be determined in any cell expressing HSF1, either constitutively or by genomic engineering, and by any appropriate assay. However, when a reference or control is needed in order to determine whether a given RNAi agent inhibits the expression of the HSF1 gene by a certain degree and therefore is encompassed by the instant disclosure, the assays provided in the Examples below shall serve as such reference.

For example, in certain instances, expression of a HSF1 gene is suppressed by at least about 10%, 15%, 20%, 25%, 30%, 35%, 40%, 45%, or 50% by administration of a RNAi agent featured in the present disclosure. In some embodiments, a HSF1 gene is suppressed by at least about 60%, 70%, or 80% by administration of a RNAi agent featured in the present disclosure. In some embodiments, a HSF1 gene is suppressed by at least about 85%, 90%, or 95% or more by administration of a RNAi agent, as described herein.

The ability of a RNAi agent to suppress HSF1 can be first tested in vitro (e.g., using test cells such as H441).

RNAi agents which can suppress HSF1 in vitro can then be tested for immunostimulation using, for example, a PBMC (peripheral blood mononuclear cell) assay. RNAi agents can also be tested in animal tests. Test and control animals include those which over-express or under-express HSF1. RNAi agents which suppress or alter the level, activity and/or expression of HSF1 can be used in medicaments to treat various HSF1-related diseases.

By "lower" in the context of HSF1 or a symptom of a HSF1-related disease is meant a statistically significant decrease in such level. The decrease can be, for example, at least 10%, at least 20%, at least 30%, at least 40% or more. If, for a particular disease, or for an individual suffering from a particular disease, the levels or expression of HSF1 are elevated, treatment with a HSF1 RNAi agent of the present disclosure can particularly reduce the level or expression of HSF1 to a level considered in the literature as within the range of normal for an individual without such disorder. The level or expression of HSF1 can be measured by evaluation of mRNA (e.g., via Northern blots or PCR), or protein (e.g., Western blots). The effect of a RNAi agent on HSF1 expression can be determined by measuring HSF1 gene transcription rates (e.g., via Northern blots; or reverse transcriptase polymerase chain reaction or real-time polymerase chain reaction). Direct measurements can be made of levels of HSF1, e.g. by Western blots of tissues in which HSF1 is expressed.

As used herein, "down-regulates" refers to any statistically significant decrease in a biological activity and/or expression of HSF1, including full blocking of the activity (i.e., complete inhibition) and/or expression. For example, "down-regulation" can refer to a decrease of at least about 10, 20, 30, 40, 50, 60, 70, 80, 90 or 100% in HSF1 level, activity and/or expression.

As used herein, the term "inhibit" or "inhibiting" HSF1 refers to any statistically significant decrease in biological level, activity and/or expression of HSF1, including full blocking of the activity and/or expression. For example, "inhibition" can refer to a decrease of at least about 10, 20, 30, 40, 50, 60, 70, 80, 90 or 100% in HSF1 level, activity and/or expression. As used herein, the term "inhibit" similarly refers to a significant decrease in level, activity and/or expression, while referring to any other biological agent or composition.

By "level", it is meant that the HSF1 RNAi agent can alter the level of HSF1, e.g., the level of HSF1 mRNA or the level of HSF1 protein, or the level of activity of HSF1.

Some diseases, such as some viral diseases and cancers, are characterized by excessive HSF1 activity or levels. Particularly in one embodiment, in the case of a disease characterized by over-expression and/or hyper-activity of HSF1, administration of a RNAi agent to HSF1 reduces the level, expression and/or activity of HSF1. Thus, in various embodiments, administration of a RNAi agent to HSF1 particularly establishes or re-establishes a normal or approximately normal level of HSF1 activity, expression and/or level.

By "normal" or "approximately normal" in terms of level, expression and/or activity, is meant at least: about 50%, about 60%, about 70%, about 80%, about 90%, and/or about 100%; and/or no more than: about 100%, about 120%, about 130%, about 140%, or about 150% of the level, expression or activity of HSF1 in a healthy cell, tissue, or organ. Particularly in one embodiment, administration of the appropriate amount of the appropriate HSF1 RNAi agent restores HSF1 level, activity and/or expression to about 50% to about 150%, more particularly about 60% to about 140%, more particularly to about 70% to about 130%, more particularly to about 80% to about 120%, more particularly to about 90% to about 110%, and most particularly to about 100% of that of a healthy cell, tissue or organ.

In addition, in various embodiments, depending on the disease condition and biological context, it is acceptable to use the RNAi agents of the present disclosure to establish a level of HSF1 expression, activity and/or level which is below the normal level, or above the normal level.

Treatments Involving HSF1 RNAi Agents.

As used herein in the context of HSF1 expression, the terms "treat," "treatment," and the like, refer to relief from or alleviation of pathological processes mediated by HSF1 expression. In the context of the present disclosure insofar as it relates to any of the other conditions recited herein below (other than pathological processes mediated by HSF1 expression), the terms "treat," "treatment," and the like mean to relieve or alleviate at least one symptom associated with such condition, or to slow or reverse the progression or anticipated progression of such condition, such as slowing the progression of a lipid disorder, such as atherosclerosis.

By "lower" in the context of a disease marker or symptom is meant a statistically significant decrease in such level. The decrease can be, for example, at least 10%, at least 20%, at least 30%, at least 40% or more. If, for a particular disease, or for an individual suffering from a particular disease, the levels or expression of HSF1 are elevated, treatment with an HSF1 RNAi agent of the present disclosure can preferably reduce the level or expression of HSF1 to a level considered in the literature as within the range of normal for an individual without such disorder.

The level or expression of HSF1 can be measured by evaluation of mRNA (e.g., via Northern blots or PCR), or protein (e.g., Western blots). The effect of an RNAi agent on HSF1 expression can be determined by measuring HSF1 gene transcription rates (e.g., via Northern blots; or reverse transcriptase polymerase chain reaction or real-time polymerase chain reaction). RT-PCR has been used to show that mRNA levels of HSF1 are high in kidney, pancreas and prostate, and medium in liver and spleen. Brauner-Osborne et al. 2001. Biochim. Biophys. Acta 1518: 237-248. Direct measurements can be made of levels of HSF1 (which is expressed by the cell surface), e.g. by Western blots of tissues in which HSF1 is expressed.

RNAi agents to HSF1 can thus be used to treat HSF1-related diseases, particularly those diseases associated with altered (particularly, raised) expression, activity and/or levels of HSF1.

Use of RNAi Agents for Treatment of HSF1-Related Diseases.

The RNAi agents to HSF1 described herein can be formulated into pharmaceutical compositions which can be administered to humans or non-human animals. These compositions can comprise one or more RNAi agents, and, optionally, additional treatments useful for treating HSF1-related diseases. They can be administered as part of an early/preventative treatment, and can be administered in a therapeutically-effective dosage. The pharmaceutical composition can comprise a pharmaceutical carrier and can be administered by any method known in the art. These various aspects of the present disclosure are described in additional detail below.

RNAi agents to HSF1 can be administered to humans and non-human animals for treatment of HSF1-related diseases.

In one embodiment of the disclosure, the compositions comprising a HSF1 RNAi agent can be administered to non-human animals. For example, the compositions can be given to chickens, turkeys, livestock animals (such as sheep, pigs, horses, cattle, etc.), companion animals (e.g., cats and dogs) and can have efficacy in treatment of cancer and viral diseases. In each case, the RNAi agent to HSF1 would be selected to match the sequence of the HSF1 of the genome of the animal, and to, preferably, contain at least 1 nt mismatch from all other genes in that animal's genome. The RNAi agents of the present disclosure can thus be used in treatment of HSF1-related diseases in humans and non-human animals.

As used herein in the context of HSF1 expression, the terms "treat," "treatment," and the like, refer to relief from or alleviation of pathological processes mediated by HSF1 expression. In the context of the present disclosure insofar as it relates to any of the other conditions recited herein below (other than pathological processes mediated by HSF1 expression), the terms "treat," "treatment," and the like mean to relieve or alleviate at least one symptom associated with such condition, or to slow or reverse the progression or anticipated progression of such condition, such as slowing the progression of a lipid disorder, such as atherosclerosis.

By "treatment" is meant prophylaxis, therapy, cure, or any other change in a patient's condition indicating improvement or absence of degradation of physical condition. By "treatment" is meant treatment of HSF1-related disease (e.g., cancer or viral disease), or any appropriate treatment of any other ailment the patient has. As used herein, the terms "treatment" and "treat" refer to both prophylactic or preventative treatment and curative or disease-modifying treatment, including treatment of patients at risk of contracting a disease or suspected of having a disease, as well as patients already ill or diagnosed as suffering from a condition. The terms "treatment" and "treat" also refer to the maintenance and/or promotion of health in an individual not suffering from a disease but who may be susceptible to developing an unhealthy condition, such as nitrogen imbalance or muscle loss. In one embodiment, "treatment" does not encompass prevention of a disease state. Thus, the present disclosure is useful for suppressing expression of HSF1 and/or treating an HSF1-related disease in an individual afflicted by an HSF1-related disease, or an individual susceptible to an HSF1-related disease. An individual "afflicted" by an HSF1-related disease has demonstrated detectable symptoms characteristics of the disease, or had otherwise been shown clinically to have been exposed to or to carry HSF1-related disease pathogens or markers. As non-limiting examples, an individual afflicted by an HSF1-related disease can show outward symptoms; or can show no outward symptoms but can be shown with a clinical test to carry protein markers associated with an HSF1-related disease, or proteins or genetic material associated with a pathogen in the blood.

Treatment of some HSF1-related diseases may be more efficacious if administered early rather than later. Thus, in one particular embodiment, the RNAi agent to HSF1 is administered early, prior to disease manifestation, and/or as a preventative agent, rather than administered after disease establishment.

Treatments of HSF1-related diseases can comprise various treatments, comprising a HSF1 RNAi agent, and optionally further comprising an additional treatment, which can be a method (or procedure), or an additional composition (e.g., an agent or additional RNAi agent).

Dosages and Effective Amounts of RNAi Agents.

The RNAi agents of the present disclosure are administered in a dosage of a therapeutically effective amount to a patient in need thereof.

An "effective amount" or a "therapeutically effective amount" is an amount that treats a disease or medical condition of an individual, or, more generally, provides a nutritional, physiological or medical benefit to an individual. As used herein, the phrases "therapeutically effective amount" and "prophylactically effective amount" refer to an amount that provides a therapeutic benefit in the treatment, prevention, or management of pathological processes mediated by HSF1 expression or an overt symptom of pathological processes mediated by HSF1 expression. The specific amount that is therapeutically effective can be readily determined by an ordinary medical practitioner, and may vary depending on factors known in the art, such as, e.g., the type of pathological processes mediated by HSF1 expression, the patient's history and age, the stage of pathological processes mediated by HSF1 expression, and administration of other agents that inhibit pathological processes mediated by HSF1.

In various embodiments of the disclosure, the patient is at least about 1, 5, 10, 20, 30, 40, 50, 55, 60, 65, 70, or 75 years of age. In various embodiments, the patient has not yet been born, but receives treatment(s) prior to birth. In various embodiments, the patient is no more than about 1, 5, 10, 20, 30, 40, 50, 55, 60, 65, 70, 75, 80, 90, or 100 years of age. In various embodiments the patient has a body weight of at least about 20, 30, 40, 50, 60, 70, 80, 90, 100, 120, 140, 160, 180, 200, 220, 240, 260, 280, 300, 320, 340, 360, 380 or 400 lbs. In various embodiments, the patient has a body weight of no more than about 20, 30, 40, 50, 60, 70, 80, 90, 100, 120, 140, 160, 180, 200, 220, 240, 260, 280, 300, 320, 340, 360, 380 or 400 lbs.

In various embodiments of the disclosure, the dosage [measuring only the active ingredient(s)] can be at least about 1, 5, 10, 25, 50, 100, 200, 250, 300, 250, 400, 450, 500, 550, 600, 650, 700, 750, 800, 850, 900, 950 or 1000 ng, 1, 5, 10, 25, 50, 100, 200, 250, 300, 250, 400, 450, 500, 550, 600, 650, 700, 750, 800, 850, 900, 950 or 1000 micrograms, 1, 5, 10, 25, 50, 100, 200, 250, 300, 250, 400, 450, 500, 550, 600, 650, 700, 750, 800, 850, 900, 950 or 1000 mg. In various embodiments, the dosage can be no more than about 10, 25, 50, 100, 200, 250, 300, 250, 400, 450, 500, 550, 600, 650, 700, 750, 800, 850, 900, 950 or 1000 mg. In various embodiments, the dosage can be administered at least more than once a day, daily, more than once a weekly, weekly, bi-weekly, monthly, and/or every 2, 3, 4, 5, 6, 7, 8, 9, 10, 11 or 12 months, or a combination thereof.

In various embodiments, the dosage is correlated to the body weight or body surface area of the individual. The actual dosage level can be varied to obtain an amount of active agent which is effective for a particular patient, composition and mode of administration, without being toxic to the patient. The selected dose will depend on a variety of pharmacokinetic factors, including the activity of the particular RNAi agent employed, the route of administration, the rate of excretion of the RNAi agent, the duration of the treatment, other drugs, compounds and/or materials used in combination with the RNAi agent, the age, sex, weight, condition, general health and prior medical history of the patient, and like factors well known in the medical arts. A physician or veterinarian having ordinary skill in the art can readily determine the effective amount of the RNAi agent required. A suitable dose will be that amount which is the lowest dose effective to produce a therapeutic effect, or a dose low enough to produce a therapeutic effect without causing side effects.

In addition to a therapeutically-effective dosage of one or more RNAi agents to HSF1, the pharmaceutical compositions of the present disclosure can comprise or be used in conjunction with an additional disease treatment which works synergistically with the RNAi agent. For example, the pharmaceutical composition can comprise an additional antagonist to HSF1.

Additional Embodiments of RNAi Agents to HSF1.

In a particular embodiment, the present disclosure encompasses a composition comprising one or more HSF1 RNAi agents. In one embodiment, the present disclosure comprises a RNAi agent comprising a sense strand and an antisense strand. In one embodiment, the antisense strand consists of, consists essentially of, or comprises the sequence of the antisense strand of a RNAi agent listed, e.g., in Tables A1, 1, 2, 3, 4, 5, 6, or 7. In one embodiment, the antisense strand consists of, consists essentially of, or comprises a sequence with 0, 1, 2, or 3 mismatches from that of the antisense strand of any RNAi agent listed, e.g., in Tables A1, 1, 2, 3, 4, 5, 6, or 7. In one embodiment, the antisense strand consists of the sequence of the antisense strand of a RNAi agent listed, e.g., in Tables A1, 1, 2, 3, 4, 5, 6, or 7, and further comprises 0, 1, 2, 3, 4, 5, 6, 7, 8, 9, or 10 nucleotides. In one embodiment, the antisense strand consists of a sequence with 0, 1, 2, or 3 mismatches from that of the antisense strand of a RNAi agent listed, e.g., in Tables A1, 1, 2, 3, 4, 5, 6, or 7, and further comprises 0, 1, 2, 3, 4, 5, 6, 7, 8, 9, or 10 nucleotides.

In another embodiment, the composition of the claimed disclosure does not comprise any particular individual RNAi agent listed, e.g., in Tables A1, 1, 2, 3, 4, 5, 6, or 7. In another embodiment of the present disclosure, the RNAi agent to HSF1 does not comprise any specific sequence of any HSF1 RNAi agent disclosed in the patent or scientific literature, e.g., Published U.S. Patent App. No. US-2011-0166058-A1. In one embodiment, the disclosure encompasses a RNAi agent to HSF1 which comprises a sequence of a HSF1 RNAi agent previously disclosed in the patent or scientific literature (e.g., Published U.S. Patent App. No. US-2011-0166058-A1), however with a different set of modifications than that disclosed in the patent or scientific literature.

Specific Embodiments of RNAi Agents to HSF1.

In a particular specific embodiment, the present disclosure is a composition comprising one or more HSF1 RNAi agents disclosed or provided herein, e.g., in Tables A1, 1, 2, 3, 4, 5, 6, or 7, wherein the sequence of the first strand and the second strand of the RNAi agent consists or comprises the sequence of the first and second strand of any HSF1 RNAi agent disclosed herein, or modified or unmodified variants thereof.

In various embodiments, the disclosure pertains to:

An RNAi agent comprising a first and a second strand, wherein the sequence of the first strand of the RNAi agent is the sequence of the first strand of, and the sequence of the second strand of the RNAi agent is the sequence of the second strand of: hs_HSF1_175_A22_S26 (SEQ ID NOs: 180 and 264; or SEQ ID NOs: 348 and 432), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_175_A25_S27 (SEQ ID NOs: 192 and 276; or SEQ ID NOs: 360 and 444), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_175_A81_S26 (SEQ ID NOs: 204 and 288; or SEQ ID NOs: 372 and 456), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_175_A48_S26 (SEQ ID NOs: 216 and 300; or SEQ ID NOs: 384 and 468), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_175_A82_S36 (SEQ ID NOs: 228 and 312; or SEQ ID NOs: 396 and 480), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_175_A83_S36 (SEQ ID NOs: 240 and 324; or SEQ ID NOs: 408 and 492), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_175_A84_S36 (SEQ ID NOs: 252 and 336; or SEQ ID NOs: 420 and 504), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_517_A22_S26 (SEQ ID NOs: 172 and 256; or SEQ ID NOs: 340 and 424), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_517_A25_S27 (SEQ ID NOs: 184 and 268; or SEQ ID NOs: 352 and 436), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_517_A81_S26 (SEQ ID NOs: 196 and 280; or SEQ ID NOs: 364 and 448), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_517_A48_S26 (SEQ ID NOs: 208 and 292; or SEQ ID NOs: 376 and 460), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_517_A82_S36 (SEQ ID NOs: 220 and 304; or SEQ ID NOs: 388 and 472), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_517_A83_S36 (SEQ ID NOs: 232 and 316; or SEQ ID NOs: 400 and 484), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_517_A84_S36 (SEQ ID NOs: 244 and 328; or SEQ ID NOs: 412 and 496), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_562_A22_S26 (SEQ ID NOs: 169 and 253; or SEQ ID NOs: 337 and 421), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_562_A25_S27 (SEQ ID NOs: 181 and 265; or SEQ ID NOs: 349 and 433), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_562_A81_S26 (SEQ ID NOs: 193 and 277; or SEQ ID NOs: 361 and 445), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_562_A48_S26 (SEQ ID NOs: 205 and 289; or SEQ ID NOs: 373 and 457), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_562_A82_S36 (SEQ ID NOs: 217 and 301; or SEQ ID NOs: 385 and 469), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_562_A83_S36 (SEQ ID NOs: 229 and 313; or SEQ ID NOs: 397 and 481), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_562_A84_S36 (SEQ ID NOs: 241 and 325; or SEQ ID NOs: 409 and 493), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_751_A22_S26 (SEQ ID NOs: 170 and 254; or SEQ ID NOs: 338 and 422), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_751_A25_S27 (SEQ ID NOs: 182 and 266; or SEQ ID NOs: 350 and 434), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_751_A81_S26 (SEQ ID NOs: 194 and 278; or SEQ ID NOs: 362 and 446), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_751_A48_S26 (SEQ ID NOs: 206 and 290; or SEQ ID NOs: 374 and 458), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_751_A82_S36 (SEQ ID NOs: 218 and 302; or SEQ ID NOs: 386 and 470), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_751_A83_S36 (SEQ ID NOs: 230 and 314; or SEQ ID NOs: 398 and 482), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_751_A84_S36 (SEQ ID NOs: 242 and 326; or SEQ ID NOs: 410 and 494), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_755_A22_S26 (SEQ ID NOs: 171 and 255; or SEQ ID NOs: 339 and 423), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_755_A25_S27 (SEQ ID NOs: 183 and 267; or SEQ ID NOs: 351 and 435), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_755_A81_S26 (SEQ ID NOs: 195 and 279; or SEQ ID NOs: 363 and 447), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_755_A48_S26 (SEQ ID NOs: 207 and 291; or SEQ ID NOs: 375 and 459), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_755_A82_S36 (SEQ ID NOs: 219 and 303; or SEQ ID NOs: 387 and 471), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_755_A83_S36 (SEQ ID NOs: 231 and 315; or SEQ ID NOs: 399 and 483), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_755_A84_S36 (SEQ ID NOs: 243 and 327; or SEQ ID NOs: 411 and 495), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_846_A22_S26 (SEQ ID NOs: 173 and 257; or SEQ ID NOs: 341 and 425), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_846_A25_S27 (SEQ ID NOs: 185 and 269; or SEQ ID NOs: 353 and 437), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_846_A81_S26 (SEQ ID NOs: 197 and 281; or SEQ ID NOs: 365 and 449), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_846_A48_S26 (SEQ ID NOs: 209 and 293; or SEQ ID NOs: 377 and 461), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_846_A82_S36 (SEQ ID NOs: 221 and 305; or SEQ ID NOs: 389 and 473), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_846_A83_S36 (SEQ ID NOs: 233 and 317; or SEQ ID NOs: 401 and 485), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_846_A84_S36 (SEQ ID NOs: 245 and 329; or SEQ ID NOs: 413 and 497), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_1360_A22_S26 (SEQ ID NOs: 174 and 258; or SEQ ID NOs: 342 and 426), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_1360_A25_S27 (SEQ ID NOs: 186 and 270; or SEQ ID NOs: 354 and 438), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_1360_A81_S26 (SEQ ID NOs: 198 and 282; or SEQ ID NOs: 366 and 450), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_1360_A48_S26 (SEQ ID NOs: 210 and 294; or SEQ ID NOs: 378 and 462), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_1360_A82_S36 (SEQ ID NOs: 222 and 306; or SEQ ID NOs: 390 and 474), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_1360_A83_S36 (SEQ ID NOs: 234 and 318; or SEQ ID NOs: 402 and 486), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_1360_A84_S36 (SEQ ID NOs: 246 and 330; or SEQ ID NOs: 414 and 498), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_2030_A22_S26 (SEQ ID NOs: 175 and 259; or SEQ ID NOs: 343 and 427), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of hs_HSF1_2030_A25_S27 (SEQ ID NOs: 187 and 271; or SEQ ID NOs: 355 and 439), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_2030_A81_S26 (SEQ ID NOs: 199 and 283; or SEQ ID NOs: 367 and 451), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_2030_A48_S26 (SEQ ID NOs: 211 and 295; or SEQ ID NOs: 379 and 463), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_2030_A82_S36 (SEQ ID NOs: 223 and 307; or SEQ ID NOs: 391 and 475), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_2030_A83_S36 (SEQ ID NOs: 235 and 319; or SEQ ID NOs: 403 and 487), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_2030_A84_S36 (SEQ ID NOs: 247 and 331; or SEQ ID NOs: 415 and 499), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_2034_A22_S26 (SEQ ID NOs: 176 and 260; or SEQ ID NOs: 344 and 428), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_2034_A25_S27 (SEQ ID NOs: 188 and 272; or SEQ ID NOs: 356 and 440), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_2034_A81_S26 (SEQ ID NOs: 200 and 284; or SEQ ID NOs: 368 and 452), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of hs_HSF1_2034_A48_S26 (SEQ ID NOs: 212 and 296; or SEQ ID NOs: 380 and 464), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_2034_A82_S36 (SEQ ID NOs: 224 and 308; or SEQ ID NOs: 392 and 476), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_2034_A83_S36 (SEQ ID NOs: 236 and 320; or SEQ ID NOs: 404 and 488), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_2034_A84_S36 (SEQ ID NOs: 248 and 332; or SEQ ID NOs: 416 and 500), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_2138_A22_S26 (SEQ ID NOs: 177 and 261; or SEQ ID NOs: 345 and 429), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_2138_A25_S27 (SEQ ID NOs: 189 and 273; or SEQ ID NOs: 357 and 441), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_2138_A81_S26 (SEQ ID NOs: 201 and 285; or SEQ ID NOs: 369 and 453), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_2138_A48_S26 (SEQ ID NOs: 213 and 297; or SEQ ID NOs: 381 and 465), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_2138_A82_S36 (SEQ ID NOs: 225 and 309; or SEQ ID NOs: 393 and 477), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of hs_HSF1_2138_A83_S36 (SEQ ID NOs: 237 and 321; or SEQ ID NOs: 405 and 489), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_2138_A84_S36 (SEQ ID NOs: 249 and 333; or SEQ ID NOs: 417 and 501), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_2153_A22_S26 (SEQ ID NOs: 178 and 262; or SEQ ID NOs: 346 and 430), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_2153_A25_S27 (SEQ ID NOs: 190 and 274; or SEQ ID NOs: 358 and 442), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_2153_A81_S26 (SEQ ID NOs: 202 and 286; or SEQ ID NOs: 370 and 454), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_2153_A48_S26 (SEQ ID NOs: 214 and 298; or SEQ ID NOs: 382 and 466), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_2153_A82_S36 (SEQ ID NOs: 226 and 310; or SEQ ID NOs: 394 and 478), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_2153_A83_S36 (SEQ ID NOs: 238 and 322; or SEQ ID NOs: 406 and 490), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_2153_A84_S36 (SEQ ID NOs: 250 and 334; or SEQ ID NOs: 418 and 502), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of hs_HSF1_2154_A22_S26 (SEQ ID NOs: 179 and 263; or SEQ ID NOs: 347 and 431), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_2154_A25_S27 (SEQ ID NOs: 191 and 275; or SEQ ID NOs: 359 and 443), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_2154_A81_S26 (SEQ ID NOs: 203 and 287; or SEQ ID NOs: 371 and 455), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_2154_A48_S26 (SEQ ID NOs: 215 and 299; or SEQ ID NOs: 383 and 467), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_2154_A82_S36 (SEQ ID NOs: 227 and 311; or SEQ ID NOs: 395 and 479), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_2154_A83_S36 (SEQ ID NOs: 239 and 323; or SEQ ID NOs: 407 and 491), or modified or unmodified variants thereof.

An RNAi agent comprising a first and a second strand, wherein the sequence of the first strand of the RNAi agent is the sequence of the first strand of, and the sequence of the second strand of the RNAi agent is the sequence of the second strand of: hs_HSF1_2154_A84_S36 (SEQ ID NOs: 251 and 335; or SEQ ID NOs: 419 and 503), or modified or unmodified variants thereof.

In various embodiments, the disclosure pertains to:

An RNAi agent comprising a first and a second strand, wherein the sequence of the first strand comprises the sequence of the first strand of, and the sequence of the second strand comprises the sequence of the second strand of: hs_HSF1_175_A22_S26 (SEQ ID NOs: 180 and 264; or SEQ ID NOs: 348 and 432), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_175_A25_S27 (SEQ ID NOs: 192 and 276; or SEQ ID NOs: 360 and 444), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_175_A81_S26 (SEQ ID NOs: 204 and 288; or SEQ ID NOs: 372 and 456), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_175_A48_S26 (SEQ ID NOs: 216 and 300; or SEQ ID NOs: 384 and 468), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_175_A82_S36 (SEQ ID NOs: 228 and 312; or SEQ ID NOs: 396 and 480), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_175_A83_S36 (SEQ ID NOs: 240 and 324; or SEQ ID NOs: 408 and 492), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_175_A84_S36 (SEQ ID NOs: 252 and 336; or SEQ ID NOs: 420 and 504), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_517_A22_S26 (SEQ ID NOs: 172 and 256; or SEQ ID NOs: 340 and 424), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_517_A25_S27 (SEQ ID NOs: 184 and 268; or SEQ ID NOs: 352 and 436), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_517_A81_S26 (SEQ ID NOs: 196 and 280; or SEQ ID NOs: 364 and 448), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_517_A48_S26 (SEQ ID NOs: 208 and 292; or SEQ ID NOs: 376 and 460), or modified or unmodified variants thereof.

An RNAi agent comprising a first and a second strand, wherein the sequence of the first strand comprises the sequence of the first strand of, and the sequence of the second strand comprises the sequence of the second strand of hs_HSF1_517_A82_S36 (SEQ ID NOs: 220 and 304; or SEQ ID NOs: 388 and 472), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_517_A83_S36 (SEQ ID NOs: 232 and 316; or SEQ ID NOs: 400 and 484), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_517_A84_S36 (SEQ ID NOs: 244 and 328; or SEQ ID NOs: 412 and 496), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_562_A22_S26 (SEQ ID NOs: 169 and 253; or SEQ ID NOs: 337 and 421), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_562_A25_S27 (SEQ ID NOs: 181 and 265; or SEQ ID NOs: 349 and 433), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_562_A81_S26 (SEQ ID NOs: 193 and 277; or SEQ ID NOs: 361 and 445), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_562_A48_S26 (SEQ ID NOs: 205 and 289; or SEQ ID NOs: 373 and 457), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_562_A82_S36 (SEQ ID NOs: 217 and 301; or SEQ ID NOs: 385 and 469), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_562_A83_S36 (SEQ ID NOs: 229 and 313; or SEQ ID NOs: 397 and 481), or modified or unmodified variants thereof.

An RNAi agent comprising a first and a second strand, wherein the sequence of the first strand comprises the sequence of the first strand of, and the sequence of the second strand comprises the sequence of the second strand of hs_HSF1_562_A84_S36 (SEQ ID NOs: 241 and 325; or SEQ ID NOs: 409 and 493), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_751_A22_S26 (SEQ ID NOs: 170 and 254; or SEQ ID NOs: 338 and 422), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_751_A25_S27 (SEQ ID NOs: 182 and 266; or SEQ ID NOs: 350 and 434), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_751_A81_S26 (SEQ ID NOs: 194 and 278; or SEQ ID NOs: 362 and 446), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_751_A48_S26 (SEQ ID NOs: 206 and 290; or SEQ ID NOs: 374 and 458), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_751_A82_S36 (SEQ ID NOs: 218 and 302; or SEQ ID NOs: 386 and 470), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_751_A83_S36 (SEQ ID NOs: 230 and 314; or SEQ ID NOs: 398 and 482), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_751_A84_S36 (SEQ ID NOs: 242 and 326; or SEQ ID NOs: 410 and 494), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_755_A22_S26 (SEQ ID NOs: 171 and 255; or SEQ ID NOs: 339 and 423), or modified or unmodified variants thereof.

An RNAi agent comprising a first and a second strand, wherein the sequence of the first strand comprises the sequence of the first strand of, and the sequence of the second strand comprises the sequence of the second strand of hs_HSF1_755_A25_S27 (SEQ ID NOs: 183 and 267; or SEQ ID NOs: 351 and 435), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_755_A81_S26 (SEQ ID NOs: 195 and 279; or SEQ ID NOs: 363 and 447), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_755_A48_S26 (SEQ ID NOs: 207 and 291; or SEQ ID NOs: 375 and 459), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_755_A82_S36 (SEQ ID NOs: 219 and 303; or SEQ ID NOs: 387 and 471), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_755_A83_S36 (SEQ ID NOs: 231 and 315; or SEQ ID NOs: 399 and 483), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_755_A84_S36 (SEQ ID NOs: 243 and 327; or SEQ ID NOs: 411 and 495), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_846_A22_S26 (SEQ ID NOs: 173 and 257; or SEQ ID NOs: 341 and 425), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_846_A25_S27 (SEQ ID NOs: 185 and 269; or SEQ ID NOs: 353 and 437), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_846_A81_S26 (SEQ ID NOs: 197 and 281; or SEQ ID NOs: 365 and 449), or modified or unmodified variants thereof.

An RNAi agent comprising a first and a second strand, wherein the sequence of the first strand comprises the sequence of the first strand of, and the sequence of the second strand comprises the sequence of the second strand of hs_HSF1_846_A48_S26 (SEQ ID NOs: 209 and 293; or SEQ ID NOs: 377 and 461), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_846_A82_S36 (SEQ ID NOs: 221 and 305; or SEQ ID NOs: 389 and 473), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_846_A83_S36 (SEQ ID NOs: 233 and 317; or SEQ ID NOs: 401 and 485), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_846_A84_S36 (SEQ ID NOs: 245 and 329; or SEQ ID NOs: 413 and 497), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_1360_A22_S26 (SEQ ID NOs: 174 and 258; or SEQ ID NOs: 342 and 426), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_1360_A25_S27 (SEQ ID NOs: 186 and 270; or SEQ ID NOs: 354 and 438), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_1360_A81_S26 (SEQ ID NOs: 198 and 282; or SEQ ID NOs: 366 and 450), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_1360_A48_S26 (SEQ ID NOs: 210 and 294; or SEQ ID NOs: 378 and 462), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_1360_A82_S36 (SEQ ID NOs: 222 and 306; or SEQ ID NOs: 390 and 474), or modified or unmodified variants thereof.

An RNAi agent comprising a first and a second strand, wherein the sequence of the first strand comprises the sequence of the first strand of, and the sequence of the second strand comprises the sequence of the second strand of hs_HSF1_1360_A83_S36 (SEQ ID NOs: 234 and 318; or SEQ ID NOs: 402 and 486), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_1360_A84_S36 (SEQ ID NOs: 246 and 330; or SEQ ID NOs: 414 and 498), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_2030_A22_S26 (SEQ ID NOs: 175 and 259; or SEQ ID NOs: 343 and 427), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_2030_A25_S27 (SEQ ID NOs: 187 and 271; or SEQ ID NOs: 355 and 439), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_2030_A81_S26 (SEQ ID NOs: 199 and 283; or SEQ ID NOs: 367 and 451), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_2030_A48_S26 (SEQ ID NOs: 211 and 295; or SEQ ID NOs: 379 and 463), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_2030_A82_S36 (SEQ ID NOs: 223 and 307; or SEQ ID NOs: 391 and 475), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_2030_A83_S36 (SEQ ID NOs: 235 and 319; or SEQ ID NOs: 403 and 487), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_2030_A84_S36 (SEQ ID NOs: 247 and 331; or SEQ ID NOs: 415 and 499), or modified or unmodified variants thereof.

An RNAi agent comprising a first and a second strand, wherein the sequence of the first strand comprises the sequence of the first strand of, and the sequence of the second strand comprises the sequence of the second strand of hs_HSF1_2034_A22_S26 (SEQ ID NOs: 176 and 260; or SEQ ID NOs: 344 and 428), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_2034_A25_S27 (SEQ ID NOs: 188 and 272; or SEQ ID NOs: 356 and 440), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_2034_A81_S26 (SEQ ID NOs: 200 and 284; or SEQ ID NOs: 368 and 452), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_2034_A48_S26 (SEQ ID NOs: 212 and 296; or SEQ ID NOs: 380 and 464), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_2034_A82_S36 (SEQ ID NOs: 224 and 308; or SEQ ID NOs: 392 and 476), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_2034_A83_S36 (SEQ ID NOs: 236 and 320; or SEQ ID NOs: 404 and 488), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_2034_A84_S36 (SEQ ID NOs: 248 and 332; or SEQ ID NOs: 416 and 500), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_2138_A22_S26 (SEQ ID NOs: 177 and 261; or SEQ ID NOs: 345 and 429), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_2138_A25_S27 (SEQ ID NOs: 189 and 273; or SEQ ID NOs: 357 and 441), or modified or unmodified variants thereof.

An RNAi agent comprising a first and a second strand, wherein the sequence of the first strand comprises the sequence of the first strand of, and the sequence of the second strand comprises the sequence of the second strand of hs_HSF1_2138_A81_S26 (SEQ ID NOs: 201 and 285; or SEQ ID NOs: 369 and 453), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_2138_A48_S26 (SEQ ID NOs: 213 and 297; or SEQ ID NOs: 381 and 465), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_2138_A82_S36 (SEQ ID NOs: 225 and 309; or SEQ ID NOs: 393 and 477), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_2138_A83_S36 (SEQ ID NOs: 237 and 321; or SEQ ID NOs: 405 and 489), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_2138_A84_S36 (SEQ ID NOs: 249 and 333; or SEQ ID NOs: 417 and 501), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_2153_A22_S26 (SEQ ID NOs: 178 and 262; or SEQ ID NOs: 346 and 430), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_2153_A25_S27 (SEQ ID NOs: 190 and 274; or SEQ ID NOs: 358 and 442), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_2153_A81_S26 (SEQ ID NOs: 202 and 286; or SEQ ID NOs: 370 and 454), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_2153_A48_S26 (SEQ ID NOs: 214 and 298; or SEQ ID NOs: 382 and 466), or modified or unmodified variants thereof.

An RNAi agent comprising a first and a second strand, wherein the sequence of the first strand comprises the sequence of the first strand of, and the sequence of the second strand comprises the sequence of the second strand of hs_HSF1_2153_A82_S36 (SEQ ID NOs: 226 and 310; or SEQ ID NOs: 394 and 478), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_2153_A83_S36 (SEQ ID NOs: 238 and 322; or SEQ ID NOs: 406 and 490), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_2153_A84_S36 (SEQ ID NOs: 250 and 334; or SEQ ID NOs: 418 and 502), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_2154_A22_S26 (SEQ ID NOs: 179 and 263; or SEQ ID NOs: 347 and 431), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_2154_A25_S27 (SEQ ID NOs: 191 and 275; or SEQ ID NOs: 359 and 443), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_2154_A81_S26 (SEQ ID NOs: 203 and 287; or SEQ ID NOs: 371 and 455), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_2154_A48_S26 (SEQ ID NOs: 215 and 299; or SEQ ID NOs: 383 and 467), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_2154_A82_S36 (SEQ ID NOs: 227 and 311; or SEQ ID NOs: 395 and 479), or modified or unmodified variants thereof.

An RNAi agent comprising a first and a second strand, wherein the sequence of the first strand comprises the sequence of the first strand of, and the sequence of the second strand comprises the sequence of the second strand of: hs_HSF1_2154_A83_S36 (SEQ ID NOs: 239 and 323; or SEQ ID NOs: 407 and 491), or modified or unmodified variants thereof.

An RNAi agent comprising a first and a second strand, wherein the sequence of the first strand comprises the sequence of the first strand of, and the sequence of the second strand comprises the sequence of the second strand of hs_HSF1_2154_A84_S36 (SEQ ID NOs: 251 and 335; or SEQ ID NOs: 419 and 503), or modified or unmodified variants thereof.

In various embodiments, wherein it is said that the sequence of a particular strand is the sequence of a particular SEQ ID NO., it is meant that the sequence of that particular strand consists of the sequence of the referenced SEQ ID NO.

Additional Particular Specific Embodiments

In various embodiments, the disclosure comprises a RNAi agent comprising a first and a second strand, wherein the first strand comprises at least 15 contiguous nucleotides differing by 0, 1, 2, or 3 nt (e.g., 0, 1, 2 or 3 mismatches) from a first strand, and the second strand comprises at least 15 contiguous nucleotides differing by 0, 1, 2, or 3 nt (e.g., 0, 1, 2 or 3 mismatches) from the second strand of any one or more RNAi agent disclosed herein.

A mismatch is defined herein as a difference between the base sequence or length when two sequences are maximally aligned and compared. A mismatch is defined as a position wherein the base of one sequence does not match the base of the other sequence. Thus, a mismatch is counted, for example, if a position in one sequence has a particular base (e.g., A), and the corresponding position on the other sequence has a different base (e.g., G).

A mismatch is also counted, e.g., if a position in one sequence has a base (e.g., A), and the corresponding position on the other sequence has no base (e.g., that position is an abasic nucleotide which comprises a phosphate-sugar backbone but no base). A single-stranded nick in either sequence (or in the sense or antisense strand) is not counted as mismatch. Thus, as a non-limiting example, no mismatch would be counted if one sequence comprises the sequence AG, but the other sequence comprises the sequence AG with a single-stranded nick between the A and the G. A base modification is also not considered a mismatch. Thus, if one sequence comprises a C, and the other sequence comprises a modified C (e.g., 2'-modification) at the same position, no mismatch would be counted.

Neither a 5'-endcap nor a 3' end cap is considered in counting mismatches. Thus a first duplex which identical in sequence to a second duplex has zero mismatches, even if one duplex had an end cap (e.g., a 3' end cap) and the other duplex did not or had a different endcap, or had the same endcap in a different location.

Various embodiments are further delineated below.

The disclosure encompasses:

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_175_A22_S26, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_175_A25_S27, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_175_A81_S26, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_175_A48_S26, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_175_A82_S36, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_175_A83_S36, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_175_A84_S36, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_517_A22_S26, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_517_A25_S27, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_517_A81_S26, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_517_A48_S26, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_517_A82_S36, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_517_A83_S36, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_517_A84_S36, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_562_A22_S26, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_562_A25_S27, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_562_A81_S26, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_562_A48_S26, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_562_A82_S36, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_562_A83_S36, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_562_A84_S36, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_751_A22_S26, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_751_A25_S27, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_751_A81_S26, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_751_A48_S26, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_751_A82_S36, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_751_A83_S36, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_751_A84_S36, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_755_A22_S26, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_755_A25_S27, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_755_A81_S26, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_755_A48_S26, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_755_A82_S36, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_755_A83_S36, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_755_A84_S36, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_846_A22_S26, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_846_A25_S27, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_846_A81_S26, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_846_A48_S26, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_846_A82_S36, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_846_A83_S36, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_846_A84_S36, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_1360_A22_S26, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_1360_A25_S27, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_1360_A81_S26, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_1360_A48_S26, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_1360_A82_S36, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_1360_A83_S36, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_1360_A84_S36, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_2030_A22_S26, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_2030_A25_S27, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_2030_A81_S26, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_2030_A48_S26, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_2030_A82_S36, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_2030_A83_S36, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_2030_A84_S36, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_2034_A22_S26, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_2034_A25_S27, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_2034_A81_S26, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_2034_A48_S26, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_2034_A82_S36, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_2034_A83_S36, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_2034_A84_S36, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_2138_A22_S26, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_2138_A25_S27, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_2138_A81_S26, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_2138_A48_S26, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_2138_A82_S36, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_2138_A83_S36, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_2138_A84_S36, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_2153_A22_S26, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_2153_A25_S27, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_2153_A81_S26, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_2153_A48_S26, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_2153_A82_S36, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_2153_A83_S36, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_2153_A84_S36, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_2154_A22_S26, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_2154_A25_S27, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_2154_A81_S26, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_2154_A48_S26, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_2154_A82_S36, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_2154_A83_S36, or a modified or unmodified variant thereof.

An RNAi agent comprising a first and a second strand, wherein the first strand comprises at least 15 contiguous nucleotides differing by 0, 1, 2, or 3 nt from a first strand, and the second strand comprises at least 15 contiguous nucleotides differing by 0, 1, 2, or 3 nt from the second strand of: hs_HSF1_2154_A84_S36, or a modified or unmodified variant thereof.

In various embodiments wherein a RNAi agent is said to comprise a first strand and/or a second strand comprising a particular sequence (or a portion thereof which is least 15 contiguous nucleotides differing by 0, 1, 2, or 3 nt), it is meant that the cited strand can be longer than the referenced sequence, for example, it can be up to about 30 nucleotides in length, or further comprise any number of nucleotides, e.g., 1, 2, 3, 4, 5, 6, 7, 8, 9, 10, etc.

Additional Particular Specific Embodiments

In various embodiments, the disclosure comprises a RNAi agent comprising a sense and an antisense strand, wherein the antisense strand comprises at least 15 contiguous nucleotides differing by 0, 1, 2, or 3 nt from the antisense strand of any RNAi agent disclosed herein.

Thus, in various embodiments the disclosure encompasses:

An RNAi agent comprising a sense and an antisense strand, wherein the antisense strand comprises at least 15 contiguous nucleotides differing by 0, 1, 2, or 3 nt from the antisense strand of: hs_HSF1_175_A22_S26, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_175_A25_S27, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_175_A81_S26, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_175_A48_S26, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_175_A82_S36, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_175_A83_S36, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_175_A84_S36, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_517_A22_S26, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_517_A25_S27, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_517_A81_S26, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_517_A48_S26, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_517_A82_S36, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_517_A83_S36, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_517_A84_S36, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_562_A22_S26, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_562_A25_S27, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_562_A81_S26, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_562_A48_S26, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_562_A82_S36, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_562_A83_S36, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_562_A84 S36, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_751_A22_S26, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_751_A25_S27, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_751_A81_S26, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_751_A48_S26, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_751_A82_S36, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_751_A83_S36, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_751_A84_S36, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_755_A22_S26, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_755_A25_S27, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_755_A81_S26, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_755_A48_S26, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_755_A82_S36, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_755_A83_S36, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_755_A84_S36, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_846_A22_S26, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_846_A25_S27, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_846_A81_S26, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_846_A48_S26, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_846_A82_S36, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_846_A83_S36, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_846_A84_S36, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_1360_A22_S26, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_1360_A25_S27, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_1360_A81_S26, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_1360_A48_S26, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_1360_A82_S36, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_1360_A83_S36, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_1360_A84 S36, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_2030_A22_S26, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_2030_A25_S27, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_2030_A81_S26, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_2030_A48_S26, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_2030_A82_S36, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_2030_A83_S36, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_2030_A84_S36, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_2034_A22_S26, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_2034_A25_S27, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_2034_A81_S26, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_2034_A48_S26, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_2034_A82_S36, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_2034_A83_S36, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_2034_A84_S36, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_2138_A22_S26, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_2138_A25_S27, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_2138_A81_S26, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_2138_A48_S26, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_2138_A82_S36, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_2138_A83_S36, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_2138_A84_S36, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_2153_A22_S26, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_2153_A25_S27, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_2153_A81_S26, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_2153_A48_S26, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_2153_A82_S36, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_2153_A83_S36, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_2153_A84_S36, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_2154_A22_S26, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_2154_A25_S27, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_2154_A81_S26, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_2154_A48_S26, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_2154_A82_S36, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_2154_A83_S36, or a modified or unmodified variant thereof.

An RNAi agent comprising a sense and an antisense strand, wherein the antisense strand comprises at least 15 contiguous nucleotides differing by 0, 1, 2, or 3 nt from the antisense strand of: hs_HSF1_2154_A84 S36, or a modified or unmodified variant thereof.

In various embodiments wherein a RNAi agent is said to comprise a first strand and/or a second strand comprising a particular sequence (or a portion thereof which is least 15 contiguous nucleotides differing by 0, 1, 2, or 3 nt), it is meant that the cited strand can be longer than the referenced sequence, for example, it can be up to about 30 nucleotides in length, or further comprise any number of nucleotides, e.g., about 1, 2, 3, 4, 5, 6, 7, 8, 9, 10, etc.

Additional Particular Embodiments

In various embodiments, the disclosure comprises a RNAi agent comprising a sense and an antisense strand, wherein the antisense strand comprises or consists of the antisense strand of any RNAi agent disclosed herein.

Thus, the following are provided as examples of the various embodiments.

The disclosure encompasses:

An RNAi agent comprising a sense and an antisense strand, wherein the sequence of the antisense strand comprises or consists of the sequence of the antisense strand of: hs_HSF1_175_A22_S26, or a modified or unmodified variant thereof.

An RNAi agent comprising a sense and an antisense strand, wherein the sequence of the antisense strand comprises or consists of the sequence of the antisense strand of hs_HSF1_175_A25_S27, or a modified or unmodified variant thereof.

An RNAi agent comprising a sense and an antisense strand, wherein the sequence of the antisense strand comprises or consists of the sequence of the antisense strand of: hs_HSF1_175_A81_S26, or a modified or unmodified variant thereof.

An RNAi agent comprising a sense and an antisense strand, wherein the sequence of the antisense strand comprises or consists of the sequence of the antisense strand of: hs_HSF1_175_A48_S26, or a modified or unmodified variant thereof.

An RNAi agent comprising a sense and an antisense strand, wherein the sequence of the antisense strand comprises or consists of the sequence of the antisense strand of: hs_HSF1_175_A82_S36, or a modified or unmodified variant thereof.

An RNAi agent comprising a sense and an antisense strand, wherein the sequence of the antisense strand comprises or consists of the sequence of the antisense strand of: hs_HSF1_175_A83_S36, or a modified or unmodified variant thereof.

An RNAi agent comprising a sense and an antisense strand, wherein the sequence of the antisense strand comprises or consists of the sequence of the antisense strand of: hs_HSF1_175_A84_S36, or a modified or unmodified variant thereof.

An RNAi agent comprising a sense and an antisense strand, wherein the sequence of the antisense strand comprises or consists of the sequence of the antisense strand of: hs_HSF1_517_A22_S26, or a modified or unmodified variant thereof.

An RNAi agent comprising a sense and an antisense strand, wherein the sequence of the antisense strand comprises or consists of the sequence of the antisense strand of: hs_HSF1_517_A25_S27, or a modified or unmodified variant thereof.

An RNAi agent comprising a sense and an antisense strand, wherein the sequence of the antisense strand comprises or consists of the sequence of the antisense strand of: hs_HSF1_517_A81_S26, or a modified or unmodified variant thereof.

An RNAi agent comprising a sense and an antisense strand, wherein the sequence of the antisense strand comprises or consists of the sequence of the antisense strand of: hs_HSF1_517_A48_S26, or a modified or unmodified variant thereof.

An RNAi agent comprising a sense and an antisense strand, wherein the sequence of the antisense strand comprises or consists of the sequence of the antisense strand of: hs_HSF1_517_A82_S36, or a modified or unmodified variant thereof.

An RNAi agent comprising a sense and an antisense strand, wherein the sequence of the antisense strand comprises or consists of the sequence of the antisense strand of: hs_HSF1_517_A83_S36, or a modified or unmodified variant thereof.

An RNAi agent comprising a sense and an antisense strand, wherein the sequence of the antisense strand comprises or consists of the sequence of the antisense strand of hs_HSF1_517_A84_S36, or a modified or unmodified variant thereof.

An RNAi agent comprising a sense and an antisense strand, wherein the sequence of the antisense strand comprises or consists of the sequence of the antisense strand of: hs_HSF1_562_A22_S26, or a modified or unmodified variant thereof.

An RNAi agent comprising a sense and an antisense strand, wherein the sequence of the antisense strand comprises or consists of the sequence of the antisense strand of: hs_HSF1_562_A25_S27, or a modified or unmodified variant thereof.

An RNAi agent comprising a sense and an antisense strand, wherein the sequence of the antisense strand comprises or consists of the sequence of the antisense strand of: hs_HSF1_562_A81_S26, or a modified or unmodified variant thereof.

An RNAi agent comprising a sense and an antisense strand, wherein the sequence of the antisense strand comprises or consists of the sequence of the antisense strand of: hs_HSF1_562_A48_S26, or a modified or unmodified variant thereof.

An RNAi agent comprising a sense and an antisense strand, wherein the sequence of the antisense strand comprises or consists of the sequence of the antisense strand of: hs_HSF1_562_A82_S36, or a modified or unmodified variant thereof.

An RNAi agent comprising a sense and an antisense strand, wherein the sequence of the antisense strand comprises or consists of the sequence of the antisense strand of: hs_HSF1_562_A83_S36, or a modified or unmodified variant thereof.

An RNAi agent comprising a sense and an antisense strand, wherein the sequence of the antisense strand comprises or consists of the sequence of the antisense strand of: hs_HSF1_562_A84_S36, or a modified or unmodified variant thereof.

An RNAi agent comprising a sense and an antisense strand, wherein the sequence of the antisense strand comprises or consists of the sequence of the antisense strand of: hs_HSF1_751_A22_S26, or a modified or unmodified variant thereof.

An RNAi agent comprising a sense and an antisense strand, wherein the sequence of the antisense strand comprises or consists of the sequence of the antisense strand of: hs_HSF1_751_A25_S27, or a modified or unmodified variant thereof.

An RNAi agent comprising a sense and an antisense strand, wherein the sequence of the antisense strand comprises or consists of the sequence of the antisense strand of: hs_HSF1_751_A81_S26, or a modified or unmodified variant thereof.

An RNAi agent comprising a sense and an antisense strand, wherein the sequence of the antisense strand comprises or consists of the sequence of the antisense strand of: hs_HSF1_751_A48_S26, or a modified or unmodified variant thereof.

An RNAi agent comprising a sense and an antisense strand, wherein the sequence of the antisense strand comprises or consists of the sequence of the antisense strand of hs_HSF1_751_A82_S36, or a modified or unmodified variant thereof.

An RNAi agent comprising a sense and an antisense strand, wherein the sequence of the antisense strand comprises or consists of the sequence of the antisense strand of: hs_HSF1_751_A83_S36, or a modified or unmodified variant thereof.

An RNAi agent comprising a sense and an antisense strand, wherein the sequence of the antisense strand comprises or consists of the sequence of the antisense strand of: hs_HSF1_751_A84_S36, or a modified or unmodified variant thereof.

An RNAi agent comprising a sense and an antisense strand, wherein the sequence of the antisense strand comprises or consists of the sequence of the antisense strand of: hs_HSF1_755_A22_S26, or a modified or unmodified variant thereof.

An RNAi agent comprising a sense and an antisense strand, wherein the sequence of the antisense strand comprises or consists of the sequence of the antisense strand of: hs_HSF1_755_A25_S27, or a modified or unmodified variant thereof.

An RNAi agent comprising a sense and an antisense strand, wherein the sequence of the antisense strand comprises or consists of the sequence of the antisense strand of: hs_HSF1_755_A81_S26, or a modified or unmodified variant thereof.

An RNAi agent comprising a sense and an antisense strand, wherein the sequence of the antisense strand comprises or consists of the sequence of the antisense strand of: hs_HSF1_755_A48_S26, or a modified or unmodified variant thereof.

An RNAi agent comprising a sense and an antisense strand, wherein the sequence of the antisense strand comprises or consists of the sequence of the antisense strand of: hs_HSF1_755_A82_S36, or a modified or unmodified variant thereof.

An RNAi agent comprising a sense and an antisense strand, wherein the sequence of the antisense strand comprises or consists of the sequence of the antisense strand of: hs_HSF1_755_A83_S36, or a modified or unmodified variant thereof.

An RNAi agent comprising a sense and an antisense strand, wherein the sequence of the antisense strand comprises or consists of the sequence of the antisense strand of: hs_HSF1_755_A84_S36, or a modified or unmodified variant thereof.

An RNAi agent comprising a sense and an antisense strand, wherein the sequence of the antisense strand comprises or consists of the sequence of the antisense strand of: hs_HSF1_846_A22_S26, or a modified or unmodified variant thereof.

An RNAi agent comprising a sense and an antisense strand, wherein the sequence of the antisense strand comprises or consists of the sequence of the antisense strand of: hs_HSF1_846_A25_S27, or a modified or unmodified variant thereof.

An RNAi agent comprising a sense and an antisense strand, wherein the sequence of the antisense strand comprises or consists of the sequence of the antisense strand of hs_HSF1_846_A81_S26, or a modified or unmodified variant thereof.

An RNAi agent comprising a sense and an antisense strand, wherein the sequence of the antisense strand comprises or consists of the sequence of the antisense strand of: hs_HSF1_846_A48_S26, or a modified or unmodified variant thereof.

An RNAi agent comprising a sense and an antisense strand, wherein the sequence of the antisense strand comprises or consists of the sequence of the antisense strand of: hs_HSF1_846_A82_S36, or a modified or unmodified variant thereof.

An RNAi agent comprising a sense and an antisense strand, wherein the sequence of the antisense strand comprises or consists of the sequence of the antisense strand of: hs_HSF1_846_A83_S36, or a modified or unmodified variant thereof.

An RNAi agent comprising a sense and an antisense strand, wherein the sequence of the antisense strand comprises or consists of the sequence of the antisense strand of: hs_HSF1_846_A84_S36, or a modified or unmodified variant thereof.

An RNAi agent comprising a sense and an antisense strand, wherein the sequence of the antisense strand comprises or consists of the sequence of the antisense strand of: hs_HSF1_1360_A22_S26, or a modified or unmodified variant thereof.

An RNAi agent comprising a sense and an antisense strand, wherein the sequence of the antisense strand comprises or consists of the sequence of the antisense strand of: hs_HSF1_1360_A25_S27, or a modified or unmodified variant thereof.

An RNAi agent comprising a sense and an antisense strand, wherein the sequence of the antisense strand comprises or consists of the sequence of the antisense strand of: hs_HSF1_1360_A81_S26, or a modified or unmodified variant thereof.

An RNAi agent comprising a sense and an antisense strand, wherein the sequence of the antisense strand comprises or consists of the sequence of the antisense strand of: hs_HSF1_1360_A48_S26, or a modified or unmodified variant thereof.

An RNAi agent comprising a sense and an antisense strand, wherein the sequence of the antisense strand comprises or consists of the sequence of the antisense strand of: hs_HSF1_1360_A82_S36, or a modified or unmodified variant thereof.

An RNAi agent comprising a sense and an antisense strand, wherein the sequence of the antisense strand comprises or consists of the sequence of the antisense strand of: hs_HSF1_1360_A83_S36, or a modified or unmodified variant thereof.

An RNAi agent comprising a sense and an antisense strand, wherein the sequence of the antisense strand comprises or consists of the sequence of the antisense strand of: hs_HSF1_1360_A84 S36, or a modified or unmodified variant thereof.

An RNAi agent comprising a sense and an antisense strand, wherein the sequence of the antisense strand comprises or consists of the sequence of the antisense strand of hs_HSF1_2030_A22_S26, or a modified or unmodified variant thereof.

An RNAi agent comprising a sense and an antisense strand, wherein the sequence of the antisense strand comprises or consists of the sequence of the antisense strand of: hs_HSF1_2030_A25_S27, or a modified or unmodified variant thereof.

An RNAi agent comprising a sense and an antisense strand, wherein the sequence of the antisense strand comprises or consists of the sequence of the antisense strand of: hs_HSF1_2030_A81_S26, or a modified or unmodified variant thereof.

An RNAi agent comprising a sense and an antisense strand, wherein the sequence of the antisense strand comprises or consists of the sequence of the antisense strand of: hs_HSF1_2030_A48_S26, or a modified or unmodified variant thereof.

An RNAi agent comprising a sense and an antisense strand, wherein the sequence of the antisense strand comprises or consists of the sequence of the antisense strand of: hs_HSF1_2030_A82_S36, or a modified or unmodified variant thereof.

An RNAi agent comprising a sense and an antisense strand, wherein the sequence of the antisense strand comprises or consists of the sequence of the antisense strand of: hs_HSF1_2030_A83_S36, or a modified or unmodified variant thereof.

An RNAi agent comprising a sense and an antisense strand, wherein the sequence of the antisense strand comprises or consists of the sequence of the antisense strand of: hs_HSF1_2030_A84_S36, or a modified or unmodified variant thereof.

An RNAi agent comprising a sense and an antisense strand, wherein the sequence of the antisense strand comprises or consists of the sequence of the antisense strand of: hs_HSF1_2034_A22_S26, or a modified or unmodified variant thereof.

An RNAi agent comprising a sense and an antisense strand, wherein the sequence of the antisense strand comprises or consists of the sequence of the antisense strand of: hs_HSF1_2034_A25_S27, or a modified or unmodified variant thereof.

An RNAi agent comprising a sense and an antisense strand, wherein the sequence of the antisense strand comprises or consists of the sequence of the antisense strand of: hs_HSF1_2034_A81_S26, or a modified or unmodified variant thereof.

An RNAi agent comprising a sense and an antisense strand, wherein the sequence of the antisense strand comprises or consists of the sequence of the antisense strand of: hs_HSF1_2034_A48_S26, or a modified or unmodified variant thereof.

An RNAi agent comprising a sense and an antisense strand, wherein the sequence of the antisense strand comprises or consists of the sequence of the antisense strand of: hs_HSF1_2034_A82_S36, or a modified or unmodified variant thereof.

An RNAi agent comprising a sense and an antisense strand, wherein the sequence of the antisense strand comprises or consists of the sequence of the antisense strand of hs_HSF1_2034_A83_S36, or a modified or unmodified variant thereof.

An RNAi agent comprising a sense and an antisense strand, wherein the sequence of the antisense strand comprises or consists of the sequence of the antisense strand of: hs_HSF1_2034_A84_S36, or a modified or unmodified variant thereof.

An RNAi agent comprising a sense and an antisense strand, wherein the sequence of the antisense strand comprises or consists of the sequence of the antisense strand of: hs_HSF1_2138_A22_S26, or a modified or unmodified variant thereof.

An RNAi agent comprising a sense and an antisense strand, wherein the sequence of the antisense strand comprises or consists of the sequence of the antisense strand of: hs_HSF1_2138_A25_S27, or a modified or unmodified variant thereof.

An RNAi agent comprising a sense and an antisense strand, wherein the sequence of the antisense strand comprises or consists of the sequence of the antisense strand of: hs_HSF1_2138_A81_S26, or a modified or unmodified variant thereof.

An RNAi agent comprising a sense and an antisense strand, wherein the sequence of the antisense strand comprises or consists of the sequence of the antisense strand of: hs_HSF1_2138_A48_S26, or a modified or unmodified variant thereof.

An RNAi agent comprising a sense and an antisense strand, wherein the sequence of the antisense strand comprises or consists of the sequence of the antisense strand of: hs_HSF1_2138_A82_S36, or a modified or unmodified variant thereof.

An RNAi agent comprising a sense and an antisense strand, wherein the sequence of the antisense strand comprises or consists of the sequence of the antisense strand of: hs_HSF1_2138_A83_S36, or a modified or unmodified variant thereof.

An RNAi agent comprising a sense and an antisense strand, wherein the sequence of the antisense strand comprises or consists of the sequence of the antisense strand of: hs_HSF1_2138_A84_S36, or a modified or unmodified variant thereof.

An RNAi agent comprising a sense and an antisense strand, wherein the sequence of the antisense strand comprises or consists of the sequence of the antisense strand of: hs_HSF1_2153_A22_S26, or a modified or unmodified variant thereof.

An RNAi agent comprising a sense and an antisense strand, wherein the sequence of the antisense strand comprises or consists of the sequence of the antisense strand of: hs_HSF1_2153_A25_S27, or a modified or unmodified variant thereof.

An RNAi agent comprising a sense and an antisense strand, wherein the sequence of the antisense strand comprises or consists of the sequence of the antisense strand of: hs_HSF1_2153_A81_S26, or a modified or unmodified variant thereof.

An RNAi agent comprising a sense and an antisense strand, wherein the sequence of the antisense strand comprises or consists of the sequence of the antisense strand of hs_HSF1_2153_A48_S26, or a modified or unmodified variant thereof.

An RNAi agent comprising a sense and an antisense strand, wherein the sequence of the antisense strand comprises or consists of the sequence of the antisense strand of: hs_HSF1_2153_A82_S36, or a modified or unmodified variant thereof.

An RNAi agent comprising a sense and an antisense strand, wherein the sequence of the antisense strand comprises or consists of the sequence of the antisense strand of: hs_HSF1_2153_A83_S36, or a modified or unmodified variant thereof.

An RNAi agent comprising a sense and an antisense strand, wherein the sequence of the antisense strand comprises or consists of the sequence of the antisense strand of: hs_HSF1_2153_A84_S36, or a modified or unmodified variant thereof.

An RNAi agent comprising a sense and an antisense strand, wherein the sequence of the antisense strand comprises or consists of the sequence of the antisense strand of: hs_HSF1_2154_A22_S26, or a modified or unmodified variant thereof.

An RNAi agent comprising a sense and an antisense strand, wherein the sequence of the antisense strand comprises or consists of the sequence of the antisense strand of: hs_HSF1_2154_A25_S27, or a modified or unmodified variant thereof.

An RNAi agent comprising a sense and an antisense strand, wherein the sequence of the antisense strand comprises or consists of the sequence of the antisense strand of: hs_HSF1_2154_A81_S26, or a modified or unmodified variant thereof.

An RNAi agent comprising a sense and an antisense strand, wherein the sequence of the antisense strand comprises or consists of the sequence of the antisense strand of: hs_HSF1_2154_A48_S26, or a modified or unmodified variant thereof.

An RNAi agent comprising a sense and an antisense strand, wherein the sequence of the antisense strand comprises or consists of the sequence of the antisense strand of: hs_HSF1_2154_A82_S36, or a modified or unmodified variant thereof.

An RNAi agent comprising a sense and an antisense strand, wherein the sequence of the antisense strand comprises or consists of the sequence of the antisense strand of: hs_HSF1_2154_A83_S36, or a modified or unmodified variant thereof.

An RNAi agent comprising a sense and an antisense strand, wherein the sequence of the antisense strand comprises or consists of the sequence of the antisense strand of: hs_HSF1_2154_A84_S36, or a modified or unmodified variant thereof.

In various embodiments, the disclosure comprises a RNAi agent comprising a sense and an antisense strand, wherein the antisense strand comprises at least 15 contiguous nucleotides differing by 0, 1, 2, or 3 nt from the antisense strand of any RNAi agent disclosed herein, or modified or unmodified variants thereof, wherein the antisense strand optionally further comprises about 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_175_A22_S26 (SEQ ID NOs: 180 and 264; or SEQ ID NOs: 348 and 432), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_175_A25_S27 (SEQ ID NOs: 192 and 276; or SEQ ID NOs: 360 and 444), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_175_A81_S26 (SEQ ID NOs: 204 and 288; or SEQ ID NOs: 372 and 456), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_175_A48_S26 (SEQ ID NOs: 216 and 300; or SEQ ID NOs: 384 and 468), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_175_A82_S36 (SEQ ID NOs: 228 and 312; or SEQ ID NOs: 396 and 480), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_175_A83_S36 (SEQ ID NOs: 240 and 324; or SEQ ID NOs: 408 and 492), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_175_A84_S36 (SEQ ID NOs: 252 and 336; or SEQ ID NOs: 420 and 504), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_517_A22_S26 (SEQ ID NOs: 172 and 256; or SEQ ID NOs: 340 and 424), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_517_A25_S27 (SEQ ID NOs: 184 and 268; or SEQ ID NOs: 352 and 436), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_517_A81_S26 (SEQ ID NOs: 196 and 280; or SEQ ID NOs: 364 and 448), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_517_A48_S26 (SEQ ID NOs: 208 and 292; or SEQ ID NOs: 376 and 460), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_517_A82_S36 (SEQ ID NOs: 220 and 304; or SEQ ID NOs: 388 and 472), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_517_A83_S36 (SEQ ID NOs: 232 and 316; or SEQ ID NOs: 400 and 484), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_517_A84_S36 (SEQ ID NOs: 244 and 328; or SEQ ID NOs: 412 and 496), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_562_A22_S26 (SEQ ID NOs: 169 and 253; or SEQ ID NOs: 337 and 421), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_562_A25_S27 (SEQ ID NOs: 181 and 265; or SEQ ID NOs: 349 and 433), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_562_A81_S26 (SEQ ID NOs: 193 and 277; or SEQ ID NOs: 361 and 445), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_562_A48_S26 (SEQ ID NOs:

205 and 289; or SEQ ID NOs: 373 and 457), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_562_A82_S36 (SEQ ID NOs: 217 and 301; or SEQ ID NOs: 385 and 469), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_562_A83_S36 (SEQ ID NOs: 229 and 313; or SEQ ID NOs: 397 and 481), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_562_A84_S36 (SEQ ID NOs: 241 and 325; or SEQ ID NOs: 409 and 493), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_751_A22_S26 (SEQ ID NOs: 170 and 254; or SEQ ID NOs: 338 and 422), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_751_A25_S27 (SEQ ID NOs: 182 and 266; or SEQ ID NOs: 350 and 434), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_751_A81_S26 (SEQ ID NOs: 194 and 278; or SEQ ID NOs: 362 and 446), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_751_A48_S26 (SEQ ID NOs: 206 and 290; or SEQ ID NOs: 374 and 458), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_751_A82_S36 (SEQ ID NOs: 218 and 302; or SEQ ID NOs: 386 and 470), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_751_A83_S36 (SEQ ID NOs: 230 and 314; or SEQ ID NOs: 398 and 482), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_751_A84_S36 (SEQ ID NOs: 242 and 326; or SEQ ID NOs: 410 and 494), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_755_A22_S26 (SEQ ID NOs: 171 and 255; or SEQ ID NOs: 339 and 423), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_755_A25_S27 (SEQ ID NOs: 183 and 267; or SEQ ID NOs: 351 and 435), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_755_A81_S26 (SEQ ID NOs: 195 and 279; or SEQ ID NOs: 363 and 447), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_755_A48_S26 (SEQ ID NOs: 207 and 291; or SEQ ID NOs: 375 and 459), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_755_A82_S36 (SEQ ID NOs: 219 and 303; or SEQ ID NOs: 387 and 471), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_755_A83_S36 (SEQ ID NOs: 231 and 315; or SEQ ID NOs: 399 and 483), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_755_A84_S36 (SEQ ID NOs: 243 and 327; or SEQ ID NOs: 411 and 495), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_846_A22_S26 (SEQ ID NOs: 173 and 257; or SEQ ID NOs: 341 and 425), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_846_A25_S27 (SEQ ID NOs: 185 and 269; or SEQ ID NOs: 353 and 437), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_846_A81_S26 (SEQ ID NOs: 197 and 281; or SEQ ID NOs: 365 and 449), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_846_A48_S26 (SEQ ID NOs: 209 and 293; or SEQ ID NOs: 377 and 461), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_846_A82_S36 (SEQ ID NOs: 221 and 305; or SEQ ID NOs: 389 and 473), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_846_A83_S36 (SEQ ID NOs: 233 and 317; or SEQ ID NOs: 401 and 485), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_846_A84_S36 (SEQ ID NOs: 245 and 329; or SEQ ID NOs: 413 and 497), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_1360_A22_S26 (SEQ ID NOs: 174 and 258; or SEQ ID NOs: 342 and 426), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_1360_A25_S27 (SEQ ID NOs: 186 and 270; or SEQ ID NOs: 354 and 438), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_1360_A81_S26 (SEQ ID NOs: 198 and 282; or SEQ ID NOs: 366 and 450), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_1360_A48_S26 (SEQ ID NOs: 210 and 294; or SEQ ID NOs: 378 and 462), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_1360_A82_S36 (SEQ ID NOs: 222 and 306; or SEQ ID NOs: 390 and 474), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_1360_A83_S36 (SEQ ID NOs: 234 and 318; or SEQ ID NOs: 402 and 486), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_1360_A84_S36 (SEQ ID NOs: 246 and 330; or SEQ ID NOs: 414 and 498), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_2030_A22_S26 (SEQ ID NOs: 175 and 259; or SEQ ID NOs: 343 and 427), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_2030_A25_S27 (SEQ ID NOs: 187 and 271; or SEQ ID NOs: 355 and 439), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_2030_A81_S26 (SEQ ID NOs: 199 and 283; or SEQ ID NOs: 367 and 451), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_2030_A48_S26 (SEQ ID NOs: 211 and 295; or SEQ ID NOs: 379 and 463), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_2030_A82_S36 (SEQ ID NOs: 223 and 307; or SEQ ID NOs: 391 and 475), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_2030_A83_S36 (SEQ ID NOs: 235 and 319; or SEQ ID NOs: 403 and 487), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_2030_A84_S36 (SEQ ID NOs: 247 and 331; or SEQ ID NOs: 415 and 499), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_2034_A22_S26 (SEQ ID NOs: 176 and 260; or SEQ ID NOs: 344 and 428), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_2034_A25_S27 (SEQ ID NOs: 188 and 272; or SEQ ID NOs: 356 and 440), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_2034_A81_S26 (SEQ ID NOs: 200 and 284; or SEQ ID NOs: 368 and 452), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_2034_A48_S26 (SEQ ID NOs: 212 and 296; or SEQ ID NOs: 380 and 464), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_2034_A82_S36 (SEQ ID NOs: 224 and 308; or SEQ ID NOs: 392 and 476), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_2034_A83_S36 (SEQ ID NOs: 236 and 320; or SEQ ID NOs: 404 and 488), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_2034_A84_S36 (SEQ ID NOs: 248 and 332; or SEQ ID NOs: 416 and 500), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_2138_A22_S26 (SEQ ID NOs: 177 and 261; or SEQ ID NOs: 345 and 429), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_2138_A25_S27 (SEQ ID NOs: 189 and 273; or SEQ ID NOs: 357 and 441), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_2138_A81_S26 (SEQ ID NOs: 201 and 285; or SEQ ID NOs: 369 and 453), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_2138_A48_S26 (SEQ ID NOs: 213 and 297; or SEQ ID NOs: 381 and 465), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_2138_A82_S36 (SEQ ID NOs: 225 and 309; or SEQ ID NOs: 393 and 477), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_2138_A83_S36 (SEQ ID NOs: 237 and 321; or SEQ ID NOs: 405 and 489), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_2138_A84_S36 (SEQ ID NOs: 249 and 333; or SEQ ID NOs: 417 and 501), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_2153_A22_S26 (SEQ ID NOs: 178 and 262; or SEQ ID NOs: 346 and 430), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_2153_A25_S27 (SEQ ID NOs: 190 and 274; or SEQ ID NOs: 358 and 442), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_2153_A81_S26 (SEQ ID NOs: 202 and 286; or SEQ ID NOs: 370 and 454), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_2153_A48_S26 (SEQ ID NOs: 214 and 298; or SEQ ID NOs: 382 and 466), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_2153_A82_S36 (SEQ ID NOs: 226 and 310; or SEQ ID NOs: 394 and 478), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_2153_A83_S36 (SEQ ID NOs: 238 and 322; or SEQ ID NOs: 406 and 490), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_2153_A84_S36 (SEQ ID NOs: 250 and 334; or SEQ ID NOs: 418 and 502), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_2154_A22_S26 (SEQ ID NOs: 179 and 263; or SEQ ID NOs: 347 and 431), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_2154_A25_S27 (SEQ ID NOs: 191 and 275; or SEQ ID NOs: 359 and 443), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_2154_A81_S26 (SEQ ID NOs: 203 and 287; or SEQ ID NOs: 371 and 455), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_2154_A48_S26 (SEQ ID NOs: 215 and 299; or SEQ ID NOs: 383 and 467), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_2154_A82_S36 (SEQ ID NOs: 227 and 311; or SEQ ID NOs: 395 and 479), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_2154_A83_S36 (SEQ ID NOs: 239 and 323; or SEQ ID NOs: 407 and 491), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

An RNAi agent comprising a sense and an antisense strand, wherein the antisense strand comprises at least 15 contiguous nucleotides differing by 0, 1, 2, or 3 nt from the antisense strand of: hs_HSF1_2154_A84_S36 (SEQ ID NOs: 251 and 335; or SEQ ID NOs: 419 and 503), or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

In one embodiment, the disclosure comprises any one or more of the RNAi agent listed herein.

Additional Particular Specific Embodiments

Certain RNAi agents to HSF1 are disclosed in the scientific literature, e.g., in Rossi et al. 2006 Cancer Res. 66:7678-85; Dokladny et al. 2008 Am. J. Pathology 72:659-70; Jacobs et al. 2007 J. Biol. Chem. 282: 33412-20; Page et al. 2006 Mol. Biosystems 2:627-39; Zhao et al. 2007 Diabetes 56: 1436-1444; and Du et al. 2009 J. Cell. Phys. 218:631-637. The compositions of this disclosure do not cover these RNAi agents to the extent that they are identical in both sequence and modifications.

Other particular specific embodiments include compositions comprising 1, 2, 3, 4, or more of these RNAi agents. Another embodiment is a composition comprising any single RNAi agent, along with any other RNAi agents which overlap it. Another embodiment comprises two, three, four or more HSF1 RNAi agents which do not overlap and thus target different parts of the RNA molecule. When two or more RNAi agents are used, they can be administered simultaneously or sequentially.

Another particular specific embodiment comprises an RNAi agent, wherein the RNAi agent comprises a sense strand comprising at least 15 contiguous nucleotides (identical in sequence) to the sense strand of any of the listed RNAi agents, and an antisense strand comprising at least 15 contiguous nucleotides (identical in sequence) to the antisense strand of the same RNAi agent. In another embodiment, the composition comprises one, two, three, four, or more such RNAi agents.

In one embodiment, the composition comprises an RNAi agent which comprises an antisense strand comprising at least 15 contiguous nucleotides differing by 0, 1, 2 or 3 mismatches from the antisense strand of a RNAi agent described herein.

In one embodiment, the composition comprises an RNAi agent which comprises an antisense strand comprising at least 15 contiguous nucleotides differing by 0, 1, 2 or 3 mismatches from the antisense strand of a RNAi agent described herein.

In another embodiment, the composition comprises an RNAi agent which comprises a sense strand comprising at least 15 contiguous nucleotides differing by 0, 1, 2, or 3 mismatches from the sense strand of one of the listed RNAi agents, and an antisense strand comprising at least 15 contiguous nucleotides differing by 0, 1, 2 or 3 mismatches from the antisense strand of the same RNAi agent.

A "mismatch" is defined herein as a difference between the base sequence or length when two sequences are maximally aligned and compared. As a non-limiting example, a mismatch is counted if a difference exists between the base at a particular location in one sequence and the base at the corresponding position in another sequence (e.g., between the sequence of a given RNAi agent and an RNAi agent listed herein). Thus, a mismatch is counted, for example, if a position in one sequence has a particular base (e.g., A), and the corresponding position on the other sequence has a different base (e.g., G, C or U). A mismatch is also counted, e.g., if a position in one sequence has a base (e.g., A), and the corresponding position on the other sequence has no base (e.g., that position is an abasic nucleotide which comprises a phosphate-sugar backbone but no base). A single-stranded nick in either sequence (or in the sense or antisense strand) is not counted as mismatch. Thus, as a non-limiting example, no mismatch would be counted if one sequence comprises the sequence A-G, but the other sequence comprises the sequence A-G with a single-stranded nick between the A and the G. A base modification is also not considered a mismatch. If one sequence comprises a C, and the other sequence comprises a modified C (e.g., with a 2'-modification) at the same position, no mismatch would be counted. Thus, modifications of a nucleotide other than replacement or alteration of the base would not constitute a mismatch. For example, no mismatch would occur between a nucleotide which is A, and a nucleotide which is A with a 5' modification (e.g., those illustrated in FIG. 1) and/or a 2'-modification. The key feature of a mismatch (base replacement) is that it would not be able to base-pair with the corresponding base on the opposite strand. Thus, substitution of U with T would not constitute a mismatch. Substitution of a RNA nucleotide with a DNA would also not constitute a mismatch, provided that the base is not changed. In addition, terminal overhangs such as "TT" or "UU" or "dTdT" or "sdTsdT" are not counted when counting the number of mismatches; the terminal "UU" and "dTdT" overhangs are also not included when calculating "15 contiguous nucleotides." This is because Elbashir et al. 2001 Nature 411: 494-498 showed that a terminal dinucleotide, such as dithymidine, does not contribute to target recognition. In addition, terminal caps (e.g., a 5' or 3' end cap) are not considered in counting mismatches.

In these embodiments, a mismatch is defined as a position wherein the base of one sequence does not match the base of the other sequence.

In another embodiment, the composition comprises 1, 2, 3, 4, or more such RNAi agents.

In another embodiment, the composition comprises an RNAi agent which comprises a sense strand comprising at least 15 contiguous nucleotides differing by 0, 1, 2 or 3 mismatches from the sense strand of one of the listed RNAi agents, and an antisense strand comprising at least 15 contiguous nucleotides differing by 0, 1, 2 or 3 mismatches from the antisense strand of the same RNAi agent.

EXAMPLES

Example 1. Sequences of RNAi Agents to HSF1

Table A1, above, provides a list correlating the nickname of a RNAi agent to HSF1 to SEQ ID NOs. of the target sequence, and unmodified and modified variants. The actual sequences are provided below.

Table 1 provides the sequences of the target sequences (antisense and sense).

Table 2 provides example unmodified variants of the RNAi agents to HSF1 (antisense and sense).

Table 3 provides example modified variants of the RNAi agents to HSF1 (antisense and sense). Seven different chemical modification formats are presented for several nucleotide duplex sequences. For each of these, the prefix of the duplex nickname indicates the position (nt) in the HSF1 transcript. Thus, hs_HSF1_562_ begins at nt 562 of the HSF1 transcript. (Thus, all RNAI agents with the same prefix (e.g., hs_HSF1_562_) have the same nucleotide sequence despite differences in chemical modifications. The suffix (e.g., A22_S26) indicates a particular rule set used to design the set of chemical modifications.

Example 1A. HSF1 RNAi Agent Sequences and Target Sequences

Table 1. HSF1 RNAi Agent Target Sequences.

Provided are the nicknames of HSF1 RNAi agents, along with the Antisense (AS) and Sense (S) sequences to the target sequences (wherein each sequence nickname begins with hs_HSF1_*, where * is the nickname provided in each row; e.g., "175_A22_S26" is the same as "hs_HSF1_ 175_A22_S26", etc.). Note that the target sequences are presented as DNA (with DNA nucleotides and T instead of U). The corresponding RNAi agents would comprise the corresponding RNA sequence (with RNA nucleotides and U instead of T). The RNAi agents can, optionally, further comprise a terminal UU or TT on either or both strands, and can comprise modifications, as indicated below by example sets of modifications.

In various embodiments, the phraseology related to "an RNAi agent (with a sequence) of Table 1", "an RNAi agent comprising a first strand and a second strand, wherein the sequence of the first strand comprises (or is) the sequence of a strand of Table 1", and the like, indicate that a strand of the RNAi agent comprises (or has) a RNA sequence corresponding to a disclosed DNA sequence. For example, referring to Table 1, below, RNAi agent (duplex) 175_A22_S26 would comprise one strand having the RNA sequence of UCCAUCUCGAGCAAGGAGG (SEQ ID NO: 514) and one strand having the RNA sequence of CCUCCUUGCUCGAGAUGGA (SEQ ID NO: 515). Example RNAi agents corresponding to these target sequences are provided in Table 2.

TABLE 1

HSF1 RNAi Agent Target Sequences.

| Nickname | Original Antisense Sequence | SEQ ID NO: | Original Sense Sequence | SEQ ID NO: |
|---|---|---|---|---|
| 175_A22_S26 | TCCATCTCGAGCAAGGAGG | 12 | CCTCCTTGCTCGAGATGGA | 96 |
| 175_A25_S27 | TCCATCTCGAGCAAGGAGG | 24 | CCTCCTTGCTCGAGATGGA | 108 |
| 175_A81_S26 | TCCATCTCGAGCAAGGAGG | 36 | CCTCCTTGCTCGAGATGGA | 120 |
| 175_A48_S26 | TCCATCTCGAGCAAGGAGG | 48 | CCTCCTTGCTCGAGATGGA | 132 |
| 175_A82_S36 | TCCATCTCGAGCAAGGAGG | 60 | CCTCCTTGCTCGAGATGGA | 144 |
| 175_A83_S36 | TCCATCTCGAGCAAGGAGG | 72 | CCTCCTTGCTCGAGATGGA | 156 |

TABLE 1 -continued

HSF1 RNAi Agent Target Sequences.

| Nickname | Original Antisense Sequence | SEQ ID NO: | Original Sense Sequence | SEQ ID NO: |
|---|---|---|---|---|
| 175_A84_S36 | TCCATCTCGAGCAAGGAGG | 84 | CCTCCTTGCTCGAGATGGA | 168 |
| 517_A22_S26 | TTGATGTTCTCAAGGAGCT | 4 | AGCTCCTTGAGAACATCAA | 88 |
| 517_A25_S27 | TTGATGTTCTCAAGGAGCT | 16 | AGCTCCTTGAGAACATCAA | 100 |
| 517_A81_S26 | TTGATGTTCTCAAGGAGCT | 28 | AGCTCCTTGAGAACATCAA | 112 |
| 517_A48_S26 | TTGATGTTCTCAAGGAGCT | 40 | AGCTCCTTGAGAACATCAA | 124 |
| 517_A82_S36 | TTGATGTTCTCAAGGAGCT | 52 | AGCTCCTTGAGAACATCAA | 136 |
| 517_A83_S36 | TTGATGTTCTCAAGGAGCT | 64 | AGCTCCTTGAGAACATCAA | 148 |
| 517_A84_S36 | TTGATGTTCTCAAGGAGCT | 76 | AGCTCCTTGAGAACATCAA | 160 |
| 562_A22_S26 | TTTATGTCTTCACTCTTCA | 1 | TGAAGAGTGAAGACATAAA | 85 |
| 562_A25_S27 | TTTATGTCTTCACTCTTCA | 13 | TGAAGAGTGAAGACATAAA | 97 |
| 562_A81_S26 | TTTATGTCTTCACTCTTCA | 25 | TGAAGAGTGAAGACATAAA | 109 |
| 562_A48_S26 | TTTATGTCTTCACTCTTCA | 37 | TGAAGAGTGAAGACATAAA | 121 |
| 562_A82_S36 | TTTATGTCTTCACTCTTCA | 49 | TGAAGAGTGAAGACATAAA | 133 |
| 562_A83_S36 | TTTATGTCTTCACTCTTCA | 61 | TGAAGAGTGAAGACATAAA | 145 |
| 562_A84_S36 | TTTATGTCTTCACTCTTCA | 73 | TGAAGAGTGAAGACATAAA | 157 |
| 751_A22_S26 | ATCAGGAACTGAATGAGCT | 2 | AGCTCATTCAGTTCCTGAT | 86 |
| 751_A25_S27 | ATCAGGAACTGAATGAGCT | 14 | AGCTCATTCAGTTCCTGAT | 98 |
| 751_A81_S26 | ATCAGGAACTGAATGAGCT | 26 | AGCTCATTCAGTTCCTGAT | 110 |
| 751_A48_S26 | ATCAGGAACTGAATGAGCT | 38 | AGCTCATTCAGTTCCTGAT | 122 |
| 751_A82_S36 | ATCAGGAACTGAATGAGCT | 50 | AGCTCATTCAGTTCCTGAT | 134 |
| 751_A83_S36 | ATCAGGAACTGAATGAGCT | 62 | AGCTCATTCAGTTCCTGAT | 146 |
| 751_A84_S36 | ATCAGGAACTGAATGAGCT | 74 | AGCTCATTCAGTTCCTGAT | 158 |
| 755_A22_S26 | TGAGATCAGGAACTGAATG | 3 | CATTCAGTTCCTGATCTCA | 87 |
| 755_A25_S27 | TGAGATCAGGAACTGAATG | 15 | CATTCAGTTCCTGATCTCA | 99 |
| 755_A81_S26 | TGAGATCAGGAACTGAATG | 27 | CATTCAGTTCCTGATCTCA | 111 |
| 755_A48_S26 | TGAGATCAGGAACTGAATG | 39 | CATTCAGTTCCTGATCTCA | 123 |
| 755_A82_S36 | TGAGATCAGGAACTGAATG | 51 | CATTCAGTTCCTGATCTCA | 135 |
| 755_A83_S36 | TGAGATCAGGAACTGAATG | 63 | CATTCAGTTCCTGATCTCA | 147 |
| 755_A84_S36 | TGAGATCAGGAACTGAATG | 75 | CATTCAGTTCCTGATCTCA | 159 |
| 846_A22_S26 | TATACTTGGGCATGGAATG | 5 | CATTCCATGCCCAAGTATA | 89 |
| 846_A25_S27 | TATACTTGGGCATGGAATG | 17 | CATTCCATGCCCAAGTATA | 101 |
| 846_A81_S26 | TATACTTGGGCATGGAATG | 29 | CATTCCATGCCCAAGTATA | 113 |
| 846_A48_S26 | TATACTTGGGCATGGAATG | 41 | CATTCCATGCCCAAGTATA | 125 |
| 846_A82_S36 | TATACTTGGGCATGGAATG | 53 | CATTCCATGCCCAAGTATA | 137 |
| 846_A83_S36 | TATACTTGGGCATGGAATG | 65 | CATTCCATGCCCAAGTATA | 149 |
| 846_A84_S36 | TATACTTGGGCATGGAATG | 77 | CATTCCATGCCCAAGTATA | 161 |
| 1360_A22_S26 | TTATCCAGGTTGGAGTCCA | 6 | TGGACTCCAACCTGGATAA | 90 |
| 1360_A25_S27 | TTATCCAGGTTGGAGTCCA | 18 | TGGACTCCAACCTGGATAA | 102 |

TABLE 1 -continued

HSF1 RNAi Agent Target Sequences.

| Nickname | Original Antisense Sequence | SEQ ID NO: | Original Sense Sequence | SEQ ID NO: |
|---|---|---|---|---|
| 1360_A81_S26 | TTATCCAGGTTGGAGTCCA | 30 | TGGACTCCAACCTGGATAA | 114 |
| 1360_A48_S26 | TTATCCAGGTTGGAGTCCA | 42 | TGGACTCCAACCTGGATAA | 126 |
| 1360_A82_S36 | TTATCCAGGTTGGAGTCCA | 54 | TGGACTCCAACCTGGATAA | 138 |
| 1360_A83_S36 | TTATCCAGGTTGGAGTCCA | 66 | TGGACTCCAACCTGGATAA | 150 |
| 1360_A84_S36 | TTATCCAGGTTGGAGTCCA | 78 | TGGACTCCAACCTGGATAA | 162 |
| 2030_A22_S26 | ATTCTGACTATGAACAACC | 7 | GGTTGTTCATAGTCAGAAT | 91 |
| 2030_A25_S27 | ATTCTGACTATGAACAACC | 19 | GGTTGTTCATAGTCAGAAT | 103 |
| 2030_A81_S26 | ATTCTGACTATGAACAACC | 31 | GGTTGTTCATAGTCAGAAT | 115 |
| 2030_A48_S26 | ATTCTGACTATGAACAACC | 43 | GGTTGTTCATAGTCAGAAT | 127 |
| 2030_A82_S36 | ATTCTGACTATGAACAACC | 55 | GGTTGTTCATAGTCAGAAT | 139 |
| 2030_A83_S36 | ATTCTGACTATGAACAACC | 67 | GGTTGTTCATAGTCAGAAT | 151 |
| 2030_A84_S36 | ATTCTGACTATGAACAACC | 79 | GGTTGTTCATAGTCAGAAT | 163 |
| 2034_A22_S26 | TACAATTCTGACTATGAAC | 8 | GTTCATAGTCAGAATTGTA | 92 |
| 2034_A25_S27 | TACAATTCTGACTATGAAC | 20 | GTTCATAGTCAGAATTGTA | 104 |
| 2034_A81_S26 | TACAATTCTGACTATGAAC | 32 | GTTCATAGTCAGAATTGTA | 116 |
| 2034_A48_S26 | TACAATTCTGACTATGAAC | 44 | GTTCATAGTCAGAATTGTA | 128 |
| 2034_A82_S36 | TACAATTCTGACTATGAAC | 56 | GTTCATAGTCAGAATTGTA | 140 |
| 2034_A83_S36 | TACAATTCTGACTATGAAC | 68 | GTTCATAGTCAGAATTGTA | 152 |
| 2034_A84_S36 | TACAATTCTGACTATGAAC | 80 | GTTCATAGTCAGAATTGTA | 164 |
| 2138_A22_S26 | TCTGTTTATAGATCTCTGC | 9 | GCAGAGATCTATAAACAGA | 93 |
| 2138_A25_S27 | TCTGTTTATAGATCTCTGC | 21 | GCAGAGATCTATAAACAGA | 105 |
| 2138_A81_S26 | TCTGTTTATAGATCTCTGC | 33 | GCAGAGATCTATAAACAGA | 117 |
| 2138_A48_S26 | TCTGTTTATAGATCTCTGC | 45 | GCAGAGATCTATAAACAGA | 129 |
| 2138_A82_S36 | TCTGTTTATAGATCTCTGC | 57 | GCAGAGATCTATAAACAGA | 141 |
| 2138_A83_S36 | TCTGTTTATAGATCTCTGC | 69 | GCAGAGATCTATAAACAGA | 153 |
| 2138_A84_S36 | TCTGTTTATAGATCTCTGC | 81 | GCAGAGATCTATAAACAGA | 165 |
| 2153_A22_S26 | TTAGCATAGAGCCTGTCTG | 10 | CAGACAGGCTCTATGCTAA | 94 |
| 2153_A25_S27 | TTAGCATAGAGCCTGTCTG | 22 | CAGACAGGCTCTATGCTAA | 106 |
| 2153_A81_S26 | TTAGCATAGAGCCTGTCTG | 34 | CAGACAGGCTCTATGCTAA | 118 |
| 2153_A48_S26 | TTAGCATAGAGCCTGTCTG | 46 | CAGACAGGCTCTATGCTAA | 130 |
| 2153_A82_S36 | TTAGCATAGAGCCTGTCTG | 58 | CAGACAGGCTCTATGCTAA | 142 |
| 2153_A83_S36 | TTAGCATAGAGCCTGTCTG | 70 | CAGACAGGCTCTATGCTAA | 154 |
| 2153_A84_S36 | TTAGCATAGAGCCTGTCTG | 82 | CAGACAGGCTCTATGCTAA | 166 |
| 2154_A22_S26 | TTTAGCATAGAGCCTGTCT | 11 | AGACAGGCTCTATGCTAAA | 95 |
| 2154_A25_S27 | TTTAGCATAGAGCCTGTCT | 23 | AGACAGGCTCTATGCTAAA | 107 |
| 2154_A81_S26 | TTTAGCATAGAGCCTGTCT | 35 | AGACAGGCTCTATGCTAAA | 119 |
| 2154_A48_S26 | TTTAGCATAGAGCCTGTCT | 47 | AGACAGGCTCTATGCTAAA | 131 |
| 2154_A82_S36 | TTTAGCATAGAGCCTGTCT | 59 | AGACAGGCTCTATGCTAAA | 143 |

TABLE 1 -continued

HSF1 RNAi Agent Target Sequences.

| Nickname | Original Antisense Sequence | SEQ ID NO: | Original Sense Sequence | SEQ ID NO: |
|---|---|---|---|---|
| 2154_A83_S36 | TTTAGCATAGAGCCTGTCT | 71 | AGACAGGCTCTATGCTAAA | 155 |
| 2154_A84_S36 | TTTAGCATAGAGCCTGTCT | 83 | AGACAGGCTCTATGCTAAA | 167 |

Example 1B. HSF1 RNAi Agent Sequences.
(Unmodified)

TABLE 2

HSF1 RNAi Agent Sequences. (Example Unmodified)
Table 2. Unmodified variants

| Nickname | Original Antisense Sequence (Generic RNA View) | SEQ ID NO: | Original Sense Sequence (Generic RNA View) | SEQ ID NO: |
|---|---|---|---|---|
| 175_A22_S26 | UCCAUCUCGAGCAAGGAGG | 180 | CCUCCUUGCUCGAGAUGGA | 264 |
| 175_A25_S27 | UCCAUCUCGAGCAAGGAGG | 192 | CCUCCUUGCUCGAGAUGGA | 276 |
| 175_A81_S26 | UCCAUCUCGAGCAAGGAGG | 204 | CCUCCUUGCUCGAGAUGGA | 288 |
| 175_A48_S26 | UCCAUCUCGAGCAAGGAGG | 216 | CCUCCUUGCUCGAGAUGGA | 300 |
| 175_A82_S36 | UCCAUCUCGAGCAAGGAGG | 228 | CCUCCUUGCUCGAGAUGGA | 312 |
| 175_A83_S36 | UCCAUCUCGAGCAAGGAGG | 240 | CCUCCUUGCUCGAGAUGGA | 324 |
| 175_A84_S36 | UCCAUCUCGAGCAAGGAGG | 252 | CCUCCUUGCUCGAGAUGGA | 336 |
| 517_A22_S26 | UUGAUGUUCUCAAGGAGCU | 172 | AGCUCCUUGAGAACAUCAA | 256 |
| 517_A25_S27 | UUGAUGUUCUCAAGGAGCU | 184 | AGCUCCUUGAGAACAUCAA | 268 |
| 517_A81_S26 | UUGAUGUUCUCAAGGAGCU | 196 | AGCUCCUUGAGAACAUCAA | 280 |
| 517_A48_S26 | UUGAUGUUCUCAAGGAGCU | 208 | AGCUCCUUGAGAACAUCAA | 292 |
| 517_A82_S36 | UUGAUGUUCUCAAGGAGCU | 220 | AGCUCCUUGAGAACAUCAA | 304 |
| 517_A83_S36 | UUGAUGUUCUCAAGGAGCU | 232 | AGCUCCUUGAGAACAUCAA | 316 |
| 517_A84_S36 | UUGAUGUUCUCAAGGAGCU | 244 | AGCUCCUUGAGAACAUCAA | 328 |
| 562_A22_S26 | UUUAUGUCUUCACUCUUCA | 169 | UGAAGAGUGAAGACAUAAA | 253 |
| 562_A25_S27 | UUUAUGUCUUCACUCUUCA | 181 | UGAAGAGUGAAGACAUAAA | 265 |
| 562_A81_S26 | UUUAUGUCUUCACUCUUCA | 193 | UGAAGAGUGAAGACAUAAA | 277 |
| 562_A48_S26 | UUUAUGUCUUCACUCUUCA | 205 | UGAAGAGUGAAGACAUAAA | 289 |
| 562_A82_S36 | UUUAUGUCUUCACUCUUCA | 217 | UGAAGAGUGAAGACAUAAA | 301 |
| 562_A83_S36 | UUUAUGUCUUCACUCUUCA | 229 | UGAAGAGUGAAGACAUAAA | 313 |
| 562_A84_S36 | UUUAUGUCUUCACUCUUCA | 241 | UGAAGAGUGAAGACAUAAA | 325 |
| 751_A22_S26 | AUCAGGAACUGAAUGAGCU | 170 | AGCUCAUUCAGUUCCUGAU | 254 |
| 751_A25_S27 | AUCAGGAACUGAAUGAGCU | 182 | AGCUCAUUCAGUUCCUGAU | 266 |
| 751_A81_S26 | AUCAGGAACUGAAUGAGCU | 194 | AGCUCAUUCAGUUCCUGAU | 278 |
| 751_A48_S26 | AUCAGGAACUGAAUGAGCU | 206 | AGCUCAUUCAGUUCCUGAU | 290 |
| 751_A82_S36 | AUCAGGAACUGAAUGAGCU | 218 | AGCUCAUUCAGUUCCUGAU | 302 |
| 751_A83_S36 | AUCAGGAACUGAAUGAGCU | 230 | AGCUCAUUCAGUUCCUGAU | 314 |
| 751_A84_S36 | AUCAGGAACUGAAUGAGCU | 242 | AGCUCAUUCAGUUCCUGAU | 326 |

TABLE 2 -continued

HSF1 RNAi Agent Sequences. (Example Unmodified)
Table 2. Unmodified variants

| Nickname | Original Antisense Sequence (Generic RNA View) | SEQ ID NO: | Original Sense Sequence (Generic RNA View) | SEQ ID NO: |
| --- | --- | --- | --- | --- |
| 755_A22_S26 | UGAGAUCAGGAACUGAAUG | 171 | CAUUCAGUUCCUGAUCUCA | 255 |
| 755_A25_S27 | UGAGAUCAGGAACUGAAUG | 183 | CAUUCAGUUCCUGAUCUCA | 267 |
| 755_A81_S26 | UGAGAUCAGGAACUGAAUG | 195 | CAUUCAGUUCCUGAUCUCA | 279 |
| 755_A48_S26 | UGAGAUCAGGAACUGAAUG | 207 | CAUUCAGUUCCUGAUCUCA | 291 |
| 755_A82_S36 | UGAGAUCAGGAACUGAAUG | 219 | CAUUCAGUUCCUGAUCUCA | 303 |
| 755_A83_S36 | UGAGAUCAGGAACUGAAUG | 231 | CAUUCAGUUCCUGAUCUCA | 315 |
| 755_A84_S36 | UGAGAUCAGGAACUGAAUG | 243 | CAUUCAGUUCCUGAUCUCA | 327 |
| 846_A22_S26 | UAUACUUGGGCAUGGAAUG | 173 | CAUUCCAUGCCCAAGUAUA | 257 |
| 846_A25_S27 | UAUACUUGGGCAUGGAAUG | 185 | CAUUCCAUGCCCAAGUAUA | 269 |
| 846_A81_S26 | UAUACUUGGGCAUGGAAUG | 197 | CAUUCCAUGCCCAAGUAUA | 281 |
| 846_A48_S26 | UAUACUUGGGCAUGGAAUG | 209 | CAUUCCAUGCCCAAGUAUA | 293 |
| 846_A82_S36 | UAUACUUGGGCAUGGAAUG | 221 | CAUUCCAUGCCCAAGUAUA | 305 |
| 846_A83_S36 | UAUACUUGGGCAUGGAAUG | 233 | CAUUCCAUGCCCAAGUAUA | 317 |
| 846_A84_S36 | UAUACUUGGGCAUGGAAUG | 245 | CAUUCCAUGCCCAAGUAUA | 329 |
| 1360_A22_S26 | UUAUCCAGGUUGGAGUCCA | 174 | UGGACUCCAACCUGGAUAA | 258 |
| 1360_A25_S27 | UUAUCCAGGUUGGAGUCCA | 186 | UGGACUCCAACCUGGAUAA | 270 |
| 1360_A81_S26 | UUAUCCAGGUUGGAGUCCA | 198 | UGGACUCCAACCUGGAUAA | 282 |
| 1360_A48_S26 | UUAUCCAGGUUGGAGUCCA | 210 | UGGACUCCAACCUGGAUAA | 294 |
| 1360_A82_S36 | UUAUCCAGGUUGGAGUCCA | 222 | UGGACUCCAACCUGGAUAA | 306 |
| 1360_A83_S36 | UUAUCCAGGUUGGAGUCCA | 234 | UGGACUCCAACCUGGAUAA | 318 |
| 1360_A84_S36 | UUAUCCAGGUUGGAGUCCA | 246 | UGGACUCCAACCUGGAUAA | 330 |
| 2030_A22_S26 | AUUCUGACUAUGAACAACC | 175 | GGUUGUUCAUAGUCAGAAU | 259 |
| 2030_A25_S27 | AUUCUGACUAUGAACAACC | 187 | GGUUGUUCAUAGUCAGAAU | 271 |
| 2030_A81_S26 | AUUCUGACUAUGAACAACC | 199 | GGUUGUUCAUAGUCAGAAU | 283 |
| 2030_A48_S26 | AUUCUGACUAUGAACAACC | 211 | GGUUGUUCAUAGUCAGAAU | 295 |
| 2030_A82_S36 | AUUCUGACUAUGAACAACC | 223 | GGUUGUUCAUAGUCAGAAU | 307 |
| 2030_A83_S36 | AUUCUGACUAUGAACAACC | 235 | GGUUGUUCAUAGUCAGAAU | 319 |
| 2030_A84_S36 | AUUCUGACUAUGAACAACC | 247 | GGUUGUUCAUAGUCAGAAU | 331 |
| 2034_A22_S26 | UACAAUUCUGACUAUGAAC | 176 | GUUCAUAGUCAGAAUUGUA | 260 |
| 2034_A25_S27 | UACAAUUCUGACUAUGAAC | 188 | GUUCAUAGUCAGAAUUGUA | 272 |
| 2034_A81_S26 | UACAAUUCUGACUAUGAAC | 200 | GUUCAUAGUCAGAAUUGUA | 284 |
| 2034_A48_S26 | UACAAUUCUGACUAUGAAC | 212 | GUUCAUAGUCAGAAUUGUA | 296 |
| 2034_A82_S36 | UACAAUUCUGACUAUGAAC | 224 | GUUCAUAGUCAGAAUUGUA | 308 |
| 2034_A83_S36 | UACAAUUCUGACUAUGAAC | 236 | GUUCAUAGUCAGAAUUGUA | 320 |
| 2034_A84_S36 | UACAAUUCUGACUAUGAAC | 248 | GUUCAUAGUCAGAAUUGUA | 332 |
| 2138_A22_S26 | UCUGUUUAUAGAUCUcuGC | 177 | GCAGAGAUCUAUAAACAGA | 261 |
| 2138_A25_S27 | UCUGUUUAUAGAUCUcuGC | 189 | GCAGAGAUCUAUAAACAGA | 273 |

TABLE 2 -continued

HSF1 RNAi Agent Sequences. (Example Unmodified)
Table 2. Unmodified variants

| Nickname | Original Antisense Sequence (Generic RNA View) | SEQ ID NO: | Original Sense Sequence (Generic RNA View) | SEQ ID NO: |
|---|---|---|---|---|
| 2138_A81_S26 | UCUGUUUAUAGAUCUcuGC | 201 | GCAGAGAUCUAUAAACAGA | 285 |
| 2138_A48_S26 | UCUGUUUAUAGAUCUcuGC | 213 | GCAGAGAUCUAUAAACAGA | 297 |
| 2138_A82_S36 | UCUGUUUAUAGAUCUcuGC | 225 | GCAGAGAUCUAUAAACAGA | 309 |
| 2138_A83_S36 | UCUGUUUAUAGAUCUCUGC | 237 | GCAGAGAUCUAUAAACAGA | 321 |
| 2138_A84_S36 | UCUGUUUAUAGAUCUCUGC | 249 | GCAGAGAUCUAUAAACAGA | 333 |
| 2153_A22_S26 | UUAGCAUAGAGCCUGUCUG | 178 | CAGACAGGCUCUAUGCUAA | 262 |
| 2153_A25_S27 | UUAGCAUAGAGCCUGUCUG | 190 | CAGACAGGCUCUAUGCUAA | 274 |
| 2153_A81_S26 | UUAGCAUAGAGCCUGUCUG | 202 | CAGACAGGCUCUAUGCUAA | 286 |
| 2153_A48_S26 | UUAGCAUAGAGCCUGUCUG | 214 | CAGACAGGCUCUAUGCUAA | 298 |
| 2153_A82_S36 | UUAGCAUAGAGCCUGUCUG | 226 | CAGACAGGCUCUAUGCUAA | 310 |
| 2153_A83_S36 | UUAGCAUAGAGCCUGUCUG | 238 | CAGACAGGCUCUAUGCUAA | 322 |
| 2153_A84_S36 | UUAGCAUAGAGCCUGUCUG | 250 | CAGACAGGCUCUAUGCUAA | 334 |
| 2154_A22_S26 | UUUAGCAUAGAGCCUGUCU | 179 | AGACAGGCUCUAUGCUAAA | 263 |
| 2154_A25_S27 | UUUAGCAUAGAGCCUGUCU | 191 | AGACAGGCUCUAUGCUAAA | 275 |
| 2154_A81_S26 | UUUAGCAUAGAGCCUGUCU | 203 | AGACAGGCUCUAUGCUAAA | 287 |
| 2154_A48_S26 | UUUAGCAUAGAGCCUGUCU | 215 | AGACAGGCUCUAUGCUAAA | 299 |
| 2154_A82_S36 | UUUAGCAUAGAGCCUGUCU | 227 | AGACAGGCUCUAUGCUAAA | 311 |
| 2154_A83_S36 | UUUAGCAUAGAGCCUGUCU | 239 | AGACAGGCUCUAUGCUAAA | 323 |
| 2154_A84_S36 | UUUAGCAUAGAGCCUGUCU | 251 | AGACAGGCUCUAUGCUAAA | 335 |

Provided are the nicknames and unmodified variants of RNAi agents (wherein each sequence nickname begins with hs_HSF1_*, where * is the nickname provided in each row; e.g., "175_A22_S26" is the same as "hs_HSF1_175_A22_S26", etc.).

Note that the sequences in Table 2 represent the HSF1 portion of sense and antisense strands of various RNAi agents. Each strand can further comprise a UU dinucleotide at one or both 3' ends, as shown in Table 3.

Example 1C. HSF1 RNAi Agent Sequences. (Modified)

Table 3. HSF1 RNAi Agent Sequences. (Example Modified)

Provided are nicknames and example modified variants for HSF1 RNAi agents. Each of several RNAi agent duplexes is presented in seven different chemical modification formats. Abbreviations are as follows:

002 DNA
004 2'Ome
005 2'MOE

Thus, U004 indicates a nucleotide with a U base with a 2'Ome modification; U002 indicates a nucleotide with a U base which is DNA; U005 indicates a base with a U base with a 2'MOE modification. Similarly, other nucleotides are modified, e.g., C004 indicates a nucleotide with a C base and a 2'Ome modification. Example modified nucleotides are shown in FIG. 1. Also note that the sequences in Table 3 comprise a UU dinucleotide; this not part of the HSF1 sequence.

TABLE 3

Example modified variants

| Nickname | Antisense Sequence (Short View) | SEQ ID NO: | Sense Sequence (Short View) | SEQ ID NO: |
|---|---|---|---|---|
| 175_A22_S26 | UCC004 AUCUCGAGC004 AAGGAGGU004 U004 | 348 | C004 C004 U004 C004 C004 U004 U004 GC004 U004 C004 GAGAU004 GGAU004 U004 | 432 |
| 175_A25_S27 | UCCAUCUCGAGCAAGGAGGU004 U004 | 360 | CCUCCUUGCUCGAGAUGGAU004 U004 | 444 |

TABLE 3 -continued

Example modified variants

| Nickname | Antisense Sequence (Short View) | SEQ ID NO: | Sense Sequence (Short View) | SEQ ID NO: |
|---|---|---|---|---|
| 175_A81_S26 | UCC004 AU004 C004 U004 C004 GAGC004 AAGGAGGU004 U004 | 372 | C004 C004 U004 C004 C004 U004 U004 GC004 C004 U004 C004 GAGAU004 GGAU004 U004 | 456 |
| 175_A48_S26 | U002 CC004 AUCUCGAGC004 AAGGAGGU004 | 384 | C004 C004 U004 C004 U004 C004 U004 U004 GC004 U004 C004 GAGAU004 GGAU004 U004 | 468 |
| 175_A82_S36 | U002 0C004 AUCUCGAGC004 AAGGAG005 G005 U004 U004 | 396 | C005 C005 0C004 CUUG004 CUCG004 AGA004 UGG005 A005 U004 C004 | 480 |
| 175_A83_S36 | U002 0C004 AUCU004 CGA004 GCAAG004 GAG005 G005 C004 C004 | 408 | C005 C005 UC004 CUUG004 CUCG004 AGA004 UGG005 A005 U004 U004 | 492 |
| 175_A84_S36 | U002 0C005 AUCU005 CGA005 GCAAG005 GAG005 G005 C004 C004 | 420 | C005 C005 UC004 CUUG004 CUCG004 AGA004 UGG005 A005 U004 U004 | 504 |
| 517_A22_S26 | UUGAUGUUCUC004 AAGGAGCUU004 U004 | 340 | AGC004 C004 C004 C004 U004 U004 GAGAAC004 AU004 C004 AAU004 C004 | 424 |
| 517_A25_S27 | UUGAUGUUCUCAAGGAGCUU004 U004 | 352 | AGCUCCUUGAGAACAUCAAU004 U004 | 436 |
| 517_A81_S26 | UUGAU004 GU004 U004 C004 C004 C004 AAGGAGC004 C004 C004 C004 | 364 | AGC004 C004 C004 C004 U004 U004 GAGAAC004 AU004 C004 AAU004 C004 | 448 |
| 517_A48_S26 | U002 UGAUGUUCUC004 AAGGAGCUU004 U004 | 376 | AGC004 C004 C004 C004 U004 U004 GAGAAC004 AU004 C004 AAU004 C004 | 460 |
| 517_A82_S36 | U002 UGAUGUUCUC004 AAGGAGC005 U005 C004 C004 | 388 | A005 G005 CU004 CCUU004 GAGA004 ACA004 UCA005 A005 U004 U004 | 472 |
| 517_A83_S36 | U002 UG004 AUGU004 UCU004 CAAGG004 AGC005 C005 C004 C004 | 400 | A005 G005 CU004 CCUU004 GAGA004 ACA004 UCA005 A005 U004 U004 | 484 |
| 517_A84_S36 | U002 UG005 AUGU005 UCU005 CAAGG005 AGC005 U005 C004 C004 | 412 | A005 G005 CU004 CCUU004 GAGA004 ACA004 UCA005 A005 U004 U004 | 496 |
| 562_A22_S26 | UUU004 AUGUCUUC004 ACUCUUC004 AU004 U004 | 337 | U004 GAAGAGU004 GAAGAC004 AU004 AAAU004 U004 | 421 |
| 562_A25_S27 | UUUAUGUCUUCACUCUUCAU004 U004 | 349 | UGAAGAGUGAAGACAUAAAU004 U004 | 433 |
| 562_A81_S26 | UUU004 AU004 GU004 C004 U004 U004 C004 ACUC004 U004 U004 C004 AU004 U004 | 361 | U004 GAAGAGU004 GAAGAC004 AU004 AAAU004 U004 | 445 |
| 562_A48_S26 | U002 UU004 AUGUCUUC004 ACUCUUC004 AU004 U004 | 373 | U004 GAAGAGU004 GAAGAC004 AU004 AAAU004 U004 | 457 |
| 562_A82_S36 | U002 UU004 AUGUCUUC004 ACUCUUC005 A005 U004 U004 | 385 | U005 G005 AA004 GAGU004 GAAG004 ACA004 UAA005 A005 U004 U004 | 469 |
| 562_A83_S36 | U002 UU004 AUGU004 CUU004 CACUC004 UUC005 A005 U004 U004 | 397 | U005 G005 AA004 GAGU004 GAAG004 ACA004 UAA005 A005 U004 U004 | 481 |

TABLE 3 -continued

Example modified variants

| Nickname | Antisense Sequence (Short View) | SEQ ID NO: | Sense Sequence (Short View) | SEQ ID NO: |
|---|---|---|---|---|
| 562_ A84_S36 | U002 UU005 AUGU005 CUU005 CACUC005 UUC005 A005 U004 U004 | 409 | U005 G005 AA004 GAGU004 GAAG004 ACA004 UAA005 A005 U004 U004 | 493 |
| 751_ A22_S26 | AUC004 AGGAACUGAAUGAGCUU004 U004 | 338 | AGC004 U004 C004 AU004 U004 C004 AGU004 U004 C004 C004 U004 GAU004 U004 U004 | 422 |
| 751_ A25_S27 | AUCAGGAACUGAAUGAGCUU004 U004 | 350 | AGCUCAUUCAGUUCCUGAUU004 U004 | 434 |
| 751_ A81_S26 | AUC004 AGGAAC004 U004 GAAUGAGC004 U004 U004 U004 | 362 | AGC004 U004 C004 AU004 U004 C004 AGU004 U004 C004 C004 U004 GAU004 U004 U004 | 446 |
| 751_ A48_S26 | A002 UC004 AGGAACUGAAUGAGCUU004 U004 | 374 | AGC004 U004 C004 AU004 U004 C004 AGU004 U004 C004 C004 U004 GAU004 U004 U004 | 458 |
| 751_ A82_S36 | A002 UC004 AGGAACUGAAUGAGC005 U005 U004 U004 | 386 | A005 G005 CU004 CAUU004 CAGU004 UCC004 UGA005 U005 U004 U004 | 470 |
| 751_ A83_S36 | A002 UC004 AGGA004 ACU004 GAAUG004 AGC005 U005 U004 U004 | 398 | A005 G005 CU004 CAUU004 CAGU004 UCC004 UGA005 U005 U004 U004 | 482 |
| 751_ A84_S36 | A002 UC005 AGGA005 ACU005 GAAUG005 AGC005 U005 U004 U004 | 410 | A005 G005 CU004 CAUU004 CAGU004 UCC004 UGA005 U005 U004 U004 | 494 |
| 755 A22_S26 | UGAGAUC004 AGGAACUGAAUGU004 U004 | 339 | C004 AU004 U004 C004 AGU004 U004 C004 C004 U004 GAU004 C004 U004 C004 AU004 U004 | 423 |
| 755_ A25_S27 | UGAGAUCAGGAACUGAAUGU004 U004 | 351 | CAUUCAGUUCCUGAUCUCAU004 U004 | 435 |
| 755_ A81_S26 | UGAGAU004 C004 AGGAACUGAAU004 GU004 U004 | 363 | C004 AU004 U004 C004 AGU004 U004 C004 C004 U004 GAU004 C004 U004 C004 AU004 U004 | 447 |
| 755_ A48_S26 | U002 GAGAUC004 AGGAACUGAAUGU004 U004 | 375 | C004 AU004 U004 C004 AGU004 U004 C004 C004 U004 GAU004 C004 U004 C004 AU004 U004 | 459 |
| 755_ A82_S36 | U002 GAGAUC004 AGGAACUGAAU005 G005 U004 U004 | 387 | C005 A005 UU004 CAGU004 UCCU004 GAU004 CUC005 A005 U004 U004 | 471 |
| 755_ A83_S36 | U002 GA004 GAUC004 AGG004 AACUG004 AAU005 G005 U004 U004 | 399 | C005 A005 UU004 CAGU004 UCCU004 GAU004 CUC005 A005 U004 U004 | 483 |
| 755_ A84_S36 | U002 GA005 GAUC005 AGG005 AACUG005 AAU005 G005 U004 U004 | 411 | C005 A005 UU004 CAGU004 UCCU004 GAU004 CUC005 A005 U004 U004 | 495 |
| 846_ A22_S26 | U004 AU004 ACUUGGGC004 AUGGAAUGU004 U004 | 341 | C004 AU004 U004 C004 C004 AU004 GC004 C004 C004 AAGU004 AU004 AU004 U004 | 425 |
| 846_ A25_S27 | UAUACUUGGGCAUGGAAUGU004 U004 | 353 | CAUUCCAUGCCCAAGUAUAU004 U004 | 437 |

TABLE 3 -continued

Example modified variants

| Nickname | Antisense Sequence (Short View) | SEQ ID NO: | Sense Sequence (Short View) | SEQ ID NO: |
|---|---|---|---|---|
| 846_A81_S26 | UAU004 AC004 U004 U004 GGGC004 AUGGAAU004 GU004 U004 | 365 | C004 AU004 U004 C004 C004 AU004 GC004 C004 C004 AAGU004 AU004 AU004 U004 | 449 |
| 846_A48_S26 | U002 AU004 ACUUGGGC004 AUGGAAUGU004 U004 | 377 | C004 AU004 U004 C004 C004 AU004 GC004 C004 C004 AAGU004 AU004 AU004 U004 | 461 |
| 846_A82_S36 | U002 AU004 ACUUGGGC004 AUGGAAU005 G005 U004 U004 | 389 | C005 A005 UU004 CCAU004 GCCC004 AAG004 UAU005 A005 U004 U004 | 473 |
| 846_A83_S36 | U002 AU004 ACUU004 GGG004 CAUGG004 AAU005 G005 U004 U004 | 401 | C005 A005 UU004 CCAU004 GCCC004 AAG004 UAU005 A005 U004 U004 | 485 |
| 846_A84_S36 | U002 AU005 ACUU005 GGG005 CAUGG005 AAU005 G005 U004 U004 | 413 | C005 A005 UU004 CCAU004 GCCC004 AAG004 UAU005 A005 U004 U004 | 497 |
| 1360_A22_S26 | UU004 AUCC004 AGGUUGGAGUCC004 AU004 U004 | 342 | U004 GGAC004 U004 c004 C004 AAC004 C004 U004 GGAU004 AAU004 U004 | 426 |
| 1360_A25_S27 | UUAUCCAGGUUGGAGUCCAU004 U004 | 354 | UGGACUCCAACCUGGAUAAU004 U004 | 438 |
| 1360_A81_S26 | UUAU004 C004 C004 AGGU004 U004 GGAGU004 C004 C004 AU004 U004 | 366 | U004 GGAC004 U004 C004 C004 AAC004 C004 U004 GGAU004 AAU004 U004 | 450 |
| 1360_A48_S26 | U002 U004 AuCC004 AGGUUGGAGUCC004 AU004 U004 | 378 | U004 GGAC004 U004 C004 C004 AAC004 C004 U004 GGAU004 AAU004 U004 | 462 |
| 1360_A82_S36 | U002 U004 AuCC004 AGGUUGGAGUCC005 A005 U004 U004 | 390 | U005 G005 GA004 CUCC004 AACC004 UGG004 AUA005 A005 U004 U004 | 474 |
| 1360_A83_S36 | U002 UA004 UCCA004 GGU004 UGGAG004 UCC005 A005 U004 U004 | 402 | U005 G005 GA004 CUCC004 AACC004 uGG004 AuA005 A005 U004 U004 | 486 |
| 1360_A84_S36 | U002 UA005 UCCA005 GGU005 UGGAG005 UCC005 A005 U004 U004 | 414 | U005 G005 GA004 CUCC004 AACC004 UGG004 AUA005 A005 U004 U004 | 498 |
| 2030_A22_S26 | AUUCUGACU004 AUGAAC004 AACCU004 U004 | 343 | GGU004 U004 GU004 U004 C004 AU004 AGU004 C004 AGAAU004 U004 U004 | 427 |
| 2030_A25_S27 | AUUCUGACUAUGAACAACCU004 U004 | 355 | GGUUGUUCAUAGUCAGAAUU004 U004 | 439 |
| 2030_A81_S26 | AuU004 C004 U004 GAC004 U004 AU004 GAAC004 AAC004 C004 U004 U004 | 367 | GGU004 U004 GU004 U004 C004 AU004 AGU004 C004 AGAAU004 U004 U004 | 451 |
| 2030_A48_S26 | A002 UUCUGACU004 AUGAAC004 AACCU004 U004 | 379 | GGU004 U004 GU004 U004 C004 AU004 AGU004 C004 AGAAU004 U004 U004 | 463 |
| 2030_A82_S36 | A002 UUCuGACU004 AUGAAC004 AAC005 C005 U004 U004 | 391 | G005 G005 UU004 GUUC004 AUAG004 UCA004 GAA005 U005 U004 U004 | 475 |
| 2030_A83_S36 | A002 UU004 CUGA004 CUA004 UGAAC004 AAC005 C005 U004 U004 | 403 | G005 G005 UU004 GUUC004 AUAG004 UCA004 GAA005 U005 U004 U004 | 487 |
| 2030_A84_S36 | A002 UU005 CUGA005 CUA005 UGAAC005 AAC005 C005 U004 U004 | 415 | G005 G005 UU004 GUUC004 AUAG004 UCA004 GAA005 U005 U004 U004 | 499 |

TABLE 3 -continued

Example modified variants

| Nickname | Antisense Sequence (Short View) | SEQ ID NO: | Sense Sequence (Short View) | SEQ ID NO: |
|---|---|---|---|---|
| 2034_A22_S26 | U004 AC004 AAUUCUGACU004 AUGAACU004 U004 | 344 | GU004 U004 C004 AU004 AGU004 C004 AGAAU004 U004 GU004 AU004 U004 | 428 |
| 2034_A25_S27 | UACAAUUCUGACUAUGAACU004 U004 | 356 | GUUCAUAGUCAGAAUUGUAU004 U004 | 440 |
| 2034_A81_S26 | UAC004 AAU004 U004 C004 U004 GAC004 uAU004 GAAC004 U004 U004 | 368 | GU004 U004 C004 AU004 AGU004 C004 AGAAU004 U004 GU004 AU004 U004 | 452 |
| 2034_A48_S26 | U002 AC004 AAUUCUGACU004 AUGAACU004 U004 | 380 | GU004 U004 C004 AU004 AGU004 C004 AGAAU004 U004 GU004 AU004 U004 | 464 |
| 2034_A82_S36 | U002 AC004 AAUUCUGACU004 AUGAA005 C005 U004 U004 | 392 | G005 U005 UC004 AUAG004 UCAG004 AAU004 UGU005 A005 U004 U004 | 476 |
| 2034_A83_S36 | U002 AC004 AAUU004 CUG004 ACUAU004 GAA005 C005 U004 U004 | 404 | G005 U005 UC004 AUAG004 UCAG004 AAU004 UGU005 A005 U004 U004 | 488 |
| 2034_A84_S36 | U002 AC005 AAUU005 CUG005 ACUAU005 GAA005 C005 U004 U004 | 416 | G005 U005 UC004 AUAG004 UCAG004 AAU004 UGU005 A005 U004 U004 | 500 |
| 2138_A22_S26 | UCUGUUU004 AU004 AGAUCUCUGCU004 U004 | 345 | GC004 AGAGAU004 C004 U004 AU004 AAAC004 AGAU004 U004 | 429 |
| 2138_A25_S27 | UCUGUUUAUAGAUCUCUGCU004 U004 | 357 | GCAGAGAUCUAUAAACAGAU004 U004 | 441 |
| 2138_A81_S26 | UCU004 GU004 U004 U004 AU004 AGAUCU004 C004 U004 GC004 U004 U004 | 369 | GC004 AGAGAU004 C004 U004 AU004 AAAC004 AGAU004 U004 | 453 |
| 2138_A48_S26 | U002 CUGUUU004 AU004 AGAUCUCUGCU004 U004 | 381 | GC004 AGAGAU004 C004 U004 AU004 AAAC004 AGAU004 U004 | 465 |
| 2138_A82_S36 | U002 CUGUUU004 AU004 AGAUCUCUG005 C005 U004 U004 | 393 | G005 C005 AG004 AGAU004 CUAU004 AAA004 CAG005 A005 U004 U004 | 477 |
| 2138_A83_S36 | U002 CU004 GUUU004 AUA004 GAUCU004 CUG005 C005 U004 U004 | 405 | G005 C005 AG004 AGAU004 CUAU004 AAA004 CAG005 A005 U004 U004 | 489 |
| 2138_A84_S36 | U002 CU005 GUUU005 AUA005 GAUCU005 CUG005 C005 U004 U004 | 417 | G005 C005 AG004 AGAU004 CUAU004 AAA004 CAG005 A005 U004 U004 | 501 |
| 2153_A22_S26 | UU004 AGC004 AU004 AGAGCCUGUCUGU004 U004 | 346 | C004 AGAC004 AGGC004 U004 C004 U004 AU004 GC004 U004 AAU004 U004 | 430 |
| 2153_A25_S27 | UUAGCAUAGAGCCUGUCUGU004 U004 | 358 | CAGACAGGCUCUAUGCUAAU004 U004 | 442 |
| 2153_A81_S26 | UUAGC004 AU004 AGAGC004 CUGU004 C004 U004 GU004 U004 | 370 | C004 AGAC004 AGGC004 U004 C004 U004 AU004 GC004 U004 AAU004 U004 | 454 |
| 2153_A48_S26 | U002 U004 AGC004 AU004 AGAGCCUGUCUGU004 U004 | 382 | C004 AGAC004 AGGC004 U004 C004 U004 AU004 GC004 U004 AAU004 U004 | 466 |
| 2153_A82_S36 | U002 U004 AGC004 AU004 AGAGCCUGUCU005 G005 U004 U004 | 394 | C005 A005 GA004 CAGG004 CUCU004 AUG004 CUA005 A005 U004 U004 | 478 |

TABLE 3 -continued

Example modified variants

| Nickname | Antisense Sequence (Short View) | SEQ ID NO: | Sense Sequence (Short View) | SEQ ID NO: |
|---|---|---|---|---|
| 2153_A83_S36 | U002 UA004 GCAU004 AGA004 GCCUG004 UCU005 G005 U004 U004 | 406 | C005 A005 GA004 CAGG004 CUCU004 AUG004 CUA005 A005 U004 U004 | 490 |
| 2153_A84_S36 | U002 UA005 GCAU005 AGA005 GCCUG005 UCU005 G005 U004 U004 | 418 | C005 A005 GA004 CAGG004 CUCU004 AUG004 CUA005 A005 U004 U004 | 502 |
| 2154_A22_S26 | UUU004 AGC004 AU004 AGAGCCUGUCUU004 U004 | 347 | AGAC004 AGGC004 U004 C004 U004 AU004 GC004 U004 AAAU004 U004 | 431 |
| 2154_A25_S27 | UUUAGCAUAGAGCCUGUCUU004 U004 | 359 | AGACAGGCUCUAUGCUAAAU004 U004 | 443 |
| 2154_A81_S26 | UUU004 AGC004 AU004 AGAGCCU004 GU004 C004 U004 U004 U004 | 371 | AGAC004 AGGC004 U004 C004 U004 AU004 GC004 U004 AAAU004 U004 | 455 |
| 2154_A48_S26 | U002 UU004 AGC004 AU004 AGAGCCUGUCUU004 U004 | 383 | AGAC004 AGGC004 U004 C004 U004 AU004 GC004 U004 AAAU004 U004 | 467 |
| 2154_A82_S36 | U002 UU004 AGC004 AU004 AGAGCCUGUC005 U005 U004 U004 | 395 | A005 G005 AC004 AGGC004 UCUA004 UGC004 UAA005 A005 U004 U004 | 479 |
| 2154_A83_S36 | U002 UU004 AGCA004 UAG004 AGCCU004 GUC005 U005 U004 U004 | 407 | A005 G005 AC004 AGGC004 UCUA004 UGC004 UAA005 A005 U004 U004 | 491 |
| 2154_A84_S36 | U002 UU005 AGCA005 UAG005 AGCCU005 GUC005 U005 U004 U004 | 419 | A005 G005 AC004 AGGC004 UCUA004 UGC004 UAA005 A005 U004 U004 | 503 |

Example 1D. Groups of Overlapping HSF1 RNAi Agent Sequences

Some of the RNAi agents listed herein overlap each other in sequence. Table 4, below, provides a compilation of some of the groups of overlapping RNAi agents, wherein each member of a group overlaps each other member of the same group by at least 12 nt.

In various embodiments, the disclosure relates to groups of RNAi agents with overlapping sequences. Thus, the disclosure encompasses groups of RNAi agents wherein each RNAi agent in the group overlaps with each other RNAi agent in the same group by at least 5, 6, 7, 8, 9, 10, 11, 12, 13, 14, 15, 16, 17, 18, 19 or more nucleotides. Particularly, in one embodiment, the overlap is at least 12 nt. Groups of sequences that overlap are shown in Table 4.

TABLE 4

Overlapping sequences in HSF1 RNAi agents.

| Antisense Sequence Overlap | SEQ ID NO: | Sense Sequence Overlap | SEQ ID NO: | Groups of Overlapping RNAi Agents to HSF1 |
|---|---|---|---|---|
| ATCAGGAAC TGAATG | 507 | CATTCAGTT CCTGAT | 510 | 751_A22_S26 751_A25_S27 751_A81_S26 751_A48_S26 751_A82_S36 751_A83_S36 751_A84_S36 |
| | | | | 755_A22_S26 755_A25_S27 755_A81_S26 755_A48_S26 755_A82_S36 755_A83_S36 755_A84_S36 |
| ATTCTGACT ATGAAC | 508 | GTTCATAGT CAGAAT | 511 | 2030_A22_S26 2030_A25_S27 2030_A81_S26 2030_A48_S26 2030_A82_S36 2030_A83_S36 2030_A84_S36 2034_A22_S26 2034_A25_S27 2034_A81_S26 2034_A48_S26 2034_A82_S36 2034_A83_S36 2034_A84_S36 |
| TTAGCATAGA GCCTGTCTG | 509 | AGACAGGCT CTATGCTAA | 512 | 2153_A22_S26 2153_A25_S27 2153_A81_S26 2153_A48_S26 2153_A82_S36 |

TABLE 4 -continued

Overlapping sequences in HSF1 RNAi agents.

| Antisense Sequence Overlap | SEQ ID NO: | Sense Sequence Overlap | SEQ ID NO: | Groups of Overlapping RNAi Agents to HSF1 |
|---|---|---|---|---|
| | | | | 2153_A83_S36 |
| | | | | 2153_A84_S36 |
| | | | | 2154_A22_S26 |
| | | | | 2154_A25_S27 |
| | | | | 2154_A81_S26 |
| | | | | 2154_A48_S26 |
| | | | | 2154_A82_S36 |
| | | | | 2154_A83_S36 |
| | | | | 2154_A84_S36 |

This Table presents sets of HSF1 RNAi agents (last column) wherein all the RNAi agents within each set comprise the same overlapping sequence in the antisense strand (first column) or sense strand (second column).
In the column "Groups of Overlapping RNAi Agents to HSF1", groups of overlapping RNAi agents are presented by nickname. As in other Tables, the nicknames are preceded by "hs_HSF1_"; thus, for example, "A22_S26" is the same as "hs_HSF1_751_A22_S26", etc.
The present disclosure contemplates any group of overlapping RNAi agents disclosed herein (e.g., 751_A22_S26, 751_A25_S27, 751_A81_S26, 751_A48_S26, 751_A82_S36, 751_A83_S36, 751_A84_S36, 755_A22_S26, 755_A25_S27, 755_A81_S26, 755_A48_S26, 755_A82_S36, 755_A83_S36, and 755_A84_S36) or any portion or subgroup of that group (e.g., 751_A22_S26, 751_A25_S27, and 751_A81_S26; and/or 755_A82_S36, 755_A83_S36, and 755_A84_S36 and/or 755_A84_S36, 755_A22_S26, 755_A25_S27, and 755_A81_S26), etc.

Tables 2, 3 and 4 show, for example, that all RNAi agents with the prefix hs_HSF1_751 and hs_HSF1_755 (e.g., hs_HSF1_751_A22_S26, hs_HSF1_751_A25_S27, hs_HSF1_751_A81_S26, hs_HSF1_751_A48_S26, hs_HSF1_751_A82_S36, hs_HSF1_751_A83_S36, hs_HSF1_751_A84_S36, hs_HSF1_755_A22_S26, hs_HSF1_755_A25_S27, hs_HSF1_755_A81_S26, hs_HSF1_755_A48_S26, hs_HSF1_755_A82_S36, hs_HSF1_755_A83_S36, and hs_HSF1_755_A84_S36, modified variants thereof, etc.) share the common technical feature of the sequence of CATTCAGTTCCTGAT (SEQ ID NO: 510) in the sense strand, and the sequence of ATCAGGAACTGAATG (SEQ ID NO: 507) in the antisense strand.

The disclosure thus encompasses various embodiments comprising groups of overlapping RNAi agents, for example (1) RNAi agents comprising the sequences of CATTCAGTTCCTGAT (SEQ ID NO: 510) or ATCAGGAACTGAATG (SEQ ID NO: 507) (e.g., any combination of or all of hs_HSF1_751_A22_S26; hs_HSF1_751_A25_S27; hs_HSF1_751_A81_S26; hs_HSF1_751_A48_S26; hs_HSF1_751_A82_S36; hs_HSF1_751_A83_S36; hs_HSF1_751_A84_S36; hs_HSF1_755_A22_S26; hs_HSF1_755_A25_S27; hs_HSF1_755_A81_S26; hs_HSF1_755_A48_S26; and hs_HSF1_755_A82_S36; and hs_HSF1_755_A83_S36; hs_HSF1_755_A84_S36, and modified variants thereof); (2) RNAi agents comprising the sequences of CATTCAGTTCCTGAT (SEQ ID NO: 510) or ATCAGGAACTGAATG (SEQ ID NO: 507); (3) RNAi agents comprising a first strand and/or a second strand comprising a sequence of CATTCAGTTCCTGAT (SEQ ID NO: 510) or ATCAGGAACTGAATG (SEQ ID NO: 507); (4) RNAi agents comprising a sense strand and/or a antisense strand comprising 15 contiguous nt with 0 to 3 mismatches from a sequence of CATTCAGTTCCTGAT (SEQ ID NO: 510) or ATCAGGAACTGAATG (SEQ ID NO: 507); (5) RNAi agents comprising a first strand comprising 15 contiguous nt with 0 to 3 mismatches from a sequence of CATTCAGTTCCTGAT (SEQ ID NO: 510); (6) RNAi agents comprising a strand comprising 15 contiguous nt with 0 to 3 mismatches from a sequence of ATCAGGAACTGAATG (SEQ ID NO: 507); etc. The disclosure also encompasses similar embodiments reflecting all the overlapping groups of RNAi agents as described in Table A2.

Variants of RNAi agents (e.g., comprising different modifications, caps, etc.) are disclosed herein, e.g., in Tables A1, 1, 2, 3, 4, 5, 6, or 7. In these texts and tables, for example, hs_HSF1_751_A22_S26 shares the same sequence as hs_HSF1_751_A25_S27, and hs_HSF1_751_A81_S26, though the RNAi agents may differ in their modifications, caps (e.g., 5' and/or 3' caps), etc. However, any overlapping group comprising a RNAi agent of a given sequence also comprises any other RNAi agent which has the same sequence, but different variations in modifications, caps, etc. Thus, any group of overlapping RNAi agents that includes hs_HSF1_751_A22_S26 also includes HSF1_751_A25_S27, hs_HSF1_751_A81_S26 and other variants of the same sequence (e.g., with different modifications, caps, etc.). More embodiments are provided herein, and are included in the scope of each group of RNAi agents of the disclosure.

Example 2. Activity of RNAi Agents to HSF1

RNAi agent activity is tested in vitro in HeLa cells (Example 2A), GTL-16 cells (Example 2B) and SK-BR-3 (SKBR3) cells (Example 2C).

In various assays, the transfection agent is RNAiMAX.

To establish a dose-response for a RNAi agent, the starting concentration is 10 nM, with various 1:3 dilutions for a 9-point single agent dose response curve.

The timepoint for measuring KD (gene knockdown) is 48 hours.

Media is changed at 24 hours.

Additional details are provided in the protocols in Example 3.

Example 2A. Activity of RNAi Agents to HSF1 in HeLa Cells

For in vitro experiments, RNAi agent dose-response activity is measured in HeLa cells. HeLa cells are transfected with RNAi agents at 1, 5 or 10 nM. HSF1 qRT-PCR protocols were performed at 48 hours after transfection.

Figure 2A:
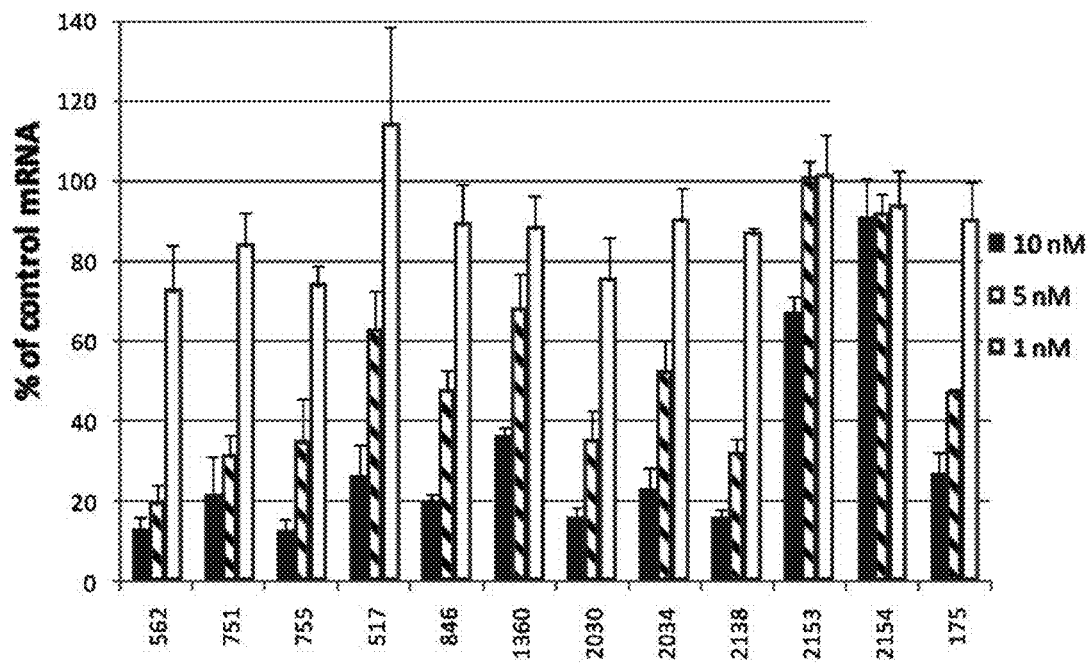
FIGS. 2A to 2G show the activity of various HSF1 RNAi agents in HeLa cells in vitro, as detailed in Example 2A.

Results are shown in FIG. 2A for A22_S26 modification formats for HSF1 RNAi agents hs_HSF1_175_; hs_HSF1_517_; hs_HSF1_562_; hs_HSF1_751_; hs_HSF1_755_; hs_HSF1_846; hs_HSF1_1360_; hs_HSF1_2030_; hs_HSF1_2034_; hs_HSF1_2138_; hs_HSF1_2153_; and hs_HSF1_2154_. Vertical bars indicate residual gene activity; e.g., for hs_HSF1_562, residual gene activity at 10 nM is <20%, indicating that gene knockdown is >80%.

Figure 2B:
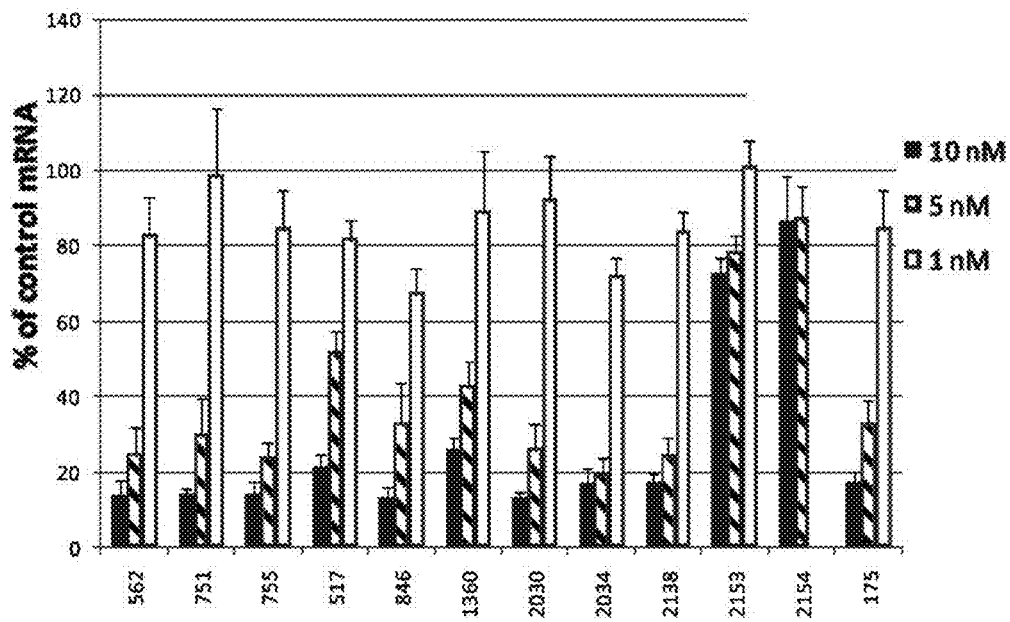

FIG. 2B shows activity for A25_S27 variants of these sequences.

Figure 2C:
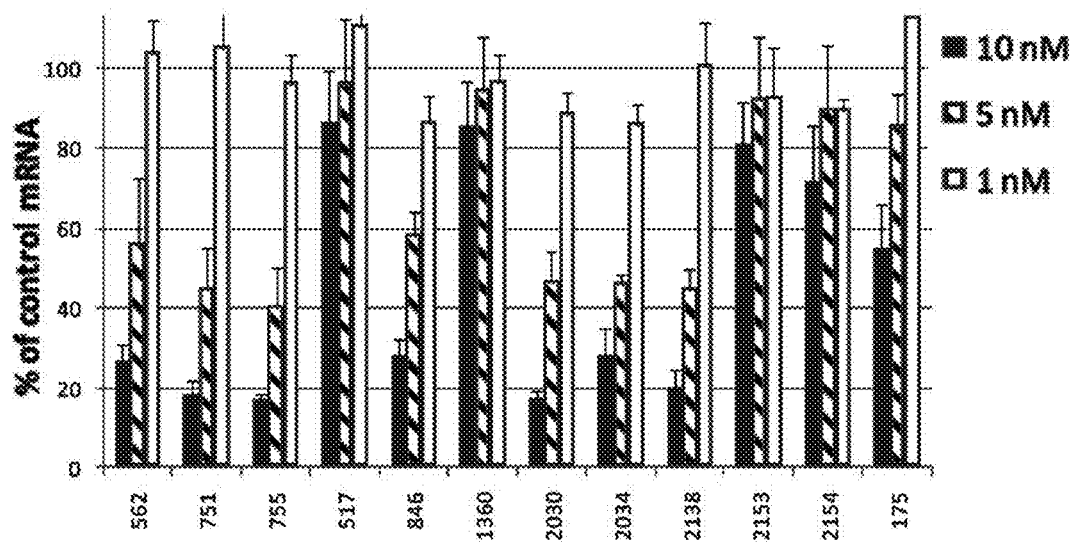

FIG. 2C shows activity for AV14_S26 [also known as A_LO_V14_S26 or A81_S26] variants of these sequences.

Figure 2D:
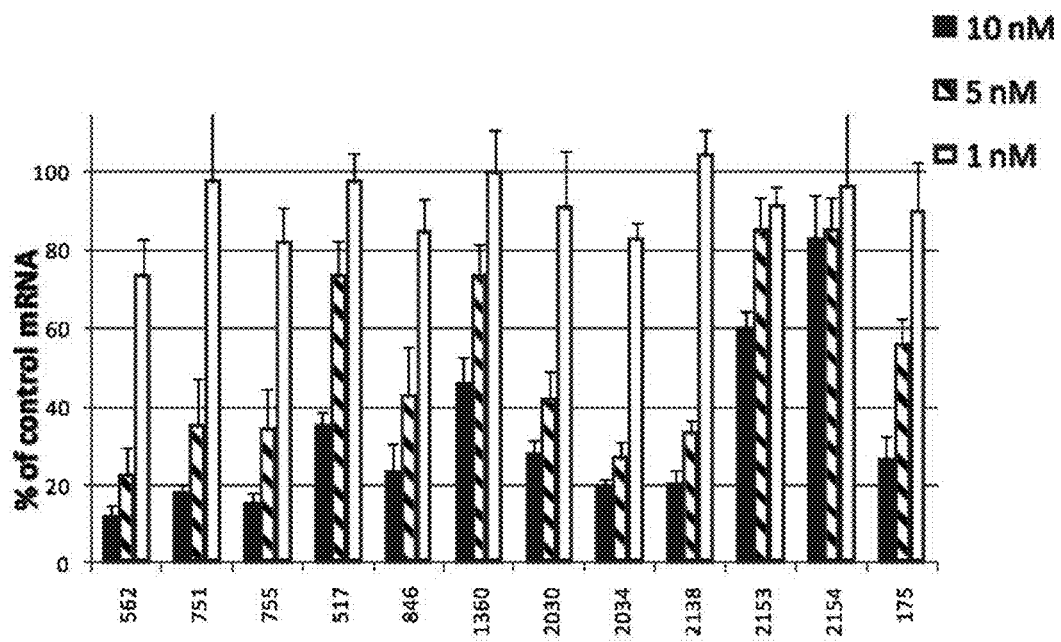

FIG. 2D shows activity for A48_S26 variants of these sequences.

Figure 2E:
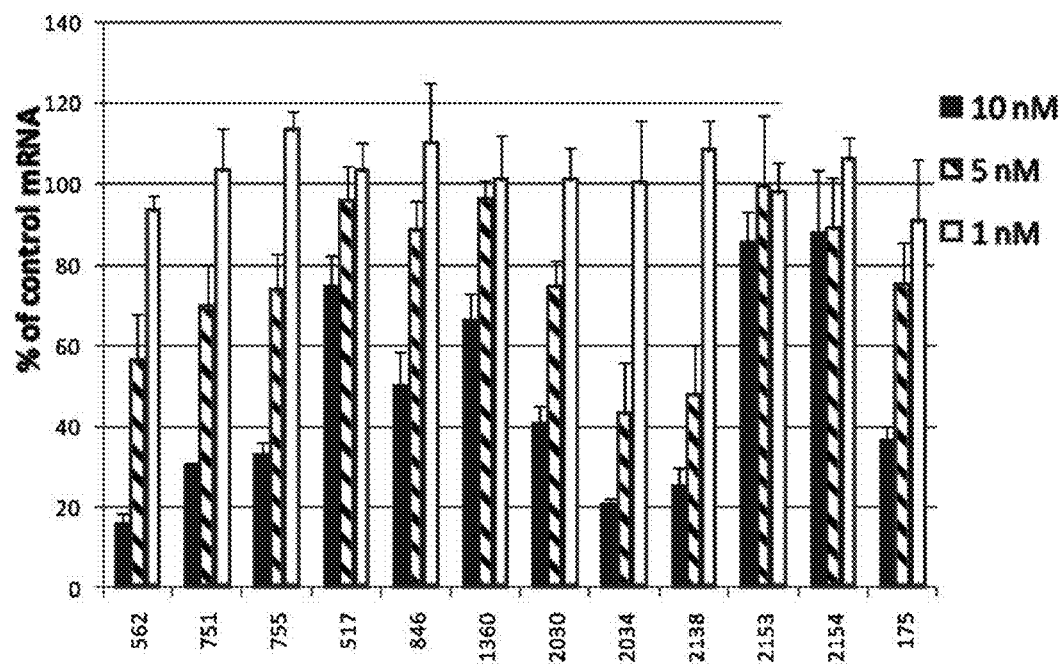

FIG. 2E shows activity for AV15_SV7 (A82_S50, also known as A_LO_V15 S_LO_V7) variants of these sequences.

Figure 2F:
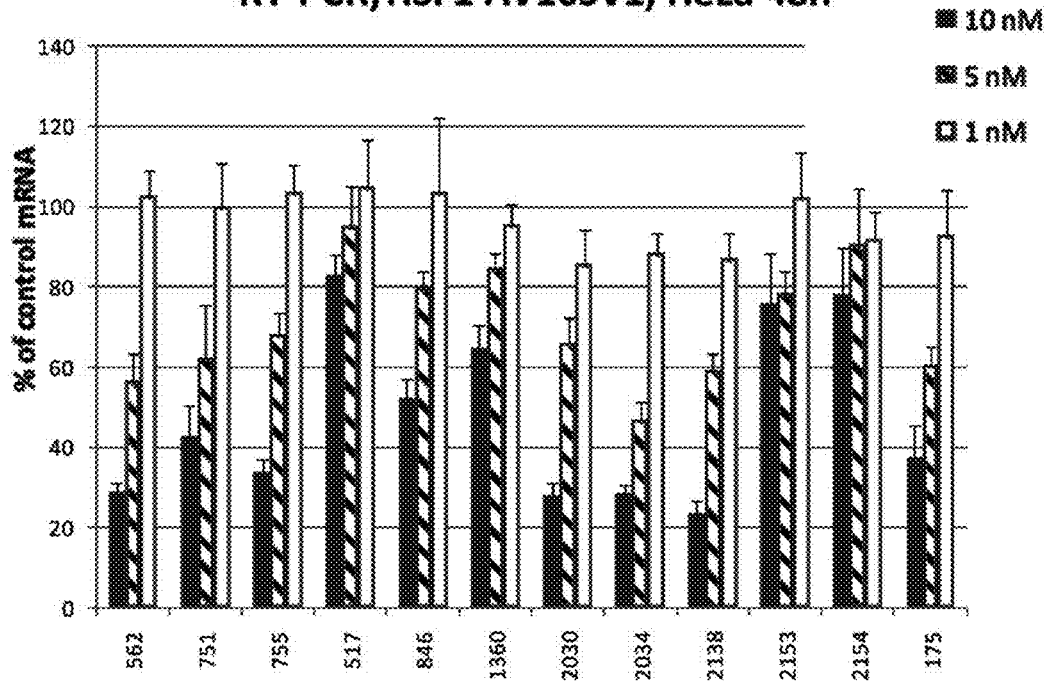

FIG. 2F shows activity for AV16_SV1 (A83_S36, also known as A_LO_V16 S_LO_V1) variants of these sequences.

Figure 2G:
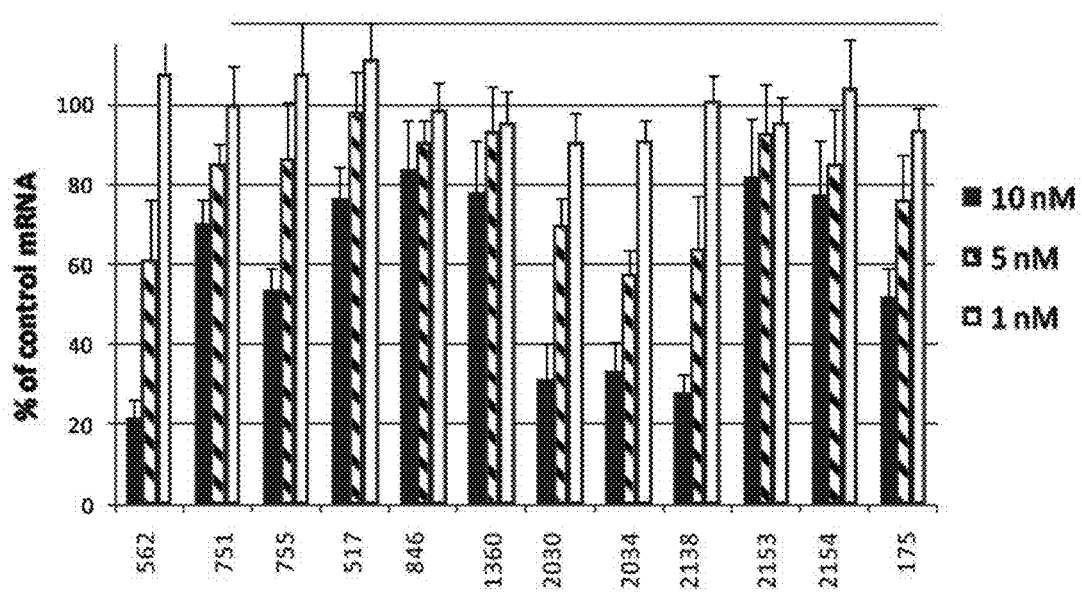

FIG. 2G shows activity for AV17_SV1 (A84_S36, also known as A_LO_V17 S_LO_V1) variants of these sequences.

The results in FIGS. 2A to 2G show that at least one variant of each of hs_HSF1_175_; hs_HSF1_517_; hs_HSF1_562_; hs_HSF1_751_; hs_HSF1_755_; hs_HSF1_846_; hs_HSF1_1360_; hs_HSF1_2030_; hs_HSF1_2034_; and hs_HSF1_2138_ was effective in mediating RNA interference against HeLa cells in vitro.

Example 2B. Activity of HSF1 RNAi Agents in GTL-16 Cells

HSF1 RNAi agents are tested in vitro on GTL-16 cells. The results are shown in Table 5, below.

This Table provides the EC50 for proliferation, the EC50 for knockdown, and % knockdown at 10 nM. Thus, for hs_HSF1_846_A25_S27, the EC50 for proliferation is >10 nM, the EC50 for 50% knockdown is 0.03 nM; and the % knockdown at 10 nM is 80% (indicating 20% residual gene activity). "-" indicates that this data point was not performed.

The table is arranged with the most potent RNAi agents (lowest EC50 knockdown in nM) at the top.

TABLE 5

| siRNAs | EC50 Proliferation (nM) | EC50 Knockdown (nM) | % Knockdown at 10 nM |
| --- | --- | --- | --- |
| hsHSF1_846_A25_S27 | >10 | 0.03 | 80 |
| hsHSF1_751_A25_S27 | >10 | 0.04 | 80 |
| hsHSF1_755_A25_S27 | >10 | 0.04 | 80 |
| hsHSF1_2138_A25_S27 | >10 | 0.05 | 80 |
| hsHSF1_2030_A25_S27 | >10 | 0.06 | 80 |
| hsHSF1_562_A25_S27 | >10 | 0.10 | 70 |
| hsHSF1_846_A48_S26 | >10 | 0.17 | 70 |
| hsHSF1_2030_A22_S26 | >10 | 0.19 | 70 |
| hsHSF1_846_A22_S26 | >10 | 0.26 | 70 |
| hsHSF1_751_A22_S26 | >10 | 0.63 | 70 |
| hsHSF1_751_A_LO_V14_S26 | >10 | 0.04 | 60 |
| hsHSF1_2030_A48_S26 | >10 | 0.05 | 60 |
| hsHSF1_175_A25_S27 | >10 | 0.09 | 60 |
| hsHSF1_2138_A22_S26 | >10 | 0.23 | 60 |
| hsHSF1_755_A22_S26 | >10 | 0.62 | 60 |
| hsHSF1_562_A22_S26 | >10 | 0.73 | 60 |
| hsHSF1_2034_A25_S27 | >10 | 0.05 | 50 |
| hsHSF1_2138_A_LO_V16_S_LO_V1 | >10 | 0.13 | 50 |
| hsHSF1_751_A48_S26 | >10 | 0.38 | 50 |
| hsHSF1_755_A_LO_V14_S26 | >10 | 0.89 | 50 |
| hsHSF1_562_A48_S26 | >10 | 0.05 | 40 |
| hsHSF1_2138_A_LO_V14_S26 | >10 | 0.06 | 40 |
| hsHSF1_2034_A22_S26 | >10 | 1.90 | 60 |
| hsHSF1_2030_A_LO_V14_S26 | >10 | 3.61 | 50 |
| hsHSF1_846_A_LO_V14_S26 | >10 | 8.40 | 60 |
| hsHSF1_175_A22_S26 | >10 | >10 | 50 |
| hsHSF1_562_A_LO_V14_S26 | >10 | >10 | — |
| hsHSF1_2034_A_LO_V14_S26 | >10 | >10 | 20 |
| hsHSF1_755_A48_S26 | >10 | >10 | 30 |
| hsHSF1_2034_A48_S26 | >10 | >10 | 30 |
| hsHSF1_2138_A48_S26 | >10 | >10 | 60 |
| hsHSF1_175_A48_S26 | >10 | >10 | 50 |
| hsHSF1_2034_A_LO_V16_S_LO_V1 | >10 | >10 | 50 |

Example 2C. Activity of HSF1 RNAi Agents in SK-BR-3 Cells

HSF1 RNAi agents are tested in vitro on SK-BR-3 (SKBR3) cells. The results are shown in Table 6, below. RNAiMAX is 0.3 ul. 7 day CTG assay is performed, as is a 4 day KD (gene knockdown) assay.

TABLE 6

Activity of HSF1 RNAi Agents in SK-BR-3 Cells in vitro.

| SiRNAs | % Inhibition at 10 nM | % Knockdown at 10 nM |
| --- | --- | --- |
| hsHSF1_846_A22_S26 | 0 | 92 |
| hsHSF1_2138_A22_S26 | 8 | 92 |
| hsHSF1_751_A48_S26 | 20 | 92 |
| hsHSF1_751_A22_S26 | 25 | 95 |
| hsHSF1_846_A48_S26 | 25 | 94 |
| hsHSF1_751_A_LO_V14_S26 | 35 | 92 |
| hsHSF1_2030_A48_S26 | 40 | 94 |
| hsHSF1_2030_A22_S26 | 50 | 93 |

Example 2D. Activity of HSF1 RNAi Agents in GTL-16 and SK-BR-3 Cells

Table 7 provides a comparison of the activity of selected HSF1 RNAi agents in GTL-16 and SK-BR-3 cells in vitro.

TABLE 7

| SiRNAs | % Inhibition in GTL-16 | % Knockdown in GTL-16 | % Inhibition in SK-BR-3 | % Knockdown in SK-BR-3 |
| --- | --- | --- | --- | --- |
| hsHSF1_846_A22_S26 | 0 | 70 | 0 | 92 |
| hsHSF1_2138_A22_S26 | 0 | 60 | 8 | 92 |
| hsHSF1_751_A48_S26 | 0 | 50 | 20 | 92 |
| hsHSF1_751_A22_S26 | 0 | 70 | 25 | 95 |
| hsHSF1_846_A48_S26 | 8 | 70 | 25 | 94 |
| hsHSF1_751_A_LO_V14_S26 | 8 | 60 | 35 | 92 |
| hsHSF1_2030_A48_S26 | 5 | 60 | 40 | 94 |
| hsHSF1_2030_A22_S26 | 6 | 70 | 50 | 93 |

Example 3. Specificity of HSF1 RNAi Agents to HSF1

RNAi agent hs_HSF1_2138, shown by experimental data discussed above to be effective in mediating RNAi against HSF1, was found to have a 19-mer complementarity to a portion of the sense strand of another gene, DGAT1 mRNA.

hs_HSF1_2138, PBS (phosphate-buffered saline, a negative control), hs_HSF1_544 or HSF-544-1 (hs_HSF_562], HSF1_2120-1 [hs_HSF1_2138] and the unrelated luc (luciferase, another negative control) were tested for RNA interference in vivo in Hep3B subcutaneous tumors in test animals. RNAi agents were delivered in a lipid nanoparticle.

The results showed that hs_HSF_562 (about 75% gene knockdown) and hs_HSF1_2138 (about 73% gene knockdown) both mediated RNAi against HSF1 but not significantly against DGAT1, with RNAi in the range of only about 20% for both hs_HSF_562 and hs_HSF1_2138.

As for the controls, PBS did not knockdown either HSF1 or DGAT1 expression. The luciferase RNAi agent was also ineffective in knocking down either HSF1 or DGAT1 expression.

These results show that hs_HSF1_2138 (which was shown above to mediate RNAi against HSF1) did not mediate RNAi against DGAT1, despite having a 19-mer complementary to the DGAT1 mRNA.

Similar results are also obtained using the same RNAi agents in HeLa cells in vitro.

Example 4. Experimental Protocols

This Example details experimental protocols for screening of duplexes in gene knockdown and cell proliferation assays. This Example describes: (A) the overall screening procedure for measuring the effects of duplexes on HSF1 gene knockdown and cell proliferation; (B) the cDNA synthesis procedure for measuring gene knockdown; and (C) the proliferation CTG (PROMEGA CELL TITER GLO™ luminescent cell viability assay) assay procedure.

A. Overall Screening Procedure for Measuring Effects of Duplexes on Knockdown and Cell Proliferation.

The overall screening procedure involves these steps: inputting platemap to template (to program the TECAN FREEDOM EVO™ robotic worktable in preparing initial multi-well plates); creating the master block (by the TECAN); aliquoting 20 ul per cell plate (performed by PERKIN ELMER JANUS™ automated workstation); cell plating; changing media at 24 hours; measuring knockdown at 48 hours (performed by ZYMARK CALIPER SCI-CLONE ALH3000™ liquid handing system); and measuring cell proliferation with CTG assay.

Details: The total number of duplexes screened is 33. A 9-point dose response is performed, starting with a concentration of 10 nM and 1:3 dilutions for 9-point single agent dose response. The number of cell lines tested is 2 (GTL-16 and SK-BR-3). The timepoint for measuring knockdown is 48 hours. The timepoints for measuring proliferation are 5 days and 10 days.

Additional Details: The transfection agent is RNAiMax. OptiMem I media is also used. The volume of transfection reagent=0.1 ul/well×100 wells×number of cell plates to be screened+Dead volume for 2 plates. The volume of OptiMem I media=9.9 ul/well×100 wells×number of cell plates to be screened+Dead volume for 2 plates. For example, for 2 blocks and 2 cell lines, the transfection reagent needed=200 ul, and OptiMem I media needed=19.8 ml. This mix is incubated for 10 min. at room temperature. 1.8 ul of siRNA as per plate map in the workbook is aliquoted to column 2 of 96-well U-bottom plate. A siRNA aliquoted plate is prepared and put into position. An empty 96-well U-bottom plate is prepared and placed into position. The method is run to create a block with siRNA+transfection reagent and incubated for 20 minutes at room temperature.

B. cDNA Synthesis for TAQMAN™ Assay System for Measuring Knockdown Mediated by Duplexes This procedure involves the following steps (CELLS-TO-CT™ kit from Applied Biosystems): 1×PBS is placed at 4 degrees or on ice. Lysis buffer is prepared by mixing 49.5 ul/well of lysis solution+0.5 ul/well of DNAse I and aliquoting to U-bottom 96-well plate. Plates are checked for confluency or contamination. Stop solution, 2×RT buffer and 20× RT-enzyme mix are thawed. Stop solution is aliquoted to 96-well PCR plate and 10 ul of dead volume is added. Cells in contaminated wells are disposed of.

cDNA is generated via RT (reverse transcription). This procedure involves the following steps: RT mastermix plates are prepared. Mix is made and aliquoted 16 ul/well to 96-well PCR plate and plates are placed on ice. 10 ul of 2×RT buffer, 1 ul of 20× RT Enzyme mix, and 5 ul of DNAase RNAse free ultrapure water is used per well. CALIPER SCICLONE ALH3000™ liquid handing system is used to apirate media and add 50 ul of cold 1×PBS (phosphate-buffered saline solution) to 4 plates that undergo lysis and RT steps. Plates are transferred to ice. PBS is aspirated. Cell plates, lysis, RT and stop solution plates are placed on deck per the layout. A method is run on the ALH3000™ liquid handling system, where it transfers prealiquoted lysis buffer, stop solution and RT-mix to cell plates for generating cDNA for knockdown. Plates are transferred to a BIORAD™ PCR machine and the PCR method run. Cell plates are stored at −80 C for processing for lysis, stop reactions and RT reactions, if required to repeat the experiment.

The TAQMAN™ Assay is performed. This procedure involves the following steps: cDNA plates are thawed and centrifuged at 3000 rpm (revolutions per minutes) for 3 min. 2× Taqman universal master mix and 20× beta-actin are added. Appropriate probes are added and aliquoted to 96 well PCR plates and the assay run.

C. Proliferation CTG Reads.

The following steps are used in the CTG procedure: After the plates are incubated either day 4 or day 5 (as per the project), 100 ul of PROMEGA CELL TITER GLO™ (CTG) luminescent cell viability assay solution is added. The plates are shaken for 15-20 min. on plate shaker and read. The data is collected and saved.

EQUIVALENTS

A composition of embodiment 1 is a composition comprising a RNAi agent for inhibition of HSF1 comprising a sense strand and an antisense strand, wherein the antisense strand comprises at least 15 contiguous nucleotides differing by 0, 1, 2, or 3 nucleotides from the antisense strand of a RNAi agent specific to HSF1 provided in Table A1.

The composition of embodiment 1, wherein the composition further comprises a second RNAi agent to HSF1.

The composition of embodiment 1, wherein the antisense strand is 30 or fewer nucleotides in length.

The composition of embodiment 1, wherein the sense strand and the antisense strand form a duplex region 15 to 30 nucleotide pairs in length.

The composition of embodiment 1, wherein the antisense strand and the sense strand are independently 19 to 23 nucleotides in length.

The composition of embodiment 1, wherein the RNAi agent comprises a modification that causes the RNAi agent to have increased stability in a biological sample or environment.

The composition of embodiment 1, wherein the RNAi agent comprises at least one modified backbone and/or at least one 2'-modified nucleotide.

The composition of embodiment 1, wherein the RNAi agent comprises:

a) at least one 5'-uridine-adenine-3' (5'-ua-3') dinucleotide, wherein the uridine is a 2'-modified nucleotide; and/or b) at least one 5'-uridine-guanine-3' (5'-ug-3') dinucleotide, wherein the 5'-uridine is a 2'-modified nucleotide; and/or c) at least one 5'-cytidine-adenine-3' (5'-ca-3') dinucleotide, wherein the 5'-cytidine is a 2'-modified nucleotide; and/or d) at least one 5'-uridine-uridine-3' (5'-uu-3') dinucleotide, wherein the 5'-uridine is a 2'-modified nucleotide.

The composition of embodiment 1, wherein the RNAi agent comprises a 2'-modification selected from the group consisting of: 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA).

The composition of embodiment 1, wherein the RNAi agent comprises a blunt end.

The composition of embodiment 1, wherein the RNAi agent comprises a 3' end cap.

The composition of embodiment 1, wherein the RNAi agent comprises a 3' end cap and a blunt end.

The composition of embodiment 1, wherein the RNAi agent comprises a 3' end cap and at least one 2' modification.

The composition of embodiment 1, wherein the RNAi agent comprises a 5' end cap.

The composition of embodiment 1, wherein the RNAi agent comprises a 5' end cap and a 3' end cap.

The composition of embodiment 1, wherein the RNAi agent comprises a 3' end cap, a blunt end and a 5' end cap.

The composition of embodiment 1, wherein the RNAi agent comprises any one or more of: at least one 2' modification, a 3' end cap, a 5' end cap, and a blunt end.

The composition of embodiment 1, wherein the RNAi agent comprises an overhang having 1 to 4 unpaired nucleotides.

The composition of embodiment 1, wherein the RNAi agent comprises an overhang at the 3'-end of the antisense strand of the RNAi agent.

The composition of embodiment 1, wherein the RNAi agent is ligated to one or more agent selected from: one or more diagnostic compound, reporter group, cross-linking agent, nuclease-resistance conferring moiety, natural or unusual nucleobase, lipophilic molecule, cholesterol, lipid, lectin, steroid, uvaol, hecigenin, diosgenin, terpene, triterpene, sarsasapogenin, Friedelin, epifriedelanol-derivatized lithocholic acid, vitamin, carbohydrate, dextran, pullulan, chitin, chitosan, synthetic carbohydrate, oligo lactate 15-mer, natural polymer, low- or medium-molecular weight polymer, inulin, cyclodextrin, hyaluronic acid, protein, protein-binding agent, integrin-targeting molecule, polycationic, peptide, polyamine, peptide mimic, and/or transferrin.

The composition of embodiment 1, wherein the RNAi agent is capable of inhibiting expression of the HSF1 gene by at least about 60% at a concentration of 10 nM in HeLa, GTL-16, or SK-BR-3 cells in vitro.

The composition of embodiment 1, wherein the RNAi agent is capable of inhibiting expression of the HSF1 gene by at least about 70% at a concentration of 10 nM in HeLa, GTL-16, or SK-BR-3 cells in vitro.

The composition of embodiment 1, wherein the RNAi agent is capable of inhibiting expression of the HSF1 gene by at least about 80% at a concentration of 10 nM in HeLa, GTL-16, or SK-BR-3 cells in vitro.

The composition of embodiment 1, wherein the RNAi agent is capable of inhibiting expression of the HSF1 gene by at least about 90% at a concentration of 10 nM in HeLa, GTL-16, or SK-BR-3 cells in vitro.

The composition of embodiment 1, wherein the RNAi has an EC50 of no more than about 0.1 nM.

The composition of embodiment 1, wherein the RNAi has an EC50 of no more than about 0.01 nM.

The composition of embodiment 1, wherein the RNAi has an EC50 of no more than about 0.001 nM.

A composition of embodiment 2 is a composition comprising a RNAi agent for inhibition of HSF1 comprising a first strand and a second strand, wherein the first strand and second strand comprise at least 15 contiguous nucleotides differing by 0, 1, 2, or 3 nucleotides from the first and second strand, respectively, of a RNAi agent specific to HSF1 provided in Table A1.

The composition of embodiment 2, wherein the composition comprises a second RNAi agent to HSF1.

The composition of embodiment 2, wherein the second strand is 30 or fewer nucleotides in length.

The composition of embodiment 2, wherein the first strand and the second strand form a duplex region 15 to 30 nucleotide pairs in length.

The composition of embodiment 2, wherein the first strand and the second strand are independently 19 to 23 nucleotides in length.

The composition of embodiment 2, wherein the RNAi agent comprises a modification that causes the RNAi agent to have increased stability in a biological sample or environment.

The composition of embodiment 2, wherein the RNAi agent comprises a phosphorothioate and/or a 2'-modified nucleotide.

The composition of embodiment 2, wherein the RNAi agent comprises:

at least one 5'-uridine-adenine-3' (5'-ua-3') dinucleotide, wherein the uridine is a 2'-modified nucleotide; and/or at least one 5'-uridine-guanine-3' (5'-ug-3') dinucleotide, wherein the 5'-uridine is a 2'-modified nucleotide;

and/or at least one 5'-cytidine-adenine-3' (5'-ca-3') dinucleotide, wherein the 5'-cytidine is a 2'-modified nucleotide;

and/or at least one 5'-uridine-uridine-3' (5'-uu-3') dinucleotide, wherein the 5'-uridine is a 2'-modified nucleotide.

The composition of embodiment 2, wherein the RNAi agent comprises one or more 2'-modifications selected from the group consisting of:

2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA).

The composition of embodiment 2, wherein the RNAi agent comprises a blunt end.

The composition of embodiment 2, wherein the RNAi agent comprises a 3' end cap.

The composition of embodiment 2, wherein the RNAi agent comprises a 3' end cap and a blunt end.

The composition of embodiment 2, wherein the RNAi agent comprises a 3' end cap and at least one 2' modification.

The composition of embodiment 2, wherein the RNAi agent comprises a 5' end cap.

The composition of embodiment 2, wherein the RNAi agent comprises a 5' end cap and a 3' end cap.

The composition of embodiment 2, wherein the RNAi agent comprises a 3' end cap, a blunt end and a 5' end cap.

The composition of embodiment 2, wherein the RNAi agent comprises any one or more of: at least one 2' modification, a 3' end cap, a 5' end cap, and a blunt end.

The composition of embodiment 2, wherein the RNAi agent comprises an overhang having 1 to 4 unpaired nucleotides.

The composition of embodiment 2, wherein the RNAi agent comprises an overhang at the 3'-end of the antisense strand.

The composition of embodiment 2, wherein the RNAi agent is ligated to one or more agents, the agent selected from a: one or more diagnostic compound, reporter group, cross-linking agent, nuclease-resistance conferring moiety, natural or unusual nucleobase, lipophilic molecule, cholesterol, lipid, lectin, steroid, uvaol, hecigenin, diosgenin, terpene, triterpene, sarsasapogenin, Friedelin, epifriedelanol-derivatized lithocholic acid, vitamin, carbohydrate, dextran, pullulan, chitin, chitosan, synthetic carbohydrate, oligo lactate 15-mer, natural polymer, low- or medium-molecular weight polymer, inulin, cyclodextrin, hyaluronic acid, protein, protein-binding agent, integrin-targeting molecule, polycationic, peptide, polyamine, peptide mimic, and/or transferrin.

The composition of embodiment 2, wherein the RNAi agent is capable of inhibiting expression of the HSF1 gene by at least about 60% at a concentration of 10 nM in HeLa, GTL-16, or SK-BR-3 cells in vitro.

The composition of embodiment 2, wherein the RNAi agent is capable of inhibiting expression of the HSF1 gene by at least about 70% at a concentration of 10 nM in HeLa, GTL-16, or SK-BR-3 cells in vitro.

The composition of embodiment 2, wherein the RNAi agent is capable of inhibiting expression of the HSF1 gene by at least about 80% at a concentration of 10 nM in HeLa, GTL-16, or SK-BR-3 cells in vitro.

The composition of embodiment 2, wherein the RNAi agent is capable of inhibiting expression of the HSF1 gene by at least about 90% at a concentration of 10 nM in HeLa, GTL-16, or SK-BR-3 cells in vitro.

The composition of embodiment 2, wherein the RNAi has an EC50 of no more than about 0.1 nM.

The composition of embodiment 2, wherein the RNAi has an EC50 of no more than about 0.01 nM.

The composition of embodiment 2, wherein the RNAi has an EC50 of no more than about 0.001 nM.

A method of embodiment 3 is a method comprising a method of treating a HSF1-related disease in an individual, comprising the step of administering to the individual a therapeutically effective amount of a composition comprising a RNAi agent for inhibition of HSF1 comprising a sense strand and an antisense strand, wherein the antisense strand comprises at least 15 contiguous nucleotides differing by 0, 1, 2, or 3 nucleotides from the antisense strand of a RNAi agent specific to HSF1 provided in Table A1.

The method of embodiment 3, wherein the HSF1-related disease is cancer, or autoimmune, or a viral disease.

The method of embodiment 3, wherein the HSF1-related disease is cancer.

The method of embodiment 3, wherein the method further comprises the step of administering an additional treatment for cancer, or autoimmune, or a viral disease.

The method of embodiment 3, wherein the composition comprises a second RNAi agent to HSF1.

The method of embodiment 3, wherein the method further comprises the step of administering an additional RNAi agent to HSF1.

The method of embodiment 3, further comprising the administration of an additional treatment.

The method of embodiment 3, further comprising the administration of an additional treatment and wherein the additional treatment is a composition.

The method of embodiment 3, further comprising the administration of an additional treatment and wherein the additional treatment is a composition, and wherein the composition is a HSP90 inhibitor.

The method of embodiment 3, further comprising the administration of an additional treatment and wherein the additional treatment is a composition, and wherein the composition is a HSP90 inhibitor, and wherein the HSP90 inhibitor is AUY922.

The method of embodiment 3, further comprising the administration of an additional treatment and wherein the additional treatment is a method.

The method of embodiment 3, further comprising the administration of an additional treatment and wherein the additional treatment and the RNAi agent can be administered in any order.

The method of embodiment 3, wherein the antisense strand is 30 or fewer nucleotides in length.

The method of embodiment 3, wherein the sense strand and the antisense strand form a duplex region 15 to 30 nucleotide pairs in length.

The method of embodiment 3, wherein the sense strand and the antisense strand are independently 19 to 23 nucleotides in length.

The method of embodiment 3, wherein the RNAi agent comprises a modification that causes the RNAi agent to have increased stability in a biological sample or environment.

The method of embodiment 3, wherein the RNAi agent comprises a phosphorothioate and/or a 2'-modified nucleotide.

The method of embodiment 3, wherein the RNAi agent comprises:
at least one 5'-uridine-adenine-3' (5'-ua-3') dinucleotide, wherein the uridine is a 2'-modified nucleotide; and/or at least one 5'-uridine-guanine-3' (5'-ug-3') dinucleotide, wherein the 5'-uridine is a 2'-modified nucleotide;
and/or at least one 5'-cytidine-adenine-3' (5'-ca-3') dinucleotide, wherein the 5'-cytidine is a 2'-modified nucleotide;
and/or at least one 5'-uridine-uridine-3' (5'-uu-3') dinucleotide, wherein the 5'-uridine is a 2'-modified nucleotide.

The method of embodiment 3, wherein the RNAi agent comprises one or more 2'-modifications selected from the group consisting of:
2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA).

The method of embodiment 3, wherein the RNAi agent comprises a blunt end.

The method of embodiment 3, wherein the RNAi agent comprises a 3' end cap.

The method of embodiment 3, wherein the RNAi agent comprises a 3' end cap and a blunt end.

The method of embodiment 3, wherein the RNAi agent comprises a 3' end cap and at least one 2' modification.

The method of embodiment 3, wherein the RNAi agent comprises a 5' end cap.

The method of embodiment 3, wherein the RNAi agent comprises a 5' end cap and a 3' end cap.

The method of embodiment 3, wherein the RNAi agent comprises a 3' end cap, a blunt end and a 5' end cap.

The method of embodiment 3, wherein the RNAi agent comprises any one or more of: at least one 2' modification, a 3' end cap, a 5' end cap, and a blunt end.

A method of embodiment 4 is a method comprising a method of inhibiting the expression of the HSF1 gene in an individual, comprising the step of administering to the individual a therapeutically effective amount of a composition comprising a RNAi agent for inhibition of HSF1 comprising a sense strand and an antisense strand, wherein the antisense strand comprises at least 15 contiguous nucleotides differing by 0, 1, 2, or 3 nucleotides from the antisense strand of a RNAi agent specific to HSF1 provided in Table A1.

The method of embodiment 4, wherein the individual is afflicted with or susceptible to a HSF1-related disease.

The method of embodiment 4, wherein the HSF1-related disease is cancer, or autoimmune, or a viral disease.

The method of embodiment 4, wherein the HSF1-related disease is cancer.

The method of embodiment 4, further comprising the administration of an additional treatment.

The method of embodiment 4, further comprising the administration of an additional treatment.

The method of embodiment 4, wherein the additional treatment is a composition.

The method of embodiment 4, further comprising the administration of an additional treatment.

The method of embodiment 4, wherein the additional treatment is a method.

The method of embodiment 4, further comprising the administration of an additional treatment.

The method of embodiment 4, wherein the additional treatment and the RNAi agent can be administered in any order.

The method of embodiment 4, further comprising the administration of an additional treatment.

The method of embodiment 4, wherein the additional treatment is a HSP90 inhibitor.

The method of embodiment 4, further comprising the administration of an additional treatment.

The method of embodiment 4, wherein the additional treatment is a HSP90 inhibitor and wherein the HSP90 inhibitor is AUY922.

The method of embodiment 4, wherein the antisense strand is 30 or fewer nucleotides in length.

The method of embodiment 4, wherein the sense strand and the antisense strand form a duplex region 15 to 30 nucleotide pairs in length.

The method of embodiment 4, wherein the sense strand and the antisense strand are independently 19 to 23 nucleotides in length.

The method of embodiment 4, wherein the RNAi agent comprises a modification that causes the RNAi agent to have increased stability in a biological sample or environment.

The method of embodiment 4, wherein the RNAi agent comprises a phosphorothioate and/or a 2'-modified nucleotide.

The method of embodiment 4, wherein the RNAi agent comprises:

at least one 5'-uridine-adenine-3' (5'-ua-3') dinucleotide, wherein the uridine is a 2'-modified nucleotide; and/or at least one 5'-uridine-guanine-3' (5'-ug-3') dinucleotide, wherein the 5'-uridine is a 2'-modified nucleotide;

and/or at least one 5'-cytidine-adenine-3' (5'-ca-3') dinucleotide, wherein the 5'-cytidine is a 2'-modified nucleotide;

and/or at least one 5'-uridine-uridine-3' (5'-uu-3') dinucleotide, wherein the 5'-uridine is a 2'-modified nucleotide.

The method of embodiment 3, wherein the RNAi agent comprises one or more 2'-modifications selected from the group consisting of:

2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA).

The method of embodiment 4, wherein the RNAi agent comprises a blunt end.

The method of embodiment 4, wherein the RNAi agent comprises a 3' end cap.

The method of embodiment 4, wherein the RNAi agent comprises a 3' end cap and a blunt end.

The method of embodiment 4, wherein the RNAi agent comprises a 3' end cap and at least one 2' modification.

The method of embodiment 4, wherein the RNAi agent comprises a 5' end cap.

The method of embodiment 4, wherein the RNAi agent comprises a 5' end cap and a 3' end cap.

The method of embodiment 4, wherein the RNAi agent comprises a 3' end cap, a blunt end and a 5' end cap.

The method of embodiment 4, wherein the RNAi agent comprises any one or more of: at least one 2' modification, a 3' end cap, a 5' end cap, and a blunt end.

A composition of embodiment 5 comprises a medicament for use in an RNAi formulation comprising a RNAi agent for inhibition of HSF1 comprising a sense strand and an antisense strand, wherein the antisense strand comprises at least 15 contiguous nucleotides differing by 0, 1, 2, or 3 nucleotides from the antisense strand of a RNAi agent specific to HSF1 provided in Table A1.

Any composition above in a pharmaceutically effective formulation.

The composition according to embodiment 5, for use in a method of treating a HSF1-related disease in an individual, the method comprising the step of administering to the individual a therapeutically effective amount of a composition according to embodiment 5.

The use of a composition according to embodiment 5, in the manufacture of a medicament for the treatment of a HSF1-related disease.

The use of a composition according to embodiment 5, wherein the HSF1-related disease is cancer, or autoimmune, or a viral disease.

The composition of embodiment 5, wherein all the pyrimidines are 2' O-methyl-modified nucleotides.

The composition of embodiment 5, wherein all the pyrimidines are 2' O-methyl-modified nucleotides.

The composition of embodiment 5, wherein the composition comprises a second RNAi agent to HSF1.

The composition of embodiment 5, wherein the second strand is 30 or fewer nucleotides in length.

The composition of embodiment 5, wherein the first strand and the second strand form a duplex region 15 to 30 nucleotide pairs in length.

The composition of embodiment 5, wherein the first strand and the second strand are independently 19 to 23 nucleotides in length.

The composition of embodiment 5, wherein the RNAi agent comprises a modification that causes the RNAi agent to have increased stability in a biological sample or environment.

The composition of embodiment 5, wherein the RNAi agent comprises a phosphorothioate and/or a 2'-modified nucleotide.

The composition of embodiment 5, wherein the RNAi agent comprises:

at least one 5'-uridine-adenine-3' (5'-ua-3') dinucleotide, wherein the uridine is a 2'-modified nucleotide; and/or at least one 5'-uridine-guanine-3' (5'-ug-3') dinucleotide, wherein the 5'-uridine is a 2'-modified nucleotide;

and/or at least one 5'-cytidine-adenine-3' (5'-ca-3') dinucleotide, wherein the 5'-cytidine is a 2'-modified nucleotide;

and/or at least one 5'-uridine-uridine-3' (5'-uu-3') dinucleotide, wherein the 5'-uridine is a 2'-modified nucleotide.

The composition of embodiment 5, wherein the RNAi agent comprises one or more 2'-modifications selected from the group consisting of:

2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA).

The composition of embodiment 5, wherein the RNAi agent comprises a blunt end.

The composition of embodiment 5, wherein the RNAi agent comprises a 3' end cap.

The composition of embodiment 5, wherein the RNAi agent comprises a 3' end cap and a blunt end.

The composition of embodiment 5, wherein the RNAi agent comprises a 3' end cap and at least one 2' modification.

The composition of embodiment 5, wherein the RNAi agent comprises a 5' end cap.

The composition of embodiment 5, wherein the RNAi agent comprises a 5' end cap and a 3' end cap.

The composition of embodiment 5, wherein the RNAi agent comprises a 3' end cap, a blunt end and a 5' end cap.

The composition of embodiment 5, wherein the RNAi agent comprises any one or more of: at least one 2' modification, a 3' end cap, a 5' end cap, and a blunt end.

The composition of embodiment 5, wherein the RNAi agent comprises an overhang having 1 to 4 unpaired nucleotides.

The composition of embodiment 5, wherein the RNAi agent comprises an overhang at the 3'-end of the antisense strand.

The composition of embodiment 5, wherein the RNAi agent is ligated to one or more agents, the agent selected from a: one or more diagnostic compound, reporter group, cross-linking agent, nuclease-resistance conferring moiety, natural or unusual nucleobase, lipophilic molecule, cholesterol, lipid, lectin, steroid, uvaol, hecigenin, diosgenin, terpene, triterpene, sarsasapogenin, Friedelin, epifriedelanol-derivatized lithocholic acid, vitamin, carbohydrate, dextran, pullulan, chitin, chitosan, synthetic carbohydrate, oligo lactate 15-mer, natural polymer, low- or medium-molecular weight polymer, inulin, cyclodextrin, hyaluronic acid, protein, protein-binding agent, integrin-targeting molecule, polycationic, peptide, polyamine, peptide mimic, and/or transferrin.

The composition of embodiment 5, wherein the RNAi agent is capable of inhibiting expression of the HSF1 gene by at least about 60% at a concentration of 10 nM in HeLa, GTL-16, or SK-BR-3 cells in vitro.

The composition of embodiment 5, wherein the RNAi agent is capable of inhibiting expression of the HSF1 gene by at least about 70% at a concentration of 10 nM in HeLa, GTL-16, or SK-BR-3 cells in vitro.

The composition of embodiment 5, wherein the RNAi agent is capable of inhibiting expression of the HSF1 gene by at least about 80% at a concentration of 10 nM in HeLa, GTL-16, or SK-BR-3 cells in vitro.

The composition of embodiment 5, wherein the RNAi agent is capable of inhibiting expression of the HSF1 gene by at least about 90% at a concentration of 10 nM in HeLa, GTL-16, or SK-BR-3 cells in vitro.

The composition of embodiment 5, wherein the RNAi has an EC50 of no more than about 0.1 nM.

The composition of embodiment 5, wherein the RNAi has an EC50 of no more than about 0.01 nM.

The composition of embodiment 5, wherein the RNAi has an EC50 of no more than about 0.001 nM.

A composition of embodiment 6 is a composition comprising a RNAi agent for inhibition of HSF1 comprising a first strand and a second strand, wherein the sequence of the first strand comprises the sequence of the first strand of a RNAi agent specific to HSF1 provided in Table A1.

A composition of embodiment 6 is a composition comprising a RNAi agent for inhibition of HSF1 comprising a first strand and a second strand, wherein the sequence of the first strand comprises the sequence of the first strand of a RNAi agent specific to HSF1 provided in Table A1, the sequence of the first strand further comprising up to about 6 additional nucleotides.

The composition of embodiment 6, wherein the composition further comprises a second RNAi agent to HSF1.

The composition of embodiment 6, wherein the antisense strand is 30 or fewer nucleotides in length.

The composition of embodiment 6, wherein the sense strand and the antisense strand form a duplex region 15 to 30 nucleotide pairs in length.

The composition of embodiment 6, wherein the antisense strand and the sense strand are independently 19 to 23 nucleotides in length.

The composition of embodiment 6, wherein the RNAi agent comprises a modification that causes the RNAi agent to have increased stability in a biological sample or environment.

The composition of embodiment 6, wherein the RNAi agent comprises at least one modified backbone and/or at least one 2'-modified nucleotide.

The composition of embodiment 6, wherein the RNAi agent comprises:

a) at least one 5'-uridine-adenine-3' (5'-ua-3') dinucleotide, wherein the uridine is a 2'-modified nucleotide; and/or b) at least one 5'-uridine-guanine-3' (5'-ug-3') dinucleotide, wherein the 5'-uridine is a 2'-modified nucleotide; and/or c) at least one 5'-cytidine-adenine-3' (5'-ca-3') dinucleotide, wherein the 5'-cytidine is a 2'-modified nucleotide; and/or d) at least one 5'-uridine-uridine-3' (5'-uu-3') dinucleotide, wherein the 5'-uridine is a 2'-modified nucleotide.

The composition of embodiment 6, wherein the RNAi agent comprises a 2'-modification selected from the group consisting of: 2'-deoxy, 2'-deoxy-2'-fluoro, 2'-O-methyl, 2'-O-methoxyethyl(2'-O-MOE), 2'-O-aminopropyl (2'-O-AP), 2'-O-dimethylaminoethyl (2'-O-DMAOE), 2'-O-dimethylaminopropyl (T-O-DMAP), 2'-O-dimethylaminoethyloxyethyl (T-O-DMAEOE), and 2'-O—N-methylacetamido (2'-O-NMA).

The composition of embodiment 6, wherein the RNAi agent comprises a blunt end.

The composition of embodiment 6, wherein the RNAi agent comprises an overhang having 1 to 4 unpaired nucleotides.

The composition of embodiment 6, wherein the RNAi agent comprises an overhang at the 3'-end of the antisense strand of the RNAi agent.

The composition of embodiment 6, wherein the RNAi agent is ligated to one or more agent selected from: one or more diagnostic compound, reporter group, cross-linking agent, nuclease-resistance conferring moiety, natural or unusual nucleobase, lipophilic molecule, cholesterol, lipid, lectin, steroid, uvaol, hecigenin, diosgenin, terpene, sarsasapogenin, Friedelin, epifriedelanol-derivatized lithocholic acid, vitamin, carbohydrate, dextran, pullulan, chitin, chitosan, synthetic carbohydrate, oligo lactate 15-mer, natural polymer, low- or medium-molecular weight polymer, inulin, cyclodextrin, hyaluronic acid, protein, protein-binding agent, integrin-targeting molecule, polycationic, peptide, polyamine, peptide mimic, and/or transferrin.

The composition of embodiment 6, wherein the RNAi agent is capable of inhibiting expression of the HSF1 gene by at least about 60% at a concentration of 10 nM in HeLa, GTL-16, or SK-BR-3 cells in vitro.

The composition of embodiment 6, wherein the RNAi agent is capable of inhibiting expression of the HSF1 gene by at least about 70% at a concentration of 10 nM in HeLa, GTL-16, or SK-BR-3 cells in vitro.

The composition of embodiment 6, wherein the RNAi agent is capable of inhibiting expression of the HSF1 gene by at least about 80% at a concentration of 10 nM in HeLa, GTL-16, or SK-BR-3 cells in vitro.

The composition of embodiment 6, wherein the RNAi agent is capable of inhibiting expression of the HSF1 gene by at least about 90% at a concentration of 10 nM in HeLa, GTL-16, or SK-BR-3 cells in vitro.

The composition of embodiment 6, wherein the RNAi has an EC50 of no more than about 0.1 nM.

The composition of embodiment 6, wherein the RNAi has an EC50 of no more than about 0.01 nM.

The composition of embodiment 6, wherein the RNAi has an EC50 of no more than about 0.001 nM.

The composition of embodiment 6, wherein the RNAi agent comprises a blunt end.

The composition of embodiment 6, wherein the RNAi agent comprises a 3' end cap.

The composition of embodiment 6, wherein the RNAi agent comprises a 3' end cap and a blunt end.

The composition of embodiment 6, wherein the RNAi agent comprises a 3' end cap and at least one 2' modification.

The composition of embodiment 6, wherein the RNAi agent comprises a 5' end cap.

The composition of embodiment 6, wherein the RNAi agent comprises a 5' end cap and a 3' end cap.

The composition of embodiment 6, wherein the RNAi agent comprises a 3' end cap, a blunt end and a 5' end cap.

The composition of embodiment 6, wherein the RNAi agent comprises any one or more of: at least one 2' modification, a 3' end cap, a 5' end cap, and a blunt end.

A composition of embodiment 7 is a composition comprising a RNAi agent for inhibition of HSF1 comprising a first strand and a second strand, wherein the sequence of the first strand is the sequence of the first strand of a RNAi agent specific to HSF1 provided in Table A1.

The composition of embodiment 7, wherein the composition further comprises a second RNAi agent to HSF1.

The composition of embodiment 7, wherein the antisense strand is 30 or fewer nucleotides in length.

The composition of embodiment 7, wherein the sense strand and the antisense strand form a duplex region 15 to 30 nucleotide pairs in length.

The composition of embodiment 7, wherein the antisense strand and the sense strand are independently 19 to 23 nucleotides in length.

The composition of embodiment 7, wherein the RNAi agent comprises a modification that causes the RNAi agent to have increased stability in a biological sample or environment.

The composition of embodiment 7, wherein the RNAi agent comprises at least one modified backbone and/or at least one 2'-modified nucleotide.

The composition of embodiment 7, wherein the RNAi agent comprises:

a) at least one 5'-uridine-adenine-3' (5'-ua-3') dinucleotide, wherein the uridine is a 2'-modified nucleotide; and/or b) at least one 5'-uridine-guanine-3' (5'-ug-3') dinucleotide, wherein the 5'-uridine is a 2'-modified nucleotide; and/or c) at least one 5'-cytidine-adenine-3' (5'-ca-3') dinucleotide, wherein the 5'-cytidine is a 2'-modified nucleotide; and/or d) at least one 5'-uridine-uridine-3' (5'-uu-3') dinucleotide, wherein the 5'-uridine is a 2'-modified nucleotide.

The composition of embodiment 7, wherein the RNAi agent comprises a 2'-modification selected from the group consisting of: 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA).

The composition of embodiment 7, wherein the RNAi agent comprises a blunt end.

The composition of embodiment 7, wherein the RNAi agent comprises an overhang having 1 to 4 unpaired nucleotides.

The composition of embodiment 7, wherein the RNAi agent comprises an overhang at the 3'-end of the antisense strand of the RNAi agent.

The composition of embodiment 7, wherein the RNAi agent is ligated to one or more agent selected from: one or more diagnostic compound, reporter group, cross-linking agent, nuclease-resistance conferring moiety, natural or unusual nucleobase, lipophilic molecule, cholesterol, lipid, lectin, steroid, uvaol, hecigenin, diosgenin, terpene, triterpene, sarsasapogenin, Friedelin, epifriedelanol-derivatized lithocholic acid, vitamin, carbohydrate, dextran, pullulan, chitin, chitosan, synthetic carbohydrate, oligo lactate 15-mer, natural polymer, low- or medium-molecular weight polymer, inulin, cyclodextrin, hyaluronic acid, protein, protein-binding agent, integrin-targeting molecule, polycationic, peptide, polyamine, peptide mimic, and/or transferrin.

The composition of embodiment 7, wherein the RNAi agent is capable of inhibiting expression of the HSF1 gene by at least about 60% at a concentration of 10 nM in HeLa, GTL-16, or SK-BR-3 cells in vitro.

The composition of embodiment 7, wherein the RNAi agent is capable of inhibiting expression of the HSF1 gene by at least about 70% at a concentration of 10 nM in HeLa, GTL-16, or SK-BR-3 cells in vitro.

The composition of embodiment 7, wherein the RNAi agent is capable of inhibiting expression of the HSF1 gene by at least about 80% at a concentration of 10 nM in HeLa, GTL-16, or SK-BR-3 cells in vitro.

The composition of embodiment 7, wherein the RNAi agent is capable of inhibiting expression of the HSF1 gene by at least about 90% at a concentration of 10 nM in HeLa, GTL-16, or SK-BR-3 cells in vitro.

The composition of embodiment 7, wherein the RNAi has an EC50 of no more than about 0.1 nM.

The composition of embodiment 7, wherein the RNAi has an EC50 of no more than about 0.01 nM.

The composition of embodiment 7, wherein the RNAi has an EC50 of no more than about 0.001 nM.

The composition of embodiment 7, wherein the RNAi agent comprises a blunt end.

The composition of embodiment 7, wherein the RNAi agent comprises a 3' end cap.

The composition of embodiment 7, wherein the RNAi agent comprises a 3' end cap and a blunt end.

The composition of embodiment 7, wherein the RNAi agent comprises a 3' end cap and at least one 2' modification.

The composition of embodiment 7, wherein the RNAi agent comprises a 5' end cap.

The composition of embodiment 7, wherein the RNAi agent comprises a 5' end cap and a 3' end cap.

The composition of embodiment 7, wherein the RNAi agent comprises a 3' end cap, a blunt end and a 5' end cap.

The composition of embodiment 7, wherein the RNAi agent comprises any one or more of: at least one 2' modification, a 3' end cap, a 5' end cap, and a blunt end.

Unless defined otherwise, the technical and scientific terms used herein have the same meaning as that usually understood by a specialist familiar with the field to which the disclosure belongs.

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein. Unless indicated otherwise, each of the references cited herein is incorporated in its entirety by reference.

Claims to the invention are non-limiting and are provided below.

Although particular embodiments and claims have been disclosed herein in detail, this has been done by way of example for purposes of illustration only, and is not intended to be limiting with respect to the scope of the appended claims, or the scope of subject matter of claims of any corresponding future application. In particular, it is contemplated by the inventors that various substitutions, alterations, and modifications may be made to the disclosure without departing from the spirit and scope of the disclosure as defined by the claims. The choice of nucleic acid starting material, clone of interest, or library type is believed to be a matter of routine for a person of ordinary skill in the art with knowledge of the embodiments described herein. Other aspects, advantages, and modifications considered to be within the scope of the following claims. Those skilled in the art will recognize or be able to ascertain, using no more than routine experimentation, many equivalents of the specific embodiments of the invention described herein. Such equivalents are intended to be encompassed by the following claims. Redrafting of claim scope in later filed corresponding applications may be due to limitations by the patent laws of various countries and should not be interpreted as giving up subject matter of the claims.

---

We claim:

1. A composition comprising a RNAi agent for inhibiting the expression of HSF1, the RNAi agent comprising a sense strand and an antisense strand, wherein the antisense strand comprises at least 19 contiguous nucleotides differing by 0 or 1 nucleotides from:
   (i) the antisense strand sequence UUAGCAUAGAGCCUGUCUG (SEQ ID NO: 178); or
   (ii) the antisense strand sequence UUUAGCAUAGAGCCUGUCU (SEQ ID NO: 179);
wherein the antisense strand comprises at least one modified backbone and/or at least one 2'-modified nucleotide, and wherein the sense strand is at least substantially complementary to the antisense strand.

2. The composition of claim 1, wherein the composition further comprises a second RNAi agent to HSF1.

3. The composition of claim 1, wherein the RNAi agent comprises at least one phosphorothioate linkage.

4. The composition of claim 1, wherein the RNAi agent is ligated to one or more agent selected from: one or more diagnostic compound, reporter group, cross-linking agent, nuclease-resistance conferring moiety, natural or unusual nucleobase, lipophilic molecule, cholesterol, lipid, lectin, steroid, uvaol, hecigenin, diosgenin, terpene, triterpene, sarsasapogenin, Friedelin, epifriedelanol-derivatized lithocholic acid, vitamin, carbohydrate, dextran, pullulan, chitin, chitosan, synthetic carbohydrate, oligo lactate 15-mer, natural polymer, low- or medium-molecular weight polymer, inulin, cyclodextrin, hyaluronic acid, protein, protein-binding agent, integrin-targeting molecule, polycationic, peptide, polyamine, peptide mimic, and transferrin.

5. The composition of claim 1, wherein the composition is a pharmaceutically effective formulation.

6. The composition of claim 2, wherein the composition is a pharmaceutically effective formulation.

7. The composition of claim 1, wherein all the pyrimidine nucleotides of the RNAi agent are 2'-O-methyl modified nucleotides.

8. The composition of claim 1, wherein the antisense strand of the RNAi agent comprises:
   (i) the sequence UUAGCAUAGAGCCUGUCUG (SEQ ID NO: 178); or
   (ii) the sequence UUUAGCAUAGAGCCUGUCU (SEQ ID NO: 179).

9. The composition of claim 1, wherein the sense strand of the RNAi agent comprises at least 19 contiguous nucleotides differing by 0, 1, 2, or 3 nucleotides from:
   (i) the sequence CAGACAGGCUCUAUGCUAA (SEQ ID NO: 262); or
   (ii) the sequence AGACAGGCUCUAUGCUAAA (SEQ ID NO: 263).

10. The composition of claim 9, wherein the sense strand of the RNAi agent comprises at least 19 contiguous nucleotides differing by 0 or 1 nucleotides from:
    (i) the sequence CAGACAGGCUCUAUGCUAA (SEQ ID NO: 262); or
    (ii) the sequence AGACAGGCUCUAUGCUAAA (SEQ ID NO: 263).

11. The composition of claim 1, wherein the RNAi agent comprises:
    (i) an antisense strand that comprises the sequence UUAGCAUAGAGCCUGUCUG (SEQ ID NO: 178) and the sense strand comprises the sequence CAGACAGGCUCUAUGCUAA (SEQ ID NO: 262); or
    (ii) an antisense strand that comprises the sequence UUUAGCAUAGAGCCUGUCU (SEQ ID NO: 179) and the sense strand comprises the sequence AGACAGGCUCUAUGCUAAA (SEQ ID NO: 263).

12. The composition of claim 11, wherein the RNAi agent comprises:
    (i) 2153_A22_S26 (SEQ ID Pair NOs: 346/430);
    (ii) 2153_A25_S27 (SEQ ID Pair NOs: 358/442);
    (iii) 2153_A81_S26 (SEQ ID Pair NOs: 370/454);
    (iv) 2153_A48_S26 (SEQ ID Pair NOs: 382/466);
    (v) 2153_A82_S36 (SEQ ID Pair NOs: 394/478);
    (vi) 2153_A83_S36 (SEQ ID Pair NOs: 406/490); or
    (vii) 2153_A84_S36 (SEQ ID Pair NOs: 418/502).

13. The composition of claim 11, wherein the RNAi agent comprises:
    (i) 2154_A22_S26 (SEQ ID Pair NOs: 347/431);
    (ii) 2154_A25_S27 (SEQ ID Pair NOs: 359/443);
    (iii) 2154_A81_S26 (SEQ ID Pair NOs: 371/455);
    (iv) 2154_A48_S26 (SEQ ID Pair NOs: 383/467);
    (v) 2154_A82_S36 (SEQ ID Pair NOs: 395/479);
    (vi) 2154_A83_S36 (SEQ ID Pair NOs: 407/491); or
    (vii) 2154_A84_S36 (SEQ ID Pair NOs: 419/503).

* * * * *

SEQUENCE LISTING

```
<160> NUMBER OF SEQ ID NOS: 515

<210> SEQ ID NO 1
<211> LENGTH: 19
<212> TYPE: DNA
<213> ORGANISM: Homo sapiens

<400> SEQUENCE: 1
tttatgtctt cactcttca                                                   19

<210> SEQ ID NO 2
<211> LENGTH: 19
<212> TYPE: DNA
<213> ORGANISM: Homo sapiens

<400> SEQUENCE: 2
atcaggaact gaatgagct                                                   19

<210> SEQ ID NO 3
<211> LENGTH: 19
<212> TYPE: DNA
<213> ORGANISM: Homo sapiens

<400> SEQUENCE: 3
tgagatcagg aactgaatg                                                   19

<210> SEQ ID NO 4
<211> LENGTH: 19
<212> TYPE: DNA
<213> ORGANISM: Homo sapiens

<400> SEQUENCE: 4
ttgatgttct caaggagct                                                   19

<210> SEQ ID NO 5
<211> LENGTH: 19
<212> TYPE: DNA
<213> ORGANISM: Homo sapiens
```

<400> SEQUENCE: 5
tatacttggg catggaatg                                                19

<210> SEQ ID NO 6
<211> LENGTH: 19
<212> TYPE: DNA
<213> ORGANISM: Homo sapiens

<400> SEQUENCE: 6
ttatccaggt tggagtcca                                                19

<210> SEQ ID NO 7
<211> LENGTH: 19
<212> TYPE: DNA
<213> ORGANISM: Homo sapiens

<400> SEQUENCE: 7
attctgacta tgaacaacc                                                19

<210> SEQ ID NO 8
<211> LENGTH: 19
<212> TYPE: DNA
<213> ORGANISM: Homo sapiens

<400> SEQUENCE: 8
tacaattctg actatgaac                                                19

<210> SEQ ID NO 9
<211> LENGTH: 19
<212> TYPE: DNA
<213> ORGANISM: Homo sapiens

<400> SEQUENCE: 9
tctgtttata gatctctgc                                                19

<210> SEQ ID NO 10
<211> LENGTH: 19
<212> TYPE: DNA
<213> ORGANISM: Homo sapiens

<400> SEQUENCE: 10
ttagcataga gcctgtctg                                                19

<210> SEQ ID NO 11
<211> LENGTH: 19
<212> TYPE: DNA
<213> ORGANISM: Homo sapiens

<400> SEQUENCE: 11
tttagcatag agcctgtct                                                19

<210> SEQ ID NO 12
<211> LENGTH: 19
<212> TYPE: DNA
<213> ORGANISM: Homo sapiens

<400> SEQUENCE: 12
tccatctcga gcaaggagg                                                19

<210> SEQ ID NO 13
<211> LENGTH: 19
<212> TYPE: DNA
<213> ORGANISM: Homo sapiens

```
<400> SEQUENCE: 13
tttatgtctt cactcttca                                              19

<210> SEQ ID NO 14
<211> LENGTH: 19
<212> TYPE: DNA
<213> ORGANISM: Homo sapiens

<400> SEQUENCE: 14
atcaggaact gaatgagct                                              19

<210> SEQ ID NO 15
<211> LENGTH: 19
<212> TYPE: DNA
<213> ORGANISM: Homo sapiens

<400> SEQUENCE: 15
tgagatcagg aactgaatg                                              19

<210> SEQ ID NO 16
<211> LENGTH: 19
<212> TYPE: DNA
<213> ORGANISM: Homo sapiens

<400> SEQUENCE: 16
ttgatgttct caaggagct                                              19

<210> SEQ ID NO 17
<211> LENGTH: 19
<212> TYPE: DNA
<213> ORGANISM: Homo sapiens

<400> SEQUENCE: 17
tatacttggg catggaatg                                              19

<210> SEQ ID NO 18
<211> LENGTH: 19
<212> TYPE: DNA
<213> ORGANISM: Homo sapiens

<400> SEQUENCE: 18
ttatccaggt tggagtcca                                              19

<210> SEQ ID NO 19
<211> LENGTH: 19
<212> TYPE: DNA
<213> ORGANISM: Homo sapiens

<400> SEQUENCE: 19
attctgacta tgaacaacc                                              19

<210> SEQ ID NO 20
<211> LENGTH: 19
<212> TYPE: DNA
<213> ORGANISM: Homo sapiens

<400> SEQUENCE: 20
tacaattctg actatgaac                                              19

<210> SEQ ID NO 21
<211> LENGTH: 19
<212> TYPE: DNA
<213> ORGANISM: Homo sapiens
```

```
<400> SEQUENCE: 21
tctgtttata gatctctgc                                                19

<210> SEQ ID NO 22
<211> LENGTH: 19
<212> TYPE: DNA
<213> ORGANISM: Homo sapiens

<400> SEQUENCE: 22
ttagcataga gcctgtctg                                                19

<210> SEQ ID NO 23
<211> LENGTH: 19
<212> TYPE: DNA
<213> ORGANISM: Homo sapiens

<400> SEQUENCE: 23
tttagcatag agcctgtct                                                19

<210> SEQ ID NO 24
<211> LENGTH: 19
<212> TYPE: DNA
<213> ORGANISM: Homo sapiens

<400> SEQUENCE: 24
tccatctcga gcaaggagg                                                19

<210> SEQ ID NO 25
<211> LENGTH: 19
<212> TYPE: DNA
<213> ORGANISM: Homo sapiens

<400> SEQUENCE: 25
tttatgtctt cactcttca                                                19

<210> SEQ ID NO 26
<211> LENGTH: 19
<212> TYPE: DNA
<213> ORGANISM: Homo sapiens

<400> SEQUENCE: 26
atcaggaact gaatgagct                                                19

<210> SEQ ID NO 27
<211> LENGTH: 19
<212> TYPE: DNA
<213> ORGANISM: Homo sapiens

<400> SEQUENCE: 27
tgagatcagg aactgaatg                                                19

<210> SEQ ID NO 28
<211> LENGTH: 19
<212> TYPE: DNA
<213> ORGANISM: Homo sapiens

<400> SEQUENCE: 28
ttgatgttct caaggagct                                                19

<210> SEQ ID NO 29
<211> LENGTH: 19
<212> TYPE: DNA
```

```
<213> ORGANISM: Homo sapiens

<400> SEQUENCE: 29
tatacttggg catggaatg                                                    19

<210> SEQ ID NO 30
<211> LENGTH: 19
<212> TYPE: DNA
<213> ORGANISM: Homo sapiens

<400> SEQUENCE: 30
ttatccaggt tggagtcca                                                    19

<210> SEQ ID NO 31
<211> LENGTH: 19
<212> TYPE: DNA
<213> ORGANISM: Homo sapiens

<400> SEQUENCE: 31
attctgacta tgaacaacc                                                    19

<210> SEQ ID NO 32
<211> LENGTH: 19
<212> TYPE: DNA
<213> ORGANISM: Homo sapiens

<400> SEQUENCE: 32
tacaattctg actatgaac                                                    19

<210> SEQ ID NO 33
<211> LENGTH: 19
<212> TYPE: DNA
<213> ORGANISM: Homo sapiens

<400> SEQUENCE: 33
tctgtttata gatctctgc                                                    19

<210> SEQ ID NO 34
<211> LENGTH: 19
<212> TYPE: DNA
<213> ORGANISM: Homo sapiens

<400> SEQUENCE: 34
ttagcataga gcctgtctg                                                    19

<210> SEQ ID NO 35
<211> LENGTH: 19
<212> TYPE: DNA
<213> ORGANISM: Homo sapiens

<400> SEQUENCE: 35
tttagcatag agcctgtct                                                    19

<210> SEQ ID NO 36
<211> LENGTH: 19
<212> TYPE: DNA
<213> ORGANISM: Homo sapiens

<400> SEQUENCE: 36
tccatctcga gcaaggagg                                                    19

<210> SEQ ID NO 37
<211> LENGTH: 19
```

<212> TYPE: DNA
<213> ORGANISM: Homo sapiens

<400> SEQUENCE: 37
tttatgtctt cactcttca                                              19

<210> SEQ ID NO 38
<211> LENGTH: 19
<212> TYPE: DNA
<213> ORGANISM: Homo sapiens

<400> SEQUENCE: 38
atcaggaact gaatgagct                                              19

<210> SEQ ID NO 39
<211> LENGTH: 19
<212> TYPE: DNA
<213> ORGANISM: Homo sapiens

<400> SEQUENCE: 39
tgagatcagg aactgaatg                                              19

<210> SEQ ID NO 40
<211> LENGTH: 19
<212> TYPE: DNA
<213> ORGANISM: Homo sapiens

<400> SEQUENCE: 40
ttgatgttct caaggagct                                              19

<210> SEQ ID NO 41
<211> LENGTH: 19
<212> TYPE: DNA
<213> ORGANISM: Homo sapiens

<400> SEQUENCE: 41
tatacttggg catggaatg                                              19

<210> SEQ ID NO 42
<211> LENGTH: 19
<212> TYPE: DNA
<213> ORGANISM: Homo sapiens

<400> SEQUENCE: 42
ttatccaggt tggagtcca                                              19

<210> SEQ ID NO 43
<211> LENGTH: 19
<212> TYPE: DNA
<213> ORGANISM: Homo sapiens

<400> SEQUENCE: 43
attctgacta tgaacaacc                                              19

<210> SEQ ID NO 44
<211> LENGTH: 19
<212> TYPE: DNA
<213> ORGANISM: Homo sapiens

<400> SEQUENCE: 44
tacaattctg actatgaac                                              19

<210> SEQ ID NO 45

```
<211> LENGTH: 19
<212> TYPE: DNA
<213> ORGANISM: Homo sapiens

<400> SEQUENCE: 45
tctgtttata gatctctgc                                                      19

<210> SEQ ID NO 46
<211> LENGTH: 19
<212> TYPE: DNA
<213> ORGANISM: Homo sapiens

<400> SEQUENCE: 46
ttagcataga gcctgtctg                                                      19

<210> SEQ ID NO 47
<211> LENGTH: 19
<212> TYPE: DNA
<213> ORGANISM: Homo sapiens

<400> SEQUENCE: 47
tttagcatag agcctgtct                                                      19

<210> SEQ ID NO 48
<211> LENGTH: 19
<212> TYPE: DNA
<213> ORGANISM: Homo sapiens

<400> SEQUENCE: 48
tccatctcga gcaaggagg                                                      19

<210> SEQ ID NO 49
<211> LENGTH: 19
<212> TYPE: DNA
<213> ORGANISM: Homo sapiens

<400> SEQUENCE: 49
tttatgtctt cactcttca                                                      19

<210> SEQ ID NO 50
<211> LENGTH: 19
<212> TYPE: DNA
<213> ORGANISM: Homo sapiens

<400> SEQUENCE: 50
atcaggaact gaatgagct                                                      19

<210> SEQ ID NO 51
<211> LENGTH: 19
<212> TYPE: DNA
<213> ORGANISM: Homo sapiens

<400> SEQUENCE: 51
tgagatcagg aactgaatg                                                      19

<210> SEQ ID NO 52
<211> LENGTH: 19
<212> TYPE: DNA
<213> ORGANISM: Homo sapiens

<400> SEQUENCE: 52
ttgatgttct caaggagct                                                      19
```

-continued

```
<210> SEQ ID NO 53
<211> LENGTH: 19
<212> TYPE: DNA
<213> ORGANISM: Homo sapiens

<400> SEQUENCE: 53
tatacttggg catggaatg                                               19

<210> SEQ ID NO 54
<211> LENGTH: 19
<212> TYPE: DNA
<213> ORGANISM: Homo sapiens

<400> SEQUENCE: 54
ttatccaggt tggagtcca                                               19

<210> SEQ ID NO 55
<211> LENGTH: 19
<212> TYPE: DNA
<213> ORGANISM: Homo sapiens

<400> SEQUENCE: 55
attctgacta tgaacaacc                                               19

<210> SEQ ID NO 56
<211> LENGTH: 19
<212> TYPE: DNA
<213> ORGANISM: Homo sapiens

<400> SEQUENCE: 56
tacaattctg actatgaac                                               19

<210> SEQ ID NO 57
<211> LENGTH: 19
<212> TYPE: DNA
<213> ORGANISM: Homo sapiens

<400> SEQUENCE: 57
tctgtttata gatctctgc                                               19

<210> SEQ ID NO 58
<211> LENGTH: 19
<212> TYPE: DNA
<213> ORGANISM: Homo sapiens

<400> SEQUENCE: 58
ttagcataga gcctgtctg                                               19

<210> SEQ ID NO 59
<211> LENGTH: 19
<212> TYPE: DNA
<213> ORGANISM: Homo sapiens

<400> SEQUENCE: 59
tttagcatag agcctgtct                                               19

<210> SEQ ID NO 60
<211> LENGTH: 19
<212> TYPE: DNA
<213> ORGANISM: Homo sapiens

<400> SEQUENCE: 60
tccatctcga gcaaggagg                                               19
```

```
<210> SEQ ID NO 61
<211> LENGTH: 19
<212> TYPE: DNA
<213> ORGANISM: Homo sapiens

<400> SEQUENCE: 61
tttatgtctt cactcttca                                                19

<210> SEQ ID NO 62
<211> LENGTH: 19
<212> TYPE: DNA
<213> ORGANISM: Homo sapiens

<400> SEQUENCE: 62
atcaggaact gaatgagct                                                19

<210> SEQ ID NO 63
<211> LENGTH: 19
<212> TYPE: DNA
<213> ORGANISM: Homo sapiens

<400> SEQUENCE: 63
tgagatcagg aactgaatg                                                19

<210> SEQ ID NO 64
<211> LENGTH: 19
<212> TYPE: DNA
<213> ORGANISM: Homo sapiens

<400> SEQUENCE: 64
ttgatgttct caaggagct                                                19

<210> SEQ ID NO 65
<211> LENGTH: 19
<212> TYPE: DNA
<213> ORGANISM: Homo sapiens

<400> SEQUENCE: 65
tatacttggg catggaatg                                                19

<210> SEQ ID NO 66
<211> LENGTH: 19
<212> TYPE: DNA
<213> ORGANISM: Homo sapiens

<400> SEQUENCE: 66
ttatccaggt tggagtcca                                                19

<210> SEQ ID NO 67
<211> LENGTH: 19
<212> TYPE: DNA
<213> ORGANISM: Homo sapiens

<400> SEQUENCE: 67
attctgacta tgaacaacc                                                19

<210> SEQ ID NO 68
<211> LENGTH: 19
<212> TYPE: DNA
<213> ORGANISM: Homo sapiens

<400> SEQUENCE: 68
tacaattctg actatgaac                                                19
```

```
<210> SEQ ID NO 69
<211> LENGTH: 19
<212> TYPE: DNA
<213> ORGANISM: Homo sapiens

<400> SEQUENCE: 69
tctgtttata gatctctgc                                                   19

<210> SEQ ID NO 70
<211> LENGTH: 19
<212> TYPE: DNA
<213> ORGANISM: Homo sapiens

<400> SEQUENCE: 70
ttagcataga gcctgtctg                                                   19

<210> SEQ ID NO 71
<211> LENGTH: 19
<212> TYPE: DNA
<213> ORGANISM: Homo sapiens

<400> SEQUENCE: 71
tttagcatag agcctgtct                                                   19

<210> SEQ ID NO 72
<211> LENGTH: 19
<212> TYPE: DNA
<213> ORGANISM: Homo sapiens

<400> SEQUENCE: 72
tccatctcga gcaaggagg                                                   19

<210> SEQ ID NO 73
<211> LENGTH: 19
<212> TYPE: DNA
<213> ORGANISM: Homo sapiens

<400> SEQUENCE: 73
tttatgtctt cactcttca                                                   19

<210> SEQ ID NO 74
<211> LENGTH: 19
<212> TYPE: DNA
<213> ORGANISM: Homo sapiens

<400> SEQUENCE: 74
atcaggaact gaatgagct                                                   19

<210> SEQ ID NO 75
<211> LENGTH: 19
<212> TYPE: DNA
<213> ORGANISM: Homo sapiens

<400> SEQUENCE: 75
tgagatcagg aactgaatg                                                   19

<210> SEQ ID NO 76
<211> LENGTH: 19
<212> TYPE: DNA
<213> ORGANISM: Homo sapiens

<400> SEQUENCE: 76
```

```
ttgatgttct caaggagct                                              19

<210> SEQ ID NO 77
<211> LENGTH: 19
<212> TYPE: DNA
<213> ORGANISM: homo sapien

<400> SEQUENCE: 77
tatacttggg catggaatg                                              19

<210> SEQ ID NO 78
<211> LENGTH: 19
<212> TYPE: DNA
<213> ORGANISM: Homo sapiens

<400> SEQUENCE: 78
ttatccaggt tggagtcca                                              19

<210> SEQ ID NO 79
<211> LENGTH: 19
<212> TYPE: DNA
<213> ORGANISM: Homo sapiens

<400> SEQUENCE: 79
attctgacta tgaacaacc                                              19

<210> SEQ ID NO 80
<211> LENGTH: 19
<212> TYPE: DNA
<213> ORGANISM: Homo sapiens

<400> SEQUENCE: 80
tacaattctg actatgaac                                              19

<210> SEQ ID NO 81
<211> LENGTH: 19
<212> TYPE: DNA
<213> ORGANISM: Homo sapiens

<400> SEQUENCE: 81
tctgtttata gatctctgc                                              19

<210> SEQ ID NO 82
<211> LENGTH: 19
<212> TYPE: DNA
<213> ORGANISM: Homo sapiens

<400> SEQUENCE: 82
ttagcataga gcctgtctg                                              19

<210> SEQ ID NO 83
<211> LENGTH: 19
<212> TYPE: DNA
<213> ORGANISM: Homo sapiens

<400> SEQUENCE: 83
tttagcatag agcctgtct                                              19

<210> SEQ ID NO 84
<211> LENGTH: 19
<212> TYPE: DNA
<213> ORGANISM: Homo sapiens

<400> SEQUENCE: 84
```
tccatctcga gcaaggagg					19

<210> SEQ ID NO 85
<211> LENGTH: 19
<212> TYPE: DNA
<213> ORGANISM: Homo sapiens

<400> SEQUENCE: 85
tgaagagtga agacataaa					19

<210> SEQ ID NO 86
<211> LENGTH: 19
<212> TYPE: DNA
<213> ORGANISM: Homo sapiens

<400> SEQUENCE: 86
agctcattca gttcctgat					19

<210> SEQ ID NO 87
<211> LENGTH: 19
<212> TYPE: DNA
<213> ORGANISM: Homo sapiens

<400> SEQUENCE: 87
cattcagttc ctgatctca					19

<210> SEQ ID NO 88
<211> LENGTH: 19
<212> TYPE: DNA
<213> ORGANISM: Homo sapiens

<400> SEQUENCE: 88
agctccttga gaacatcaa					19

<210> SEQ ID NO 89
<211> LENGTH: 19
<212> TYPE: DNA
<213> ORGANISM: Homo sapiens

<400> SEQUENCE: 89
cattccatgc ccaagtata					19

<210> SEQ ID NO 90
<211> LENGTH: 19
<212> TYPE: DNA
<213> ORGANISM: Homo sapiens

<400> SEQUENCE: 90
tggactccaa cctggataa					19

<210> SEQ ID NO 91
<211> LENGTH: 19
<212> TYPE: DNA
<213> ORGANISM: Homo sapiens

<400> SEQUENCE: 91
ggttgttcat agtcagaat					19

<210> SEQ ID NO 92
<211> LENGTH: 19
<212> TYPE: DNA
<213> ORGANISM: Homo sapiens

```
<400> SEQUENCE: 92
gttcatagtc agaattgta                                               19

<210> SEQ ID NO 93
<211> LENGTH: 19
<212> TYPE: DNA
<213> ORGANISM: Homo sapiens

<400> SEQUENCE: 93
gcagagatct ataaacaga                                               19

<210> SEQ ID NO 94
<211> LENGTH: 19
<212> TYPE: DNA
<213> ORGANISM: Homo sapiens

<400> SEQUENCE: 94
cagacaggct ctatgctaa                                               19

<210> SEQ ID NO 95
<211> LENGTH: 19
<212> TYPE: DNA
<213> ORGANISM: Homo sapiens

<400> SEQUENCE: 95
agacaggctc tatgctaaa                                               19

<210> SEQ ID NO 96
<211> LENGTH: 19
<212> TYPE: DNA
<213> ORGANISM: Homo sapiens

<400> SEQUENCE: 96
cctccttgct cgagatgga                                               19

<210> SEQ ID NO 97
<211> LENGTH: 19
<212> TYPE: DNA
<213> ORGANISM: Homo sapiens

<400> SEQUENCE: 97
tgaagagtga agacataaa                                               19

<210> SEQ ID NO 98
<211> LENGTH: 19
<212> TYPE: DNA
<213> ORGANISM: Homo sapiens

<400> SEQUENCE: 98
agctcattca gttcctgat                                               19

<210> SEQ ID NO 99
<211> LENGTH: 19
<212> TYPE: DNA
<213> ORGANISM: Homo sapiens

<400> SEQUENCE: 99
cattcagttc ctgatctca                                               19

<210> SEQ ID NO 100
<211> LENGTH: 19
<212> TYPE: DNA
<213> ORGANISM: Homo sapiens
```

```
<400> SEQUENCE: 100
agctccttga gaacatcaa                                               19

<210> SEQ ID NO 101
<211> LENGTH: 19
<212> TYPE: DNA
<213> ORGANISM: Homo sapiens

<400> SEQUENCE: 101
cattccatgc ccaagtata                                               19

<210> SEQ ID NO 102
<211> LENGTH: 19
<212> TYPE: DNA
<213> ORGANISM: Homo sapiens

<400> SEQUENCE: 102
tggactccaa cctggataa                                               19

<210> SEQ ID NO 103
<211> LENGTH: 19
<212> TYPE: DNA
<213> ORGANISM: Homo sapiens

<400> SEQUENCE: 103
ggttgttcat agtcagaat                                               19

<210> SEQ ID NO 104
<211> LENGTH: 19
<212> TYPE: DNA
<213> ORGANISM: Homo sapiens

<400> SEQUENCE: 104
gttcatagtc agaattgta                                               19

<210> SEQ ID NO 105
<211> LENGTH: 19
<212> TYPE: DNA
<213> ORGANISM: Homo sapiens

<400> SEQUENCE: 105
gcagagatct ataaacaga                                               19

<210> SEQ ID NO 106
<211> LENGTH: 19
<212> TYPE: DNA
<213> ORGANISM: Homo sapiens

<400> SEQUENCE: 106
cagacaggct ctatgctaa                                               19

<210> SEQ ID NO 107
<211> LENGTH: 19
<212> TYPE: DNA
<213> ORGANISM: Homo sapiens

<400> SEQUENCE: 107
agacaggctc tatgctaaa                                               19

<210> SEQ ID NO 108
<211> LENGTH: 19
<212> TYPE: DNA
```

<213> ORGANISM: Homo sapiens

<400> SEQUENCE: 108
cctccttgct cgagatgga                    19

<210> SEQ ID NO 109
<211> LENGTH: 19
<212> TYPE: DNA
<213> ORGANISM: Homo sapiens

<400> SEQUENCE: 109
tgaagagtga agacataaa                    19

<210> SEQ ID NO 110
<211> LENGTH: 19
<212> TYPE: DNA
<213> ORGANISM: Homo sapiens

<400> SEQUENCE: 110
agctcattca gttcctgat                    19

<210> SEQ ID NO 111
<211> LENGTH: 19
<212> TYPE: DNA
<213> ORGANISM: Homo sapiens

<400> SEQUENCE: 111
cattcagttc ctgatctca                    19

<210> SEQ ID NO 112
<211> LENGTH: 19
<212> TYPE: DNA
<213> ORGANISM: Homo sapiens

<400> SEQUENCE: 112
agctccttga gaacatcaa                    19

<210> SEQ ID NO 113
<211> LENGTH: 19
<212> TYPE: DNA
<213> ORGANISM: Homo sapiens

<400> SEQUENCE: 113
cattccatgc ccaagtata                    19

<210> SEQ ID NO 114
<211> LENGTH: 19
<212> TYPE: DNA
<213> ORGANISM: Homo sapiens

<400> SEQUENCE: 114
tggactccaa cctggataa                    19

<210> SEQ ID NO 115
<211> LENGTH: 19
<212> TYPE: DNA
<213> ORGANISM: Homo sapiens

<400> SEQUENCE: 115
ggttgttcat agtcagaat                    19

<210> SEQ ID NO 116
<211> LENGTH: 19

```
<212> TYPE: DNA
<213> ORGANISM: Homo sapiens

<400> SEQUENCE: 116
gttcatagtc agaattgta                                              19

<210> SEQ ID NO 117
<211> LENGTH: 19
<212> TYPE: DNA
<213> ORGANISM: Homo sapiens

<400> SEQUENCE: 117
gcagagatct ataaacaga                                              19

<210> SEQ ID NO 118
<211> LENGTH: 19
<212> TYPE: DNA
<213> ORGANISM: Homo sapiens

<400> SEQUENCE: 118
cagacaggct ctatgctaa                                              19

<210> SEQ ID NO 119
<211> LENGTH: 19
<212> TYPE: DNA
<213> ORGANISM: Homo sapiens

<400> SEQUENCE: 119
agacaggctc tatgctaaa                                              19

<210> SEQ ID NO 120
<211> LENGTH: 19
<212> TYPE: DNA
<213> ORGANISM: Homo sapiens

<400> SEQUENCE: 120
cctccttgct cgagatgga                                              19

<210> SEQ ID NO 121
<211> LENGTH: 19
<212> TYPE: DNA
<213> ORGANISM: Homo sapiens

<400> SEQUENCE: 121
tgaagagtga agacataaa                                              19

<210> SEQ ID NO 122
<211> LENGTH: 19
<212> TYPE: DNA
<213> ORGANISM: Homo sapiens

<400> SEQUENCE: 122
agctcattca gttcctgat                                              19

<210> SEQ ID NO 123
<211> LENGTH: 19
<212> TYPE: DNA
<213> ORGANISM: Homo sapiens

<400> SEQUENCE: 123
cattcagttc ctgatctca                                              19

<210> SEQ ID NO 124
```

```
<211> LENGTH: 19
<212> TYPE: DNA
<213> ORGANISM: Homo sapiens

<400> SEQUENCE: 124
agctccttga gaacatcaa                                                    19

<210> SEQ ID NO 125
<211> LENGTH: 19
<212> TYPE: DNA
<213> ORGANISM: Homo sapiens

<400> SEQUENCE: 125
cattccatgc ccaagtata                                                    19

<210> SEQ ID NO 126
<211> LENGTH: 19
<212> TYPE: DNA
<213> ORGANISM: Homo sapiens

<400> SEQUENCE: 126
tggactccaa cctggataa                                                    19

<210> SEQ ID NO 127
<211> LENGTH: 19
<212> TYPE: DNA
<213> ORGANISM: Homo sapiens

<400> SEQUENCE: 127
ggttgttcat agtcagaat                                                    19

<210> SEQ ID NO 128
<211> LENGTH: 19
<212> TYPE: DNA
<213> ORGANISM: Homo sapiens

<400> SEQUENCE: 128
gttcatagtc agaattgta                                                    19

<210> SEQ ID NO 129
<211> LENGTH: 19
<212> TYPE: DNA
<213> ORGANISM: Homo sapiens

<400> SEQUENCE: 129
gcagagatct ataaacaga                                                    19

<210> SEQ ID NO 130
<211> LENGTH: 19
<212> TYPE: DNA
<213> ORGANISM: Homo sapiens

<400> SEQUENCE: 130
cagacaggct ctatgctaa                                                    19

<210> SEQ ID NO 131
<211> LENGTH: 19
<212> TYPE: DNA
<213> ORGANISM: Homo sapiens

<400> SEQUENCE: 131
agacaggctc tatgctaaa                                                    19
```

```
<210> SEQ ID NO 132
<211> LENGTH: 19
<212> TYPE: DNA
<213> ORGANISM: Homo sapiens

<400> SEQUENCE: 132
cctccttgct cgagatgga                                                    19

<210> SEQ ID NO 133
<211> LENGTH: 19
<212> TYPE: DNA
<213> ORGANISM: Homo sapiens

<400> SEQUENCE: 133
tgaagagtga agacataaa                                                    19

<210> SEQ ID NO 134
<211> LENGTH: 19
<212> TYPE: DNA
<213> ORGANISM: Homo sapiens

<400> SEQUENCE: 134
agctcattca gttcctgat                                                    19

<210> SEQ ID NO 135
<211> LENGTH: 19
<212> TYPE: DNA
<213> ORGANISM: Homo sapiens

<400> SEQUENCE: 135
cattcagttc ctgatctca                                                    19

<210> SEQ ID NO 136
<211> LENGTH: 19
<212> TYPE: DNA
<213> ORGANISM: Homo sapiens

<400> SEQUENCE: 136
agctccttga gaacatcaa                                                    19

<210> SEQ ID NO 137
<211> LENGTH: 19
<212> TYPE: DNA
<213> ORGANISM: Homo sapiens

<400> SEQUENCE: 137
cattccatgc ccaagtata                                                    19

<210> SEQ ID NO 138
<211> LENGTH: 19
<212> TYPE: DNA
<213> ORGANISM: Homo sapiens

<400> SEQUENCE: 138
tggactccaa cctggataa                                                    19

<210> SEQ ID NO 139
<211> LENGTH: 19
<212> TYPE: DNA
<213> ORGANISM: Homo sapiens

<400> SEQUENCE: 139
ggttgttcat agtcagaat                                                    19
```

```
<210> SEQ ID NO 140
<211> LENGTH: 19
<212> TYPE: DNA
<213> ORGANISM: Homo sapiens

<400> SEQUENCE: 140
gttcatagtc agaattgta                                              19

<210> SEQ ID NO 141
<211> LENGTH: 19
<212> TYPE: DNA
<213> ORGANISM: Homo sapiens

<400> SEQUENCE: 141
gcagagatct ataaacaga                                              19

<210> SEQ ID NO 142
<211> LENGTH: 19
<212> TYPE: DNA
<213> ORGANISM: Homo sapiens

<400> SEQUENCE: 142
cagacaggct ctatgctaa                                              19

<210> SEQ ID NO 143
<211> LENGTH: 19
<212> TYPE: DNA
<213> ORGANISM: Homo sapiens

<400> SEQUENCE: 143
agacaggctc tatgctaaa                                              19

<210> SEQ ID NO 144
<211> LENGTH: 19
<212> TYPE: DNA
<213> ORGANISM: Homo sapiens

<400> SEQUENCE: 144
cctccttgct cgagatgga                                              19

<210> SEQ ID NO 145
<211> LENGTH: 19
<212> TYPE: DNA
<213> ORGANISM: Homo sapiens

<400> SEQUENCE: 145
tgaagagtga agacataaa                                              19

<210> SEQ ID NO 146
<211> LENGTH: 19
<212> TYPE: DNA
<213> ORGANISM: Homo sapiens

<400> SEQUENCE: 146
agctcattca gttcctgat                                              19

<210> SEQ ID NO 147
<211> LENGTH: 19
<212> TYPE: DNA
<213> ORGANISM: Homo sapiens

<400> SEQUENCE: 147
cattcagttc ctgatctca                                              19
```

<210> SEQ ID NO 148
<211> LENGTH: 19
<212> TYPE: DNA
<213> ORGANISM: Homo sapiens

<400> SEQUENCE: 148
agctccttga gaacatcaa                                                  19

<210> SEQ ID NO 149
<211> LENGTH: 19
<212> TYPE: DNA
<213> ORGANISM: Homo sapiens

<400> SEQUENCE: 149
cattccatgc ccaagtata                                                  19

<210> SEQ ID NO 150
<211> LENGTH: 19
<212> TYPE: DNA
<213> ORGANISM: Homo sapiens

<400> SEQUENCE: 150
tggactccaa cctggataa                                                  19

<210> SEQ ID NO 151
<211> LENGTH: 19
<212> TYPE: DNA
<213> ORGANISM: Homo sapiens

<400> SEQUENCE: 151
ggttgttcat agtcagaat                                                  19

<210> SEQ ID NO 152
<211> LENGTH: 19
<212> TYPE: DNA
<213> ORGANISM: Homo sapiens

<400> SEQUENCE: 152
gttcatagtc agaattgta                                                  19

<210> SEQ ID NO 153
<211> LENGTH: 19
<212> TYPE: DNA
<213> ORGANISM: Homo sapiens

<400> SEQUENCE: 153
gcagagatct ataaacaga                                                  19

<210> SEQ ID NO 154
<211> LENGTH: 19
<212> TYPE: DNA
<213> ORGANISM: Homo sapiens

<400> SEQUENCE: 154
cagacaggct ctatgctaa                                                  19

<210> SEQ ID NO 155
<211> LENGTH: 19
<212> TYPE: DNA
<213> ORGANISM: Homo sapiens

<400> SEQUENCE: 155
agacaggctc tatgctaaa                                                19

<210> SEQ ID NO 156
<211> LENGTH: 19
<212> TYPE: DNA
<213> ORGANISM: Homo sapiens

<400> SEQUENCE: 156
cctccttgct cgagatgga                                                19

<210> SEQ ID NO 157
<211> LENGTH: 19
<212> TYPE: DNA
<213> ORGANISM: Homo sapiens

<400> SEQUENCE: 157
tgaagagtga agacataaa                                                19

<210> SEQ ID NO 158
<211> LENGTH: 19
<212> TYPE: DNA
<213> ORGANISM: Homo sapiens

<400> SEQUENCE: 158
agctcattca gttcctgat                                                19

<210> SEQ ID NO 159
<211> LENGTH: 19
<212> TYPE: DNA
<213> ORGANISM: Homo sapiens

<400> SEQUENCE: 159
cattcagttc ctgatctca                                                19

<210> SEQ ID NO 160
<211> LENGTH: 19
<212> TYPE: DNA
<213> ORGANISM: Homo sapiens

<400> SEQUENCE: 160
agctccttga gaacatcaa                                                19

<210> SEQ ID NO 161
<211> LENGTH: 19
<212> TYPE: DNA
<213> ORGANISM: Homo sapiens

<400> SEQUENCE: 161
cattccatgc ccaagtata                                                19

<210> SEQ ID NO 162
<211> LENGTH: 19
<212> TYPE: DNA
<213> ORGANISM: Homo sapiens

<400> SEQUENCE: 162
tggactccaa cctggataa                                                19

<210> SEQ ID NO 163
<211> LENGTH: 19
<212> TYPE: DNA
<213> ORGANISM: Homo sapiens

<400> SEQUENCE: 163

```
ggttgttcat agtcagaat                                                19

<210> SEQ ID NO 164
<211> LENGTH: 19
<212> TYPE: DNA
<213> ORGANISM: Homo sapiens

<400> SEQUENCE: 164
gttcatagtc agaattgta                                                19

<210> SEQ ID NO 165
<211> LENGTH: 19
<212> TYPE: DNA
<213> ORGANISM: Homo sapiens

<400> SEQUENCE: 165
gcagagatct ataaacaga                                                19

<210> SEQ ID NO 166
<211> LENGTH: 19
<212> TYPE: DNA
<213> ORGANISM: Homo sapiens

<400> SEQUENCE: 166
cagacaggct ctatgctaa                                                19

<210> SEQ ID NO 167
<211> LENGTH: 19
<212> TYPE: DNA
<213> ORGANISM: Homo sapiens

<400> SEQUENCE: 167
agacaggctc tatgctaaa                                                19

<210> SEQ ID NO 168
<211> LENGTH: 19
<212> TYPE: DNA
<213> ORGANISM: Homo sapiens

<400> SEQUENCE: 168
cctccttgct cgagatgga                                                19

<210> SEQ ID NO 169
<211> LENGTH: 19
<212> TYPE: RNA
<213> ORGANISM: Homo sapiens

<400> SEQUENCE: 169
uuuaugucuu cacucuuca                                                19

<210> SEQ ID NO 170
<211> LENGTH: 19
<212> TYPE: RNA
<213> ORGANISM: Homo sapiens

<400> SEQUENCE: 170
aucaggaacu gaaugagcu                                                19

<210> SEQ ID NO 171
<211> LENGTH: 19
<212> TYPE: RNA
<213> ORGANISM: Homo sapiens
```

```
<400> SEQUENCE: 171
ugagaucagg aacugaaug                                                 19

<210> SEQ ID NO 172
<211> LENGTH: 19
<212> TYPE: RNA
<213> ORGANISM: Homo sapiens

<400> SEQUENCE: 172
uugauguucu caaggagcu                                                 19

<210> SEQ ID NO 173
<211> LENGTH: 19
<212> TYPE: RNA
<213> ORGANISM: Homo sapiens

<400> SEQUENCE: 173
uauacuuggg cauggaaug                                                 19

<210> SEQ ID NO 174
<211> LENGTH: 19
<212> TYPE: RNA
<213> ORGANISM: Homo sapiens

<400> SEQUENCE: 174
uuauccaggu uggagucca                                                 19

<210> SEQ ID NO 175
<211> LENGTH: 19
<212> TYPE: RNA
<213> ORGANISM: Homo sapiens

<400> SEQUENCE: 175
auucugacua ugaacaacc                                                 19

<210> SEQ ID NO 176
<211> LENGTH: 19
<212> TYPE: RNA
<213> ORGANISM: Homo sapiens

<400> SEQUENCE: 176
uacaauucug acuaugaac                                                 19

<210> SEQ ID NO 177
<211> LENGTH: 19
<212> TYPE: RNA
<213> ORGANISM: Homo sapiens

<400> SEQUENCE: 177
ucuguuuaua gaucucugc                                                 19

<210> SEQ ID NO 178
<211> LENGTH: 19
<212> TYPE: RNA
<213> ORGANISM: Homo sapiens

<400> SEQUENCE: 178
uuagcauaga gccugucug                                                 19

<210> SEQ ID NO 179
<211> LENGTH: 19
<212> TYPE: RNA
<213> ORGANISM: Homo sapiens
```

```
<400> SEQUENCE: 179
uuuagcauag agccugucu                                                19

<210> SEQ ID NO 180
<211> LENGTH: 19
<212> TYPE: RNA
<213> ORGANISM: Homo sapiens

<400> SEQUENCE: 180
uccaucucga gcaaggagg                                                19

<210> SEQ ID NO 181
<211> LENGTH: 19
<212> TYPE: RNA
<213> ORGANISM: Homo sapiens

<400> SEQUENCE: 181
uuuaugucuu cacucuuca                                                19

<210> SEQ ID NO 182
<211> LENGTH: 19
<212> TYPE: RNA
<213> ORGANISM: Homo sapiens

<400> SEQUENCE: 182
aucaggaacu gaaugagcu                                                19

<210> SEQ ID NO 183
<211> LENGTH: 19
<212> TYPE: RNA
<213> ORGANISM: Homo sapiens

<400> SEQUENCE: 183
ugagaucagg aacugaaug                                                19

<210> SEQ ID NO 184
<211> LENGTH: 19
<212> TYPE: RNA
<213> ORGANISM: Homo sapiens

<400> SEQUENCE: 184
uugauguucu caaggagcu                                                19

<210> SEQ ID NO 185
<211> LENGTH: 19
<212> TYPE: RNA
<213> ORGANISM: Homo sapiens

<400> SEQUENCE: 185
uauacuuggg cauggaaug                                                19

<210> SEQ ID NO 186
<211> LENGTH: 19
<212> TYPE: RNA
<213> ORGANISM: Homo sapiens

<400> SEQUENCE: 186
uuauccaggu uggagucca                                                19

<210> SEQ ID NO 187
<211> LENGTH: 19
<212> TYPE: RNA
```

```
<213> ORGANISM: Homo sapiens

<400> SEQUENCE: 187
auucugacua ugaacaacc                                              19

<210> SEQ ID NO 188
<211> LENGTH: 19
<212> TYPE: RNA
<213> ORGANISM: Homo sapiens

<400> SEQUENCE: 188
uacaauucug acuaugaac                                              19

<210> SEQ ID NO 189
<211> LENGTH: 19
<212> TYPE: RNA
<213> ORGANISM: Homo sapiens

<400> SEQUENCE: 189
ucuguuuaua gaucucugc                                              19

<210> SEQ ID NO 190
<211> LENGTH: 19
<212> TYPE: RNA
<213> ORGANISM: Homo sapiens

<400> SEQUENCE: 190
uuagcauaga gccugucug                                              19

<210> SEQ ID NO 191
<211> LENGTH: 19
<212> TYPE: RNA
<213> ORGANISM: Homo sapiens

<400> SEQUENCE: 191
uuuagcauag agccugucu                                              19

<210> SEQ ID NO 192
<211> LENGTH: 19
<212> TYPE: RNA
<213> ORGANISM: Homo sapiens

<400> SEQUENCE: 192
uccaucucga gcaaggagg                                              19

<210> SEQ ID NO 193
<211> LENGTH: 19
<212> TYPE: RNA
<213> ORGANISM: Homo sapiens

<400> SEQUENCE: 193
uuuaugucuu cacucuuca                                              19

<210> SEQ ID NO 194
<211> LENGTH: 19
<212> TYPE: RNA
<213> ORGANISM: Homo sapiens

<400> SEQUENCE: 194
aucaggaacu gaaugagcu                                              19

<210> SEQ ID NO 195
<211> LENGTH: 19
```

```
<212> TYPE: RNA
<213> ORGANISM: Homo sapiens

<400> SEQUENCE: 195
ugagaucagg aacugaaug                                            19

<210> SEQ ID NO 196
<211> LENGTH: 19
<212> TYPE: RNA
<213> ORGANISM: Homo sapiens

<400> SEQUENCE: 196
uugauguucu caaggagcu                                            19

<210> SEQ ID NO 197
<211> LENGTH: 19
<212> TYPE: RNA
<213> ORGANISM: Homo sapiens

<400> SEQUENCE: 197
uauacuuggg cauggaaug                                            19

<210> SEQ ID NO 198
<211> LENGTH: 19
<212> TYPE: RNA
<213> ORGANISM: Homo sapiens

<400> SEQUENCE: 198
uuauccaggu uggagucca                                            19

<210> SEQ ID NO 199
<211> LENGTH: 19
<212> TYPE: RNA
<213> ORGANISM: Homo sapiens

<400> SEQUENCE: 199
auucugacua ugaacaacc                                            19

<210> SEQ ID NO 200
<211> LENGTH: 19
<212> TYPE: RNA
<213> ORGANISM: Homo sapiens

<400> SEQUENCE: 200
uacaauucug acuaugaac                                            19

<210> SEQ ID NO 201
<211> LENGTH: 19
<212> TYPE: RNA
<213> ORGANISM: Homo sapiens

<400> SEQUENCE: 201
ucuguuuaua gaucucugc                                            19

<210> SEQ ID NO 202
<211> LENGTH: 19
<212> TYPE: RNA
<213> ORGANISM: Homo sapiens

<400> SEQUENCE: 202
uuagcauaga gccugucug                                            19

<210> SEQ ID NO 203
```

```
<211> LENGTH: 19
<212> TYPE: RNA
<213> ORGANISM: Homo sapiens

<400> SEQUENCE: 203
uuuagcauag agccugucu                                                19

<210> SEQ ID NO 204
<211> LENGTH: 19
<212> TYPE: RNA
<213> ORGANISM: Homo sapiens

<400> SEQUENCE: 204
uccaucucga gcaaggagg                                                19

<210> SEQ ID NO 205
<211> LENGTH: 19
<212> TYPE: RNA
<213> ORGANISM: Homo sapiens

<400> SEQUENCE: 205
uuuaugucuu cacucuuca                                                19

<210> SEQ ID NO 206
<211> LENGTH: 19
<212> TYPE: RNA
<213> ORGANISM: Homo sapiens

<400> SEQUENCE: 206
aucaggaacu gaaugagcu                                                19

<210> SEQ ID NO 207
<211> LENGTH: 19
<212> TYPE: RNA
<213> ORGANISM: Homo sapiens

<400> SEQUENCE: 207
ugagaucagg aacugaaug                                                19

<210> SEQ ID NO 208
<211> LENGTH: 19
<212> TYPE: RNA
<213> ORGANISM: Homo sapiens

<400> SEQUENCE: 208
uugauguucu caaggagcu                                                19

<210> SEQ ID NO 209
<211> LENGTH: 19
<212> TYPE: RNA
<213> ORGANISM: Homo sapiens

<400> SEQUENCE: 209
uauacuuggg cauggaaug                                                19

<210> SEQ ID NO 210
<211> LENGTH: 19
<212> TYPE: RNA
<213> ORGANISM: Homo sapiens

<400> SEQUENCE: 210
uuauccaggu uggagucca                                                19
```

```
<210> SEQ ID NO 211
<211> LENGTH: 19
<212> TYPE: RNA
<213> ORGANISM: Homo sapiens

<400> SEQUENCE: 211
auucugacua ugaacaacc                                               19

<210> SEQ ID NO 212
<211> LENGTH: 19
<212> TYPE: RNA
<213> ORGANISM: Homo sapiens

<400> SEQUENCE: 212
uacaauucug acuaugaac                                               19

<210> SEQ ID NO 213
<211> LENGTH: 19
<212> TYPE: RNA
<213> ORGANISM: Homo sapiens

<400> SEQUENCE: 213
ucuguuuaua gaucucugc                                               19

<210> SEQ ID NO 214
<211> LENGTH: 19
<212> TYPE: RNA
<213> ORGANISM: Homo sapiens

<400> SEQUENCE: 214
uuagcauaga gccugucug                                               19

<210> SEQ ID NO 215
<211> LENGTH: 19
<212> TYPE: RNA
<213> ORGANISM: Homo sapiens

<400> SEQUENCE: 215
uuuagcauag agccugucu                                               19

<210> SEQ ID NO 216
<211> LENGTH: 19
<212> TYPE: RNA
<213> ORGANISM: Homo sapiens

<400> SEQUENCE: 216
uccaucucga gcaaggagg                                               19

<210> SEQ ID NO 217
<211> LENGTH: 19
<212> TYPE: RNA
<213> ORGANISM: Homo sapiens

<400> SEQUENCE: 217
uuuaugucuu cacucuuca                                               19

<210> SEQ ID NO 218
<211> LENGTH: 19
<212> TYPE: RNA
<213> ORGANISM: Homo sapiens

<400> SEQUENCE: 218
aucaggaacu gaaugagcu                                               19
```

<210> SEQ ID NO 219
<211> LENGTH: 19
<212> TYPE: RNA
<213> ORGANISM: Homo sapiens

<400> SEQUENCE: 219
ugagaucagg aacugaaug                                              19

<210> SEQ ID NO 220
<211> LENGTH: 19
<212> TYPE: RNA
<213> ORGANISM: Homo sapiens

<400> SEQUENCE: 220
uugauguucu caaggagcu                                              19

<210> SEQ ID NO 221
<211> LENGTH: 19
<212> TYPE: RNA
<213> ORGANISM: Homo sapiens

<400> SEQUENCE: 221
uauacuuggg cauggaaug                                              19

<210> SEQ ID NO 222
<211> LENGTH: 19
<212> TYPE: RNA
<213> ORGANISM: Homo sapiens

<400> SEQUENCE: 222
uuauccaggu uggagucca                                              19

<210> SEQ ID NO 223
<211> LENGTH: 19
<212> TYPE: RNA
<213> ORGANISM: Homo sapiens

<400> SEQUENCE: 223
auucugacua ugaacaacc                                              19

<210> SEQ ID NO 224
<211> LENGTH: 19
<212> TYPE: RNA
<213> ORGANISM: Homo sapiens

<400> SEQUENCE: 224
uacaauucug acuaugaac                                              19

<210> SEQ ID NO 225
<211> LENGTH: 19
<212> TYPE: RNA
<213> ORGANISM: Homo sapiens

<400> SEQUENCE: 225
ucuguuuaua gaucucugc                                              19

<210> SEQ ID NO 226
<211> LENGTH: 19
<212> TYPE: RNA
<213> ORGANISM: Homo sapiens

<400> SEQUENCE: 226
uuagcauaga gccugucug                                              19

<210> SEQ ID NO 227
<211> LENGTH: 19
<212> TYPE: RNA
<213> ORGANISM: Homo sapiens

<400> SEQUENCE: 227
uuuagcauag agccugucu                                                      19

<210> SEQ ID NO 228
<211> LENGTH: 19
<212> TYPE: RNA
<213> ORGANISM: Homo sapiens

<400> SEQUENCE: 228
uccaucucga gcaaggagg                                                      19

<210> SEQ ID NO 229
<211> LENGTH: 19
<212> TYPE: RNA
<213> ORGANISM: Homo sapiens

<400> SEQUENCE: 229
uuuaugucuu cacucuuca                                                      19

<210> SEQ ID NO 230
<211> LENGTH: 19
<212> TYPE: RNA
<213> ORGANISM: Homo sapiens

<400> SEQUENCE: 230
aucaggaacu gaaugagcu                                                      19

<210> SEQ ID NO 231
<211> LENGTH: 19
<212> TYPE: RNA
<213> ORGANISM: Homo sapiens

<400> SEQUENCE: 231
ugagaucagg aacugaaug                                                      19

<210> SEQ ID NO 232
<211> LENGTH: 19
<212> TYPE: RNA
<213> ORGANISM: Homo sapiens

<400> SEQUENCE: 232
uugauguucu caaggagcu                                                      19

<210> SEQ ID NO 233
<211> LENGTH: 19
<212> TYPE: RNA
<213> ORGANISM: Homo sapiens

<400> SEQUENCE: 233
uauacuuggg cauggaaug                                                      19

<210> SEQ ID NO 234
<211> LENGTH: 19
<212> TYPE: RNA
<213> ORGANISM: Homo sapiens

<400> SEQUENCE: 234
uuauccaggu uggagucca                                                19

<210> SEQ ID NO 235
<211> LENGTH: 19
<212> TYPE: RNA
<213> ORGANISM: Homo sapiens

<400> SEQUENCE: 235
auucugacua ugaacaacc                                                19

<210> SEQ ID NO 236
<211> LENGTH: 19
<212> TYPE: RNA
<213> ORGANISM: Homo sapiens

<400> SEQUENCE: 236
uacaauucug acuaugaac                                                19

<210> SEQ ID NO 237
<211> LENGTH: 19
<212> TYPE: RNA
<213> ORGANISM: Homo sapiens

<400> SEQUENCE: 237
ucuguuuaua gaucucugc                                                19

<210> SEQ ID NO 238
<211> LENGTH: 19
<212> TYPE: RNA
<213> ORGANISM: Homo sapiens

<400> SEQUENCE: 238
uuagcauaga gccugucug                                                19

<210> SEQ ID NO 239
<211> LENGTH: 19
<212> TYPE: RNA
<213> ORGANISM: Homo sapiens

<400> SEQUENCE: 239
uuuagcauag agccugucu                                                19

<210> SEQ ID NO 240
<211> LENGTH: 19
<212> TYPE: RNA
<213> ORGANISM: Homo sapiens

<400> SEQUENCE: 240
uccaucucga gcaaggagg                                                19

<210> SEQ ID NO 241
<211> LENGTH: 19
<212> TYPE: RNA
<213> ORGANISM: Homo sapiens

<400> SEQUENCE: 241
uuuaugucuu cacucuuca                                                19

<210> SEQ ID NO 242
<211> LENGTH: 19
<212> TYPE: RNA
<213> ORGANISM: Homo sapiens

<400> SEQUENCE: 242

| | |
|---|---|
| aucaggaacu gaaugagcu | 19 |

<210> SEQ ID NO 243
<211> LENGTH: 19
<212> TYPE: RNA
<213> ORGANISM: Homo sapiens
<400> SEQUENCE: 243

| | |
|---|---|
| ugagaucagg aacugaaug | 19 |

<210> SEQ ID NO 244
<211> LENGTH: 19
<212> TYPE: RNA
<213> ORGANISM: Homo sapiens
<400> SEQUENCE: 244

| | |
|---|---|
| uugauguucu caaggagcu | 19 |

<210> SEQ ID NO 245
<211> LENGTH: 19
<212> TYPE: RNA
<213> ORGANISM: homo sapien
<400> SEQUENCE: 245

| | |
|---|---|
| uauacuuggg cauggaaug | 19 |

<210> SEQ ID NO 246
<211> LENGTH: 19
<212> TYPE: RNA
<213> ORGANISM: Homo sapiens
<400> SEQUENCE: 246

| | |
|---|---|
| uuauccaggu uggagucca | 19 |

<210> SEQ ID NO 247
<211> LENGTH: 19
<212> TYPE: RNA
<213> ORGANISM: Homo sapiens
<400> SEQUENCE: 247

| | |
|---|---|
| auucugacua ugaacaacc | 19 |

<210> SEQ ID NO 248
<211> LENGTH: 19
<212> TYPE: RNA
<213> ORGANISM: Homo sapiens
<400> SEQUENCE: 248

| | |
|---|---|
| uacaauucug acuaugaac | 19 |

<210> SEQ ID NO 249
<211> LENGTH: 19
<212> TYPE: RNA
<213> ORGANISM: Homo sapiens
<400> SEQUENCE: 249

| | |
|---|---|
| ucuguuuaua gaucucugc | 19 |

<210> SEQ ID NO 250
<211> LENGTH: 19
<212> TYPE: RNA
<213> ORGANISM: Homo sapiens

```
<400> SEQUENCE: 250
uuagcauaga gccugucug                                              19

<210> SEQ ID NO 251
<211> LENGTH: 19
<212> TYPE: RNA
<213> ORGANISM: Homo sapiens

<400> SEQUENCE: 251
uuuagcauag agccugucu                                              19

<210> SEQ ID NO 252
<211> LENGTH: 19
<212> TYPE: RNA
<213> ORGANISM: Homo sapiens

<400> SEQUENCE: 252
uccaucucga gcaaggagg                                              19

<210> SEQ ID NO 253
<211> LENGTH: 19
<212> TYPE: RNA
<213> ORGANISM: Homo sapiens

<400> SEQUENCE: 253
ugaagaguga agacauaaa                                              19

<210> SEQ ID NO 254
<211> LENGTH: 19
<212> TYPE: RNA
<213> ORGANISM: Homo sapiens

<400> SEQUENCE: 254
agcucauuca guuccugau                                              19

<210> SEQ ID NO 255
<211> LENGTH: 19
<212> TYPE: RNA
<213> ORGANISM: Homo sapiens

<400> SEQUENCE: 255
cauucaguuc cugaucuca                                              19

<210> SEQ ID NO 256
<211> LENGTH: 19
<212> TYPE: RNA
<213> ORGANISM: Homo sapiens

<400> SEQUENCE: 256
agcuccuuga gaacaucaa                                              19

<210> SEQ ID NO 257
<211> LENGTH: 19
<212> TYPE: RNA
<213> ORGANISM: Homo sapiens

<400> SEQUENCE: 257
cauuccaugc ccaaguaua                                              19

<210> SEQ ID NO 258
<211> LENGTH: 19
<212> TYPE: RNA
<213> ORGANISM: Homo sapiens
```

```
<400> SEQUENCE: 258
uggacuccaa ccuggauaa                                              19

<210> SEQ ID NO 259
<211> LENGTH: 19
<212> TYPE: RNA
<213> ORGANISM: Homo sapiens

<400> SEQUENCE: 259
gguuguucau agucagaau                                              19

<210> SEQ ID NO 260
<211> LENGTH: 19
<212> TYPE: RNA
<213> ORGANISM: Homo sapiens

<400> SEQUENCE: 260
guucauaguc agaauugua                                              19

<210> SEQ ID NO 261
<211> LENGTH: 19
<212> TYPE: RNA
<213> ORGANISM: Homo sapiens

<400> SEQUENCE: 261
gcagagaucu auaaacaga                                              19

<210> SEQ ID NO 262
<211> LENGTH: 19
<212> TYPE: RNA
<213> ORGANISM: Homo sapiens

<400> SEQUENCE: 262
cagacaggcu cuaugcuaa                                              19

<210> SEQ ID NO 263
<211> LENGTH: 19
<212> TYPE: RNA
<213> ORGANISM: Homo sapiens

<400> SEQUENCE: 263
agacaggcuc uaugcuaaa                                              19

<210> SEQ ID NO 264
<211> LENGTH: 19
<212> TYPE: RNA
<213> ORGANISM: Homo sapiens

<400> SEQUENCE: 264
ccuccuugcu cgagaugga                                              19

<210> SEQ ID NO 265
<211> LENGTH: 19
<212> TYPE: RNA
<213> ORGANISM: Homo sapiens

<400> SEQUENCE: 265
ugaagaguga agacauaaa                                              19

<210> SEQ ID NO 266
<211> LENGTH: 19
<212> TYPE: RNA
```

```
<213> ORGANISM: Homo sapiens

<400> SEQUENCE: 266
agcucauuca guccugau                                                  19

<210> SEQ ID NO 267
<211> LENGTH: 19
<212> TYPE: RNA
<213> ORGANISM: Homo sapiens

<400> SEQUENCE: 267
cauucaguuc cugaucuca                                                 19

<210> SEQ ID NO 268
<211> LENGTH: 19
<212> TYPE: RNA
<213> ORGANISM: Homo sapiens

<400> SEQUENCE: 268
agcuccuuga gaacaucaa                                                 19

<210> SEQ ID NO 269
<211> LENGTH: 19
<212> TYPE: RNA
<213> ORGANISM: Homo sapiens

<400> SEQUENCE: 269
cauuccaugc ccaaguaua                                                 19

<210> SEQ ID NO 270
<211> LENGTH: 19
<212> TYPE: RNA
<213> ORGANISM: Homo sapiens

<400> SEQUENCE: 270
uggacuccaa ccuggauaa                                                 19

<210> SEQ ID NO 271
<211> LENGTH: 19
<212> TYPE: RNA
<213> ORGANISM: Homo sapiens

<400> SEQUENCE: 271
gguuguucau agucagaau                                                 19

<210> SEQ ID NO 272
<211> LENGTH: 19
<212> TYPE: RNA
<213> ORGANISM: Homo sapiens

<400> SEQUENCE: 272
guucauaguc agaauugua                                                 19

<210> SEQ ID NO 273
<211> LENGTH: 19
<212> TYPE: RNA
<213> ORGANISM: Homo sapiens

<400> SEQUENCE: 273
gcagagaucu auaaacaga                                                 19

<210> SEQ ID NO 274
<211> LENGTH: 19
```

```
<212> TYPE: RNA
<213> ORGANISM: Homo sapiens

<400> SEQUENCE: 274
cagacaggcu cuaugcuaa                                                19

<210> SEQ ID NO 275
<211> LENGTH: 19
<212> TYPE: RNA
<213> ORGANISM: Homo sapiens

<400> SEQUENCE: 275
agacaggcuc uaugcuaaa                                                19

<210> SEQ ID NO 276
<211> LENGTH: 19
<212> TYPE: RNA
<213> ORGANISM: Homo sapiens

<400> SEQUENCE: 276
ccuccuugcu cgagaugga                                                19

<210> SEQ ID NO 277
<211> LENGTH: 19
<212> TYPE: RNA
<213> ORGANISM: Homo sapiens

<400> SEQUENCE: 277
ugaagaguga agacauaaa                                                19

<210> SEQ ID NO 278
<211> LENGTH: 19
<212> TYPE: RNA
<213> ORGANISM: Homo sapiens

<400> SEQUENCE: 278
agcucauuca guuccugau                                                19

<210> SEQ ID NO 279
<211> LENGTH: 19
<212> TYPE: RNA
<213> ORGANISM: Homo sapiens

<400> SEQUENCE: 279
cauucaguuc cugaucuca                                                19

<210> SEQ ID NO 280
<211> LENGTH: 19
<212> TYPE: RNA
<213> ORGANISM: Homo sapiens

<400> SEQUENCE: 280
agcuccuuga gaacaucaa                                                19

<210> SEQ ID NO 281
<211> LENGTH: 19
<212> TYPE: RNA
<213> ORGANISM: Homo sapiens

<400> SEQUENCE: 281
cauuccaugc ccaaguaua                                                19

<210> SEQ ID NO 282
```

```
<211> LENGTH: 19
<212> TYPE: RNA
<213> ORGANISM: Homo sapiens

<400> SEQUENCE: 282
uggacuccaa ccuggauaa                                                      19

<210> SEQ ID NO 283
<211> LENGTH: 19
<212> TYPE: RNA
<213> ORGANISM: Homo sapiens

<400> SEQUENCE: 283
gguuguucau agucagaau                                                      19

<210> SEQ ID NO 284
<211> LENGTH: 19
<212> TYPE: RNA
<213> ORGANISM: Homo sapiens

<400> SEQUENCE: 284
guucauaguc agaauugua                                                      19

<210> SEQ ID NO 285
<211> LENGTH: 19
<212> TYPE: RNA
<213> ORGANISM: Homo sapiens

<400> SEQUENCE: 285
gcagagaucu auaaacaga                                                      19

<210> SEQ ID NO 286
<211> LENGTH: 19
<212> TYPE: RNA
<213> ORGANISM: Homo sapiens

<400> SEQUENCE: 286
cagacaggcu cuaugcuaa                                                      19

<210> SEQ ID NO 287
<211> LENGTH: 19
<212> TYPE: RNA
<213> ORGANISM: Homo sapiens

<400> SEQUENCE: 287
agacaggcuc uaugcuaaa                                                      19

<210> SEQ ID NO 288
<211> LENGTH: 19
<212> TYPE: RNA
<213> ORGANISM: homo sapien

<400> SEQUENCE: 288
ccuccuugcu cgagaugga                                                      19

<210> SEQ ID NO 289
<211> LENGTH: 19
<212> TYPE: RNA
<213> ORGANISM: Homo sapiens

<400> SEQUENCE: 289
ugaagaguga agacauaaa                                                      19
```

```
<210> SEQ ID NO 290
<211> LENGTH: 19
<212> TYPE: RNA
<213> ORGANISM: Homo sapiens

<400> SEQUENCE: 290
agcucauuca guuccugau                                                19

<210> SEQ ID NO 291
<211> LENGTH: 19
<212> TYPE: RNA
<213> ORGANISM: Homo sapiens

<400> SEQUENCE: 291
cauucaguuc cugaucuca                                                19

<210> SEQ ID NO 292
<211> LENGTH: 19
<212> TYPE: RNA
<213> ORGANISM: Homo sapiens

<400> SEQUENCE: 292
agcuccuuga gaacaucaa                                                19

<210> SEQ ID NO 293
<211> LENGTH: 19
<212> TYPE: RNA
<213> ORGANISM: Homo sapiens

<400> SEQUENCE: 293
cauuccaugc ccaaguaua                                                19

<210> SEQ ID NO 294
<211> LENGTH: 19
<212> TYPE: RNA
<213> ORGANISM: Homo sapiens

<400> SEQUENCE: 294
uggacuccaa ccuggauaa                                                19

<210> SEQ ID NO 295
<211> LENGTH: 19
<212> TYPE: RNA
<213> ORGANISM: Homo sapiens

<400> SEQUENCE: 295
gguuguucau agucagaau                                                19

<210> SEQ ID NO 296
<211> LENGTH: 19
<212> TYPE: RNA
<213> ORGANISM: Homo sapiens

<400> SEQUENCE: 296
guucauaguc agaauugua                                                19

<210> SEQ ID NO 297
<211> LENGTH: 19
<212> TYPE: RNA
<213> ORGANISM: Homo sapiens

<400> SEQUENCE: 297
gcagagaucu auaaacaga                                                19
```

```
<210> SEQ ID NO 298
<211> LENGTH: 19
<212> TYPE: RNA
<213> ORGANISM: Homo sapiens

<400> SEQUENCE: 298
cagacaggcu cuaugcuaa                                            19

<210> SEQ ID NO 299
<211> LENGTH: 19
<212> TYPE: RNA
<213> ORGANISM: Homo sapiens

<400> SEQUENCE: 299
agacaggcuc uaugcuaaa                                            19

<210> SEQ ID NO 300
<211> LENGTH: 19
<212> TYPE: RNA
<213> ORGANISM: Homo sapiens

<400> SEQUENCE: 300
ccuccuugcu cgagaugga                                            19

<210> SEQ ID NO 301
<211> LENGTH: 19
<212> TYPE: RNA
<213> ORGANISM: Homo sapiens

<400> SEQUENCE: 301
ugaagaguga agacauaaa                                            19

<210> SEQ ID NO 302
<211> LENGTH: 19
<212> TYPE: RNA
<213> ORGANISM: Homo sapiens

<400> SEQUENCE: 302
agcucauuca guuccugau                                            19

<210> SEQ ID NO 303
<211> LENGTH: 19
<212> TYPE: RNA
<213> ORGANISM: Homo sapiens

<400> SEQUENCE: 303
cauucaguuc cugaucuca                                            19

<210> SEQ ID NO 304
<211> LENGTH: 19
<212> TYPE: RNA
<213> ORGANISM: Homo sapiens

<400> SEQUENCE: 304
agcuccuuga gaacaucaa                                            19

<210> SEQ ID NO 305
<211> LENGTH: 19
<212> TYPE: RNA
<213> ORGANISM: Homo sapiens

<400> SEQUENCE: 305
cauuccaugc ccaaguaua                                            19
```

<210> SEQ ID NO 306
<211> LENGTH: 19
<212> TYPE: RNA
<213> ORGANISM: Homo sapiens

<400> SEQUENCE: 306
uggacuccaa ccuggauaa                                                    19

<210> SEQ ID NO 307
<211> LENGTH: 19
<212> TYPE: RNA
<213> ORGANISM: Homo sapiens

<400> SEQUENCE: 307
gguuguucau agucagaau                                                    19

<210> SEQ ID NO 308
<211> LENGTH: 19
<212> TYPE: RNA
<213> ORGANISM: Homo sapiens

<400> SEQUENCE: 308
guucauaguc agaauugua                                                    19

<210> SEQ ID NO 309
<211> LENGTH: 19
<212> TYPE: RNA
<213> ORGANISM: Homo sapiens

<400> SEQUENCE: 309
gcagagaucu auaaacaga                                                    19

<210> SEQ ID NO 310
<211> LENGTH: 19
<212> TYPE: RNA
<213> ORGANISM: Homo sapiens

<400> SEQUENCE: 310
cagacaggcu cuaugcuaa                                                    19

<210> SEQ ID NO 311
<211> LENGTH: 19
<212> TYPE: RNA
<213> ORGANISM: Homo sapiens

<400> SEQUENCE: 311
agacaggcuc uaugcuaaa                                                    19

<210> SEQ ID NO 312
<211> LENGTH: 19
<212> TYPE: RNA
<213> ORGANISM: Homo sapiens

<400> SEQUENCE: 312
ccuccuugcu cgagaugga                                                    19

<210> SEQ ID NO 313
<211> LENGTH: 19
<212> TYPE: RNA
<213> ORGANISM: Homo sapiens

<400> SEQUENCE: 313
ugaagaguga agacauaaa                                              19

<210> SEQ ID NO 314
<211> LENGTH: 19
<212> TYPE: RNA
<213> ORGANISM: Homo sapiens

<400> SEQUENCE: 314
agcucauuca guuccugau                                              19

<210> SEQ ID NO 315
<211> LENGTH: 19
<212> TYPE: RNA
<213> ORGANISM: Homo sapiens

<400> SEQUENCE: 315
cauucaguuc cugaucuca                                              19

<210> SEQ ID NO 316
<211> LENGTH: 19
<212> TYPE: RNA
<213> ORGANISM: Homo sapiens

<400> SEQUENCE: 316
agcuccuuga gaacaucaa                                              19

<210> SEQ ID NO 317
<211> LENGTH: 19
<212> TYPE: RNA
<213> ORGANISM: Homo sapiens

<400> SEQUENCE: 317
cauuccaugc ccaaguaua                                              19

<210> SEQ ID NO 318
<211> LENGTH: 19
<212> TYPE: RNA
<213> ORGANISM: Homo sapiens

<400> SEQUENCE: 318
uggacuccaa ccuggauaa                                              19

<210> SEQ ID NO 319
<211> LENGTH: 19
<212> TYPE: RNA
<213> ORGANISM: Homo sapiens

<400> SEQUENCE: 319
gguuguucau agucagaau                                              19

<210> SEQ ID NO 320
<211> LENGTH: 19
<212> TYPE: RNA
<213> ORGANISM: Homo sapiens

<400> SEQUENCE: 320
guucauaguc agaauugua                                              19

<210> SEQ ID NO 321
<211> LENGTH: 19
<212> TYPE: RNA
<213> ORGANISM: Homo sapiens

<400> SEQUENCE: 321

| | | |
|---|---|---|
| gcagagaucu auaaacaga | | 19 |

<210> SEQ ID NO 322
<211> LENGTH: 19
<212> TYPE: RNA
<213> ORGANISM: Homo sapiens

<400> SEQUENCE: 322

| | | |
|---|---|---|
| cagacaggcu cuaugcuaa | | 19 |

<210> SEQ ID NO 323
<211> LENGTH: 19
<212> TYPE: RNA
<213> ORGANISM: Homo sapiens

<400> SEQUENCE: 323

| | | |
|---|---|---|
| agacaggcuc uaugcuaaa | | 19 |

<210> SEQ ID NO 324
<211> LENGTH: 19
<212> TYPE: RNA
<213> ORGANISM: Homo sapiens

<400> SEQUENCE: 324

| | | |
|---|---|---|
| ccuccuugcu cgagaugga | | 19 |

<210> SEQ ID NO 325
<211> LENGTH: 19
<212> TYPE: RNA
<213> ORGANISM: Homo sapiens

<400> SEQUENCE: 325

| | | |
|---|---|---|
| ugaagaguga agacauaaa | | 19 |

<210> SEQ ID NO 326
<211> LENGTH: 19
<212> TYPE: RNA
<213> ORGANISM: Homo sapiens

<400> SEQUENCE: 326

| | | |
|---|---|---|
| agcucauuca guuccugau | | 19 |

<210> SEQ ID NO 327
<211> LENGTH: 19
<212> TYPE: RNA
<213> ORGANISM: Homo sapiens

<400> SEQUENCE: 327

| | | |
|---|---|---|
| agcucauuca guuccugau | | 19 |

<210> SEQ ID NO 328
<211> LENGTH: 19
<212> TYPE: RNA
<213> ORGANISM: Homo sapiens

<400> SEQUENCE: 328

| | | |
|---|---|---|
| agcuccuuga gaacaucaa | | 19 |

<210> SEQ ID NO 329
<211> LENGTH: 19
<212> TYPE: RNA
<213> ORGANISM: Homo sapiens

```
<400> SEQUENCE: 329
cauuccaugc ccaaguaua                                                    19

<210> SEQ ID NO 330
<211> LENGTH: 19
<212> TYPE: RNA
<213> ORGANISM: Homo sapiens

<400> SEQUENCE: 330
uggacuccaa ccuggauaa                                                    19

<210> SEQ ID NO 331
<211> LENGTH: 19
<212> TYPE: RNA
<213> ORGANISM: Homo sapiens

<400> SEQUENCE: 331
gguuguucau agucagaau                                                    19

<210> SEQ ID NO 332
<211> LENGTH: 19
<212> TYPE: RNA
<213> ORGANISM: Homo sapiens

<400> SEQUENCE: 332
guucauaguc agaauugua                                                    19

<210> SEQ ID NO 333
<211> LENGTH: 19
<212> TYPE: RNA
<213> ORGANISM: Homo sapiens

<400> SEQUENCE: 333
gcagagaucu auaaacaga                                                    19

<210> SEQ ID NO 334
<211> LENGTH: 19
<212> TYPE: RNA
<213> ORGANISM: Homo sapiens

<400> SEQUENCE: 334
cagacaggcu cuaugcuaa                                                    19

<210> SEQ ID NO 335
<211> LENGTH: 19
<212> TYPE: RNA
<213> ORGANISM: Homo sapiens

<400> SEQUENCE: 335
agacaggcuc uaugcuaaa                                                    19

<210> SEQ ID NO 336
<211> LENGTH: 19
<212> TYPE: RNA
<213> ORGANISM: Homo sapiens

<400> SEQUENCE: 336
ccuccuugcu cgagaugga                                                    19

<210> SEQ ID NO 337
<211> LENGTH: 21
<212> TYPE: RNA
<213> ORGANISM: Artificial
```

```
<220> FEATURE:
<223> OTHER INFORMATION: RNAi agent sequence

<400> SEQUENCE: 337
uuuaugucuu cacucuucau u                                              21

<210> SEQ ID NO 338
<211> LENGTH: 21
<212> TYPE: RNA
<213> ORGANISM: Artificial
<220> FEATURE:
<223> OTHER INFORMATION: RNAi agent sequence

<400> SEQUENCE: 338
aucaggaacu gaaugagcuu u                                              21

<210> SEQ ID NO 339
<211> LENGTH: 21
<212> TYPE: RNA
<213> ORGANISM: Artificial
<220> FEATURE:
<223> OTHER INFORMATION: RNAi agent sequence

<400> SEQUENCE: 339
ugagaucagg aacugaaugu u                                              21

<210> SEQ ID NO 340
<211> LENGTH: 21
<212> TYPE: RNA
<213> ORGANISM: Artificial
<220> FEATURE:
<223> OTHER INFORMATION: RNAi agent sequence

<400> SEQUENCE: 340
uugauguucu caaggagcuu u                                              21

<210> SEQ ID NO 341
<211> LENGTH: 21
<212> TYPE: RNA
<213> ORGANISM: Artificial
<220> FEATURE:
<223> OTHER INFORMATION: RNAi agent sequence

<400> SEQUENCE: 341
uauacuuggg cauggaaugu u                                              21

<210> SEQ ID NO 342
<211> LENGTH: 21
<212> TYPE: RNA
<213> ORGANISM: Artificial
<220> FEATURE:
<223> OTHER INFORMATION: RNAi agent sequence

<400> SEQUENCE: 342
uuauccaggu uggaguccau u                                              21

<210> SEQ ID NO 343
<211> LENGTH: 21
<212> TYPE: RNA
<213> ORGANISM: Artificial
<220> FEATURE:
<223> OTHER INFORMATION: RNAi agent sequence

<400> SEQUENCE: 343
auucugacua ugaacaaccu u                                              21
```

```
<210> SEQ ID NO 344
<211> LENGTH: 21
<212> TYPE: RNA
<213> ORGANISM: Artificial
<220> FEATURE:
<223> OTHER INFORMATION: RNAi agent sequence

<400> SEQUENCE: 344
uacaauucug acuaugaacu u                                              21

<210> SEQ ID NO 345
<211> LENGTH: 21
<212> TYPE: RNA
<213> ORGANISM: Artificial
<220> FEATURE:
<223> OTHER INFORMATION: RNAi agent sequence

<400> SEQUENCE: 345
ucuguuuaua gaucucugcu u                                              21

<210> SEQ ID NO 346
<211> LENGTH: 21
<212> TYPE: RNA
<213> ORGANISM: Artificial
<220> FEATURE:
<223> OTHER INFORMATION: RNAi agent sequence

<400> SEQUENCE: 346
uuagcauaga gccugucugu u                                              21

<210> SEQ ID NO 347
<211> LENGTH: 21
<212> TYPE: RNA
<213> ORGANISM: Artificial
<220> FEATURE:
<223> OTHER INFORMATION: RNAi agent sequence

<400> SEQUENCE: 347
uuuagcauag agccugucuu u                                              21

<210> SEQ ID NO 348
<211> LENGTH: 21
<212> TYPE: RNA
<213> ORGANISM: Artificial
<220> FEATURE:
<223> OTHER INFORMATION: RNAi agent sequence

<400> SEQUENCE: 348
uccaucucga gcaaggaggu u                                              21

<210> SEQ ID NO 349
<211> LENGTH: 21
<212> TYPE: RNA
<213> ORGANISM: Artificial
<220> FEATURE:
<223> OTHER INFORMATION: RNAi agent sequence

<400> SEQUENCE: 349
uuuaugucuu cacucuucau u                                              21

<210> SEQ ID NO 350
<211> LENGTH: 21
<212> TYPE: RNA
<213> ORGANISM: Artificial
<220> FEATURE:
<223> OTHER INFORMATION: RNAi agent sequence
```

```
<400> SEQUENCE: 350
aucaggaacu gaaugagcuu u                                              21

<210> SEQ ID NO 351
<211> LENGTH: 21
<212> TYPE: RNA
<213> ORGANISM: Artificial
<220> FEATURE:
<223> OTHER INFORMATION: RNAi agent sequence

<400> SEQUENCE: 351
ugagaucagg aacugaaugu u                                              21

<210> SEQ ID NO 352
<211> LENGTH: 21
<212> TYPE: RNA
<213> ORGANISM: Artificial
<220> FEATURE:
<223> OTHER INFORMATION: RNAi agent sequence

<400> SEQUENCE: 352
uugauguucu caaggagcuu u                                              21

<210> SEQ ID NO 353
<211> LENGTH: 21
<212> TYPE: RNA
<213> ORGANISM: Artificial
<220> FEATURE:
<223> OTHER INFORMATION: RNAi agent sequence

<400> SEQUENCE: 353
uauacuuggg cauggaaugu u                                              21

<210> SEQ ID NO 354
<211> LENGTH: 21
<212> TYPE: RNA
<213> ORGANISM: Artificial
<220> FEATURE:
<223> OTHER INFORMATION: RNAi agent sequence

<400> SEQUENCE: 354
uuauccaggu uggaguccau u                                              21

<210> SEQ ID NO 355
<211> LENGTH: 21
<212> TYPE: RNA
<213> ORGANISM: Artificial
<220> FEATURE:
<223> OTHER INFORMATION: RNAi agent sequence

<400> SEQUENCE: 355
auucugacua ugaacaaccu u                                              21

<210> SEQ ID NO 356
<211> LENGTH: 21
<212> TYPE: RNA
<213> ORGANISM: Artificial
<220> FEATURE:
<223> OTHER INFORMATION: RNAi agent sequence

<400> SEQUENCE: 356
uacaauucug acuaugaacu u                                              21

<210> SEQ ID NO 357
```

```
<211> LENGTH: 21
<212> TYPE: RNA
<213> ORGANISM: Artificial
<220> FEATURE:
<223> OTHER INFORMATION: RNAi agent sequence

<400> SEQUENCE: 357
ucuguuuaua gaucucugcu u                                              21

<210> SEQ ID NO 358
<211> LENGTH: 21
<212> TYPE: RNA
<213> ORGANISM: Artificial
<220> FEATURE:
<223> OTHER INFORMATION: RNAi agent sequence

<400> SEQUENCE: 358
uuagcauaga gccugucugu u                                              21

<210> SEQ ID NO 359
<211> LENGTH: 21
<212> TYPE: RNA
<213> ORGANISM: Artificial
<220> FEATURE:
<223> OTHER INFORMATION: RNAi agent sequence

<400> SEQUENCE: 359
uuuagcauag agccugucuu u                                              21

<210> SEQ ID NO 360
<211> LENGTH: 21
<212> TYPE: RNA
<213> ORGANISM: Artificial
<220> FEATURE:
<223> OTHER INFORMATION: RNAi agent sequence

<400> SEQUENCE: 360
uccaucucga gcaaggaggu u                                              21

<210> SEQ ID NO 361
<211> LENGTH: 21
<212> TYPE: RNA
<213> ORGANISM: Artificial
<220> FEATURE:
<223> OTHER INFORMATION: RNAi agent sequence

<400> SEQUENCE: 361
uuuaugucuu cacucuucau u                                              21

<210> SEQ ID NO 362
<211> LENGTH: 21
<212> TYPE: RNA
<213> ORGANISM: Artificial
<220> FEATURE:
<223> OTHER INFORMATION: RNAi agent sequence

<400> SEQUENCE: 362
aucaggaacu gaaugagcuu u                                              21

<210> SEQ ID NO 363
<211> LENGTH: 21
<212> TYPE: RNA
<213> ORGANISM: Artificial
<220> FEATURE:
<223> OTHER INFORMATION: RNAi agent sequence

<400> SEQUENCE: 363
```
ugagaucagg aacugaaugu u                                              21

<210> SEQ ID NO 364
<211> LENGTH: 21
<212> TYPE: RNA
<213> ORGANISM: Artificial
<220> FEATURE:
<223> OTHER INFORMATION: RNAi agent sequence

<400> SEQUENCE: 364
uugauguucu caaggagcuu u                                              21

<210> SEQ ID NO 365
<211> LENGTH: 21
<212> TYPE: RNA
<213> ORGANISM: Artificial
<220> FEATURE:
<223> OTHER INFORMATION: RNAi agent sequence

<400> SEQUENCE: 365
uauacuuggg cauggaaugu u                                              21

<210> SEQ ID NO 366
<211> LENGTH: 21
<212> TYPE: RNA
<213> ORGANISM: Artificial
<220> FEATURE:
<223> OTHER INFORMATION: RNAi agent sequence

<400> SEQUENCE: 366
uuauccaggu uggaguccau u                                              21

<210> SEQ ID NO 367
<211> LENGTH: 21
<212> TYPE: RNA
<213> ORGANISM: Artificial
<220> FEATURE:
<223> OTHER INFORMATION: RNAi agent sequence

<400> SEQUENCE: 367
auucugacua ugaacaaccu u                                              21

<210> SEQ ID NO 368
<211> LENGTH: 21
<212> TYPE: RNA
<213> ORGANISM: Artificial
<220> FEATURE:
<223> OTHER INFORMATION: RNAi agent sequence

<400> SEQUENCE: 368
uacaauucug acuaugaacu u                                              21

<210> SEQ ID NO 369
<211> LENGTH: 21
<212> TYPE: RNA
<213> ORGANISM: Artificial
<220> FEATURE:
<223> OTHER INFORMATION: RNAi agent sequence

<400> SEQUENCE: 369
ucuguuuaua gaucucugcu u                                              21

<210> SEQ ID NO 370
<211> LENGTH: 21
<212> TYPE: RNA

```
<213> ORGANISM: Artificial
<220> FEATURE:
<223> OTHER INFORMATION: RNAi agent sequence

<400> SEQUENCE: 370
uuagcauaga gccugucugu u                                              21

<210> SEQ ID NO 371
<211> LENGTH: 21
<212> TYPE: RNA
<213> ORGANISM: Artificial
<220> FEATURE:
<223> OTHER INFORMATION: RNAi agent sequence

<400> SEQUENCE: 371
uuuagcauag agccugucuu u                                              21

<210> SEQ ID NO 372
<211> LENGTH: 21
<212> TYPE: RNA
<213> ORGANISM: Artificial
<220> FEATURE:
<223> OTHER INFORMATION: RNAi agent sequence

<400> SEQUENCE: 372
uccaucucga gcaaggaggu u                                              21

<210> SEQ ID NO 373
<211> LENGTH: 21
<212> TYPE: RNA
<213> ORGANISM: Artificial
<220> FEATURE:
<223> OTHER INFORMATION: RNAi agent sequence

<400> SEQUENCE: 373
uuuaugucuu cacucuucau u                                              21

<210> SEQ ID NO 374
<211> LENGTH: 21
<212> TYPE: RNA
<213> ORGANISM: Artificial
<220> FEATURE:
<223> OTHER INFORMATION: RNAi agent sequence

<400> SEQUENCE: 374
aucaggaacu gaaugagcuu u                                              21

<210> SEQ ID NO 375
<211> LENGTH: 21
<212> TYPE: RNA
<213> ORGANISM: Artificial
<220> FEATURE:
<223> OTHER INFORMATION: RNAi agent sequence

<400> SEQUENCE: 375
ugagaucagg aacugaaugu u                                              21

<210> SEQ ID NO 376
<211> LENGTH: 21
<212> TYPE: RNA
<213> ORGANISM: Artificial
<220> FEATURE:
<223> OTHER INFORMATION: RNAi agent sequence

<400> SEQUENCE: 376
uugauguucu caaggagcuu u                                              21
```

<210> SEQ ID NO 377
<211> LENGTH: 21
<212> TYPE: RNA
<213> ORGANISM: Artificial
<220> FEATURE:
<223> OTHER INFORMATION: RNAi agent sequence

<400> SEQUENCE: 377
uauacuuggg cauggaaugu u                                              21

<210> SEQ ID NO 378
<211> LENGTH: 21
<212> TYPE: RNA
<213> ORGANISM: Artificial
<220> FEATURE:
<223> OTHER INFORMATION: RNAi agent sequence

<400> SEQUENCE: 378
uuauccaggu uggaguccau u                                              21

<210> SEQ ID NO 379
<211> LENGTH: 21
<212> TYPE: RNA
<213> ORGANISM: Artificial
<220> FEATURE:
<223> OTHER INFORMATION: RNAi agent sequence

<400> SEQUENCE: 379
auucugacua ugaacaaccu u                                              21

<210> SEQ ID NO 380
<211> LENGTH: 21
<212> TYPE: RNA
<213> ORGANISM: Artificial
<220> FEATURE:
<223> OTHER INFORMATION: RNAi agent sequence

<400> SEQUENCE: 380
uacaauucug acuaugaacu u                                              21

<210> SEQ ID NO 381
<211> LENGTH: 21
<212> TYPE: RNA
<213> ORGANISM: Artificial
<220> FEATURE:
<223> OTHER INFORMATION: RNAi agent sequence

<400> SEQUENCE: 381
ucuguuuaua gaucucugcu u                                              21

<210> SEQ ID NO 382
<211> LENGTH: 21
<212> TYPE: RNA
<213> ORGANISM: Artificial
<220> FEATURE:
<223> OTHER INFORMATION: RNAi agent sequence

<400> SEQUENCE: 382
uuagcauaga gccugucugu u                                              21

<210> SEQ ID NO 383
<211> LENGTH: 21
<212> TYPE: RNA
<213> ORGANISM: Artificial
<220> FEATURE:

<223> OTHER INFORMATION: RNAi agent sequence

<400> SEQUENCE: 383
uuuagcauag agccugucuu u                                          21

<210> SEQ ID NO 384
<211> LENGTH: 21
<212> TYPE: RNA
<213> ORGANISM: Artificial
<220> FEATURE:
<223> OTHER INFORMATION: RNAi agent sequence

<400> SEQUENCE: 384
uccaucucga gcaaggaggu u                                          21

<210> SEQ ID NO 385
<211> LENGTH: 21
<212> TYPE: RNA
<213> ORGANISM: Artificial
<220> FEATURE:
<223> OTHER INFORMATION: RNAi agent sequence

<400> SEQUENCE: 385
uuuaugucuu cacucuucau u                                          21

<210> SEQ ID NO 386
<211> LENGTH: 21
<212> TYPE: RNA
<213> ORGANISM: Artificial
<220> FEATURE:
<223> OTHER INFORMATION: RNAi agent sequence

<400> SEQUENCE: 386
aucaggaacu gaaugagcuu u                                          21

<210> SEQ ID NO 387
<211> LENGTH: 21
<212> TYPE: RNA
<213> ORGANISM: Artificial
<220> FEATURE:
<223> OTHER INFORMATION: RNAi agent sequence

<400> SEQUENCE: 387
ugagaucagg aacugaaugu u                                          21

<210> SEQ ID NO 388
<211> LENGTH: 21
<212> TYPE: RNA
<213> ORGANISM: Artificial
<220> FEATURE:
<223> OTHER INFORMATION: RNAi agent sequence

<400> SEQUENCE: 388
uugauguucu caaggagcuu u                                          21

<210> SEQ ID NO 389
<211> LENGTH: 21
<212> TYPE: RNA
<213> ORGANISM: Artificial
<220> FEATURE:
<223> OTHER INFORMATION: RNAi agent sequence

<400> SEQUENCE: 389
uauacuuggg cauggaaugu u                                          21

```
<210> SEQ ID NO 390
<211> LENGTH: 21
<212> TYPE: RNA
<213> ORGANISM: Artificial
<220> FEATURE:
<223> OTHER INFORMATION: RNAi agent sequence

<400> SEQUENCE: 390
uuauccaggu uggaguccau u                                              21

<210> SEQ ID NO 391
<211> LENGTH: 21
<212> TYPE: RNA
<213> ORGANISM: Artificial
<220> FEATURE:
<223> OTHER INFORMATION: RNAi agent sequence

<400> SEQUENCE: 391
auucugacua ugaacaaccu u                                              21

<210> SEQ ID NO 392
<211> LENGTH: 21
<212> TYPE: RNA
<213> ORGANISM: Artificial
<220> FEATURE:
<223> OTHER INFORMATION: RNAi agent sequence

<400> SEQUENCE: 392
uacaauucug acuaugaacu u                                              21

<210> SEQ ID NO 393
<211> LENGTH: 21
<212> TYPE: RNA
<213> ORGANISM: Artificial
<220> FEATURE:
<223> OTHER INFORMATION: RNAi agent sequence

<400> SEQUENCE: 393
ucuguuuaua gaucucugcu u                                              21

<210> SEQ ID NO 394
<211> LENGTH: 21
<212> TYPE: RNA
<213> ORGANISM: Artificial
<220> FEATURE:
<223> OTHER INFORMATION: RNAi agent sequence

<400> SEQUENCE: 394
uuagcauaga gccugucugu u                                              21

<210> SEQ ID NO 395
<211> LENGTH: 21
<212> TYPE: RNA
<213> ORGANISM: Artificial
<220> FEATURE:
<223> OTHER INFORMATION: RNAi agent sequence

<400> SEQUENCE: 395
uuuagcauag agccugucuu u                                              21

<210> SEQ ID NO 396
<211> LENGTH: 21
<212> TYPE: RNA
<213> ORGANISM: Artificial
<220> FEATURE:
<223> OTHER INFORMATION: RNAi agent sequence
```

```
<400> SEQUENCE: 396
uccaucucga gcaaggaggu u                                            21

<210> SEQ ID NO 397
<211> LENGTH: 21
<212> TYPE: RNA
<213> ORGANISM: Artificial
<220> FEATURE:
<223> OTHER INFORMATION: RNAi agent sequence

<400> SEQUENCE: 397
uuuaugucuu cacucuucau u                                            21

<210> SEQ ID NO 398
<211> LENGTH: 21
<212> TYPE: RNA
<213> ORGANISM: Artificial
<220> FEATURE:
<223> OTHER INFORMATION: RNAi agent sequence

<400> SEQUENCE: 398
aucaggaacu gaaugagcuu u                                            21

<210> SEQ ID NO 399
<211> LENGTH: 21
<212> TYPE: RNA
<213> ORGANISM: Artificial
<220> FEATURE:
<223> OTHER INFORMATION: RNAi agent sequence

<400> SEQUENCE: 399
ugagaucagg aacugaaugu u                                            21

<210> SEQ ID NO 400
<211> LENGTH: 21
<212> TYPE: RNA
<213> ORGANISM: Artificial
<220> FEATURE:
<223> OTHER INFORMATION: RNAi agent sequence

<400> SEQUENCE: 400
uugauguucu caaggagcuu u                                            21

<210> SEQ ID NO 401
<211> LENGTH: 21
<212> TYPE: RNA
<213> ORGANISM: Artificial
<220> FEATURE:
<223> OTHER INFORMATION: RNAi agent sequence

<400> SEQUENCE: 401
uauacuuggg cauggaaugu u                                            21

<210> SEQ ID NO 402
<211> LENGTH: 21
<212> TYPE: RNA
<213> ORGANISM: Artificial
<220> FEATURE:
<223> OTHER INFORMATION: RNAi agent sequence

<400> SEQUENCE: 402
uuauccaggu uggaguccau u                                            21

<210> SEQ ID NO 403
<211> LENGTH: 21
```

```
<212> TYPE: RNA
<213> ORGANISM: Artificial
<220> FEATURE:
<223> OTHER INFORMATION: RNAi agent sequence

<400> SEQUENCE: 403
auucugacua ugaacaaccu u                                              21

<210> SEQ ID NO 404
<211> LENGTH: 21
<212> TYPE: RNA
<213> ORGANISM: Artificial
<220> FEATURE:
<223> OTHER INFORMATION: RNAi agent sequence

<400> SEQUENCE: 404
uacaauucug acuaugaacu u                                              21

<210> SEQ ID NO 405
<211> LENGTH: 21
<212> TYPE: RNA
<213> ORGANISM: Artificial
<220> FEATURE:
<223> OTHER INFORMATION: RNAi agent sequence

<400> SEQUENCE: 405
ucuguuuaua gaucucugcu u                                              21

<210> SEQ ID NO 406
<211> LENGTH: 21
<212> TYPE: RNA
<213> ORGANISM: Artificial
<220> FEATURE:
<223> OTHER INFORMATION: RNAi agent sequence

<400> SEQUENCE: 406
uuagcauaga gccugucugu u                                              21

<210> SEQ ID NO 407
<211> LENGTH: 21
<212> TYPE: RNA
<213> ORGANISM: Artificial
<220> FEATURE:
<223> OTHER INFORMATION: RNAi agent sequence

<400> SEQUENCE: 407
uuuagcauag agccugucuu u                                              21

<210> SEQ ID NO 408
<211> LENGTH: 21
<212> TYPE: RNA
<213> ORGANISM: Artificial
<220> FEATURE:
<223> OTHER INFORMATION: RNAi agent sequence

<400> SEQUENCE: 408
uccaucucga gcaaggaggu u                                              21

<210> SEQ ID NO 409
<211> LENGTH: 21
<212> TYPE: RNA
<213> ORGANISM: Artificial
<220> FEATURE:
<223> OTHER INFORMATION: RNAi agent sequence

<400> SEQUENCE: 409
```
uuuaugucuu cacucuucau u                                              21

<210> SEQ ID NO 410
<211> LENGTH: 21
<212> TYPE: RNA
<213> ORGANISM: Artificial
<220> FEATURE:
<223> OTHER INFORMATION: RNAi agent sequence

<400> SEQUENCE: 410
aucaggaacu gaaugagcuu u                                              21

<210> SEQ ID NO 411
<211> LENGTH: 21
<212> TYPE: RNA
<213> ORGANISM: Artificial
<220> FEATURE:
<223> OTHER INFORMATION: RNAi agent sequence

<400> SEQUENCE: 411
ugagaucagg aacugaaugu u                                              21

<210> SEQ ID NO 412
<211> LENGTH: 21
<212> TYPE: RNA
<213> ORGANISM: Artificial
<220> FEATURE:
<223> OTHER INFORMATION: RNAi agent sequence

<400> SEQUENCE: 412
uugauguucu caaggagcuu u                                              21

<210> SEQ ID NO 413
<211> LENGTH: 21
<212> TYPE: RNA
<213> ORGANISM: Artificial
<220> FEATURE:
<223> OTHER INFORMATION: RNAi agent sequence

<400> SEQUENCE: 413
uauacuuggg cauggaaugu u                                              21

<210> SEQ ID NO 414
<211> LENGTH: 21
<212> TYPE: RNA
<213> ORGANISM: Artificial
<220> FEATURE:
<223> OTHER INFORMATION: RNAi agent sequence

<400> SEQUENCE: 414
uuauccaggu uggaguccau u                                              21

<210> SEQ ID NO 415
<211> LENGTH: 21
<212> TYPE: RNA
<213> ORGANISM: Artificial
<220> FEATURE:
<223> OTHER INFORMATION: RNAi agent sequence

<400> SEQUENCE: 415
auucugacua ugaacaaccu u                                              21

<210> SEQ ID NO 416
<211> LENGTH: 21
<212> TYPE: RNA
<213> ORGANISM: Artificial

<220> FEATURE:
<223> OTHER INFORMATION: RNAi agent sequence

<400> SEQUENCE: 416
uacaauucug acuaugaacu u                                              21

<210> SEQ ID NO 417
<211> LENGTH: 21
<212> TYPE: RNA
<213> ORGANISM: Artificial
<220> FEATURE:
<223> OTHER INFORMATION: RNAi agent sequence

<400> SEQUENCE: 417
ucuguuuaua gaucucugcu u                                              21

<210> SEQ ID NO 418
<211> LENGTH: 21
<212> TYPE: RNA
<213> ORGANISM: Artificial
<220> FEATURE:
<223> OTHER INFORMATION: RNAi agent sequence

<400> SEQUENCE: 418
uuagcauaga gccugucugu u                                              21

<210> SEQ ID NO 419
<211> LENGTH: 21
<212> TYPE: RNA
<213> ORGANISM: Artificial
<220> FEATURE:
<223> OTHER INFORMATION: RNAi agent sequence

<400> SEQUENCE: 419
uuuagcauag agccugucuu u                                              21

<210> SEQ ID NO 420
<211> LENGTH: 21
<212> TYPE: RNA
<213> ORGANISM: Artificial
<220> FEATURE:
<223> OTHER INFORMATION: RNAi agent sequence

<400> SEQUENCE: 420
uccaucucga gcaaggaggu u                                              21

<210> SEQ ID NO 421
<211> LENGTH: 21
<212> TYPE: RNA
<213> ORGANISM: Artificial
<220> FEATURE:
<223> OTHER INFORMATION: RNAi agent sequence

<400> SEQUENCE: 421
ugaagaguga agacauaaau u                                              21

<210> SEQ ID NO 422
<211> LENGTH: 21
<212> TYPE: RNA
<213> ORGANISM: Artificial
<220> FEATURE:
<223> OTHER INFORMATION: RNAi agent sequence

<400> SEQUENCE: 422
agcucauuca guuccugauu u                                              21

<210> SEQ ID NO 423
<211> LENGTH: 21
<212> TYPE: RNA
<213> ORGANISM: Artificial
<220> FEATURE:
<223> OTHER INFORMATION: RNAi agent sequence

<400> SEQUENCE: 423
cauucaguuc cugaucucau u                                              21

<210> SEQ ID NO 424
<211> LENGTH: 21
<212> TYPE: RNA
<213> ORGANISM: Artificial
<220> FEATURE:
<223> OTHER INFORMATION: RNAi agent sequence

<400> SEQUENCE: 424
agcuccuuga gaacaucaau u                                              21

<210> SEQ ID NO 425
<211> LENGTH: 21
<212> TYPE: RNA
<213> ORGANISM: Artificial
<220> FEATURE:
<223> OTHER INFORMATION: RNAi agent sequence

<400> SEQUENCE: 425 cauccaugc ccaaguauau u                                               21

<210> SEQ ID NO 426
<211> LENGTH: 21
<212> TYPE: RNA
<213> ORGANISM: Artificial
<220> FEATURE:
<223> OTHER INFORMATION: RNAi agent sequence

<400> SEQUENCE: 426
uggacuccaa ccuggauaau u                                              21

<210> SEQ ID NO 427
<211> LENGTH: 21
<212> TYPE: RNA
<213> ORGANISM: Artificial
<220> FEATURE:
<223> OTHER INFORMATION: RNAi agent sequence

<400> SEQUENCE: 427
gguuguucau agucagaauu u                                              21

<210> SEQ ID NO 428
<211> LENGTH: 21
<212> TYPE: RNA
<213> ORGANISM: Artificial
<220> FEATURE:
<223> OTHER INFORMATION: RNAi agent sequence

<400> SEQUENCE: 428
guucauaguc agaauuguau u                                              21

<210> SEQ ID NO 429
<211> LENGTH: 21
<212> TYPE: RNA
<213> ORGANISM: Artificial
<220> FEATURE:
<223> OTHER INFORMATION: RNAi agent sequence

```
<400> SEQUENCE: 429
gcagagaucu auaaacagau u                                              21

<210> SEQ ID NO 430
<211> LENGTH: 21
<212> TYPE: RNA
<213> ORGANISM: Artificial
<220> FEATURE:
<223> OTHER INFORMATION: RNAi agent sequence

<400> SEQUENCE: 430
cagacaggcu cuaugcuaau u                                              21

<210> SEQ ID NO 431
<211> LENGTH: 21
<212> TYPE: RNA
<213> ORGANISM: Artificial
<220> FEATURE:
<223> OTHER INFORMATION: RNAi agent sequence

<400> SEQUENCE: 431
agacaggcuc uaugcuaaau u                                              21

<210> SEQ ID NO 432
<211> LENGTH: 21
<212> TYPE: RNA
<213> ORGANISM: Artificial
<220> FEATURE:
<223> OTHER INFORMATION: RNAi agent sequence

<400> SEQUENCE: 432
ccuccuugcu cgagauggau u                                              21

<210> SEQ ID NO 433
<211> LENGTH: 21
<212> TYPE: RNA
<213> ORGANISM: Artificial
<220> FEATURE:
<223> OTHER INFORMATION: RNAi agent sequence

<400> SEQUENCE: 433
ugaagaguga agacauaaau u                                              21

<210> SEQ ID NO 434
<211> LENGTH: 21
<212> TYPE: RNA
<213> ORGANISM: Artificial
<220> FEATURE:
<223> OTHER INFORMATION: RNAi agent sequence

<400> SEQUENCE: 434
agcucauuca guuccugauu u                                              21

<210> SEQ ID NO 435
<211> LENGTH: 21
<212> TYPE: RNA
<213> ORGANISM: Artificial
<220> FEATURE:
<223> OTHER INFORMATION: RNAi agent sequence

<400> SEQUENCE: 435
cauucaguuc cugaucucau u                                              21

<210> SEQ ID NO 436
```

```
<211> LENGTH: 21
<212> TYPE: RNA
<213> ORGANISM: Artificial
<220> FEATURE:
<223> OTHER INFORMATION: RNAi agent sequence

<400> SEQUENCE: 436
agcuccuuga gaacaucaau u                                              21

<210> SEQ ID NO 437
<211> LENGTH: 21
<212> TYPE: RNA
<213> ORGANISM: Artificial
<220> FEATURE:
<223> OTHER INFORMATION: RNAi agent sequence

<400> SEQUENCE: 437
cauuccaugc ccaaguauau u                                              21

<210> SEQ ID NO 438
<211> LENGTH: 21
<212> TYPE: RNA
<213> ORGANISM: Artificial
<220> FEATURE:
<223> OTHER INFORMATION: RNAi agent sequence

<400> SEQUENCE: 438
uggacuccaa ccuggauaau u                                              21

<210> SEQ ID NO 439
<211> LENGTH: 21
<212> TYPE: RNA
<213> ORGANISM: Artificial
<220> FEATURE:
<223> OTHER INFORMATION: RNAi agent sequence

<400> SEQUENCE: 439
gguuguucau agucagaauu u                                              21

<210> SEQ ID NO 440
<211> LENGTH: 21
<212> TYPE: RNA
<213> ORGANISM: Artificial
<220> FEATURE:
<223> OTHER INFORMATION: RNAi agent sequence

<400> SEQUENCE: 440
guucauaguc agaauuguau u                                              21

<210> SEQ ID NO 441
<211> LENGTH: 21
<212> TYPE: RNA
<213> ORGANISM: Artificial
<220> FEATURE:
<223> OTHER INFORMATION: RNAi agent sequence

<400> SEQUENCE: 441
gcagagaucu auaaacagau u                                              21

<210> SEQ ID NO 442
<211> LENGTH: 21
<212> TYPE: RNA
<213> ORGANISM: Artificial
<220> FEATURE:
<223> OTHER INFORMATION: RNAi agent sequence

<400> SEQUENCE: 442
```
cagacaggcu cuaugcuaau u    21

```
<210> SEQ ID NO 443
<211> LENGTH: 21
<212> TYPE: RNA
<213> ORGANISM: Artificial
<220> FEATURE:
<223> OTHER INFORMATION: RNAi agent sequence

<400> SEQUENCE: 443
```
agacaggcuc uaugcuaaau u    21

```
<210> SEQ ID NO 444
<211> LENGTH: 21
<212> TYPE: RNA
<213> ORGANISM: Artificial
<220> FEATURE:
<223> OTHER INFORMATION: RNAi agent sequence

<400> SEQUENCE: 444
```
ccuccuugcu cgagauggau u    21

```
<210> SEQ ID NO 445
<211> LENGTH: 21
<212> TYPE: RNA
<213> ORGANISM: Artificial
<220> FEATURE:
<223> OTHER INFORMATION: RNAi agent sequence

<400> SEQUENCE: 445
```
ugaagaguga agacauaaau u    21

```
<210> SEQ ID NO 446
<211> LENGTH: 21
<212> TYPE: RNA
<213> ORGANISM: Artificial
<220> FEATURE:
<223> OTHER INFORMATION: RNAi agent sequence

<400> SEQUENCE: 446
```
agcucauuca guccugauu u    21

```
<210> SEQ ID NO 447
<211> LENGTH: 21
<212> TYPE: RNA
<213> ORGANISM: Artificial
<220> FEATURE:
<223> OTHER INFORMATION: RNAi agent sequence

<400> SEQUENCE: 447
```
cauucaguuc cugaucucau u    21

```
<210> SEQ ID NO 448
<211> LENGTH: 21
<212> TYPE: RNA
<213> ORGANISM: Artificial
<220> FEATURE:
<223> OTHER INFORMATION: RNAi agent sequence

<400> SEQUENCE: 448
```
agcuccuuga gaacaucaau u    21

```
<210> SEQ ID NO 449
<211> LENGTH: 21
<212> TYPE: RNA
```

```
<213> ORGANISM: Artificial
<220> FEATURE:
<223> OTHER INFORMATION: RNAi agent sequence

<400> SEQUENCE: 449
cauuccaugc ccaaguauau u                                              21

<210> SEQ ID NO 450
<211> LENGTH: 21
<212> TYPE: RNA
<213> ORGANISM: Artificial
<220> FEATURE:
<223> OTHER INFORMATION: RNAi agent sequence

<400> SEQUENCE: 450
uggacuccaa ccuggauaau u                                              21

<210> SEQ ID NO 451
<211> LENGTH: 21
<212> TYPE: RNA
<213> ORGANISM: Artificial
<220> FEATURE:
<223> OTHER INFORMATION: RNAi agent sequence

<400> SEQUENCE: 451
gguuguucau agucagaauu u                                              21

<210> SEQ ID NO 452
<211> LENGTH: 21
<212> TYPE: RNA
<213> ORGANISM: Artificial
<220> FEATURE:
<223> OTHER INFORMATION: RNAi agent sequence

<400> SEQUENCE: 452
guucauaguc agaauuguau u                                              21

<210> SEQ ID NO 453
<211> LENGTH: 21
<212> TYPE: RNA
<213> ORGANISM: Artificial
<220> FEATURE:
<223> OTHER INFORMATION: RNAi agent sequence

<400> SEQUENCE: 453
gcagagaucu auaaacagau u                                              21

<210> SEQ ID NO 454
<211> LENGTH: 21
<212> TYPE: RNA
<213> ORGANISM: Artificial
<220> FEATURE:
<223> OTHER INFORMATION: RNAi agent sequence

<400> SEQUENCE: 454
cagacaggcu cuaugcuaau u                                              21

<210> SEQ ID NO 455
<211> LENGTH: 21
<212> TYPE: RNA
<213> ORGANISM: Artificial
<220> FEATURE:
<223> OTHER INFORMATION: RNAi agent sequence

<400> SEQUENCE: 455
agacaggcuc uaugcuaaau u                                              21
```

<210> SEQ ID NO 456
<211> LENGTH: 21
<212> TYPE: RNA
<213> ORGANISM: Artificial
<220> FEATURE:
<223> OTHER INFORMATION: RNAi agent sequence

<400> SEQUENCE: 456
ccuccuugcu cgagauggau u                                              21

<210> SEQ ID NO 457
<211> LENGTH: 21
<212> TYPE: RNA
<213> ORGANISM: Artificial
<220> FEATURE:
<223> OTHER INFORMATION: RNAi agent sequence

<400> SEQUENCE: 457
ugaagaguga agacauaaau u                                              21

<210> SEQ ID NO 458
<211> LENGTH: 21
<212> TYPE: RNA
<213> ORGANISM: Artificial
<220> FEATURE:
<223> OTHER INFORMATION: RNAi agent sequence

<400> SEQUENCE: 458
agcucauuca guuccugauu u                                              21

<210> SEQ ID NO 459
<211> LENGTH: 21
<212> TYPE: RNA
<213> ORGANISM: Artificial
<220> FEATURE:
<223> OTHER INFORMATION: RNAi agent sequence

<400> SEQUENCE: 459
cauucaguuc cugaucucau u                                              21

<210> SEQ ID NO 460
<211> LENGTH: 21
<212> TYPE: RNA
<213> ORGANISM: Artificial
<220> FEATURE:
<223> OTHER INFORMATION: RNAi agent sequence

<400> SEQUENCE: 460
agcuccuuga gaacaucaau u                                              21

<210> SEQ ID NO 461
<211> LENGTH: 21
<212> TYPE: RNA
<213> ORGANISM: Artificial
<220> FEATURE:
<223> OTHER INFORMATION: RNAi agent sequence

<400> SEQUENCE: 461
cauuccaugc ccaaguauau u                                              21

<210> SEQ ID NO 462
<211> LENGTH: 21
<212> TYPE: RNA
<213> ORGANISM: Artificial
<220> FEATURE:

<223> OTHER INFORMATION: RNAi agent sequence

<400> SEQUENCE: 462
uggacuccaa ccuggauaau u                                              21

<210> SEQ ID NO 463
<211> LENGTH: 21
<212> TYPE: RNA
<213> ORGANISM: Artificial
<220> FEATURE:
<223> OTHER INFORMATION: RNAi agent sequence

<400> SEQUENCE: 463
gguuguucau agucagaauu u                                              21

<210> SEQ ID NO 464
<211> LENGTH: 21
<212> TYPE: RNA
<213> ORGANISM: Artificial
<220> FEATURE:
<223> OTHER INFORMATION: RNAi agent sequence

<400> SEQUENCE: 464
guucauaguc agaauuguau u                                              21

<210> SEQ ID NO 465
<211> LENGTH: 21
<212> TYPE: RNA
<213> ORGANISM: Artificial
<220> FEATURE:
<223> OTHER INFORMATION: RNAi agent sequence

<400> SEQUENCE: 465
gcagagaucu auaaacagau u                                              21

<210> SEQ ID NO 466
<211> LENGTH: 21
<212> TYPE: RNA
<213> ORGANISM: Artificial
<220> FEATURE:
<223> OTHER INFORMATION: RNAi agent sequence

<400> SEQUENCE: 466
cagacaggcu cuaugcuaau u                                              21

<210> SEQ ID NO 467
<211> LENGTH: 21
<212> TYPE: RNA
<213> ORGANISM: Artificial
<220> FEATURE:
<223> OTHER INFORMATION: RNAi agent sequence

<400> SEQUENCE: 467
agacaggcuc uaugcuaaau u                                              21

<210> SEQ ID NO 468
<211> LENGTH: 21
<212> TYPE: RNA
<213> ORGANISM: Artificial
<220> FEATURE:
<223> OTHER INFORMATION: RNAi agent sequence

<400> SEQUENCE: 468
ccuccuugcu cgagauggau u                                              21

```
<210> SEQ ID NO 469
<211> LENGTH: 21
<212> TYPE: RNA
<213> ORGANISM: Artificial
<220> FEATURE:
<223> OTHER INFORMATION: RNAi agent sequence

<400> SEQUENCE: 469
ugaagaguga agacauaaau u                                              21

<210> SEQ ID NO 470
<211> LENGTH: 21
<212> TYPE: RNA
<213> ORGANISM: Artificial
<220> FEATURE:
<223> OTHER INFORMATION: RNAi agent sequence

<400> SEQUENCE: 470
agcucauuca guuccugauu u                                              21

<210> SEQ ID NO 471
<211> LENGTH: 21
<212> TYPE: RNA
<213> ORGANISM: Artificial
<220> FEATURE:
<223> OTHER INFORMATION: RNAi agent sequence

<400> SEQUENCE: 471
cauucaguuc cugaucucau u                                              21

<210> SEQ ID NO 472
<211> LENGTH: 21
<212> TYPE: RNA
<213> ORGANISM: Artificial
<220> FEATURE:
<223> OTHER INFORMATION: RNAi agent sequence

<400> SEQUENCE: 472
agcuccuuga gaacaucaau u                                              21

<210> SEQ ID NO 473
<211> LENGTH: 21
<212> TYPE: RNA
<213> ORGANISM: Artificial
<220> FEATURE:
<223> OTHER INFORMATION: RNAi agent sequence

<400> SEQUENCE: 473
cauuccaugc ccaaguauau u                                              21

<210> SEQ ID NO 474
<211> LENGTH: 21
<212> TYPE: RNA
<213> ORGANISM: Artificial
<220> FEATURE:
<223> OTHER INFORMATION: RNAi agent sequence

<400> SEQUENCE: 474
uggacuccaa ccuggauaau u                                              21

<210> SEQ ID NO 475
<211> LENGTH: 21
<212> TYPE: RNA
<213> ORGANISM: Artificial
<220> FEATURE:
<223> OTHER INFORMATION: RNAi agent sequence
```

```
<400> SEQUENCE: 475
gguuguucau agucagaauu u                                              21

<210> SEQ ID NO 476
<211> LENGTH: 21
<212> TYPE: RNA
<213> ORGANISM: Artificial
<220> FEATURE:
<223> OTHER INFORMATION: RNAi agent sequence

<400> SEQUENCE: 476
guucauaguc agaauuguau u                                              21

<210> SEQ ID NO 477
<211> LENGTH: 21
<212> TYPE: RNA
<213> ORGANISM: Artificial
<220> FEATURE:
<223> OTHER INFORMATION: RNAi agent sequence

<400> SEQUENCE: 477
gcagagaucu auaaacagau u                                              21

<210> SEQ ID NO 478
<211> LENGTH: 21
<212> TYPE: RNA
<213> ORGANISM: Artificial
<220> FEATURE:
<223> OTHER INFORMATION: RNAi agent sequence

<400> SEQUENCE: 478
cagacaggcu cuaugcuaau u                                              21

<210> SEQ ID NO 479
<211> LENGTH: 21
<212> TYPE: RNA
<213> ORGANISM: Artificial
<220> FEATURE:
<223> OTHER INFORMATION: RNAi agent sequence

<400> SEQUENCE: 479
agacaggcuc uaugcuaaau u                                              21

<210> SEQ ID NO 480
<211> LENGTH: 21
<212> TYPE: RNA
<213> ORGANISM: Artificial
<220> FEATURE:
<223> OTHER INFORMATION: RNAi agent sequence

<400> SEQUENCE: 480
ccuccuugcu cgagauggau u                                              21

<210> SEQ ID NO 481
<211> LENGTH: 21
<212> TYPE: RNA
<213> ORGANISM: Artificial
<220> FEATURE:
<223> OTHER INFORMATION: RNAi agent sequence

<400> SEQUENCE: 481
ugaagaguga agacauaaau u                                              21

<210> SEQ ID NO 482
<211> LENGTH: 21
```

```
<212> TYPE: RNA
<213> ORGANISM: Artificial
<220> FEATURE:
<223> OTHER INFORMATION: RNAi agent sequence

<400> SEQUENCE: 482
agcucauuca guuccugauu u                                              21

<210> SEQ ID NO 483
<211> LENGTH: 21
<212> TYPE: RNA
<213> ORGANISM: Artificial
<220> FEATURE:
<223> OTHER INFORMATION: RNAi agent sequence

<400> SEQUENCE: 483
cauucaguuc cugaucucau u                                              21

<210> SEQ ID NO 484
<211> LENGTH: 21
<212> TYPE: RNA
<213> ORGANISM: Artificial
<220> FEATURE:
<223> OTHER INFORMATION: RNAi agent sequence

<400> SEQUENCE: 484 agcccuuga gaacaucaau u                                               21

<210> SEQ ID NO 485
<211> LENGTH: 21
<212> TYPE: RNA
<213> ORGANISM: Artificial
<220> FEATURE:
<223> OTHER INFORMATION: RNAi agent sequence

<400> SEQUENCE: 485
cauuccaugc ccaaguauau u                                              21

<210> SEQ ID NO 486
<211> LENGTH: 21
<212> TYPE: RNA
<213> ORGANISM: Artificial
<220> FEATURE:
<223> OTHER INFORMATION: RNAi agent sequence

<400> SEQUENCE: 486
uggacuccaa ccuggauaau u                                              21

<210> SEQ ID NO 487
<211> LENGTH: 21
<212> TYPE: RNA
<213> ORGANISM: Artificial
<220> FEATURE:
<223> OTHER INFORMATION: RNAi agent sequence

<400> SEQUENCE: 487
gguuguucau agucagaauu u                                              21

<210> SEQ ID NO 488
<211> LENGTH: 21
<212> TYPE: RNA
<213> ORGANISM: Artificial
<220> FEATURE:
<223> OTHER INFORMATION: RNAi agent sequence

<400> SEQUENCE: 488
```
guucauaguc agaauuguau u 21

<210> SEQ ID NO 489
<211> LENGTH: 21
<212> TYPE: RNA
<213> ORGANISM: Artificial
<220> FEATURE:
<223> OTHER INFORMATION: RNAi agent sequence

<400> SEQUENCE: 489
gcagagaucu auaaacagau u 21

<210> SEQ ID NO 490
<211> LENGTH: 21
<212> TYPE: RNA
<213> ORGANISM: Artificial
<220> FEATURE:
<223> OTHER INFORMATION: RNAi agent sequence

<400> SEQUENCE: 490
cagacaggcu cuaugcuaau u 21

<210> SEQ ID NO 491
<211> LENGTH: 21
<212> TYPE: RNA
<213> ORGANISM: Artificial
<220> FEATURE:
<223> OTHER INFORMATION: RNAi agent sequence

<400> SEQUENCE: 491
agacaggcuc uaugcuaaau u 21

<210> SEQ ID NO 492
<211> LENGTH: 21
<212> TYPE: RNA
<213> ORGANISM: Artificial
<220> FEATURE:
<223> OTHER INFORMATION: RNAi agent sequence

<400> SEQUENCE: 492
ccuccuugcu cgagauggau u 21

<210> SEQ ID NO 493
<211> LENGTH: 21
<212> TYPE: RNA
<213> ORGANISM: Artificial
<220> FEATURE:
<223> OTHER INFORMATION: RNAi agent sequence

<400> SEQUENCE: 493
ugaagaguga agacauaaau u 21

<210> SEQ ID NO 494
<211> LENGTH: 21
<212> TYPE: RNA
<213> ORGANISM: Artificial
<220> FEATURE:
<223> OTHER INFORMATION: RNAi agent sequence

<400> SEQUENCE: 494
agcucauuca guuccugauu u 21

<210> SEQ ID NO 495
<211> LENGTH: 21
<212> TYPE: RNA
<213> ORGANISM: Artificial

```
<220> FEATURE:
<223> OTHER INFORMATION: RNAi agent sequence

<400> SEQUENCE: 495
cauucaguuc cugaucucau u                                              21

<210> SEQ ID NO 496
<211> LENGTH: 21
<212> TYPE: RNA
<213> ORGANISM: Artificial
<220> FEATURE:
<223> OTHER INFORMATION: RNAi agent sequence

<400> SEQUENCE: 496 agcccuuga gaacaucaau u                                               21

<210> SEQ ID NO 497
<211> LENGTH: 21
<212> TYPE: RNA
<213> ORGANISM: Artificial
<220> FEATURE:
<223> OTHER INFORMATION: RNAi agent sequence

<400> SEQUENCE: 497
cauuccaugc ccaaguauau u                                              21

<210> SEQ ID NO 498
<211> LENGTH: 21
<212> TYPE: RNA
<213> ORGANISM: Artificial
<220> FEATURE:
<223> OTHER INFORMATION: RNAi agent sequence

<400> SEQUENCE: 498
uggacuccaa ccuggauaau u                                              21

<210> SEQ ID NO 499
<211> LENGTH: 21
<212> TYPE: RNA
<213> ORGANISM: Artificial
<220> FEATURE:
<223> OTHER INFORMATION: RNAi agent sequence

<400> SEQUENCE: 499
gguuguucau agucagaauu u                                              21

<210> SEQ ID NO 500
<211> LENGTH: 21
<212> TYPE: RNA
<213> ORGANISM: Artificial
<220> FEATURE:
<223> OTHER INFORMATION: RNAi agent sequence

<400> SEQUENCE: 500
guucauaguc agaauuguau u                                              21

<210> SEQ ID NO 501
<211> LENGTH: 21
<212> TYPE: RNA
<213> ORGANISM: Artificial
<220> FEATURE:
<223> OTHER INFORMATION: RNAi agent sequence

<400> SEQUENCE: 501
gcagagaucu auaaacagau u                                              21
```

```
<210> SEQ ID NO 502
<211> LENGTH: 21
<212> TYPE: RNA
<213> ORGANISM: Artificial
<220> FEATURE:
<223> OTHER INFORMATION: RNAi agent sequence

<400> SEQUENCE: 502
cagacaggcu cuaugcuaau u                                              21

<210> SEQ ID NO 503
<211> LENGTH: 21
<212> TYPE: RNA
<213> ORGANISM: Artificial
<220> FEATURE:
<223> OTHER INFORMATION: RNAi agent sequence

<400> SEQUENCE: 503
agacaggcuc uaugcuaaau u                                              21

<210> SEQ ID NO 504
<211> LENGTH: 21
<212> TYPE: RNA
<213> ORGANISM: Artificial
<220> FEATURE:
<223> OTHER INFORMATION: RNAi agent sequence

<400> SEQUENCE: 504
ccuccuugcu cgagauggau u                                              21

<210> SEQ ID NO 505
<211> LENGTH: 529
<212> TYPE: PRT
<213> ORGANISM: Homo sapiens

<400> SEQUENCE: 505
```

Met Asp Leu Pro Val Gly Pro Gly Ala Ala Gly Pro Ser Asn Val Pro
 1               5                  10                  15

Ala Phe Leu Thr Lys Leu Trp Thr Leu Val Ser Asp Pro Asp Thr Asp
            20                  25                  30

Ala Leu Ile Cys Trp Ser Pro Ser Gly Asn Ser Phe His Val Phe Asp
        35                  40                  45

Gln Gly Gln Phe Ala Lys Glu Val Leu Pro Lys Tyr Phe Lys His Asn
    50                  55                  60

Asn Met Ala Ser Phe Val Arg Gln Leu Asn Met Tyr Gly Phe Arg Lys
65                  70                  75                  80

Val Val His Ile Glu Gln Gly Gly Leu Val Lys Pro Glu Arg Asp Asp
                85                  90                  95

Thr Glu Phe Gln His Pro Cys Phe Leu Arg Gly Gln Glu Gln Leu Leu
            100                 105                 110

Glu Asn Ile Lys Arg Lys Val Thr Ser Val Ser Thr Leu Lys Ser Glu
        115                 120                 125

Asp Ile Lys Ile Arg Gln Asp Ser Val Thr Lys Leu Leu Thr Asp Val
    130                 135                 140

Gln Leu Met Lys Gly Lys Gln Glu Cys Met Asp Ser Lys Leu Leu Ala
145                 150                 155                 160

Met Lys His Glu Asn Glu Ala Leu Trp Arg Glu Val Ala Ser Leu Arg
                165                 170                 175

Gln Lys His Ala Gln Gln Gln Lys Val Val Asn Lys Leu Ile Gln Phe
            180                 185                 190

Leu Ile Ser Leu Val Gln Ser Asn Arg Ile Leu Gly Val Lys Arg Lys
            195                 200                 205

Ile Pro Leu Met Leu Asn Asp Ser Gly Ser Ala His Ser Met Pro Lys
210                 215                 220

Tyr Ser Arg Gln Phe Ser Leu Glu His Val His Gly Ser Gly Pro Tyr
225                 230                 235                 240

Ser Ala Pro Ser Pro Ala Tyr Ser Ser Ser Leu Tyr Ala Pro Asp
            245                 250                 255

Ala Val Ala Ser Ser Gly Pro Ile Ile Ser Asp Ile Thr Glu Leu Ala
            260                 265                 270

Pro Ala Ser Pro Met Ala Ser Pro Gly Gly Ser Ile Asp Glu Arg Pro
            275                 280                 285

Leu Ser Ser Ser Pro Leu Val Arg Val Lys Glu Glu Pro Pro Ser Pro
            290                 295                 300

Pro Gln Ser Pro Arg Val Glu Glu Ala Ser Pro Gly Arg Pro Ser Ser
305                 310                 315                 320

Val Asp Thr Leu Leu Ser Pro Thr Ala Leu Ile Asp Ser Ile Leu Arg
            325                 330                 335

Glu Ser Glu Pro Ala Pro Ala Ser Val Thr Ala Leu Thr Asp Ala Arg
            340                 345                 350

Gly His Thr Asp Thr Glu Gly Arg Pro Pro Ser Pro Pro Thr Ser
            355                 360                 365

Thr Pro Glu Lys Cys Leu Ser Val Ala Cys Leu Asp Lys Asn Glu Leu
370                 375                 380

Ser Asp His Leu Asp Ala Met Asp Ser Asn Leu Asp Asn Leu Gln Thr
385                 390                 395                 400

Met Leu Ser Ser His Gly Phe Ser Val Asp Thr Ser Ala Leu Leu Asp
            405                 410                 415

Leu Phe Ser Pro Ser Val Thr Val Pro Asp Met Ser Leu Pro Asp Leu
            420                 425                 430

Asp Ser Ser Leu Ala Ser Ile Gln Glu Leu Leu Ser Pro Gln Glu Pro
            435                 440                 445

Pro Arg Pro Pro Glu Ala Glu Asn Ser Ser Pro Asp Ser Gly Lys Gln
450                 455                 460

Leu Val His Tyr Thr Ala Gln Pro Leu Phe Leu Asp Pro Gly Ser
465                 470                 475                 480

Val Asp Thr Gly Ser Asn Asp Leu Pro Val Leu Phe Glu Leu Gly Glu
            485                 490                 495

Gly Ser Tyr Phe Ser Glu Gly Asp Gly Phe Ala Glu Asp Pro Thr Ile
            500                 505                 510

Ser Leu Leu Thr Gly Ser Glu Pro Pro Lys Ala Lys Asp Pro Thr Val
            515                 520                 525

Ser

<210> SEQ ID NO 506
<211> LENGTH: 2137
<212> TYPE: DNA
<213> ORGANISM: Cynomolgus monkey
<220> FEATURE:
<221> NAME/KEY: misc_feature
<222> LOCATION: (68)..(156)
<223> OTHER INFORMATION: n is a, c, g, or t
<220> FEATURE:
<221> NAME/KEY: misc_feature
<222> LOCATION: (202)..(202)
<223> OTHER INFORMATION: n is a, c, g, or t
<220> FEATURE:
<221> NAME/KEY: misc_feature
<222> LOCATION: (508)..(508)
<223> OTHER INFORMATION: n is a, c, g, or t

<400> SEQUENCE: 506

| | | | | | |
|---|---|---|---|---|---|
| cgcgcccgtt | gcaagatggc | ggcggcaaag | ctgggccttg | gggctggggg | ggcgcagggg | 60 |
| gaggcggnnn | nnnnnnnnnn | nnnnnnnnnn | nnnnnnnnnn | nnnnnnnnnn | nnnnnnnnnn | 120 |
| nnnnnnnnnn | nnnnnnnnnn | nnnnnnnnnn | nnnnnncgag | atggatctgc | ccgtgggccc | 180 |
| cggtgcggcg | ggcccagca | ancgtcccgg | ccttcctgac | caagctgtgg | accctcgtga | 240 |
| gcgacccgga | caccgacgcg | ctcatctgct | ggagcccgag | tgggaacagc | ttccatgtgt | 300 |
| tcgaccaggg | ccagtttgcc | aaggaggtgc | tgcccaagta | tttcaagcac | aacaacatgg | 360 |
| ccagcttcgt | gcggcagctc | aacatgtatg | gtttccggaa | agtggtccac | atcgagcagg | 420 |
| gtggcctggt | caagccagag | agagacgaca | cggagttcca | gcaccgtgc | ttcctgcgcg | 480 |
| gccaggagca | gctccttgag | aacatcanag | aggaaagtga | ccagtgtgtc | caccctgaag | 540 |
| agtgaagaca | taaagatccg | tcaggacagt | gtcaccaagc | tgctgacgga | cgtgcagctg | 600 |
| atgaagggga | agcaggagtg | catggactcc | aagctcctgg | ccatgaagca | tgagaatgag | 660 |
| gctctgtggc | gggaggtggc | cagccttcgg | cagaagcatg | cccagcaaca | gaaagtcgtc | 720 |
| aacaagctca | ttcagttcct | gatctcactg | gtgcagtcaa | accggatcct | ggggtgaag | 780 |
| agaaagatcc | ccctgatgct | gaacgacagt | ggctcagcac | attccatgcc | caagtatggc | 840 |
| cggcagttct | ccctggagca | cgtccacggc | tcgggcccct | actcggcccc | ctccccagcc | 900 |
| tacagtagct | ccagcctcta | cgcccccgat | tctgtggcca | actccggacc | catcatctcc | 960 |
| gacatcaccg | agctggctcc | tgccagcccc | gtggcctccc | ctggcgggag | catagacgag | 1020 |
| aggcccctgt | ctagcagccc | cctggtgcgt | gtcaaagagg | agcccccag | cccgcctcag | 1080 |
| agcccccggg | tagaggaggc | gagtcccggg | cgcccatctt | ccgtggacac | cctcttgtcc | 1140 |
| ccgaccgccc | tcattgactc | catcctgcgg | gagagtgaac | ctaccccgc | ctccgccaca | 1200 |
| gccctcaccg | atgccagggg | ccacacggac | accgagggcc | ggcctccctc | accccgccc | 1260 |
| acctccaccc | ctgaaaagtg | cctcagcgta | gcctgcctgg | acaagaatga | gctcagtgat | 1320 |
| cacttggatg | ctatggactc | caacctggac | aacctgcaga | ccatgctgag | cagccacggc | 1380 |
| ttcagcgtgg | acaccagcgc | cctgctggac | ctgttcagcc | cctcggtgac | cgtgcccgac | 1440 |
| atgagcctgc | ctgaccttga | cagcagcctg | gctagtatcc | aagagctcct | gtctccccag | 1500 |
| gagccctcca | ggcctcccga | ggcagagaac | agcagcccgg | attcagggaa | gcagctggtg | 1560 |
| cactacacag | cacagccact | gttcctgctc | gaccccggct | ccgtgggcac | cgggagcagc | 1620 |
| gacttgccgg | tgctgtttga | gctggggag | ggctcctact | tctccgaagg | ggacggcttc | 1680 |
| gcagaggacc | ccaccatctc | cctgctgaca | ggctcagagc | ctcccaaagc | caaggacccc | 1740 |
| actgtctcct | aggcgcccgg | gaggagctgg | gccagccgcc | cacccccacc | cccagtgcag | 1800 |
| ggctggcctt | ggggaggaag | aggcagcctc | gaggtcctgg | gcactggtgg | gttggccacc | 1860 |
| acagccccag | taggacaaac | aggggctcag | gtctgggcag | cacctctggt | caggagggtc | 1920 |
| accccggcct | cccagtctgc | cttcccccaa | cccgtgtcc | tgtggtttgg | ttggggcttc | 1980 |
| gtagccacac | ctggactgac | cctgcaggtt | gttcataatc | agaattgtat | tttggatttt | 2040 |
| tacacaactg | tcccattccc | tgttccatag | agatatacag | atatatacac | acaggtggat | 2100 |
| ggacggacaa | gacaggcaga | gatctataaa | cagacag | | | 2137 |

```
<210> SEQ ID NO 507
<211> LENGTH: 15
<212> TYPE: DNA
<213> ORGANISM: Homo sapiens

<400> SEQUENCE: 507
atcaggaact gaatg                                                    15

<210> SEQ ID NO 508
<211> LENGTH: 15
<212> TYPE: DNA
<213> ORGANISM: Homo sapiens

<400> SEQUENCE: 508
attctgacta tgaac                                                    15

<210> SEQ ID NO 509
<211> LENGTH: 19
<212> TYPE: DNA
<213> ORGANISM: Homo sapiens

<400> SEQUENCE: 509
ttagcataga gcctgtctg                                                19

<210> SEQ ID NO 510
<211> LENGTH: 15
<212> TYPE: DNA
<213> ORGANISM: Homo sapiens

<400> SEQUENCE: 510
cattcagttc ctgat                                                    15

<210> SEQ ID NO 511
<211> LENGTH: 15
<212> TYPE: DNA
<213> ORGANISM: Homo sapiens

<400> SEQUENCE: 511
gttcatagtc agaat                                                    15

<210> SEQ ID NO 512
<211> LENGTH: 18
<212> TYPE: DNA
<213> ORGANISM: Homo sapiens

<400> SEQUENCE: 512
agacaggctc tatgctaa                                                 18

<210> SEQ ID NO 513
<211> LENGTH: 2286
<212> TYPE: DNA
<213> ORGANISM: Homo sapiens

<400> SEQUENCE: 513
gcggcgggag cgcgcccgtt gcaagatggc ggcggccatg ctgggcccccg gggctgtgtg      60 tgcgcagcgg gcggcggcgc ggcccggaag gctggcgcgg cgacggcgtt agcccggccc     120
tcggcccctc tttgcggccg ctccctccgc ctattccctc cttgctcgag atggatctgc     180
ccgtgggccc cggcgcggcg gggcccagca acgtcccggc cttcctgacc aagctgtgga     240
ccctcgtgag cgaccggac accgacgcgc tcatctgctg gagcccgagc gggaacagct     300
tccacgtgtt cgaccagggc cagtttgcca aggaggtgct gcccaagtac ttcaagcaca     360
```

```
acaacatggc cagcttcgtg cggcagctca acatgtatgg cttccggaaa gtggtccact    420
tccacgtgtt cgaccagggc cagtttgcca aggaggtgct gcccaagtac ttcaagcaca    480
acaacatggc cagcttcgtg cggcagctca acatgtatgg cttccggaaa gtggtccaca    540
tcgagcaggg cggcctggtc aagccagaga gagacgacac ggagttccag cacccatgct    600
tcctgcgtgg ccaggagcag ctccttgaga acatcaagag gaaagtgacc agtgtgtcca    660
ccctgaagag tgaagacata aagatccgcc aggacagcgt caccaagctg ctgacggacg    720
tgcagctgat gaaggggaag caggagtgca tggactccaa gctcctggcc atgaagcatg    780
agaatgaggc tctgtggcgg gaggtggcca gccttcggca aagcatgcc cagcaacaga    840 aagtcgtcaa caagctcatt cagttcctga tctcactggt gcagtcaaac cggatcctgg    900
gggtgaagag aaagatcccc ctgatgctga acgacagtgg ctcagcacat tccatgccca    960
agtatagccg gcagttctcc ctggagcacg tccacggctc gggcccctac tcggccccct    1020
ccccagccta cagcagctcc agcctctacg cccctgatgc tgtggccagc tctggaccca    1080
tcatctccga catcaccgag ctggctcctg ccagccccat ggcctccccc ggcgggagca    1140
tagacgagag gccctatcc agcagccccc tggtgcgtgt caaggaggag cccccagcc    1200 cgcctcagag ccccgggta gaggaggcga gtcccgggcg cccatcttcc gtggacaccc    1260
tcttgtcccc gaccgccctc attgactcca tcctgcggga gagtgaacct gccccgcct    1320 ccgtcacagc cctcacggac gccaggggcc acacggacac cgagggccgg cctccctccc    1380
ccccgcccac ctccaccccct gaaaagtgcc tcagcgtagc ctgcctggac aagaatgagc    1440
tcagtgacca cttggatgct atggactcca acctggataa cctgcagacc atgctgagca    1500
gccacggctt cagcgtggac accagtgccc tgctggacct gttcagcccc tcggtgaccg    1560
tgcccgacat gagcctgcct gaccttgaca gcagcctggc cagtatccaa gagctcctgt    1620
ctccccagga gccccccagg cctcccgagg cagagaacag cagcccggat tcaggaagc    1680 agctggtgca ctacacagcg cagccgctgt tcctgctgga ccccggctcc gtggacaccg    1740
ggagcaacga cctgccggtg ctgtttgagc tgggagaggg ctcctacttc tccgaagggg    1800
acggcttcgc cgaggacccc accatctccc tgctgacagg ctcggagcct cccaaagcca    1860
aggaccccac tgtctcctag aggccccgga ggagctgggc cagccgccca ccccacccc    1920 cagtgcaggg ctggtcttgg ggaggcaggg cagcctcgcg gtcttgggca ctggtgggtc    1980
ggccgccata gccccagtag dacaaacggg ctcgggtctg ggcagcacct ctggtcagga    2040
gggtcaccct ggcctgccag tctgccttcc cccaaccccg tgtcctgtgg tttggttggg    2100
gcttcacagc cacacctgga ctgaccctgc aggttgttca tagtcagaat tgtattttgg    2160 attttacac aactgtcccg ttccccgctc cacagagata cacagatata tacacacagt    2220
ggatggacgg acaagacagg cagagatcta taaacagaca ggctctatgc taaaaaaaaa    2280
aaaaaa                                                               2286
```

<210> SEQ ID NO 514
<211> LENGTH: 19
<212> TYPE: RNA
<213> ORGANISM: Homo sapiens

<400> SEQUENCE: 514
uccaucucga gcaaggagg                                                  19

```
<210> SEQ ID NO 515
<211> LENGTH: 19
<212> TYPE: RNA
<213> ORGANISM: Homo sapiens

<400> SEQUENCE: 515
ccuccuugcu cgagaugga                                                    19
```